US011154614B2

(12) United States Patent
Cardosa et al.

(10) Patent No.: US 11,154,614 B2

(45) Date of Patent: Oct. 26, 2021

(54) METHOD FOR PRODUCING VIRUS LIKE PARTICLES

(71) Applicant: Integrated Research Associates, LLC, San Rafael, CA (US)

(72) Inventors: Mary Jane Cardosa, Penang (MY); Katharine Bossart, San Francisco, CA (US)

(73) Assignee: INTEGRATED RESEARCH ASSOCIATES, LLC, San Rafael, CA (US)

( * ) Notice: Subject to any disclaimer, the term of this patent is extended or adjusted under 35 U.S.C. 154(b) by 116 days.

(21) Appl. No.: 16/095,654

(22) PCT Filed: Apr. 19, 2017

(86) PCT No.: PCT/US2017/028300

§ 371 (c)(1),
(2) Date: Oct. 22, 2018

(87) PCT Pub. No.: WO2017/184696

PCT Pub. Date: Oct. 26, 2017

(65) Prior Publication Data

US 2019/0125862 A1 May 2, 2019

Related U.S. Application Data

(60) Provisional application No. 62/326,129, filed on Apr. 22, 2016.

(51) Int. Cl.

*A61K 39/29* (2006.01)
*C12N 7/00* (2006.01)

(Continued)

(52) U.S. Cl.

CPC .............. *A61K 39/29* (2013.01); *A61K 39/12* (2013.01); *A61P 31/14* (2018.01); *C12N 7/00* (2013.01);

(Continued)

(58) Field of Classification Search

None

See application file for complete search history.

(56) References Cited

U.S. PATENT DOCUMENTS

2001/0016351 A1* 8/2001 Sorge .................... C12N 15/72 435/320.1
2006/0025367 A1 2/2006 Simari
2014/0170186 A1* 6/2014 Nabel .................... A61K 39/12 424/218.1

FOREIGN PATENT DOCUMENTS

WO WO-98/21338 A1 5/1998
WO WO-03/062408 A1 7/2003

(Continued)

OTHER PUBLICATIONS

Zhu et al. Attenuated dengue 2 viruses with deletions in capsid protein derived from an infectious full-length cDNA clone. Virus Research. vol. 126, Issues 1-2, Jun. 2007, pp. 226-232. (Year: 2007).*

(Continued)

*Primary Examiner* — Michelle S Horning

(74) *Attorney, Agent, or Firm* — Mintz, Levin, Cohn, Ferris, Glovsky and Popeo, P.C.; Terri Shieh-Newton

(57) ABSTRACT

The present invention relates to the production of structural proteins and virus-like particles (VLPs) of flaviviruses and hepatitis C. Production is through use of a single expression cassette comprising a viral structural gene, a furin encoding gene and a bicistronic expression element such as an internal ribosome entry site (IRES) between the viral and furin genes. Both the viral gene and furin gene can include a partial capsid encoding sequence acting as a signal peptide to co-locate the viral protein and furin and to act as a (Continued)

membrane anchor for the viral protein and furin. A separate expression cassette comprising a non-structural viral gene can be combined with the initial cassette. The structural proteins and VLPs can be used in vaccines and in the treatment of viral infections.

21 Claims, 83 Drawing Sheets

Specification includes a Sequence Listing.

(51) Int. Cl.

| | |
|---|---|
| ***A61K 39/12*** | (2006.01) |
| ***C12N 9/64*** | (2006.01) |
| ***A61P 31/14*** | (2006.01) |
| ***C12N 15/62*** | (2006.01) |
| *A61K 39/00* | (2006.01) |

(52) U.S. Cl.

CPC ........... *C12N 9/6454* (2013.01); *C12N 15/62* (2013.01); *A61K 2039/55505* (2013.01); *C12N 2710/14143* (2013.01); *C12N 2770/24123* (2013.01); *C12N 2770/24134* (2013.01); *C12N 2770/24151* (2013.01); *C12N 2800/22* (2013.01); *C12N 2830/20* (2013.01); *C12N 2830/50* (2013.01); *C12N 2840/203* (2013.01); *Y02A 50/30* (2018.01)

(56) References Cited

FOREIGN PATENT DOCUMENTS

| | | | |
|---|---|---|---|
| WO | WO-2007/014162 | A2 | 2/2007 |
| WO | WO-2007/014162 | A3 | 2/2007 |
| WO | WO-2010/107847 | A1 | 9/2010 |
| WO | WO-2013/098655 | A2 | 7/2013 |
| WO | WO-2016/210127 | A1 | 12/2016 |

OTHER PUBLICATIONS

Samsa et al. Uncoupling cis-Acting RNA elements from coding sequences revealed a requirement of the N-terminal region of dengue virus capsid protein in virus particle formation. J Virol. Jan. 2012;86(2): 1046-58. (Year: 2012).*

Chang et al. Enhancing biosynthesis and secretion of premembrane and envelope proteins by the chimeric plasmid of dengue virus type 2 and Japanese encephalitis virus. Virology. Feb. 1, 2003;306(1): 170-80. doi: 10.1016/s0042-6822(02)00028-4. (Year: 2003).*

De Felipe. Polycistronic viral vectors. Curr Gene Ther. Sep. 2002;2(3):355-78. doi: 10.2174/1566523023347742. (Year: 2002).*

Dowd et al. Combined effects of the structural heterogeneity and dynamics of flaviviruses on antibody recognition. J Virol. Oct. 2014; 88(20): 11726-37. doi: 10.1128/JVI.01140-14. (Year: 2014).*

Galula et al. Does structurally-mature dengue virion matter in vaccine preparation in post-Dengvaxia era?. Hum Vaccin Immunother. 2019; 15(10):2328-2336. doi:10.1080/21645515.2019.1643676 (Year: 2019).*

Hsieh et al. A strong endoplasmic reticulum retention signal in the stem-anchor region of envelope glycoprotein of dengue virus type 2 affects the production of virus-like particles. Virology 374 (2008) 338-350 (Year: 2008).*

Khromykh AA, Varnavski AN, Sedlak PL, Westaway EG. Coupling between replication and packaging of flavivirus RNA: evidence derived from the use of DNA-based full-length cDNA clones of Kunjin virus. J Virol. May 2001;75(10):4633-40. (Year: 2001).*

Lindenbach et al. Flaviviridae: The Viruses and Their Replication. Fields Virology, 5th Edition. D. M. Knipe and P. M. Howley, Eds. Lippincott-Raven Publishers, Philadelphia (2007). Chapter 33, p. 1101-1133. (Year: 2007).*

Roby et al. Post-translational regulation and modifications of flavivirus structural proteins. J Gen Virol. Jul. 2015;96(Pt 7): 1551-69. (Year: 2015).*

Shen et al. Epitope resurfacing on dengue virus-like particle vaccine preparation to induce broad neutralizing antibody. Elife. Oct. 18, 2018;7:e38970. doi: 10.7554/eLife.38970. (Year: 2018).*

Wilken et al. Adaptive Immunity to Dengue Virus: Slippery Slope or Solid Ground for Rational Vaccine Design? Pathogens. Jun. 15, 2020;9(6):470. doi: 10.3390/pathogens9060470. (Year: 2020).*

International Search Report dated Jul. 11, 2017, for PCT Application No. PCT/US2017/028300, filed Apr. 19, 2017, 10 pages.

Jones, D.M. et al. (Jul. 23, 2010, e-published May 10, 2010). "Hepatitis C virus: assembly and release of virus particles," *J Biol Chem* 285(30:22733-22739.

Lobigs, M. et al. (May 25, 2010, e-published Mar. 6, 2010). "A flavivirus signal peptide balances the catalytic activity of two proteases and thereby facilitates virus morphogenesis," *Virology* 401(1):80-89.

Nelson, S. et al. (May 9, 2008). "Maturation of West Nile virus modulates sensitivity to antibody-mediated neutralization," *PLoS Pathog* 4(5):e1000060.

Patkar, C.G. et al. (Jun. 2007). "Functional requirements of the yellow fever virus capsid protein," *J Virol* 81(12):6471-6481.

Qing, M. et al. (May 2010, e-published Feb. 12, 2010). "A high-throughput assay using dengue-1 virus-like particles for drug discovery," *Antiviral Res* 86(2):163-171.

Chang, G-J. et al. (Feb. 1, 2003). "Enhancing biosynthesis and secretion of premembrane and envelope proteins by the chimeric plasmid of dengue virus type 2 and Japanese encephalitis virus," *Virology* 306(1):170-180.

De Felipe, P. (Sep. 2002). "Polycistronic viral vectors," *Curr Gene Ther* 2(3):355-378.

Dowd, K.A. et al. (Oct. 2014, e-published Jul. 30, 2014). "Combined effects of the structural heterogeneity and dynamics of flaviviruses on antibody recognition," *J Virol* 88(20:11726-11737.

Galula, J.U. et al. (2019, e-published Aug. 23, 2019). "Does structurally-mature dengue virion matter in vaccine preparation in post-Dengvaxia era?" *Human Vaccines & Immunotherapeutics* 15(10): 2328-2336.

Hsieh, S-C. et al. (May 10, 2008, e-published Feb. 5, 2008). "A strong endoplasmic reticulum retention signal in the stem-anchor region of envelope glycoprotein of dengue virus type 2 affects the production of virus-like particles," *Virology* 374:(2):338-350.

Khromykh, A.A. et al. (May 2001). "Coupling between replication and packaging of flavivirus RNA: evidence derived from the use of DNA-based full-length cDNA clones of Kunjin virus," *Journal of Virology* 75(10):4633-4640.

Lindenbach, B.D. et al. Flaviviridae: The Viruses and Their Replication, Chapter 33 *in Fields Virology*, 5th Edition. D. M. Knipe and P. M. Howley, Eds. Lippincott-Raven Publishers, Philadelphia (2007), 52 pages.

Roby, J.A. et al. (Jul. 2015, e-published Feb. 23, 2015). "Post-translational regulation and modifications of flavivirus structural proteins," *J Gen Virol* 6(Pt. 7):1551-1569.

Shen, W-F. et al. (Oct. 18, 2018). "Epitope resurfacing on dengue virus-like particle vaccine preparation to induce broad neutralizing antibody," *eLife* 7:e38970.

Wilken, L. et al. (Jun. 15, 2020). "Adaptive Immunity to Dengue Virus: Slippery Slope or Solid Ground for Rational Vaccine Design?" *Pathogens* 9(6):470.

* cited by examiner

Fig. 1A

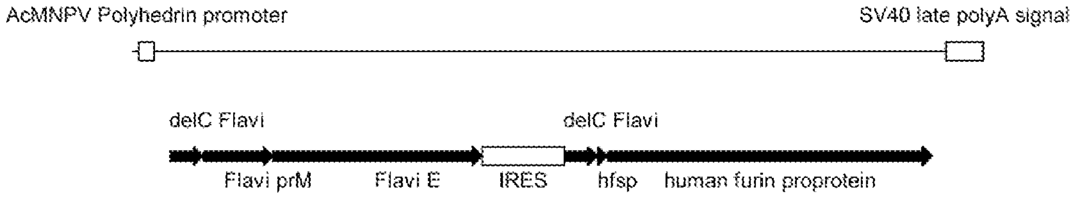

Fig. 1B

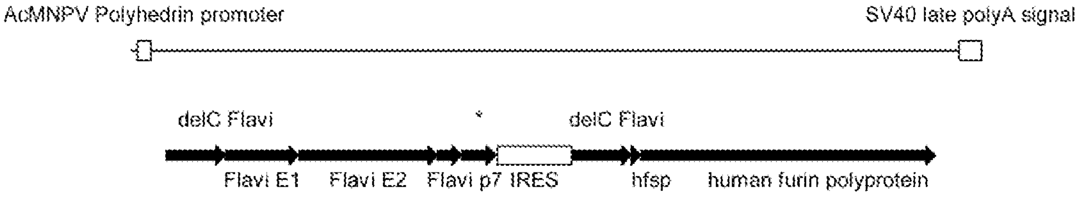

Fig. 1C

Molecule Features: (6051 bps)

| Start | End | Name | Draw As |
|---|---|---|---|
| 43 | 152 | AcMNPV Polyhedrin promoter | Region |
| 266 | 499 | delC Flavi | Gene |
| 500 | 997 | Flavi prM | Gene |
| 998 | 2482 | Flavi E | Gene |
| 2486 | 3071 | IRES | Gene |
| 3072 | 3305 | delC flavi | Gene |
| 3306 | 3377 | hfsp | Gene |
| 3378 | 5687 | human furin proprotein | Gene |
| 5786 | 6051 | SV40 late polyA signal | Region |

Fig. 1D

Molecule Features: (6663 bps)

| Start | End | Name | Draw As |
|---|---|---|---|
| 43 | 152 | AcMNPV Polyhedrin promoter | Region |
| 269 | 733 | delC Flavi | Gene |
| 734 | 1309 | Flavi E1 | Gene |
| 1310 | 2398 | Flavi E2 | Gene |
| 2399 | 2587 | Flavi p7 | Gene |
| 2588 | 2854 | * | Gene |
| 2864 | 3449 | IRES | Gene |
| 3450 | 3917 | delC Flavi | Gene |
| 3918 | 3989 | hfsp | Gene |
| 3990 | 6299 | human furin polyprotein | Gene |
| 6486 | 6663 | SV40 late polyA signal | Region |

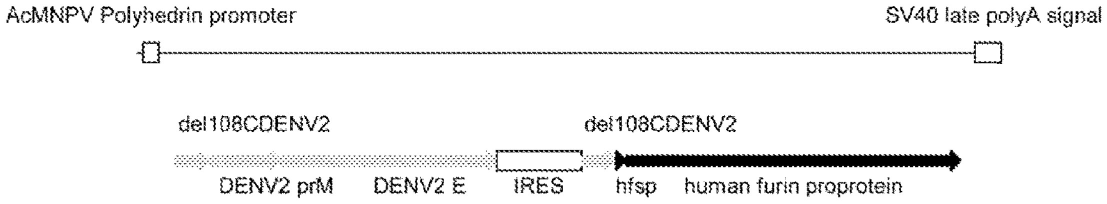

Fig. 2A

AcMNPV Polyhedrin promoter — SV40 late polyA signal del108CDENV2 — del108CDENV2
DENV2 prM — DENV2 E — IRES — hfsp — human furin proprotein

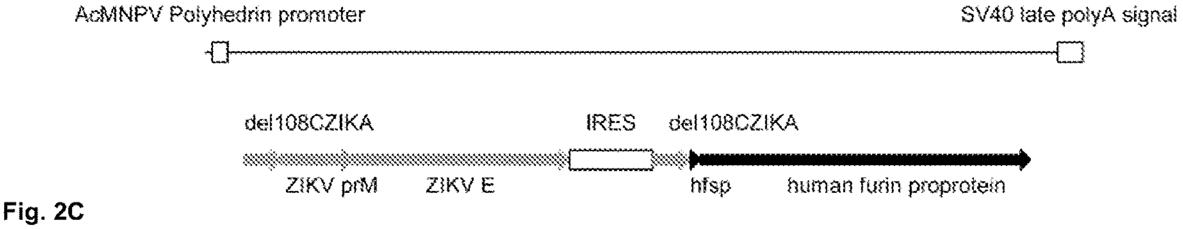

Fig. 2B

AcMNPV Polyhedrin promoter — SV40 late polyA signal del108CZIKA — IRES — del108CZIKA
ZIKV prM — ZIKV E — hfsp — human furin proprotein

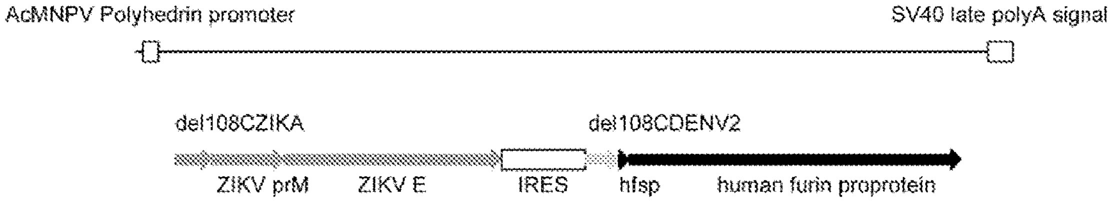

Fig. 2C

AcMNPV Polyhedrin promoter — SV40 late polyA signal del108CZIKA — del108CDENV2
ZIKV prM — ZIKV E — IRES — hfsp — human furin proprotein

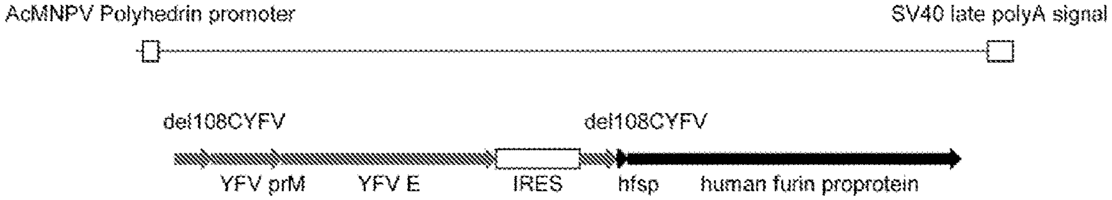

Fig. 2D

AcMNPV Polyhedrin promoter — SV40 late polyA signal del108CYFV — del108CYFV
YFV prM — YFV E — IRES — hfsp — human furin proprotein

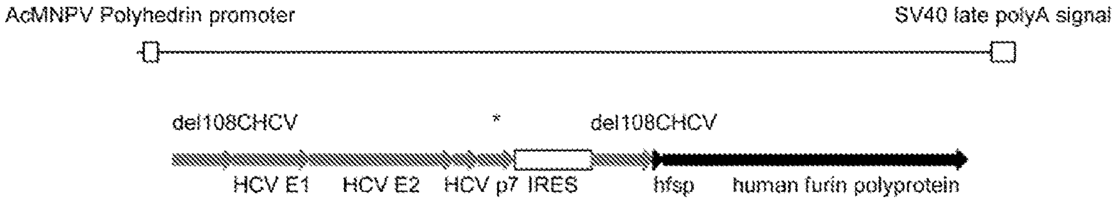

Fig. 2E

AcMNPV Polyhedrin promoter — SV40 late polyA signal del108CHCV — * — del108CHCV
HCV E1 — HCV E2 — HCV p7 — IRES — hfsp — human furin polyprotein

Fig. 2F ule Features: (6051 bps)

| Start | End | Name | Feature Key | Draw As |
|---|---|---|---|---|
| 43 | 152 | AcMNPV Polyhedrin promoter | | Region |
| 266 | 499 | del108CDENV2 | | Gene |
| 500 | 997 | DENV2 prM | | Gene |
| 998 | 2482 | DENV2 E | | Gene |
| 2486 | 3071 | IRES | | Gene |
| 3072 | 3305 | del108CDENV2 | | Gene |
| 3306 | 3377 | hfsp | | Gene |
| 3378 | 5687 | human furin proprotein | | Gene |
| 5786 | 6051 | SV40 late polyA signal | | Region |

Fig. 2G

Molecule Features: (6132 bps)

| Start | End | Name | Feature Key | Draw As |
|---|---|---|---|---|
| 43 | 152 | AcMNPV Polyhedrin promoter | | Region |
| 269 | 523 | del108CZIKA | | Gene |
| 524 | 1027 | ZIKV prM | | Gene |
| 1028 | 2539 | ZIKV E | | Gene |
| 2543 | 3128 | IRES | | Gene |
| 3129 | 3386 | del108CZIKA | | Gene |
| 3387 | 3458 | hfsp | | Gene |
| 3459 | 5768 | human furin proprotein | | Gene |
| 5954 | 6132 | SV40 late polyA signal | | Region |

Fig. 2H

Molecule Features: (6108 bps)

| Start | End | Name | Feature Key | Draw As |
|---|---|---|---|---|
| 43 | 152 | AcMNPV Polyhedrin promoter | | Region |
| 269 | 523 | del108CZIKA | | Gene |
| 524 | 1027 | ZIKV prM | | Gene |
| 1028 | 2539 | ZIKV E | | Gene |
| 2543 | 3128 | IRES | | Gene |
| 3129 | 3362 | del108CDENV2 | | Gene |
| 3363 | 3434 | hfsp | | Gene |
| 3435 | 5744 | human furin proprotein | | Gene |
| 5930 | 6108 | SV40 late polyA signal | | Region |

Primers (0 sites)

Fig. 2I

Molecule Features: (6087 bps)

| Start | End | Name | Feature Key | Draw As |
|---|---|---|---|---|
| 43 | 152 | AcMNPV Polyhedrin promoter | | Region |
| 266 | 523 | del108CYFV | | Gene |
| 524 | 1015 | YFV prM | | Gene |
| 1016 | 2497 | YFV E | | Gene |
| 2498 | 3083 | IRES | | Gene |
| 3084 | 3341 | del108CYFV | | Gene |
| 3342 | 3413 | hfsp | | Gene |
| 3414 | 5723 | human furin proprotein | | Gene |
| 5909 | 6087 | SV40 late polyA signal | | Region |

Fig. 2J

Molecule Features: (6663 bps)

| Start | End | Name | Feature Key | Draw As |
|---|---|---|---|---|
| 43 | 152 | AcMNPV Polyhedrin promoter | | Region |
| 269 | 733 | del108CHCV | | Gene |
| 734 | 1309 | HCV E1 | | Gene |
| 1310 | 2398 | HCV E2 | | Gene |
| 2399 | 2587 | HCV p7 | | Gene |
| 2588 | 2863 | * | | Gene |
| 2864 | 3449 | IRES | | Gene |
| 3450 | 3917 | del108CHCV | | Gene |
| 3918 | 3989 | hfsp | | Gene |
| 3990 | 6299 | human furin polyprotein | | Gene |
| 6486 | 6663 | SV40 late polyA signal | | Region |

Fig. 3A

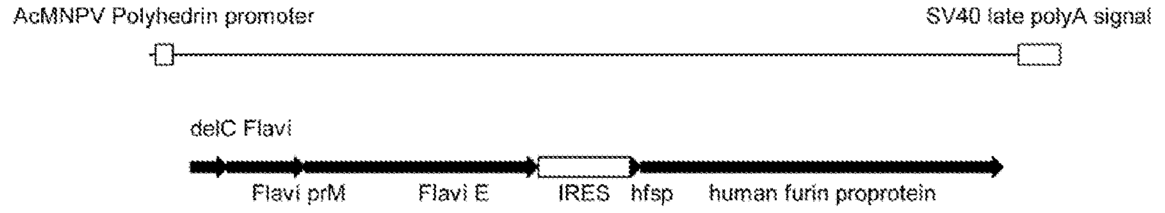

Fig. 3B

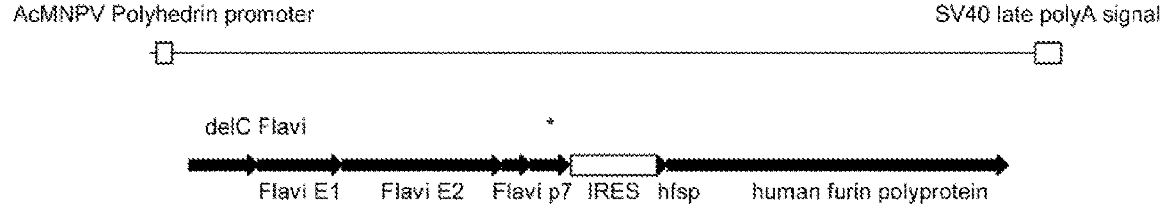

Fig. 3C

Molecule Features: (5817 bps)

| Start | End | Name | Feature Key | Draw As |
|---|---|---|---|---|
| 43 | 152 | AcMNPV Polyhedrin promoter | | Region |
| 266 | 499 | delC Flavi | | Gene |
| 500 | 997 | Flavi prM | | Gene |
| 998 | 2482 | Flavi E | | Gene |
| 2486 | 3071 | IRES | | Gene |
| 3072 | 3143 | hfsp | | Gene |
| 3144 | 5453 | human furin proprotein | | Gene |
| 5552 | 5817 | SV40 late polyA signal | | Region |

Primers (0 sites)

Fig. 3D

Molecule Features: (6195 bps)

| Start | End | Name | Feature Key | Draw As |
|---|---|---|---|---|
| 43 | 152 | AcMNPV Polyhedrin promoter | | Region |
| 269 | 733 | delC Flavi | | Gene |
| 734 | 1309 | Flavi E1 | | Gene |
| 1310 | 2398 | Flavi E2 | | Gene |
| 2399 | 2587 | Flavi p7 | | Gene |
| 2588 | 2854 | * | | Gene |
| 2864 | 3449 | IRES | | Gene |
| 3450 | 3521 | hfsp | | Gene |
| 3522 | 5831 | human furin polyprotein | | Gene |
| 6018 | 6195 | SV40 late polyA signal | | Region |

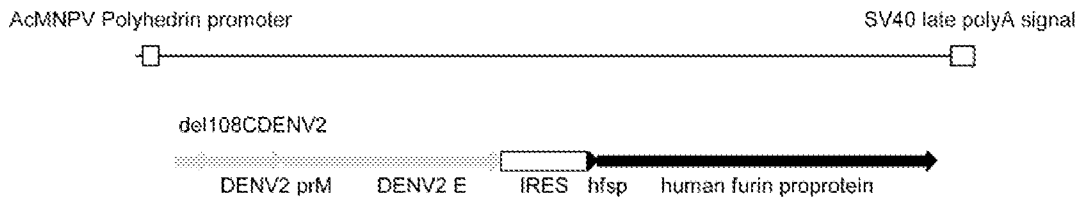

Fig. 4A

AcMNPV Polyhedrin promoter — SV40 late polyA signal del108CDENV2: DENV2 prM — DENV2 E — IRES — hfsp — human furin proprotein

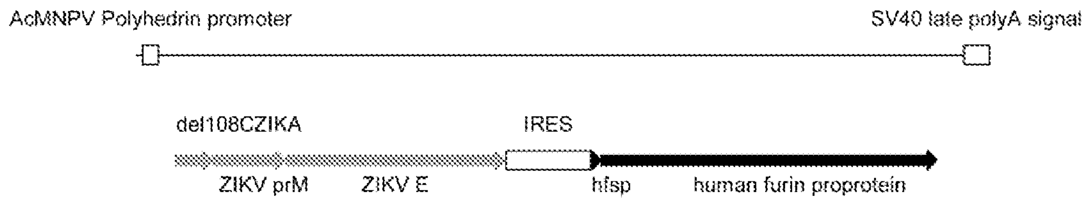

Fig. 4B

AcMNPV Polyhedrin promoter — SV40 late polyA signal del108CZIKA: ZIKV prM — ZIKV E — IRES — hfsp — human furin proprotein

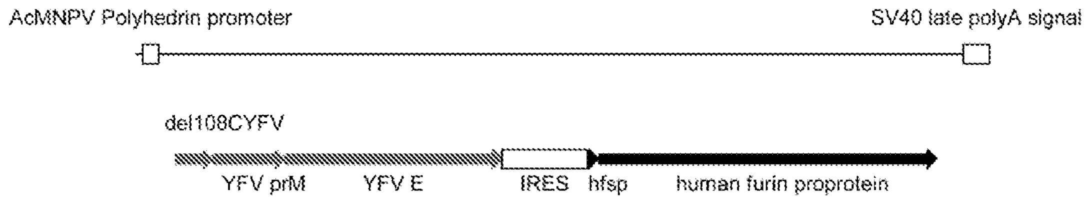

Fig. 4C

AcMNPV Polyhedrin promoter — SV40 late polyA signal del108CYFV: YFV prM — YFV E — IRES — hfsp — human furin proprotein

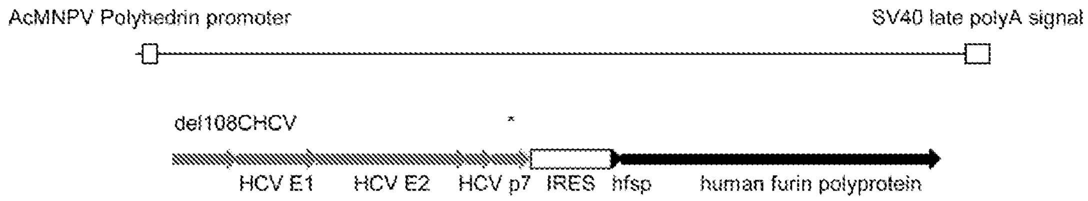

Fig. 4D

AcMNPV Polyhedrin promoter — SV40 late polyA signal del108CHCV: HCV E1 — HCV E2 — HCV p7 — IRES — hfsp — human furin polyprotein

Fig. 4E

Molecule Features: (5817 bps)

| Start | End | Name | Feature Key | Draw As |
|---|---|---|---|---|
| 43 | 152 | AcMNPV Polyhedrin promoter | | Region |
| 266 | 499 | del108CDENV2 | | Gene |
| 500 | 997 | DENV2 prM | | Gene |
| 998 | 2482 | DENV2 E | | Gene |
| 2486 | 3071 | IRES | | Gene |
| 3072 | 3143 | hfsp | | Gene |
| 3144 | 5453 | human furin proprotein | | Gene |
| 5552 | 5817 | SV40 late polyA signal | | Region |

Fig. 4F

Molecule Features: (5874 bps)

| Start | End | Name | Feature Key | Draw As |
|---|---|---|---|---|
| 43 | 152 | AcMNPV Polyhedrin promoter | | Region |
| 269 | 523 | del108CZIKA | | Gene |
| 524 | 1027 | ZIKV prM | | Gene |
| 1028 | 2539 | ZIKV E | | Gene |
| 2543 | 3128 | IRES | | Gene |
| 3129 | 3200 | hfsp | | Gene |
| 3201 | 5510 | human furin proprotein | | Gene |
| 5696 | 5874 | SV40 late polyA signal | | Region |

Fig. 4G

Molecule Features: (5829 bps)

| Start | End | Name | Feature Key | Draw As |
|---|---|---|---|---|
| 43 | 152 | AcMNPV Polyhedrin promoter | | Region |
| 266 | 523 | del108CYFV | | Gene |
| 524 | 1015 | YFV prM | | Gene |
| 1016 | 2497 | YFV E | | Gene |
| 2498 | 3083 | IRES | | Gene |
| 3084 | 3155 | hfsp | | Gene |
| 3156 | 5465 | human furin proprotein | | Gene |
| 5651 | 5829 | SV40 late polyA signal | | Region |

Fig. 4H

Molecule Features: (6195 bps)

| Start | End | Name | Feature Key | Draw As |
|---|---|---|---|---|
| 43 | 152 | AcMNPV Polyhedrin promoter | | Region |
| 269 | 733 | del108CHCV | | Gene |
| 734 | 1309 | HCV E1 | | Gene |
| 1310 | 2398 | HCV E2 | | Gene |
| 2399 | 2587 | HCV p7 | | Gene |
| 2588 | 2854 | * | | Gene |
| 2864 | 3449 | IRES | | Gene |
| 3450 | 3521 | hfsp | | Gene |
| 3522 | 5831 | human furin polyprotein | | Gene |
| 6018 | 6195 | SV40 late polyA signal | | Region |

Fig. 5A Codon Adaptation Index (CAI)
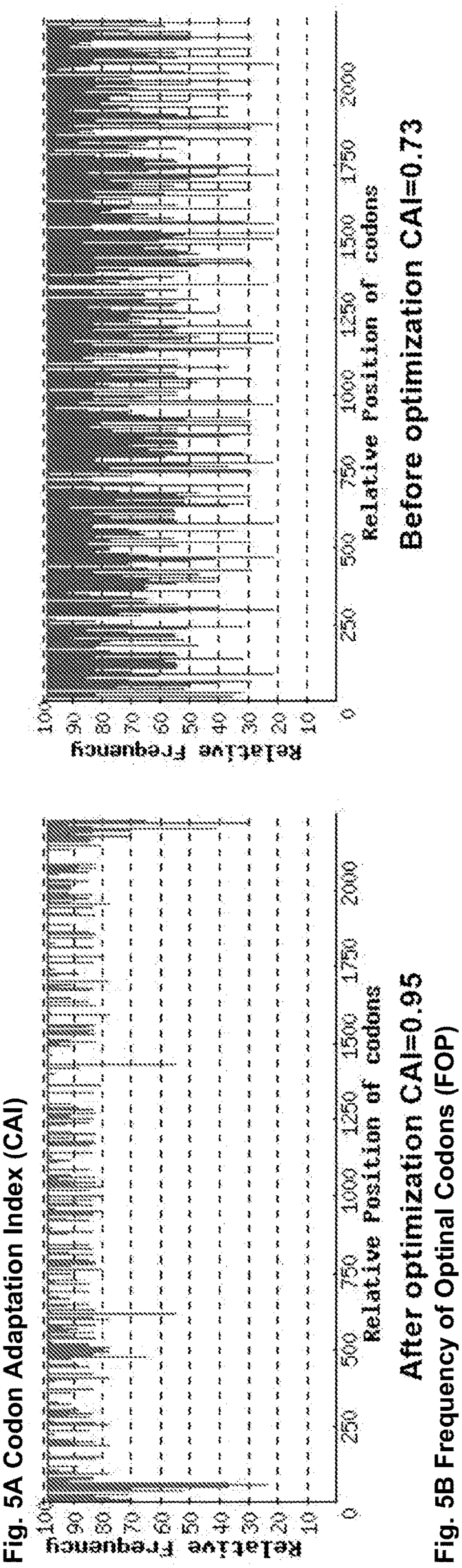
Fig. 5B Frequency of Optinal Codons (FOP)
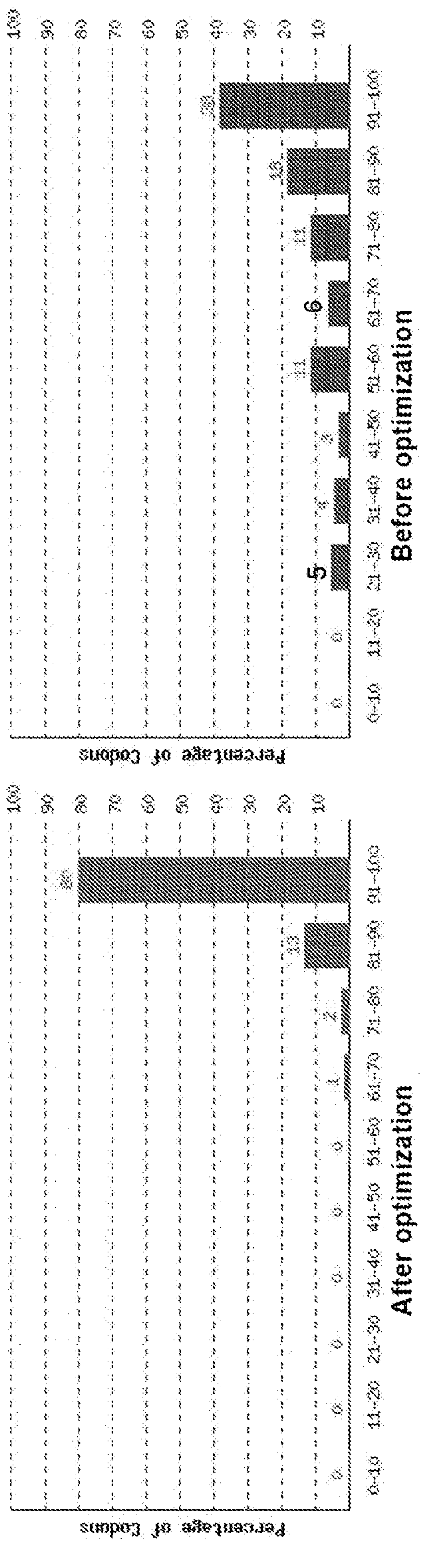

Fig. 5C GC Content Adjustmanet of DENV 2 del108C-prM-E for insect cells
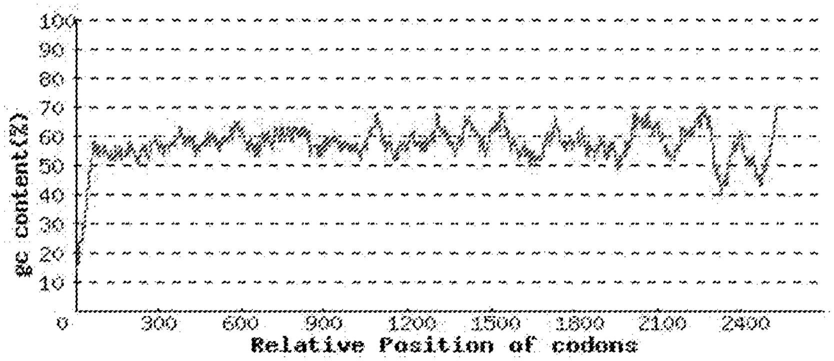
After optimization Average GC content was 57.2%
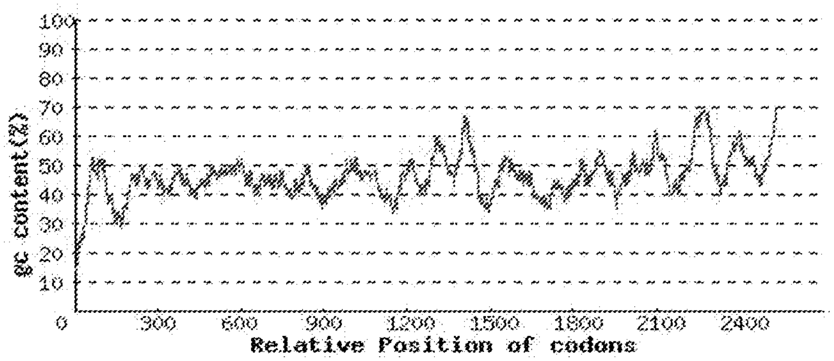
Before optimization Average GC content was 46.16%
Fig. 6A Codon Adaptation Index (CAI)
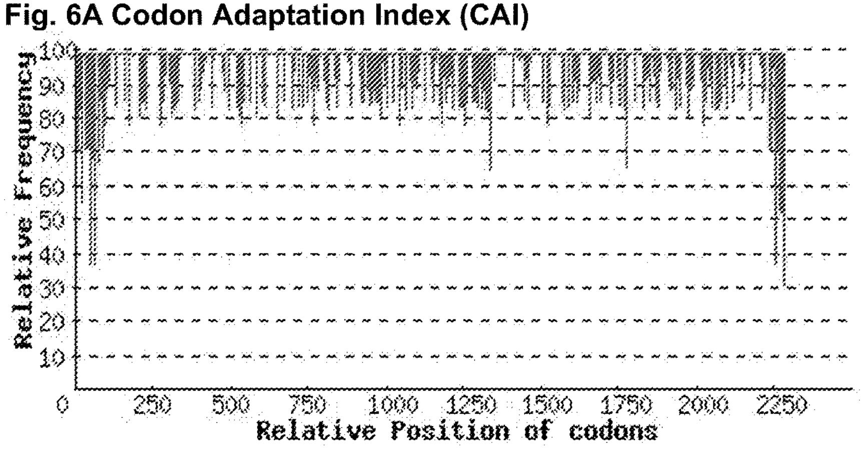
After optimization CAI=0.95
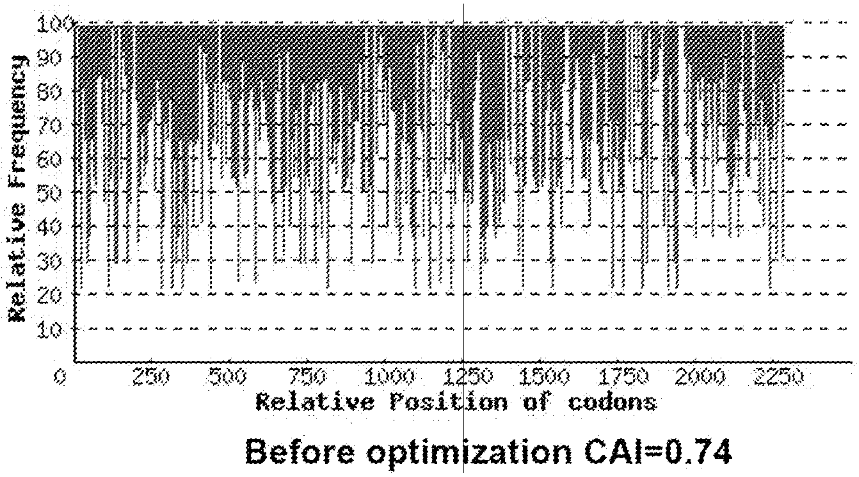
Before optimization CAI=0.74

Fig. 6B Frequency of Optimal Codons (FOP)
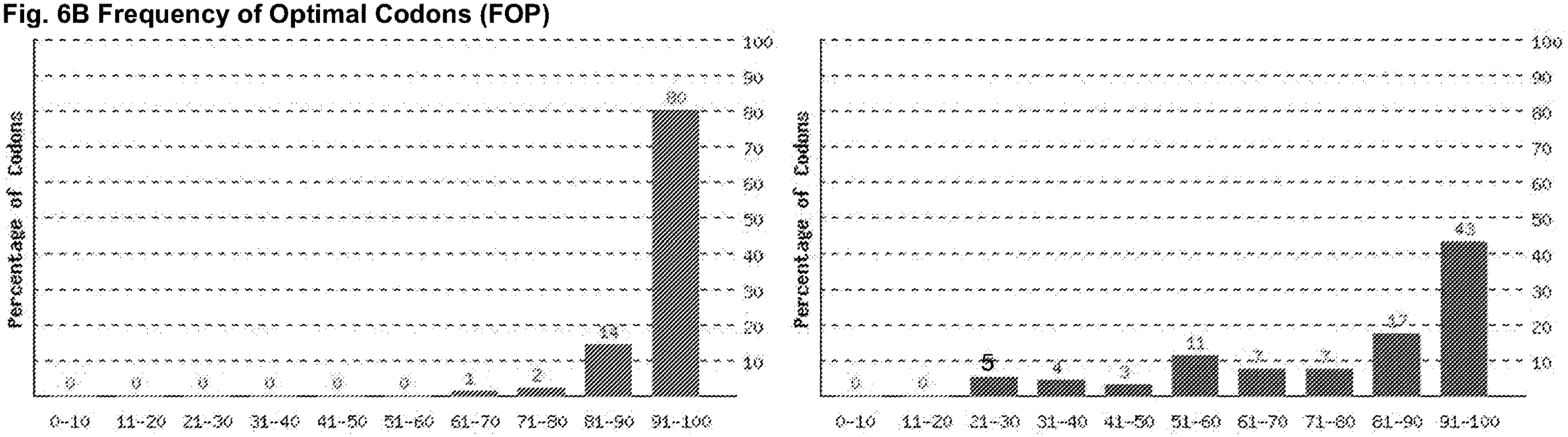
After optimization
Before optimization
Fig. 6C GC Content Adjustment of DENV del108C-prM-E for insect cells
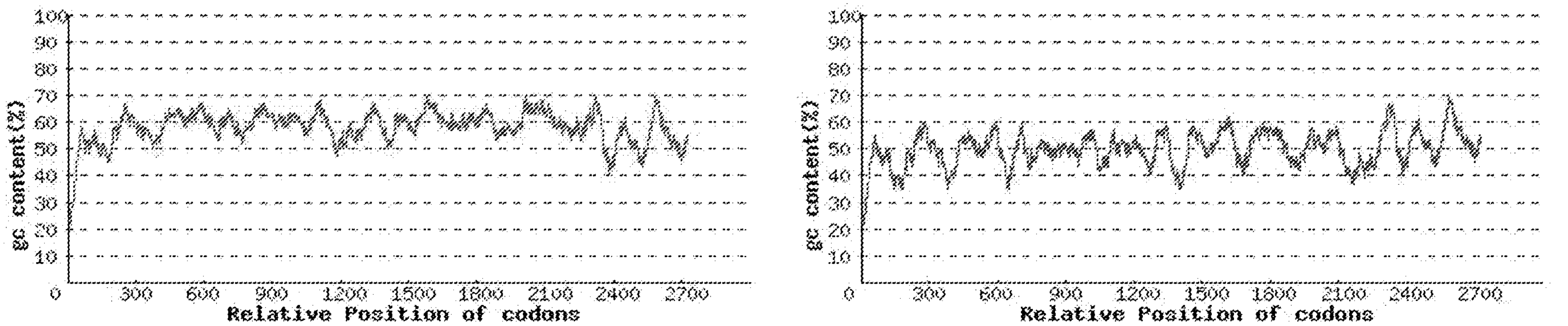
After optimization Average GC content was 58.02%
Before optimization Average GC content was 49.89%

Fig. 7A Codon Adaptation Index (CAI)
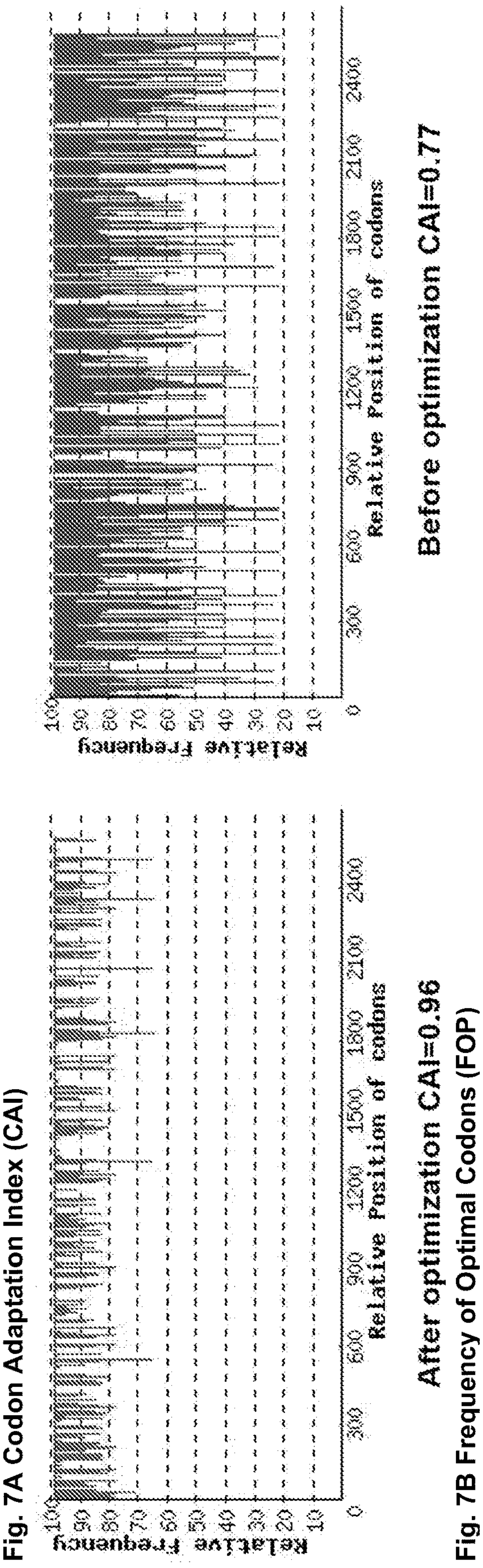
Fig. 7B Frequency of Optimal Codons (FOP)
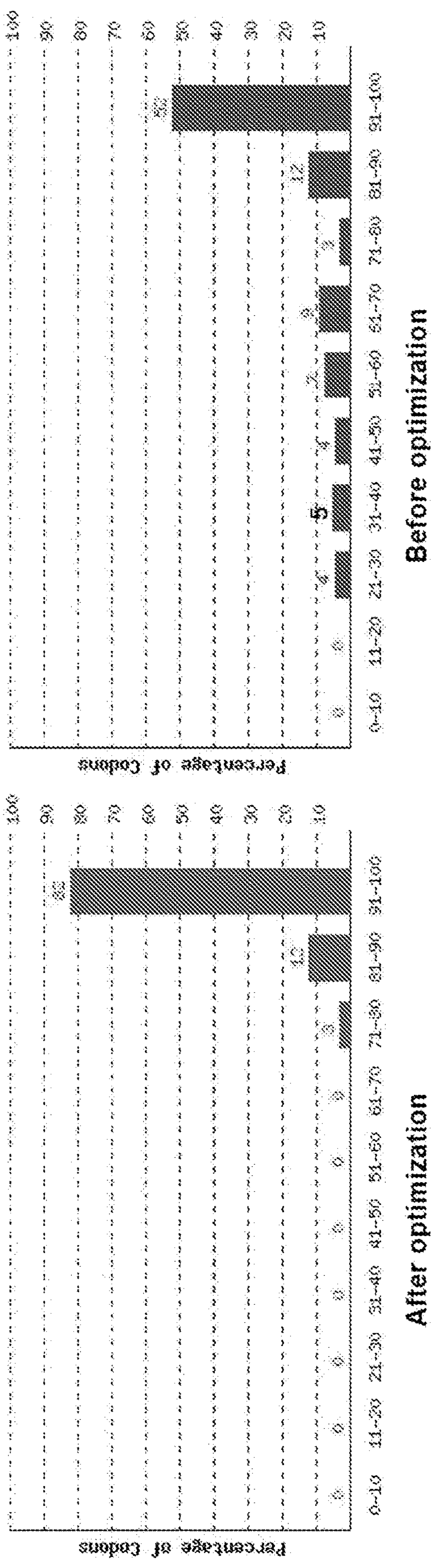

Fig. 7C GC Content Adjustment of HCV del108C-E1-E2-p7-NS2del384 ofr insect cells
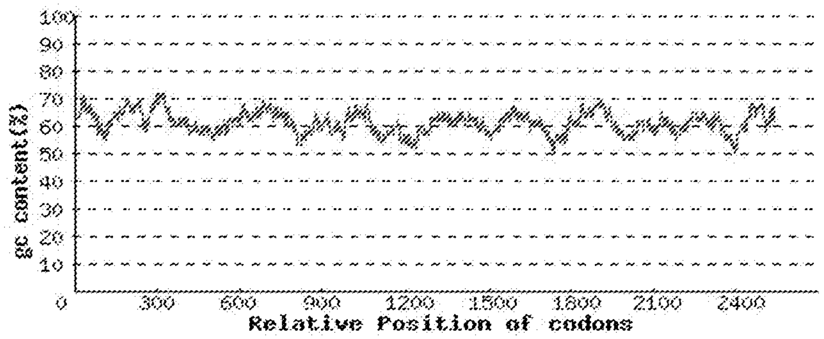
After optimization Average GC content was 61.15%
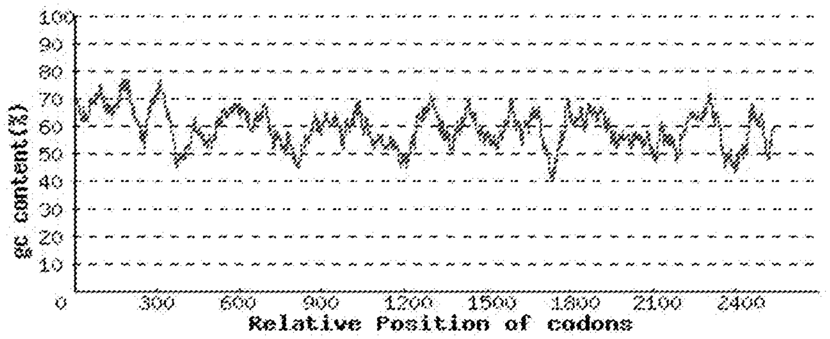
Before optimization Average GC content was 59.32%
Fig. 8A Codon Adaptation Index (CAI)
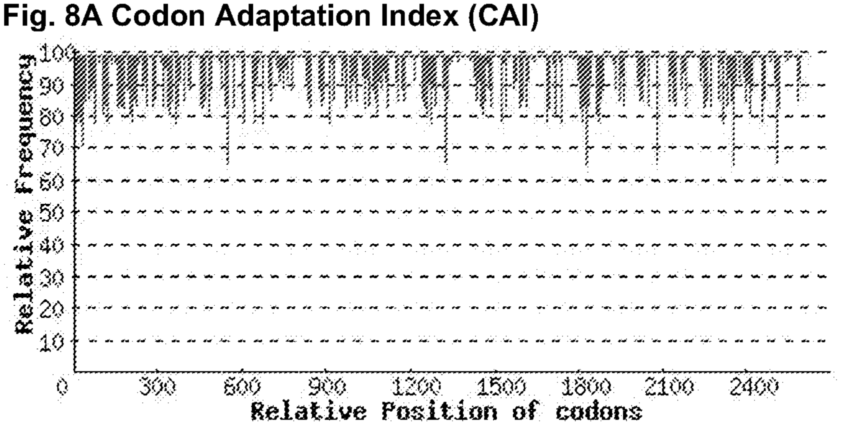
After optimization CAI=0.96
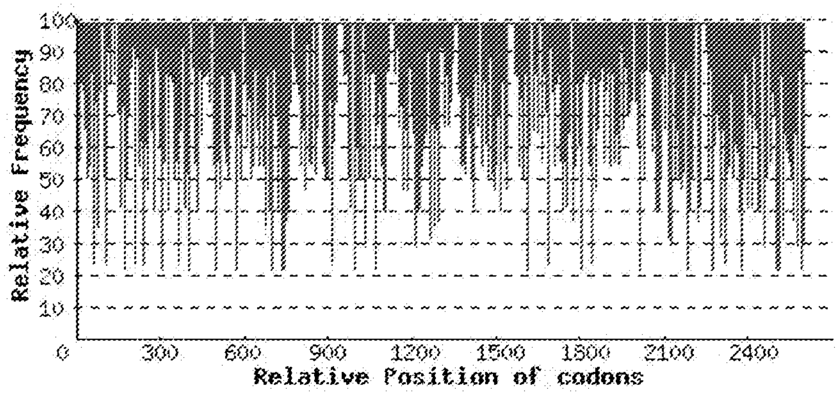
Before optimization CAI=0.77

Fig. 8B Frequency of Optimal Codons (FOP)
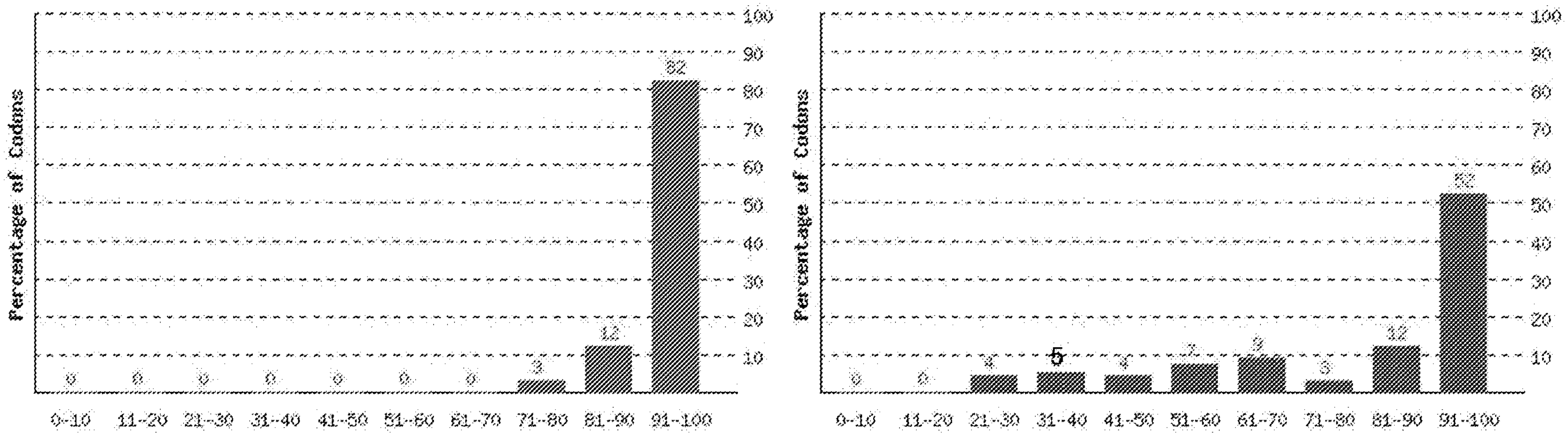
After optimization
Before optimization
Fig. 8C GC Content Adjustment of del108CDENV 2-human furin for insect cells
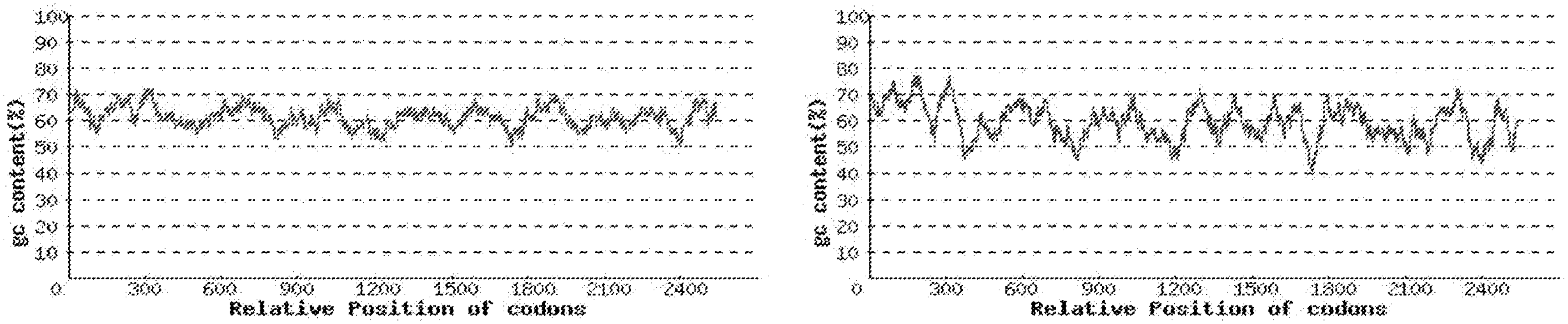
After optimization Average GC content was 61.15%
Before optimization Average GC content was 59.32%

DENV VLP & DENV NS-1 Dual Promoter Expression Cassette

ZIKV VLP & ZIKV NS-1 Dual Promoter Expression Cassettes

HSV tk polyA signal — 1 — p10 AcMNPV — ZIKV NS1 — del108CZIKA — ZIKV prM — ZIKV E — IRES — del108CZIKA — hfsp — human furin proprotein — 7637 — SV40 late polyA signal HSV tk polyA signal — 1 — p10 AcMNPV — ZIKV NS1 — del108CZIKA — ZIKV prM — ZIKV E — IRES — del108CDENV2 — hfsp — human furin proprotein — 7613 — SV40 late polyA signal

Fig. 10D

Molecule Features:

| Start | End | Name | Feature Key | Draw As |
|---|---|---|---|---|
| 283 | 1 C | HSV tk polyA signal | | Region |
| 1370 | 312 C | DENV2 NS1 | | Gene |
| 1530 | 1409 C | p10 | promoter | Region |
| 1548 | 1657 | AcMNPV | promoter | Region |
| 1771 | 2004 | del108CDENV2 | | Gene |
| 2005 | 2502 | DENV2 prM | | Gene |
| 2503 | 3987 | DENV2 E | | Gene |
| 3991 | 4576 | IRES | | Gene |
| 4577 | 4810 | del108CDENV2 | | Gene |
| 4811 | 4882 | hfsp | | Gene |
| 4883 | 7192 | human furin proprotein | | Gene |
| 7378 | 7556 | SV40 late polyA signal | | Region |

Primers (0 sites)

Fig. 10E

Molecule Features:

| Start | End | Name | Feature Key | Draw As |
|---|---|---|---|---|
| 283 | 1 C | HSV tk polyA signal | | Region |
| 1370 | 312 C | ZIKV NS1 | | Gene |
| 1530 | 1409 C | p10 | | Region |
| 1548 | 1657 | AcMNPV | promoter | Region |
| 1774 | 2028 | del108CZIKA | | Gene |
| 2029 | 2532 | ZIKV prM | | Gene |
| 2533 | 4044 | ZIKV E | | Gene |
| 4048 | 4633 | IRES | | Gene |
| 4634 | 4891 | del108CZIKA | | Gene |
| 4892 | 4963 | hfsp | | Gene |
| 4964 | 7273 | human furin proprotein | | Gene |
| 7459 | 7637 | SV40 late polyA signal | | Gene |

Fig. 10F

Molecule Features:

| Start | End | Name | Feature Key | Draw As |
|---|---|---|---|---|
| 283 | 1 C | HSV tk polyA signal | | Region |
| 1370 | 312 C | ZIKV NS1 | | Gene |
| 1530 | 1409 C | p10 | | Region |
| 1548 | 1657 | AcMNPV | promoter | Region |
| 1774 | 2028 | del108CZIKA | | Gene |
| 2029 | 2532 | ZIKV prM | | Gene |
| 2533 | 4044 | ZIKV E | | Gene |
| 4048 | 4633 | IRES | | Gene |
| 4634 | 4867 | del108CDENV2 | | Gene |
| 4868 | 4939 | hfsp | | Gene |
| 4940 | 7249 | human furin proprotein | | Gene |
| 7435 | 7613 | SV40 late polyA signal | | Region |

Primers (0 sites)

DENV VLP without del108CDENV2 upstream of human furin & DENV NS-1 Dual Promoter Expression Cassette

ZIKV VLP without del108CDENV2 upstream of human furin & ZIKV NS-1 Dual Promoter Expression Cassette

Fig. 12C

Molecule Features:

| Start | End | Name | Feature Key | Draw As |
|---|---|---|---|---|
| 283 | 1 C | HSV tk polyA signal | | Region |
| 1370 | 312 C | DENV2 NS1 | | Gene |
| 1530 | 1409 C | p10 | promoter | Region |
| 1548 | 1657 | AcMNPV | promoter | Region |
| 1771 | 2004 | del108CDENV2 | | Gene |
| 2005 | 2502 | DENV2 prM | | Gene |
| 2503 | 3987 | DENV2 E | | Gene |
| 3991 | 4576 | IRES | | Gene |
| 4577 | 4649 | hfsp | | Gene |
| 4649 | 6958 | human furin proprotein | | Gene |
| 7144 | 7322 | SV40 late polyA signal | | Region |

Primers (0 sites)

Fig. 12D

Molecule Features:

| Start | End | Name | Feature Key | Draw As |
|---|---|---|---|---|
| 283 | 1 C | HSV tk polyA signal | | Region |
| 1370 | 312 C | ZIKV NS1 | | Gene |
| 1530 | 1409 C | p10 | | Region |
| 1548 | 1657 | AcMNPV | promoter | Region |
| 1774 | 2028 | del108CZIKA | | Gene |
| 2029 | 2532 | ZIKV prM | | Gene |
| 2533 | 4044 | ZIKV E | | Gene |
| 4048 | 4633 | IRES | | Gene |
| 4634 | 4705 | hfsp | | Gene |
| 4706 | 7015 | human furin proprotein | | Gene |
| 7201 | 7379 | SV40 late polyA signal | | Region |

Primers (0 sites)

Fig. 13C
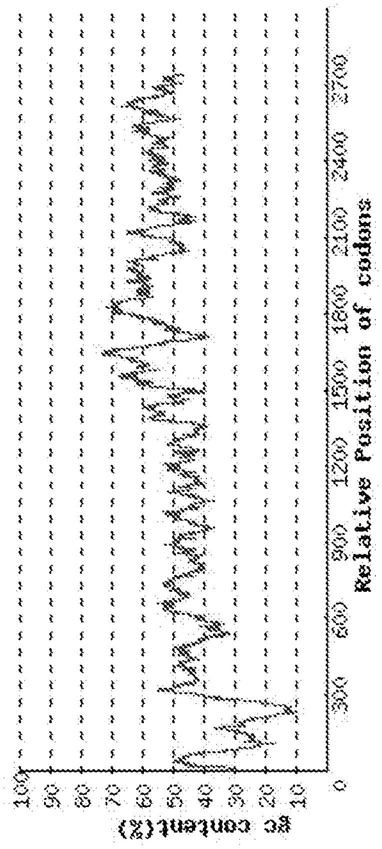
Before optimization Average GC content was 48.87%
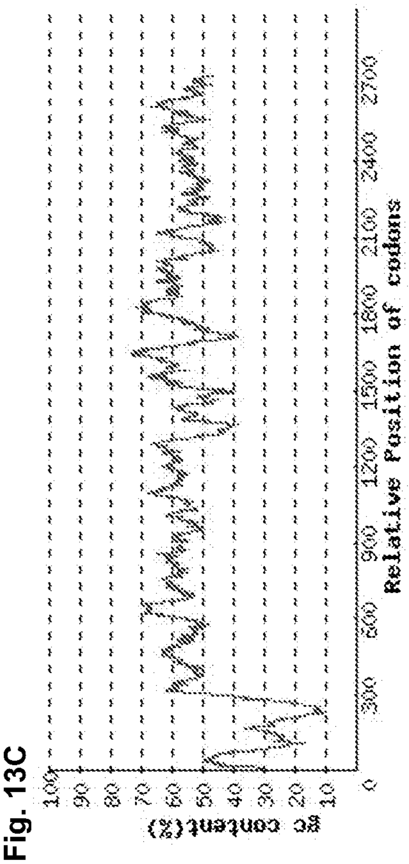
After optimization Average GC content was 53.59%

Fig. 15
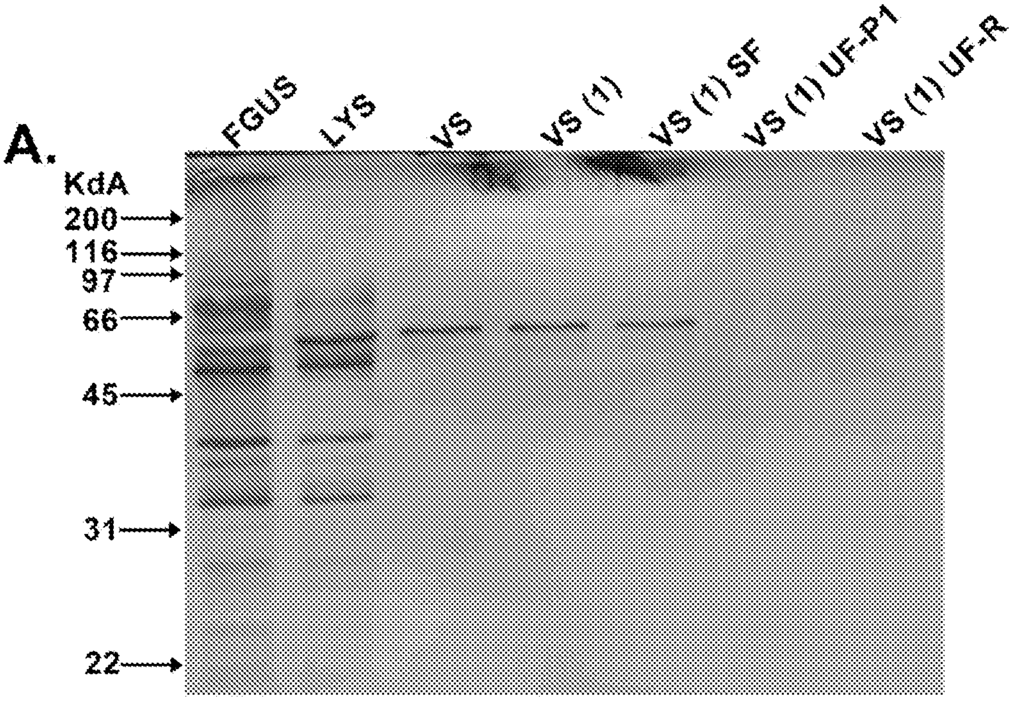
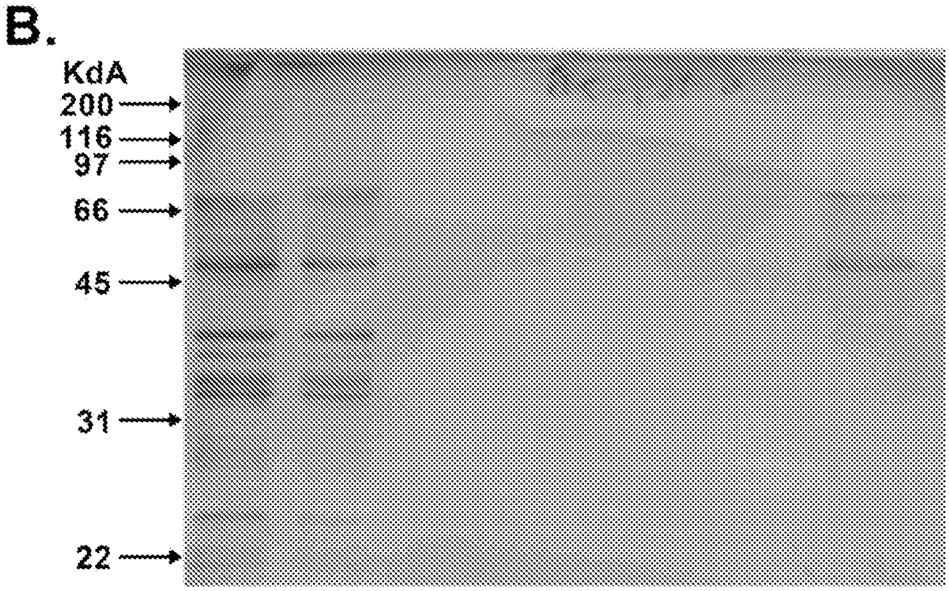

Fig. 27A

SEQ ID NO: 1. DENV2 del108C-prM-E & del108CDENV-human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgct ccagggcaga ggaccactca agctgttcat 300
ggcactcgtc gcctttctcc ggtttctcac tatcccaccc actgtcggta tcctgaagag 360
atggggcacc atcaagaaga gcaaggctat caacgtgctg cgcggattca ggaaggagat 420
cggtcgtatg ctgaacatcc tgaaccgcag gagacgtacc gctggaatga tcatcatgct 480
gatcccaacc gtgatggcct tccacctgac caccagaaac ggagagcccc acatgatcgt 540
gtctcgtcag gaaaagggca agagcctgct gttcaagacc gaggacggcg tgaacatgtg 600
caccctgatg gctatggacc tgggcgagct gtgcgaagac accatcacct acaagtgccc 660
actgctgaga cagaacgagc ccgaagacat cgactgctgg tgcaactcta ccagcacctg 720
ggtgacctac ggcacctgta ccaccactgg agagcacaga agggaaaaga gatctgtggc 780
cctggtgccc cacgtgggta tgggactgga gacccgtacc gaaacctgga tgagctccga 840
gggagcctgg aagcacgctc agagaatcga aacctggatt ctgcgtcacc ctggattcac 900
cctgatggcc gctatcctgg cttacaccat cggcaccacc aacttccagc gtgccctgat 960
cttcatcctg ctgaccgccg tggctccaag catgaccatg cgctgcatcg gcatctccaa 1020
cagggacttc gtggagggag tgtccggcgg atcttgggtg gacatcgtgc tggaacacgg 1080
ttcctgcgtg actaccatgg ccaagaacaa gcctaccctg gacttcgagc tgatcaagac 1140
cgaagccaag cagccagcta ccctgcgcaa gtactgcatc gaggccaagc tgaccaacac 1200
cactactgag tctaggtgcc caacccaggg tgaacctagc ctgaacgagg aacaggacaa 1260
gaggttcgtg tgcaagcact ctatggtgga caggggttgg ggcaacggat gcggcctgtt 1320
cggaaagggc ggcatcgtga cctgcgccat gttcacctgc aagaagaaca tggagggcaa 1380
gatcgtgcag cccgagaacc tggaatacac catcgtgatc acccctcact ctggagagga 1440
acacgctgtg ggcaacgaca ccggaaagca cggcaaggag atcaagatca cccctcagtc 1500
tagcatcacc gaggccgaac tgaccggcta cggaaccgtg accatggaat gcagccctcg 1560
caccggcctg gacttcaacg agatggtgct gctgcagatg gaaaacaagg cttggctggt 1620
gcacaggcag tggttcctgg acctgcctct gccttggctg ccaggtgctg acacccaggg 1680
cagcaactgg attcagaagg agaccctggt gaccttcaag aacccccacg ctaagaagca 1740
ggacgtggtg gtgctgggct cccaggaggg agctatgcac accgctctga ccggagccac 1800
cgaaatccag atgtcctctg gaaacctgct gttcaccggt cacctgaagt gcagactgcg 1860
tatggacaag ctgcagctga agggaatgtc ctactctatg tgcaccggca agttcaaggt 1920

FIG. 27B ggtgaaggag atcgccgaaa cccagcacgg caccatcgtg gtgagagtgc agtacgaggg 1980
tgacggcagc ccttgcaaga tcccattcga gatcatggac ctggaaaagc gccacgtgct 2040
gggcaggctg atcaccgtga accctatcgt gaccgaaaag gactccccag tgaacatcga 2100
ggctgaaccc cctttcggag actcttacgt gatcatcggt gtggagcctg gccagctgaa 2160
gctgaactgg ttcaagaagg gaagctccat cggtcagatg ttcgaaacca ccatgagagg 2220
cgctaagcgt atggccatcc tgggcgacac tgcttgggac ttcggctccc tgggcggcgt 2280
gttcacctct atcggcaagg ctctgcacca ggtgttcggc gccatctacg gagccgcttt 2340
cagcggagtg tcctggacca tgaagatcct gatcggtgtg atcatcacct ggatcggcat 2400
gaacagcagg tccacctctc tgagcgtctc tctggtcctc gtgggcgtcg tgactctcta 2460
tctcggtgtg gtcgtgcagg catgagcccc tctccctccc cccccctaa cgttactggc 2520
cgaagccgct tggaataagg ccggtgtgtg tttgtctata tgtgattttc caccatattg 2580
ccgtcttttg gcaatgtgag ggcccggaaa cctggccctg tcttcttgac gagcattcct 2640
aggggtcttt cccctctcgc caaaggaatg caaggtctgt tgaatgtcgt gaaggaagca 2700
gttcctctgg aagcttcttg aagacaaaca acgtctgtag cgaccctttg caggcagcgg 2760
aaccccccac ctggcgacag gtgcctctgc ggccaaaagc cacgtgtata agatacacct 2820
gcaaaggcgg cacaacccca gtgccacgtt gtgagttgga tagttgtgga aagagtcaaa 2880
tggctctcct caagcgtagt caacaagggg ctgaaggatg cccagaaggt accccattgt 2940
atgggaatct gatctggggc ctcggtgcac atgctttaca tgtgtttagt cgaggttaaa 3000
aaagctctag gccccccgaa ccacggggac gtggttttcc tttgaaaaac acgatgataa 3060
gcttgccaca aatgctccag ggtcgcggtc cactgaaact ctttatggct ctcgtcgcct 3120
tcctgcggtt cctcactatt cctcctactg tcggtattct gaagaggtgg ggcaccatca 3180
agaagagcaa ggccatcaac gtgctgcgcg gattcaggaa ggagatcggt aggatgctga 3240
acatcctgaa ccgcaggaga cgtaccgccg gcatgatcat catgctgatc cccaccgtga 3300
tggctatgga actgagacct tggctgctgt gggtggtggc tgctactggc accctggtgc 3360
tgctagcagc tgacgcccag ggccagaagg tgttcaccaa cacctgggct gtgagaatcc 3420
ccggcggacc tgctgtggct aacagcgtgg ctcgtaagca cggcttcctg aacctgggac 3480
agattttcgg tgactactac cacttctggc accgcggagt gaccaagagg agcctgtccc 3540
cacacagacc aaggcactcc agactgcagc gtgagcccca ggtgcagtgg ctggaacagc 3600
aggtggccaa gcgcaggacc aagagagacg tgtaccagga gcctaccgac ccaaagttcc 3660
cccagcagtg gtatctgtcc ggcgtgaccc agcgtgacct gaacgtgaag gccgcttggg 3720
ctcagggtta caccggtcac ggcatcgtgg tgtccatcct ggacgacggc atcgagaaga 3780
accaccctga cctggccggt aactacgacc caggcgcttc tttcgacgtg aacgaccagg 3840
accccgaccc tcagccaaga tacacccaga tgaacgacaa cagacatgga accagatgtg 3900
ctggtgaagt ggctgctgtg gctaacaacg gcgtgtgcgg agtgggtgtg gcctacaacg 3960

Fig. 27C ctagaatcgg tggcgtgcgt atgctggatg gagaagtgac tgatgctgtg gaagctagaa 4020
gcctgggact gaacccaaac cacatccaca tctactctgc cagctggggt ccagaggatg 4080
atggaaagac tgtggatggt cctgctagac tggctgagga agccttcttc cgcggcgtga 4140
gccagggaag gggaggtctg ggaagcatct tcgtgtgggc ttctggtaac ggcggaagag 4200
agcacgactc ctgcaactgc gacggataca ccaactctat ctacaccctg agcatcagct 4260
ccgctaccca gttcggtaac gtgccctggt actccgaagc ctgctctagc accctggcta 4320
ccacctactc ctctggcaac cagaacgaga agcagatcgt gaccaccgac ctgcgtcaga 4380
agtgcaccga atctcacact ggcacctccg cctctgctcc tctggctgct ggaatcatcg 4440
ccctgaccct ggaggctaac aagaacctga cctggcgcga catgcagcac ctggtggtgc 4500
agacctccaa gccagctcac ctgaacgcca acgactgggc taccaacggc gtgggaagga 4560
aggtgagcca ctcttacggt tacggtctgc tggatgctgg tgctatggtg gccctggctc 4620
agaactggac caccgtggcc cctcagcgca agtgcatcat cgacatcctg accgagccta 4680
aggacatcgg aaagagactg gaagtgcgta agaccgtgac cgcttgcctg ggagagccca 4740
accacatcac cagactggaa cacgcccagg ctcgtctgac cctgtcttac aacagacgtg 4800
gagacctggc catccacctg gtgtctccaa tgggcacccg cagcaccctg ctggctgcta 4860
ggccacacga ctacagcgcc gacggattca acgactgggc tttcatgacc acccactcct 4920
gggacgagga cccttctggt gaatgggtgc tggagatcga aaacaccagc gaggccaaca 4980
actacggcac cctgaccaag ttcaccctgg tgctgtacgg caccgctcct gagggactgc 5040
cagtgccccc tgaaagctcc ggttgcaaga ccctgacctc tagccaggcc tgcgtggtgt 5100
gcgaggaagg cttctccctg caccagaagt cttgcgtgca gcactgccca cccggattcg 5160
ctcctcaggt gctggacacc cactactcta ccgagaacga cgtggaaacc atcagagcca 5220
gcgtgtgcgc tccttgtcac gcttcctgtg ctacttgtca gggaccagcc ctgactgact 5280
gcctgtcctg cccatctcac gccagcctgg accccgtgga gcagacctgc tccagacagt 5340
ctcagtcctc tcgtgaaagc cctccacagc agcagccccc tagactgcca cccgaggtgg 5400
aagccggcca gagactgcgt gctggactgc tgccttctca cctgccagag gtggtggctg 5460
gtctgagctg cgctttcatc gtgctggtgt tcgtgaccgt gttcctggtg ctgcagctgc 5520
gcagcggttt ctccttcagg ggcgtgaagg tgtacaccat ggaccgcggt ctgatcagct 5580
acaagggtct gcctccagag gcttggcagg aggaatgccc atctgacagc gaagaggacg 5640
agggacgtgg agaacggact gccttcatca aagatcagag cgcactgtaa taaatcgatt 5700
taattaatag cataacccct tggggcctct aaacgggtct tgaggggttt tttggaattc 5760
acccagcttt cttgtacaaa gtggtgatag cttgtcgaga agtactagag gatcataatc 5820
agccatacca catttgtaga ggttttactt gctttaaaaa acctcccaca cctccccctg 5880
aacctgaaac ataaaatgaa tgcaattgtt gttgttaact tgtttattgc agcttataat 5940
ggttacaaat aaagcaatag catcacaaat ttcacaaata aagcattttt ttcactgcat 6000

Fig. 27D tctagttgtg gtttgtccaa actcatcaat gtatcttatc atgtctggat c 6051

FIG. 28A

SEQ ID NO: 2. DENV2 del108C-prM-E & human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
tttttttttt tggaatataa ataatatgct ccagggcaga ggaccactca agctgttcat 300
ggcactcgtc gcctttctcc ggtttctcac tatcccaccc actgtcggta tcctgaagag 360
atggggcacc atcaagaaga gcaaggctat caacgtgctg cgcggattca ggaaggagat 420
cggtcgtatg ctgaacatcc tgaaccgcag gagacgtacc gctggaatga tcatcatgct 480
gatcccaacc gtgatggcct tccacctgac caccagaaac ggagagcccc acatgatcgt 540
gtctcgtcag gaaaagggca agagcctgct gttcaagacc gaggacggcg tgaacatgtg 600
caccctgatg gctatggacc tgggcgagct gtgcgaagac accatcacct acaagtgccc 660
actgctgaga cagaacgagc ccgaagacat cgactgctgg tgcaactcta ccagcacctg 720
ggtgacctac ggcacctgta ccaccactgg agagcacaga agggaaaaga gatctgtggc 780
cctggtgccc cacgtgggta tgggactgga gacccgtacc gaaacctgga tgagctccga 840
gggagcctgg aagcacgctc agagaatcga aacctggatt ctgcgtcacc ctggattcac 900
cctgatggcc gctatcctgg cttacaccat cggcaccacc aacttccagc gtgccctgat 960
cttcatcctg ctgaccgccg tggctccaag catgaccatg cgctgcatcg gcatctccaa 1020
cagggacttc gtggagggag tgtccggcgg atcttgggtg gacatcgtgc tggaacacgg 1080
ttcctgcgtg actaccatgg ccaagaacaa gcctaccctg gacttcgagc tgatcaagac 1140
cgaagccaag cagccagcta ccctgcgcaa gtactgcatc gaggccaagc tgaccaacac 1200
cactactgag tctaggtgcc caacccaggg tgaacctagc ctgaacgagg aacaggacaa 1260
gaggttcgtg tgcaagcact ctatggtgga caggggttgg ggcaacggat gcggcctgtt 1320
cggaaagggc ggcatcgtga cctgcgccat gttcacctgc aagaagaaca tggagggcaa 1380
gatcgtgcag cccgagaacc tggaatacac catcgtgatc acccctcact ctggagagga 1440
acacgctgtg ggcaacgaca ccggaaagca cggcaaggag atcaagatca cccctcagtc 1500
tagcatcacc gaggccgaac tgaccggcta cggaaccgtg accatggaat gcagccctcg 1560
caccggcctg gacttcaacg agatggtgct gctgcagatg gaaaacaagg cttggctggt 1620
gcacaggcag tggttcctgg acctgcctct gccttggctg ccaggtgctg acacccaggg 1680
cagcaactgg attcagaagg agaccctggt gaccttcaag aacccccacg ctaagaagca 1740
ggacgtggtg gtgctgggct cccaggaggg agctatgcac accgctctga ccggagccac 1800

FIG. 28B cgaaatccag atgtcctctg gaaacctgct gttcaccggt cacctgaagt gcagactgcg 1860
tatggacaag ctgcagctga agggaatgtc ctactctatg tgcaccggca agttcaaggt 1920
ggtgaaggag atcgccgaaa cccagcacgg caccatcgtg gtgagagtgc agtacgaggg 1980
tgacggcagc ccttgcaaga tcccattcga gatcatggac ctggaaaagc gccacgtgct 2040
gggcaggctg atcaccgtga accctatcgt gaccgaaaag gactccccag tgaacatcga 2100
ggctgaaccc cctttcggag actcttacgt gatcatcggt gtggagcctg gccagctgaa 2160
gctgaactgg ttcaagaagg gaagctccat cggtcagatg ttcgaaacca ccatgagagg 2220
cgctaagcgt atggccatcc tgggcgacac tgcttgggac ttcggctccc tgggcggcgt 2280
gttcacctct atcggcaagg ctctgcacca ggtgttcggc gccatctacg gagccgcttt 2340
cagcggagtg tcctggacca tgaagatcct gatcggtgtg atcatcacct ggatcggcat 2400
gaacagcagg tccacctctc tgagcgtctc tctggtcctc gtgggcgtcg tgactctcta 2460
tctcggtgtg gtcgtgcagg catgagcccc tctccctccc cccccctaa cgttactggc 2520
cgaagccgct tggaataagg ccggtgtgtg tttgtctata tgtgattttc caccatattg 2580
ccgtcttttg gcaatgtgag ggcccggaaa cctggccctg tcttcttgac gagcattcct 2640
aggggtcttt cccctctcgc caaaggaatg caaggtctgt tgaatgtcgt gaaggaagca 2700
gttcctctgg aagcttcttg aagacaaaca acgtctgtag cgaccctttg caggcagcgg 2760
aacccccac ctggcgacag gtgcctctgc ggccaaaagc cacgtgtata agatacacct 2820
gcaaaggcgg cacaacccca gtgccacgtt gtgagttgga tagttgtgga aagagtcaaa 2880
tggctctcct caagcgtagt caacaagggg ctgaaggatg cccagaaggt accccattgt 2940
atgggaatct gatctggggc ctcggtgcac atgctttaca tgtgtttagt cgaggttaaa 3000
aaagctctag gccccccgaa ccacggggac gtggttttcc tttgaaaaac acgatgataa 3060
gcttgccaca aatggaactg agaccttggc tgctgtgggt ggtggctgct actggcaccc 3120
tggtgctgct agcagctgac gcccagggcc agaaggtgtt caccaacacc tgggctgtga 3180
gaatccccgg cggacctgct gtggctaaca gcgtggctcg taagcacggc ttcctgaacc 3240
tgggacagat tttcggtgac tactaccact tctggcaccg cggagtgacc aagaggagcc 3300
tgtccccaca cagaccaagg cactccagac tgcagcgtga gccccaggtg cagtggctgg 3360
aacagcaggt ggccaagcgc aggaccaaga gagacgtgta ccaggagcct accgacccaa 3420
agttccccca gcagtggtat ctgtccggcg tgacccagcg tgacctgaac gtgaaggccg 3480
cttgggctca gggttacacc ggtcacggca tcgtggtgtc catcctggac gacggcatcg 3540
agaagaacca ccctgacctg gccggtaact acgacccagg cgcttctttc gacgtgaacg 3600
accaggaccc cgaccctcag ccaagataca cccagatgaa cgacaacaga catggaacca 3660
gatgtgctgg tgaagtggct gctgtggcta acaacggcgt gtgcggagtg ggtgtggcct 3720
acaacgctag aatcggtggc gtgcgtatgc tggatggaga agtgactgat gctgtggaag 3780
ctagaagcct gggactgaac ccaaaccaca tccacatcta ctctgccagc tggggtccag 3840

FIG. 28C aggatgatgg aaagactgtg gatggtcctg ctagactggc tgaggaagcc ttcttccgcg 3900
gcgtgagcca gggaagggga ggtctgggaa gcatcttcgt gtgggcttct ggtaacggcg 3960
gaagagagca cgactcctgc aactgcgacg gatacaccaa ctctatctac accctgagca 4020
tcagctccgc tacccagttc ggtaacgtgc cctggtactc cgaagcctgc tctagcaccc 4080
tggctaccac ctactcctct ggcaaccaga acgagaagca gatcgtgacc accgacctgc 4140
gtcagaagtg caccgaatct cacactggca cctccgcctc tgctcctctg gctgctggaa 4200
tcatcgccct gaccctggag gctaacaaga acctgacctg gcgcgacatg cagcacctgg 4260
tggtgcagac ctccaagcca gctcacctga acgccaacga ctgggctacc aacggcgtgg 4320
gaaggaaggt gagccactct tacggttacg gtctgctgga tgctggtgct atggtggccc 4380
tggctcagaa ctggaccacc gtggcccctc agcgcaagtg catcatcgac atcctgaccg 4440
agcctaagga catcggaaag agactggaag tgcgtaagac cgtgaccgct tgcctgggag 4500
agcccaacca catcaccaga ctggaacacg cccaggctcg tctgaccctg tcttacaaca 4560
gacgtggaga cctggccatc cacctggtgt ctccaatggg cacccgcagc accctgctgg 4620
ctgctaggcc acacgactac agcgccgacg gattcaacga ctgggctttc atgaccaccc 4680
actcctggga cgaggaccct tctggtgaat gggtgctgga gatcgaaaac accagcgagg 4740
ccaacaacta cggcaccctg accaagttca ccctggtgct gtacggcacc gctcctgagg 4800
gactgccagt gccccctgaa agctccggtt gcaagaccct gacctctagc caggcctgcg 4860
tggtgtgcga ggaaggcttc tccctgcacc agaagtcttg cgtgcagcac tgcccacccg 4920
gattcgctcc tcaggtgctg gacacccact actctaccga gaacgacgtg gaaaccatca 4980
gagccagcgt gtgcgctcct tgtcacgctt cctgtgctac ttgtcaggga ccagccctga 5040
ctgactgcct gtcctgccca tctcacgcca gcctggaccc cgtggagcag acctgctcca 5100
gacagtctca gtcctctcgt gaaagccctc cacagcagca gccccctaga ctgccacccg 5160
aggtggaagc cggccagaga ctgcgtgctg gactgctgcc ttctcacctg ccagaggtgg 5220
tggctggtct gagctgcgct ttcatcgtgc tggtgttcgt gaccgtgttc ctggtgctgc 5280
agctgcgcag cggtttctcc ttcaggggcg tgaaggtgta caccatggac cgcggtctga 5340
tcagctacaa gggtctgcct ccagaggctt ggcaggagga atgcccatct gacagcgaag 5400
aggacgaggg acgtggagaa cggactgcct tcatcaaaga tcagagcgca ctgtaataaa 5460
tcgatttaat taatagcata accccttggg gcctctaaac gggtcttgag gggttttttg 5520
gaattcaccc agctttcttg tacaaagtgg tgatagcttg tcgagaagta ctagaggatc 5580
ataatcagcc ataccacatt tgtagaggtt ttacttgctt taaaaaacct cccacacctc 5640
cccctgaacc tgaaacataa aatgaatgca attgttgttg ttaacttgtt tattgcagct 5700
tataatggtt acaaataaag caatagcatc acaaatttca caaataaagc atttttttca 5760
ctgcattcta gttgtggttt gtccaaactc atcaatgtat cttatcatgt ctggatc 5817

FIG. 29A

SEQ ID NO: 3. Dual Promoter-DENV2 del108C-prM-E & del108CDENV-human furin proprotein bicistronic cassette + DENV2 NS1 gtggctatgg cagggcttgc cgccccgacg ttggctgcga gccctgggcc ttcacccgaa 60
cttgggggtt ggggtgggga aaaggaagaa acgcgggcgt attggtccca atggggtctc 120
ggtggggtat cgacagagtg ccagccctgg gaccgaaccc cgcgtttatg aacaaacgac 180
ccaacacccg tgcgttttat tctgtctttt tattgccgtc atagcgcggg ttccttccgg 240
tattgtctcc ttccgtgttt cagttagcct cccccatctc ccggtagcgc atgctctaga 300
ggcgcgcctt attaggctgt cacgagagag gacacgagat tttcttcttt ttctttcaga 360
ggacgaattt ccatgccgta ccagcatccg tcctcgccac ggtatctcag agggggcagg 420
gtgcaggacc tgcaacacca ttcggtgatc agcttgccag aagcggtggt ggtcctcagg 480
gaaggacctc tgtttccgca gtcttcggtc accaccacgg tggttccctt gcagaagtcg 540
aagtccatct caagcttgcc caggtgccat ggtccagcgg tctgggtgtg gtatccaggg 600
cggtagttgt gctggctcac ggggccagcg aagttctttg ggatgatcat ttcagactcc 660
agcactccgt tggaccacag ggtgtggctc ttgggccagt ggcagctctt cacttcgatg 720
aaagaagcct tctcgatctt ccaggtgtcg ttcagggcgg attcgatcca gtagcccatg 780
tcagcgtgca cggctctgtt gtccttgata gcggcagaca tcagcttgga gtcgcagaag 840
gcgtcctgct tctccctcag gcgcagccag atgttggtgg tgaacactcc gaagccgtag 900
tcttccacct ccaggctgtt ccaagcacgg ttggtgttag ggcattcggc ggtttcgggg 960
ccgtcgatca ggaaggtctg gttgtggctt tcggtagaca ggatcttagc cttgccccag 1020
gtcttccagg agtatctcag ctcggtgggc tgggggcgca ggctgcgctt gccagcgtgc 1080
atgatgccct tgatgtctcc ggtcatgatg gtcagcttca cttcgttctc agacaggatg 1140
tggttcagtt cgggggtgat ctgcttccac atcaggttct ccagacgggt cacagatctg 1200
atgccgcaga taccctcctg gtgggccttc tggatagcgg aggccagctt ggatgggctt 1260
tcaggctgga acttgtactg ctcggtccag gtatgcacgt tgtcggtgat aaagatgccg 1320
ctaccacact tcagttcctt gttcctccag ctgaccacgc agccgctgtc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt tttttggaa tataaataat atgctccagg gcagaggacc actcaagctg 1800
ttcatggcac tcgtcgcctt tctccggttt ctcactatcc cacccactgt cggtatcctg 1860
aagagatggg gcaccatcaa gaagagcaag gctatcaacg tgctgcgcgg attcaggaag 1920

FIG. 29B

| | |
|---|---|
| gagatcggtc gtatgctgaa catcctgaac cgcaggagac gtaccgctgg aatgatcatc | 1980 |
| atgctgatcc caaccgtgat ggccttccac ctgaccacca gaaacggaga gccccacatg | 2040 |
| atcgtgtctc gtcaggaaaa gggcaagagc ctgctgttca agaccgagga cggcgtgaac | 2100 |
| atgtgcaccc tgatggctat ggacctgggc gagctgtgcg aagacaccat cacctacaag | 2160 |
| tgcccactgc tgagacagaa cgagcccgaa gacatcgact gctggtgcaa ctctaccagc | 2220 |
| acctgggtga cctacggcac ctgtaccacc actggagagc acagaaggga aaagagatct | 2280 |
| gtggccctgg tgccccacgt gggtatggga ctggagaccc gtaccgaaac ctggatgagc | 2340 |
| tccgagggag cctggaagca cgctcagaga atcgaaacct ggattctgcg tcaccctgga | 2400 |
| ttcaccctga tggccgctat cctggcttac accatcggca ccaccaactt ccagcgtgcc | 2460 |
| ctgatcttca tcctgctgac cgccgtggct ccaagcatga ccatgcgctg catcggcatc | 2520 |
| tccaacaggg acttcgtgga gggagtgtcc ggcggatctt gggtggacat cgtgctggaa | 2580 |
| cacggttcct gcgtgactac catggccaag aacaagccta ccctggactt cgagctgatc | 2640 |
| aagaccgaag ccaagcagcc agctaccctg cgcaagtact gcatcgaggc caagctgacc | 2700 |
| aacaccacta ctgagtctag gtgcccaacc cagggtgaac ctagcctgaa cgaggaacag | 2760 |
| gacaagaggt tcgtgtgcaa gcactctatg gtggacaggg gttggggcaa cggatgcggc | 2820 |
| ctgttcggaa agggcggcat cgtgacctgc gccatgttca cctgcaagaa gaacatggag | 2880 |
| ggcaagatcg tgcagcccga gaacctggaa tacaccatcg tgatcacccc tcactctgga | 2940 |
| gaggaacacg ctgtgggcaa cgacaccgga aagcacggca aggagatcaa gatcacccct | 3000 |
| cagtctagca tcaccgaggc cgaactgacc ggctacggaa ccgtgaccat ggaatgcagc | 3060 |
| cctcgcaccg gcctggactt caacgagatg gtgctgctgc agatggaaaa caaggcttgg | 3120 |
| ctggtgcaca ggcagtggtt cctggacctg cctctgcctt ggctgccagg tgctgacacc | 3180 |
| cagggcagca actggattca gaaggagacc ctggtgacct tcaagaaccc ccacgctaag | 3240 |
| aagcaggacg tggtggtgct gggctcccag gagggagcta tgcacaccgc tctgaccgga | 3300 |
| gccaccgaaa tccagatgtc ctctggaaac ctgctgttca ccggtcacct gaagtgcaga | 3360 |
| ctgcgtatgg acaagctgca gctgaaggga atgtcctact ctatgtgcac cggcaagttc | 3420 |
| aaggtggtga aggagatcgc cgaaacccag cacggcacca tcgtggtgag agtgcagtac | 3480 |
| gagggtgacg gcagcccttg caagatccca ttcgagatca tggacctgga aaagcgccac | 3540 |
| gtgctgggca ggctgatcac cgtgaaccct atcgtgaccg aaaaggactc cccagtgaac | 3600 |
| atcgaggctg aacccccttt cggagactct tacgtgatca tcggtgtgga gcctggccag | 3660 |
| ctgaagctga actggttcaa gaagggaagc tccatcggtc agatgttcga aaccaccatg | 3720 |
| agaggcgcta agcgtatggc catcctgggc gacactgctt gggacttcgg ctccctgggc | 3780 |
| ggcgtgttca cctctatcgg caaggctctg caccaggtgt tcggcgccat ctacggagcc | 3840 |
| gctttcagcg gagtgtcctg gaccatgaag atcctgatcg gtgtgatcat cacctggatc | 3900 |
| ggcatgaaca gcaggtccac ctctctgagc gtctctctgg tcctcgtggg cgtcgtgact | 3960 |

FIG. 29C ctctatctcg gtgtggtcgt gcaggcatga gcccctctcc ctcccccccc cctaacgtta 4020
ctggccgaag ccgcttggaa taaggccggt gtgtgtttgt ctatatgtga ttttccacca 4080
tattgccgtc ttttggcaat gtgagggccc ggaaacctgg ccctgtcttc ttgacgagca 4140
ttcctagggg tctttcccct ctcgccaaag gaatgcaagg tctgttgaat gtcgtgaagg 4200
aagcagttcc tctggaagct tcttgaagac aaacaacgtc tgtagcgacc ctttgcaggc 4260
agcggaaccc cccacctggc gacaggtgcc tctgcggcca aaagccacgt gtataagata 4320
cacctgcaaa ggcggcacaa ccccagtgcc acgttgtgag ttggatagtt gtggaaagag 4380
tcaaatggct ctcctcaagc gtagtcaaca aggggctgaa ggatgcccag aaggtacccc 4440
attgtatggg aatctgatct ggggcctcgg tgcacatgct ttacatgtgt ttagtcgagg 4500
ttaaaaaagc tctaggcccc ccgaaccacg gggacgtggt tttcctttga aaaacacgat 4560
gataagcttg ccacaaatgc tccagggtcg cggtccactg aaactcttta tggctctcgt 4620
cgccttcctg cggttcctca ctattcctcc tactgtcggt attctgaaga ggtggggcac 4680
catcaagaag agcaaggcca tcaacgtgct gcgcggattc aggaaggaga tcggtaggat 4740
gctgaacatc ctgaaccgca ggagacgtac cgccggcatg atcatcatgc tgatccccac 4800
cgtgatggct atggaactga gaccttggct gctgtgggtg gtggctgcta ctggcacccct 4860
ggtgctgcta gcagctgacg cccagggcca gaaggtgttc accaacacct gggctgtgag 4920
aatccccggc ggacctgctg tggctaacag cgtggctcgt aagcacggct tcctgaacct 4980
gggacagatt ttcggtgact actaccactt ctggcaccgc ggagtgacca agaggagcct 5040
gtccccacac agaccaaggc actccagact gcagcgtgag ccccaggtgc agtggctgga 5100
acagcaggtg gccaagcgca ggaccaagag agacgtgtac caggagccta ccgacccaaa 5160
gttcccccag cagtggtatc tgtccggcgt gacccagcgt gacctgaacg tgaaggccgc 5220
ttgggctcag ggttacaccg gtcacggcat cgtggtgtcc atcctggacg acggcatcga 5280
gaagaaccac cctgacctgg ccggtaacta cgacccaggc gcttctttcg acgtgaacga 5340
ccaggacccc gaccctcagc caagatacac ccagatgaac gacaacagac atggaaccag 5400
atgtgctggt gaagtggctg ctgtggctaa caacggcgtg tgcggagtgg gtgtggccta 5460
caacgctaga atcggtggcg tgcgtatgct ggatggagaa gtgactgatg ctgtggaagc 5520
tagaagcctg ggactgaacc caaaccacat ccacatctac tctgccagct ggggtccaga 5580
ggatgatgga aagactgtgg atggtcctgc tagactggct gaggaagcct tcttccgcgg 5640
cgtgagccag ggaaggggag gtctgggaag catcttcgtg tgggcttctg gtaacggcgg 5700
aagagagcac gactcctgca actgcgacgg atacaccaac tctatctaca ccctgagcat 5760
cagctccgct acccagttcg gtaacgtgcc ctggtactcc gaagcctgct ctagcaccct 5820
ggctaccacc tactcctctg gcaaccagaa cgagaagcag atcgtgacca ccgacctgcg 5880
tcagaagtgc accgaatctc acactggcac ctccgcctct gctcctctgg ctgctggaat 5940
catcgccctg accctggagg ctaacaagaa cctgacctgg cgcgacatgc agcacctggt 6000

FIG. 29D ggtgcagacc tccaagccag ctcacctgaa cgccaacgac tgggctacca acggcgtggg 6060
aaggaaggtg agccactctt acggttacgg tctgctggat gctggtgcta tggtggccct 6120
ggctcagaac tggaccaccg tggcccctca gcgcaagtgc atcatcgaca tcctgaccga 6180
gcctaaggac atcggaaaga gactggaagt gcgtaagacc gtgaccgctt gcctgggaga 6240
gcccaaccac atcaccagac tggaacacgc ccaggctcgt ctgaccctgt cttacaacag 6300
acgtggagac ctggccatcc acctggtgtc tccaatgggc acccgcagca ccctgctggc 6360
tgctaggcca cacgactaca gcgccgacgg attcaacgac tgggctttca tgaccaccca 6420
ctcctgggac gaggaccctt ctggtgaatg ggtgctggag atcgaaaaca ccagcgaggc 6480
caacaactac ggcaccctga ccaagttcac cctggtgctg tacggcaccg ctcctgaggg 6540
actgccagtg ccccctgaaa gctccggttg caagaccctg acctctagcc aggcctgcgt 6600
ggtgtgcgag gaaggcttct ccctgcacca gaagtcttgc gtgcagcact gcccacccgg 6660
ttcgctcct caggtgctgg acacccacta ctctaccgag aacgacgtgg aaaccatcag 6720
agccagcgtg tgcgctcctt gtcacgcttc ctgtgctact tgtcagggac cagccctgac 6780
tgactgcctg tcctgcccat ctcacgccag cctggacccc gtggagcaga cctgctccag 6840
acagtctcag tcctctcgtg aaagccctcc acagcagcag ccccctagac tgccacccga 6900
ggtggaagcc ggccagagac tgcgtgctgg actgctgcct tctcacctgc cagaggtggt 6960
ggctggtctg agctgcgctt tcatcgtgct ggtgttcgtg accgtgttcc tggtgctgca 7020
gctgcgcagc ggtttctcct tcaggggcgt gaaggtgtac accatggacc gcggtctgat 7080
cagctacaag ggtctgcctc cagaggcttg gcaggaggaa tgcccatctg acagcgaaga 7140
ggacgaggga cgtggagaac ggactgcctt catcaaagat cagagcgcac tgtaataaat 7200
cgatttaatt aatagcataa ccccttgggg cctctaaacg ggtcttgagg ggttttttgg 7260
aattcaccca gctttcttgt acaaagtggt gatagcttgt cgagaagtac tagaggatca 7320
taatcagcca taccacattt gtagaggttt tacttgcttt aaaaaacctc ccacacctcc 7380
ccctgaacct gaaacataaa atgaatgcaa ttgttgttgt taacttgttt attgcagctt 7440
taatggtta caaataaagc aatagcatca caaatttcac aaataaagca ttttttcac 7500
tgcattctag ttgtggtttg tccaaactca tcaatgtatc ttatcatgtc tggatc 7556

FIG. 30A

SEQ ID NO: 4. Dual Promoter-DENV2 del108C-prM-E & human furin proprotein bicistronic cassette + DENV2 NS1 gtggctatgg cagggcttgc cgcccccgacg ttggctgcga gccctgggcc ttcacccgaa 60
cttgggggtt ggggtgggga aaaggaagaa acgcgggcgt attggtccca atggggtctc 120
ggtggggtat cgacagagtg ccagccctgg gaccgaaccc cgcgtttatg aacaaacgac 180
ccaacacccg tgcgttttat tctgtctttt tattgccgtc atagcgcggg ttccttccgg 240

FIG. 30B tattgtctcc ttccgtgttt cagttagcct cccccatctc ccggtagcgc atgctctaga 300
ggcgcgcctt attaggctgt cacgagagag gacacgagat tttcttcttt ttctttcaga 360
ggacgaattt ccatgccgta ccagcatccg tcctcgccac ggtatctcag agggggcagg 420
gtgcaggacc tgcaacacca ttcggtgatc agcttgccag aagcggtggt ggtcctcagg 480
gaaggacctc tgtttccgca gtcttcggtc accaccacgg tggttccctt gcagaagtcg 540
aagtccatct caagcttgcc caggtgccat ggtccagcgg tctgggtgtg gtatccaggg 600
cggtagttgt gctggctcac ggggccagcg aagttctttg ggatgatcat ttcagactcc 660
agcactccgt tggaccacag ggtgtggctc ttgggccagt ggcagctctt cacttcgatg 720
aaagaagcct tctcgatctt ccaggtgtcg ttcagggcgg attcgatcca gtagcccatg 780
tcagcgtgca cggctctgtt gtccttgata gcggcagaca tcagcttgga gtcgcagaag 840
gcgtcctgct tctccctcag gcgcagccag atgttggtgg tgaacactcc gaagccgtag 900
tcttccacct ccaggctgtt ccaagcacgg ttggtgttag ggcattcggc ggtttcgggg 960
ccgtcgatca ggaaggtctg gttgtggctt tcggtagaca ggatcttagc cttgccccag 1020
gtcttccagg agtatctcag ctcggtgggc tgggggcgca ggctgcgctt gccagcgtgc 1080
atgatgccct tgatgtctcc ggtcatgatg gtcagcttca cttcgttctc agacaggatg 1140
tggttcagtt cgggggtgat ctgcttccac atcaggttct ccagacgggt cacagatctg 1200
atgccgcaga taccctcctg gtgggccttc tggatagcgg aggccagctt ggatgggctt 1260
tcaggctgga acttgtactg ctcggtccag gtatgcacgt tgtcggtgat aaagatgccg 1320
ctaccacact tcagttcctt gttcctccag ctgaccacgc agccgctgtc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt tttttggaa tataaataat atgctccagg gcagaggacc actcaagctg 1800
ttcatggcac tcgtcgcctt tctccggttt ctcactatcc cacccactgt cggtatcctg 1860
aagagatggg gcaccatcaa gaagagcaag gctatcaacg tgctgcgcgg attcaggaag 1920
gagatcggtc gtatgctgaa catcctgaac cgcaggagac gtaccgctgg aatgatcatc 1980
atgctgatcc caaccgtgat ggccttccac ctgaccacca gaaacggaga gccccacatg 2040
atcgtgtctc gtcaggaaaa gggcaagagc ctgctgttca agaccgagga cggcgtgaac 2100
atgtgcaccc tgatggctat ggacctgggc gagctgtgcg aagacaccat cacctacaag 2160
tgcccactgc tgagacagaa cgagcccgaa gacatcgact gctggtgcaa ctctaccagc 2220
acctgggtga cctacggcac ctgtaccacc actggagagc acagaaggga aaagagatct 2280

FIG. 30C gtggccctgg tgccccacgt gggtatggga ctggagaccc gtaccgaaac ctggatgagc 2340
tccgagggag cctggaagca cgctcagaga atcgaaacct ggattctgcg tcaccctgga 2400
ttcaccctga tggccgctat cctggcttac accatcggca ccaccaactt ccagcgtgcc 2460
ctgatcttca tcctgctgac cgccgtggct ccaagcatga ccatgcgctg catcggcatc 2520
tccaacaggg acttcgtgga gggagtgtcc ggcggatctt gggtggacat cgtgctggaa 2580
cacggttcct gcgtgactac catggccaag aacaagccta ccctggactt cgagctgatc 2640
aagaccgaag ccaagcagcc agctaccctg cgcaagtact gcatcgaggc caagctgacc 2700
aacaccacta ctgagtctag gtgcccaacc cagggtgaac ctagcctgaa cgaggaacag 2760
gacaagaggt tcgtgtgcaa gcactctatg gtggacaggg gttggggcaa cggatgcggc 2820
ctgttcggaa agggcggcat cgtgacctgc gccatgttca cctgcaagaa gaacatggag 2880
ggcaagatcg tgcagcccga gaacctggaa tacaccatcg tgatcacccc tcactctgga 2940
gaggaacacg ctgtgggcaa cgacaccgga aagcacggca aggagatcaa gatcacccct 3000
cagtctagca tcaccgaggc cgaactgacc ggctacggaa ccgtgaccat ggaatgcagc 3060
cctcgcaccg gcctggactt caacgagatg gtgctgctgc agatggaaaa caaggcttgg 3120
ctggtgcaca ggcagtggtt cctggacctg cctctgcctt ggctgccagg tgctgacacc 3180
cagggcagca actggattca gaaggagacc ctggtgacct tcaagaaccc ccacgctaag 3240
aagcaggacg tggtggtgct gggctcccag gagggagcta tgcacaccgc tctgaccgga 3300
gccaccgaaa tccagatgtc ctctggaaac ctgctgttca ccggtcacct gaagtgcaga 3360
ctgcgtatgg acaagctgca gctgaaggga atgtcctact ctatgtgcac cggcaagttc 3420
aaggtggtga aggagatcgc cgaaacccag cacggcacca tcgtggtgag agtgcagtac 3480
gagggtgacg gcagcccttg caagatccca ttcgagatca tggacctgga aaagcgccac 3540
gtgctgggca ggctgatcac cgtgaaccct atcgtgaccg aaaaggactc cccagtgaac 3600
atcgaggctg aaccccccttt cggagactct tacgtgatca tcggtgtgga gcctggccag 3660
ctgaagctga actggttcaa gaagggaagc tccatcggtc agatgttcga aaccaccatg 3720
agaggcgcta agcgtatggc catcctgggc gacactgctt gggacttcgg ctccctgggc 3780
ggcgtgttca cctctatcgg caaggctctg caccaggtgt tcggcgccat ctacggagcc 3840
gctttcagcg gagtgtcctg gaccatgaag atcctgatcg gtgtgatcat cacctggatc 3900
ggcatgaaca gcaggtccac ctctctgagc gtctctctgg tcctcgtggg cgtcgtgact 3960
ctctatctcg gtgtggtcgt gcaggcatga gcccctctcc ctcccccccc cctaacgtta 4020
ctggccgaag ccgcttggaa taaggccggt gtgtgtttgt ctatatgtga ttttccacca 4080
tattgccgtc ttttggcaat gtgagggccc ggaaacctgg ccctgtcttc ttgacgagca 4140
ttcctagggg tctttcccct ctcgccaaag gaatgcaagg tctgttgaat gtcgtgaagg 4200
aagcagttcc tctggaagct tcttgaagac aaacaacgtc tgtagcgacc ctttgcaggc 4260
agcggaaccc cccacctggc gacaggtgcc tctgcggcca aaagccacgt gtataagata 4320

FIG. 30D cacctgcaaa ggcggcacaa ccccagtgcc acgttgtgag ttggatagtt gtggaaagag 4380
tcaaatggct ctcctcaagc gtagtcaaca aggggctgaa ggatgcccag aaggtacccc 4440
attgtatggg aatctgatct ggggcctcgg tgcacatgct ttacatgtgt ttagtcgagg 4500
ttaaaaaagc tctaggcccc ccgaaccacg gggacgtggt tttcctttga aaaacacgat 4560
gataagcttg ccacaaatgg aactgagacc ttggctgctg tgggtggtgg ctgctactgg 4620
caccctggtg ctgctagcag ctgacgccca gggccagaag gtgttcacca acacctgggc 4680
tgtgagaatc cccggcggac ctgctgtggc taacagcgtg gctcgtaagc acggcttcct 4740
gaacctggga cagattttcg gtgactacta ccacttctgg caccgcggag tgaccaagag 4800
gagcctgtcc ccacacagac caaggcactc cagactgcag cgtgagcccc aggtgcagtg 4860
gctggaacag caggtggcca agcgcaggac caagagagac gtgtaccagg agcctaccga 4920
cccaaagttc ccccagcagt ggtatctgtc cggcgtgacc cagcgtgacc tgaacgtgaa 4980
ggccgcttgg gctcagggtt acaccggtca cggcatcgtg gtgtccatcc tggacgacgg 5040
catcgagaag aaccaccctg acctggccgg taactacgac ccaggcgctt ctttcgacgt 5100
gaacgaccag gaccccgacc ctcagccaag atacacccag atgaacgaca acagacatgg 5160
aaccagatgt gctggtgaag tggctgctgt ggctaacaac ggcgtgtgcg gagtgggtgt 5220
ggcctacaac gctagaatcg gtggcgtgcg tatgctggat ggagaagtga ctgatgctgt 5280
ggaagctaga agcctgggac tgaacccaaa ccacatccac atctactctg ccagctgggg 5340
tccagaggat gatggaaaga ctgtggatgg tcctgctaga ctggctgagg aagccttctt 5400
ccgcggcgtg agccagggaa ggggaggtct gggaagcatc ttcgtgtggg cttctggtaa 5460
cggcggaaga gagcacgact cctgcaactg cgacggatac accaactcta tctacaccct 5520
gagcatcagc tccgctaccc agttcggtaa cgtgccctgg tactccgaag cctgctctag 5580
caccctggct accacctact cctctggcaa ccagaacgag aagcagatcg tgaccaccga 5640
cctgcgtcag aagtgcaccg aatctcacac tggcacctcc gcctctgctc ctctggctgc 5700
tggaatcatc gccctgaccc tggaggctaa caagaacctg acctggcgcg acatgcagca 5760
cctggtggtg cagacctcca agccagctca cctgaacgcc aacgactggg ctaccaacgg 5820
cgtgggaagg aaggtgagcc actcttacgg ttacggtctg ctggatgctg gtgctatggt 5880
ggccctggct cagaactgga ccaccgtggc ccctcagcgc aagtgcatca tcgacatcct 5940
gaccgagcct aaggacatcg gaaagagact ggaagtgcgt aagaccgtga ccgcttgcct 6000
gggagagccc aaccacatca ccagactgga acacgcccag gctcgtctga ccctgtctta 6060
caacagacgt ggagacctgg ccatccacct ggtgtctcca atgggcaccc gcagcaccct 6120
gctggctgct aggccacacg actacagcgc cgacggattc aacgactggg ctttcatgac 6180
cacccactcc tgggacgagg acccttctgg tgaatgggtg ctggagatcg aaaacaccag 6240
cgaggccaac aactacggca ccctgaccaa gttcaccctg gtgctgtacg gcaccgctcc 6300

FIG. 30E tgagggactg ccagtgcccc ctgaaagctc cggttgcaag accctgacct ctagccaggc 6360
ctgcgtggtg tgcgaggaag gcttctccct gcaccagaag tcttgcgtgc agcactgccc 6420
acccggattc gctcctcagg tgctggacac ccactactct accgagaacg acgtggaaac 6480
catcagagcc agcgtgtgcg ctccttgtca cgcttcctgt gctacttgtc agggaccagc 6540
cctgactgac tgcctgtcct gcccatctca cgccagcctg gaccccgtgg agcagacctg 6600
ctccagacag tctcagtcct ctcgtgaaag ccctccacag cagcagcccc ctagactgcc 6660
acccgaggtg gaagccggcc agagactgcg tgctggactg ctgccttctc acctgccaga 6720
ggtggtggct ggtctgagct gcgctttcat cgtgctggtg ttcgtgaccg tgttcctggt 6780
gctgcagctg cgcagcggtt tctccttcag gggcgtgaag gtgtacacca tggaccgcgg 6840
tctgatcagc tacaagggtc tgcctccaga ggcttggcag gaggaatgcc catctgacag 6900
cgaagaggac gagggacgtg gagaacggac tgccttcatc aaagatcaga gcgcactgta 6960
ataaatcgat ttaattaata gcataacccc ttggggcctc taaacgggtc ttgaggggtt 7020
ttttggaatt cacccagctt tcttgtacaa agtggtgata gcttgtcgag aagtactaga 7080
ggatcataat cagccatacc acatttgtag aggttttact tgctttaaaa aacctcccac 7140
acctccccct gaacctgaaa cataaaatga atgcaattgt tgttgttaac ttgtttattg 7200
cagcttataa tggttacaaa taaagcaata gcatcacaaa tttcacaaat aaagcatttt 7260
tttcactgca ttctagttgt ggtttgtcca aactcatcaa tgtatcttat catgtctgga 7320
tc 7322

FIG. 31A

SEQ ID NO: 5. Dual Promoter-Heterologous ZIKV del108C-prM-E & del108CDENV2-human furin proprotein bicistronic cassette + ZIKV NS1 gtggctatgg cagggcttgc cgcccgacg ttggctgcga gccctgggcc ttcacccgaa 60
cttgggggtt ggggtgggga aaaggaagaa acgcgggcgt attggtccca atggggtctc 120
ggtggggtat cgacagagtg ccagccctgg gaccgaaccc cgcgtttatg aacaaacgac 180
ccaacacccg tgcgttttat tctgtctttt tattgccgtc atagcgcggg ttccttccgg 240
tattgtctcc ttccgtgttt cagttagcct cccccatctc ccggtagcgc atgctctaga 300
ggcgcgcctt attatgcagt caccattgac cttactaagt tactttctgg ttctttcctg 360
ggccttatct ccattccata ccaacagcca tctttagccc ggaacgacag tgggggcatt 420
gtgcactccc tgcagcacca ttcctcgatc acccttccgc ttgcagtggt tgatctcaga 480
gatggtcctc ttgttccaca tgtttcctcc acgtggacct tagtgcctgg gcattcctca 540
aaccgaattt caagctcttc actgtgccat ggccctttca tttgggtcct gtagccctct 600
ctggtattgt gatggctgag tggcccagct aaagacttgg gtatgatcag atcactctct 660
tctattccat ctgtccacaa tgtgtgggac tttggccatt cacatgtttt catctcgatc 720

FIG. 31B agatgggccc tcttcagcct ccatgtgtca ttcttctcac tctcaatcca gtagcctaga 780
tcactgtgta cagcctcctt tcccttaaca gctgttccaa taacggctgg atcacactct 840
aatgaataat cttctctaac cttgagccag acactagtgt gaaataccccc gaacccatga 900
tcctccacaa gaaagctgtt ccatgctcta tgtttgagtg ggcattcctt cagtgtgtca 960
ccatccacga caaagctgtt atttgtcttt gctgctctga cgaagtacga tttcccccaa 1020
gccttccagc cgtggggcag ctcgttcaca ggcacgggca atctctgtgg acctctccac 1080
atggggtttt ttacagatcc cacaacgacc gtcagttgaa ctccattctc ttccaggatt 1140
gcgttgagct ccccttctac tgatctccac atgatgtttt ccattcttga aacagaggag 1200
atcccacaga taccatcttc ccaggcttgc ttgactgctg ctgccaatct acggggggag 1260
tcaggatggt acttgtacct gtccctccag gcttcaacgt cgttatagac gaacacccct 1320
gtaccgcatc tcgtctcctt ctttgagaag tccaccgagc accccacatc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt tttttggaa tataaataat atgctgctcg gacacggccc tattcgtatg 1800
gtgctcgcta tcctcgcctt tctcaggttt accgctatca agcctagtct gggtctcatc 1860
aacagatggg gtagcgtggg caagaaggag gctatggaaa tcatcaagaa gttcaagaag 1920
gacctggccg ctatgctgag aatcatcaac gctcgtaagg agaagaagcg caggggtgcc 1980
gacacctctg tgggaatcgt gggtctgctg ctgaccaccg ctatggctgc tgaggtgacc 2040
agaagaggct ccgcctacta catgtacctg gacaggaacg acgctggaga agccatctct 2100
ttccccacca ccctgggtat gaacaagtgc tacatccaga tcatggacct gggacacatg 2160
tgcgacgcca ccatgagcta cgagtgccca atgctggacg agggtgtgga acccgacgac 2220
gtggactgct ggtgcaacac caccagcacc tgggtggtgt acggaacctg ccaccacaag 2280
aagggtgaag ctcgcaggtc cagacgtgcc gtgaccctgc cttcccactc tacccgcaag 2340
ctgcagacca ggtcccagac ctggctggag tctcgcgaat acaccaagca cctgatccgc 2400
gtggagaact ggatcttcag gaaccctggt ttcgctctgg ccgctgctgc tatcgcttgg 2460
ctgctgggaa gctccacctc ccagaaggtc atctacctgg tcatgatcct gctgatcgcc 2520
cctgcttaca gcatcagatg catcggcgtg agcaaccgtg acttcgtgga gggcatgtct 2580
ggcggaacct gggtggacgt ggtgctggaa cacggtggct gcgtgaccgt gatggctcag 2640
gacaagccaa ccgtcgacat cgagctggtg accaccaccg tgtctaacat ggccgaggtg 2700
cgcagctact gctacgaagc cagcatcagc gacatggcct ctgacagcag gtgcccaacc 2760

FIG. 31C cagggcgaag cttacctgga caagcagtct gacacccagt acgtgtgcaa gagaaccctg 2820
gtggaccgtg gatggggtaa cggctgcgga ctgttcggca agggcagcct ggtgacctgc 2880
gctaagttcg cctgctccaa gaagatgacc ggcaagtcta tccagccaga gaacctggaa 2940
tacagaatca tgctgtctgt gcacggctcc cagcactctg gaatgatcgt gaacgacacc 3000
ggacacgaaa ccgacgaaaa cagagccaag gtggagatca cccctaactc tccacgtgcc 3060
gaagctaccc tgggaggttt cggcagcctg ggactggact gtgagcctcg taccggcctg 3120
gacttctccg acctgtacta cctgaccatg aacaacaagc actggctggt gcacaaggaa 3180
tggttccacg acatcccact gccatggcac gccggtgctg acactggaac cccacactgg 3240
aacaacaagg aggctctggt ggagttcaag gacgcccacg ctaagagaca gactgtggtg 3300
gtgctgggtt cccaggaggg tgctgtgcac accgccctgg ctggagctct ggaggctgaa 3360
atggacggtg ccaagggccg tctgtctagc ggtcacctga agtgccgcct gaagatggac 3420
aagctgaggc tgaagggcgt gtcctactct ctgtgcaccg ccgctttcac cttcaccaag 3480
atccctgctg aaaccctgca cggcaccgtg accgtggaag tgcagtacgc tggaaccgat 3540
ggtccatgca aggtgcctgc tcagatggcc gtggacatgc agaccctgac ccctgtggga 3600
cgcctgatca ccgccaaccc agtgatcacc gagtctaccg aaaacagcaa gatgatgctg 3660
gagctggacc ctcccttcgg cgacagctac atcgtgatcg gagtgggtga aaagaagatc 3720
acccaccact ggcacaggag cggcagcacc atcggcaagg ctttcgaggc taccgtgcgc 3780
ggcgctaaga gaatggccgt gctgggcgac actgcttggg acttcggaag cgtgggcgga 3840
gccctgaact ccctgggcaa gggaatccac cagatcttcg gcgccgcttt caagtccctg 3900
ttcggtggca tgagctggtt ctcccagatc ctgatcggaa ccctgctgat gtggctgggt 3960
ctgaacacca agaacggctc tatcagcctg atgtgcctcg ctctcggtgg cgtgctgatt 4020
tttctctcta ccgcagtctc cgcatgagcc cctctccctc cccccccct aacgttactg 4080
gccgaagccg cttggaataa ggccggtgtg tgtttgtcta tatgtgattt tccaccatat 4140
tgccgtcttt tggcaatgtg agggcccgga aacctggccc tgtcttcttg acgagcattc 4200
ctaggggtct ttcccctctc gccaaaggaa tgcaaggtct gttgaatgtc gtgaaggaag 4260
cagttcctct ggaagcttct tgaagacaaa caacgtctgt agcgaccctt tgcaggcagc 4320
ggaacccccc acctggcgac aggtgcctct gcggccaaaa gccacgtgta taagatacac 4380
ctgcaaaggc ggcacaaccc cagtgccacg ttgtgagttg gatagttgtg gaaagagtca 4440
aatggctctc ctcaagcgta gtcaacaagg ggctgaagga tgcccagaag gtaccccatt 4500
gtatgggaat ctgatctggg gcctcggtgc acatgcttta catgtgttta gtcgaggtta 4560
aaaaagctct aggccccccg aaccacgggg acgtggtttt cctttgaaaa acacgatgat 4620
aagcttgcca caaatgctcc agggtcgcgg tccactgaaa ctctttatgg ctctcgtcgc 4680
cttcctgcgg ttcctcacta ttcctcctac tgtcggtatt ctgaagaggt ggggcaccat 4740

FIG. 31D caagaagagc aaggccatca acgtgctgcg cggattcagg aaggagatcg gtaggatgct 4800
gaacatcctg aaccgcagga gacgtaccgc cggcatgatc atcatgctga tccccaccgt 4860
gatggctatg gaactgagac cttggctgct gtgggtggtg gctgctactg gcaccctggt 4920
gctgctagca gctgacgccc agggccagaa ggtgttcacc aacacctggg ctgtgagaat 4980
ccccggcgga cctgctgtgg ctaacagcgt ggctcgtaag cacggcttcc tgaacctggg 5040
acagattttc ggtgactact accacttctg gcaccgcgga gtgaccaaga ggagcctgtc 5100
cccacacaga ccaaggcact ccagactgca gcgtgagccc caggtgcagt ggctggaaca 5160
gcaggtggcc aagcgcagga ccaagagaga cgtgtaccag gagcctaccg acccaaagtt 5220
cccccagcag tggtatctgt ccggcgtgac ccagcgtgac ctgaacgtga aggccgcttg 5280
ggctcagggt tacaccggtc acggcatcgt ggtgtccatc ctggacgacg gcatcgagaa 5340
gaaccaccct gacctggccg gtaactacga cccaggcgct tctttcgacg tgaacgacca 5400
ggaccccgac cctcagccaa gatacaccca gatgaacgac aacagacatg gaaccagatg 5460
tgctggtgaa gtggctgctg tggctaacaa cggcgtgtgc ggagtgggtg tggcctacaa 5520
cgctagaatc ggtggcgtgc gtatgctgga tggagaagtg actgatgctg tggaagctag 5580
aagcctggga ctgaacccaa accacatcca catctactct gccagctggg gtccagagga 5640
tgatggaaag actgtggatg gtcctgctag actggctgag gaagccttct tccgcggcgt 5700
gagccaggga aggggaggtc tgggaagcat cttcgtgtgg gcttctggta acggcggaag 5760
agagcacgac tcctgcaact gcgacggata caccaactct atctacaccc tgagcatcag 5820
ctccgctacc cagttcggta acgtgccctg gtactccgaa gcctgctcta gcaccctggc 5880
taccacctac tcctctggca accagaacga gaagcagatc gtgaccaccg acctgcgtca 5940
gaagtgcacc gaatctcaca ctggcacctc cgcctctgct cctctggctg ctggaatcat 6000
cgccctgacc ctggaggcta acaagaacct gacctggcgc gacatgcagc acctggtggt 6060
gcagacctcc aagccagctc acctgaacgc caacgactgg gctaccaacg gcgtgggaag 6120
gaaggtgagc cactcttacg gttacggtct gctggatgct ggtgctatgg tggccctggc 6180
tcagaactgg accaccgtgg cccctcagcg caagtgcatc atcgacatcc tgaccgagcc 6240
taaggacatc ggaaagagac tggaagtgcg taagaccgtg accgcttgcc tgggagagcc 6300
caaccacatc accagactgg aacacgccca ggctcgtctg accctgtctt acaacagacg 6360
tggagacctg gccatccacc tggtgtctcc aatgggcacc cgcagcaccc tgctggctgc 6420
taggccacac gactacagcg ccgacggatt caacgactgg gctttcatga ccacccactc 6480
ctgggacgag gacccttctg gtgaatgggt gctggagatc gaaaacacca gcgaggccaa 6540
caactacggc accctgacca agttcaccct ggtgctgtac ggcaccgctc ctgagggact 6600
gccagtgccc cctgaaagct ccggttgcaa gaccctgacc tctagccagg cctgcgtggt 6660
gtgcgaggaa ggcttctccc tgcaccagaa gtcttgcgtg cagcactgcc cacccggatt 6720
cgctcctcag gtgctggaca cccactactc taccgagaac gacgtggaaa ccatcagagc 6780

FIG. 31E cagcgtgtgc gctccttgtc acgcttcctg tgctacttgt cagggaccag ccctgactga 6840
ctgcctgtcc tgcccatctc acgccagcct ggaccccgtg gagcagacct gctccagaca 6900
gtctcagtcc tctcgtgaaa gccctccaca gcagcagccc cctagactgc cacccgaggt 6960
ggaagccggc cagagactgc gtgctggact gctgccttct cacctgccag aggtggtggc 7020
tggtctgagc tgcgctttca tcgtgctggt gttcgtgacc gtgttcctgg tgctgcagct 7080
gcgcagcggt ttctccttca ggggcgtgaa ggtgtacacc atggaccgcg gtctgatcag 7140
ctacaagggt ctgcctccag aggcttggca ggaggaatgc ccatctgaca gcgaagagga 7200
cgagggacgt ggagaacgga ctgccttcat caaagatcag agcgcactgt aataaatcga 7260
tttaattaat agcataaccc cttggggcct ctaaacgggt cttgaggggt tttttggaat 7320
tcacccagct ttcttgtaca aagtggtgat agcttgtcga gaagtactag aggatcataa 7380
tcagccatac cacatttgta gaggttttac ttgctttaaa aaacctccca cacctccccc 7440
tgaacctgaa acataaaatg aatgcaattg ttgttgttaa cttgtttatt gcagcttata 7500
atggttacaa ataaagcaat agcatcacaa atttcacaaa taaagcattt ttttcactgc 7560
attctagttg tggtttgtcc aaactcatca atgtatctta tcatgtctgg atc 7613

FIG. 32A

SEQ ID NO: 6. Dual Promoter-Homologous ZIKV del108C-prM-E & del108CZIKV-human furin proprotein bicistronic cassette + ZIKV NS1 gtggctatgg cagggcttgc cgccccgacg ttggctgcga gccctgggcc ttcacccgaa 60
cttgggggtt ggggtgggga aaaggaagaa acgcgggcgt attggtccca atggggtctc 120
ggtggggtat cgacagagtg ccagccctgg gaccgaaccc cgcgtttatg aacaaacgac 180
ccaacacccg tgcgttttat tctgtctttt tattgccgtc atagcgcggg ttccttccgg 240
tattgtctcc ttccgtgttt cagttagcct cccccatctc ccggtagcgc atgctctaga 300
ggcgcgcctt attatgcagt caccattgac cttactaagt tactttctgg ttctttcctg 360
ggccttatct ccattccata ccaacagcca tctttagccc ggaacgacag tgggggcatt 420
gtgcactccc tgcagcacca ttcctcgatc acccttccgc ttgcagtggt tgatctcaga 480
gatggtcctc ttgttccaca tgtttcctcc acgtggacct tagtgcctgg gcattcctca 540
aaccgaattt caagctcttc actgtgccat ggccctttca tttgggtcct gtagccctct 600
ctggtattgt gatggctgag tggcccagct aaagacttgg gtatgatcag atcactctct 660
tctattccat ctgtccacaa tgtgtgggac tttggccatt cacatgtttt catctcgatc 720
agatgggccc tcttcagcct ccatgtgtca ttcttctcac tctcaatcca gtagcctaga 780
tcactgtgta cagcctcctt tcccttaaca gctgttccaa taacggctgg atcacactct 840
aatgaataat cttctctaac cttgagccag acactagtgt gaaatacccc gaacccatga 900
tcctccacaa gaaagctgtt ccatgctcta tgtttgagtg ggcattcctt cagtgtgtca 960

FIG. 32B ccatccacga caaagctgtt atttgtcttt gctgctctga cgaagtacga tttcccccaa 1020
gccttccagc cgtggggcag ctcgttcaca ggcacgggca atctctgtgg acctctccac 1080
atggggtttt ttacagatcc cacaacgacc gtcagttgaa ctccattctc ttccaggatt 1140
gcgttgagct ccccttctac tgatctccac atgatgtttt ccattcttga aacagaggag 1200
atcccacaga taccatcttc ccaggcttgc ttgactgctg ctgccaatct acggggggag 1260
tcaggatggt acttgtacct gtccctccag gcttcaacgt cgttatagac gaacacccct 1320
gtaccgcatc tcgtctcctt ctttgagaag tccaccgagc accccacatc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt ttttttggaa tataaataat atgctgctcg gacacggccc tattcgtatg 1800
gtgctcgcta tcctcgcctt tctcaggttt accgctatca agcctagtct gggtctcatc 1860
aacagatggg gtagcgtggg caagaaggag gctatggaaa tcatcaagaa gttcaagaag 1920
gacctggccg ctatgctgag aatcatcaac gctcgtaagg agaagaagcg caggggtgcc 1980
gacacctctg tgggaatcgt gggtctgctg ctgaccaccg ctatggctgc tgaggtgacc 2040
agaagaggct ccgcctacta catgtacctg gacaggaacg acgctggaga agccatctct 2100
ttccccacca ccctgggtat gaacaagtgc tacatccaga tcatggacct gggacacatg 2160
tgcgacgcca ccatgagcta cgagtgccca atgctggacg agggtgtgga acccgacgac 2220
gtggactgct ggtgcaacac caccagcacc tgggtggtgt acggaacctg ccaccacaag 2280
aagggtgaag ctcgcaggtc cagacgtgcc gtgaccctgc cttcccactc tacccgcaag 2340
ctgcagacca ggtcccagac ctggctggag tctcgcgaat acaccaagca cctgatccgc 2400
gtggagaact ggatcttcag gaaccctggt ttcgctctgg ccgctgctgc tatcgcttgg 2460
ctgctgggaa gctccacctc ccagaaggtc atctacctgg tcatgatcct gctgatcgcc 2520
cctgcttaca gcatcagatg catcggcgtg agcaaccgtg acttcgtgga gggcatgtct 2580
ggcggaacct gggtggacgt ggtgctggaa cacggtggct gcgtgaccgt gatggctcag 2640
gacaagccaa ccgtcgacat cgagctggtg accaccaccg tgtctaacat ggccgaggtg 2700
cgcagctact gctacgaagc cagcatcagc gacatggcct ctgacagcag gtgcccaacc 2760
cagggcgaag cttacctgga caagcagtct gacacccagt acgtgtgcaa gagaaccctg 2820
gtggaccgtg gatggggtaa cggctgcgga ctgttcggca agggcagcct ggtgacctgc 2880
gctaagttcg cctgctccaa gaagatgacc ggcaagtcta tccagccaga gaacctggaa 2940
tacagaatca tgctgtctgt gcacggctcc cagcactctg gaatgatcgt gaacgacacc 3000

FIG. 32C ggacacgaaa ccgacgaaaa cagagccaag gtggagatca cccctaactc tccacgtgcc 3060
gaagctaccc tgggaggttt cggcagcctg ggactggact gtgagcctcg taccggcctg 3120
gacttctccg acctgtacta cctgaccatg aacaacaagc actggctggt gcacaaggaa 3180
tggttccacg acatcccact gccatggcac gccggtgctg acactggaac cccacactgg 3240
aacaacaagg aggctctggt ggagttcaag gacgcccacg ctaagagaca gactgtggtg 3300
gtgctgggtt cccaggaggg tgctgtgcac accgccctgg ctggagctct ggaggctgaa 3360
atggacggtg ccaagggccg tctgtctagc ggtcacctga agtgccgcct gaagatggac 3420
aagctgaggc tgaagggcgt gtcctactct ctgtgcaccg ccgctttcac cttcaccaag 3480
atccctgctg aaaccctgca cggcaccgtg accgtggaag tgcagtacgc tggaaccgat 3540
ggtccatgca aggtgcctgc tcagatggcc gtggacatgc agaccctgac ccctgtggga 3600
cgcctgatca ccgccaaccc agtgatcacc gagtctaccg aaaacagcaa gatgatgctg 3660
gagctggacc ctcccttcgg cgacagctac atcgtgatcg gagtgggtga aaagaagatc 3720
acccaccact ggcacaggag cggcagcacc atcggcaagg ctttcgaggc taccgtgcgc 3780
ggcgctaaga gaatggccgt gctgggcgac actgcttggg acttcggaag cgtgggcgga 3840
gccctgaact ccctgggcaa gggaatccac cagatcttcg gcgccgcttt caagtccctg 3900
ttcggtggca tgagctggtt ctcccagatc ctgatcggaa ccctgctgat gtggctgggt 3960
ctgaacacca agaacggctc tatcagcctg atgtgcctcg ctctcggtgg cgtgctgatt 4020
tttctctcta ccgcagtctc cgcatgagcc cctctccctc ccccccccct aacgttactg 4080
gccgaagccg cttggaataa ggccggtgtg tgtttgtcta tatgtgattt tccaccatat 4140
tgccgtcttt tggcaatgtg agggcccgga aacctggccc tgtcttcttg acgagcattc 4200
taggggtct ttcccctctc gccaaaggaa tgcaaggtct gttgaatgtc gtgaaggaag 4260
cagttcctct ggaagcttct tgaagacaaa caacgtctgt agcgaccctt tgcaggcagc 4320
ggaacccccc acctggcgac aggtgcctct gcggccaaaa gccacgtgta taagatacac 4380
ctgcaaaggc ggcacaaccc cagtgccacg ttgtgagttg gatagttgtg gaaagagtca 4440
aatggctctc ctcaagcgta gtcaacaagg ggctgaagga tgcccagaag gtaccccatt 4500
gtatgggaat ctgatctggg gcctcggtgc acatgcttta catgtgttta gtcgaggtta 4560
aaaaagctct aggccccccg aaccacgggg acgtggtttt cctttgaaaa acacgatgat 4620
aagcttgcca caaatgctgc tcggacacgg ccctattcgt atggtgctcg ctatcctcgc 4680
ctttctcagg tttaccgcta tcaagcctag tctgggtctc atcaacagat ggggtagcgt 4740
gggcaagaag gaggctatgg aaatcatcaa gaagttcaag aaggacctgg ccgctatgct 4800
gagaatcatc aacgctcgta aggagaagaa gcgcaggggt gccgacacct ctgtgggaat 4860
cgtgggtctg ctgctgacca ccgctatggc tatggaactg agaccttggc tgctgtgggt 4920
ggtggctgct actggcaccc tggtgctgct agcagctgac gcccagggcc agaaggtgtt 4980
caccaacacc tgggctgtga gaatccccgg cggacctgct gtggctaaca gcgtggctcg 5040

FIG. 32D taagcacggc ttcctgaacc tgggacagat tttcggtgac tactaccact tctggcaccg 5100
cggagtgacc aagaggagcc tgtccccaca cagaccaagg cactccagac tgcagcgtga 5160
gccccaggtg cagtggctgg aacagcaggt ggccaagcgc aggaccaaga gagacgtgta 5220
ccaggagcct accgacccaa agttccccca gcagtggtat ctgtccggcg tgacccagcg 5280
tgacctgaac gtgaaggccg cttgggctca gggttacacc ggtcacggca tcgtggtgtc 5340
catcctggac gacggcatcg agaagaacca ccctgacctg gccggtaact acgacccagg 5400
cgcttctttc gacgtgaacg accaggaccc cgaccctcag ccaagataca cccagatgaa 5460
cgacaacaga catggaacca gatgtgctgg tgaagtggct gctgtggcta acaacggcgt 5520
gtgcggagtg ggtgtggcct acaacgctag aatcggtggc gtgcgtatgc tggatggaga 5580
agtgactgat gctgtggaag ctagaagcct gggactgaac ccaaaccaca tccacatcta 5640
ctctgccagc tggggtccag aggatgatgg aaagactgtg gatggtcctg ctagactggc 5700
tgaggaagcc ttcttccgcg gcgtgagcca gggaagggga ggtctgggaa gcatcttcgt 5760
gtgggcttct ggtaacggcg gaagagagca cgactcctgc aactgcgacg gatacaccaa 5820
ctctatctac accctgagca tcagctccgc tacccagttc ggtaacgtgc cctggtactc 5880
cgaagcctgc tctagcaccc tggctaccac ctactcctct ggcaaccaga acgagaagca 5940
gatcgtgacc accgacctgc gtcagaagtg caccgaatct cacactggca cctccgcctc 6000
tgctcctctg gctgctggaa tcatcgccct gaccctggag gctaacaaga acctgacctg 6060
gcgcgacatg cagcacctgg tggtgcagac ctccaagcca gctcacctga acgccaacga 6120
ctgggctacc aacggcgtgg gaaggaaggt gagccactct tacggttacg gtctgctgga 6180
tgctggtgct atggtggccc tggctcagaa ctggaccacc gtggcccctc agcgcaagtg 6240
catcatcgac atcctgaccg agcctaagga catcggaaag agactggaag tgcgtaagac 6300
cgtgaccgct tgcctgggag agcccaacca catcaccaga ctggaacacg cccaggctcg 6360
tctgaccctg tcttacaaca gacgtggaga cctggccatc cacctggtgt ctccaatggg 6420
cacccgcagc accctgctgg ctgctaggcc acacgactac agcgccgacg gattcaacga 6480
ctgggctttc atgaccaccc actcctggga cgaggaccct tctggtgaat gggtgctgga 6540
gatcgaaaac accagcgagg ccaacaacta cggcaccctg accaagttca ccctggtgct 6600
gtacggcacc gctcctgagg gactgccagt gccccctgaa agctccggtt gcaagaccct 6660
gacctctagc caggcctgcg tggtgtgcga ggaaggcttc tccctgcacc agaagtcttg 6720
cgtgcagcac tgcccacccg gattcgctcc tcaggtgctg gacacccact actctaccga 6780
gaacgacgtg gaaaccatca gagccagcgt gtgcgctcct tgtcacgctt cctgtgctac 6840
ttgtcaggga ccagccctga ctgactgcct gtcctgccca tctcacgcca gcctggaccc 6900
cgtggagcag acctgctcca gacagtctca gtcctctcgt gaaagccctc cacagcagca 6960
gccccctaga ctgccacccg aggtggaagc cggccagaga ctgcgtgctg gactgctgcc 7020
ttctcacctg ccagaggtgg tggctggtct gagctgcgct ttcatcgtgc tggtgttcgt 7080

FIG. 32E gaccgtgttc ctggtgctgc agctgcgcag cggtttctcc ttcaggggcg tgaaggtgta 7140
caccatggac cgcggtctga tcagctacaa gggtctgcct ccagaggctt ggcaggagga 7200
atgcccatct gacagcgaag aggacgaggg acgtggagaa cggactgcct tcatcaaaga 7260
tcagagcgca ctgtaataaa tcgatttaat taatagcata acccttggg gcctctaaac 7320
gggtcttgag gggtttttg gaattcaccc agctttcttg tacaaagtgg tgatagcttg 7380
tcgagaagta ctagaggatc ataatcagcc ataccacatt tgtagaggtt ttacttgctt 7440
taaaaaacct cccacacctc cccctgaacc tgaaacataa aatgaatgca attgttgttg 7500
ttaacttgtt tattgcagct tataatggtt acaaataaag caatagcatc acaaatttca 7560
caaataaagc atttttttca ctgcattcta gttgtggttt gtccaaactc atcaatgtat 7620
cttatcatgt ctggatc 7637

FIG. 33A

SEQ ID NO: 7. Dual Promoter-ZIKV del108C-prM-E & human furin proprotein bicistronic cassette + ZIKV NS1 gtggctatgg cagggcttgc cgccccgacg ttggctgcga gccctgggcc ttcacccgaa 60
cttgggggtt ggggtgggga aaaggaagaa acgcgggcgt attggtccca atggggtctc 120
ggtggggtat cgacagagtg ccagccctgg gaccgaaccc cgcgtttatg aacaaacgac 180
ccaacacccg tgcgttttat tctgtctttt tattgccgtc atagcgcggg ttccttccgg 240
tattgtctcc ttccgtgttt cagttagcct cccccatctc ccggtagcgc atgctctaga 300
ggcgcgcctt attatgcagt caccattgac cttactaagt tactttctgg ttctttcctg 360
ggccttatct ccattccata ccaacagcca tctttagccc ggaacgacag tgggggcatt 420
gtgcactccc tgcagcacca ttcctcgatc acccttccgc ttgcagtggt tgatctcaga 480
gatggtcctc ttgttccaca tgtttcctcc acgtggacct tagtgcctgg gcattcctca 540
aaccgaattt caagctcttc actgtgccat ggccctttca tttgggtcct gtagccctct 600
ctggtattgt gatggctgag tggcccagct aaagacttgg gtatgatcag atcactctct 660
tctattccat ctgtccacaa tgtgtgggac tttggccatt cacatgtttt catctcgatc 720
agatgggccc tcttcagcct ccatgtgtca ttcttctcac tctcaatcca gtagcctaga 780
tcactgtgta cagcctcctt tcccttaaca gctgttccaa taacggctgg atcacactct 840
aatgaataat cttctctaac cttgagccag acactagtgt gaaatacccc gaacccatga 900
tcctccacaa gaaagctgtt ccatgctcta tgtttgagtg ggcattcctt cagtgtgtca 960
ccatccacga caaagctgtt atttgtcttt gctgctctga cgaagtacga tttcccccaa 1020
gccttccagc cgtggggcag ctcgttcaca ggcacgggca atctctgtgg acctctccac 1080
atggggtttt ttacagatcc cacaacgacc gtcagttgaa ctccattctc ttccaggatt 1140
gcgttgagct ccccttctac tgatctccac atgatgtttt ccattcttga aacagaggag 1200

FIG. 33B atcccacaga taccatcttc ccaggcttgc ttgactgctg ctgccaatct acggggggag 1260
tcaggatggt acttgtacct gtccctccag gcttcaacgt cgttatagac gaacacccct 1320
gtaccgcatc tcgtctcctt ctttgagaag tccaccgagc accccacatc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt ttttttggaa tataaataat atgctgctcg gacacggccc tattcgtatg 1800
gtgctcgcta tcctcgcctt tctcaggttt accgctatca agcctagtct gggtctcatc 1860
aacagatggg gtagcgtggg caagaaggag gctatggaaa tcatcaagaa gttcaagaag 1920
gacctggccg ctatgctgag aatcatcaac gctcgtaagg agaagaagcg caggggtgcc 1980
gacacctctg tgggaatcgt gggtctgctg ctgaccaccg ctatggctgc tgaggtgacc 2040
agaagaggct ccgcctacta catgtacctg gacaggaacg acgctggaga agccatctct 2100
ttccccacca ccctgggtat gaacaagtgc tacatccaga tcatggacct gggacacatg 2160
tgcgacgcca ccatgagcta cgagtgccca atgctggacg agggtgtgga acccgacgac 2220
gtggactgct ggtgcaacac caccagcacc tgggtggtgt acggaacctg ccaccacaag 2280
aagggtgaag ctcgcaggtc cagacgtgcc gtgaccctgc cttcccactc tacccgcaag 2340
ctgcagacca ggtcccagac ctggctggag tctcgcgaat acaccaagca cctgatccgc 2400
gtggagaact ggatcttcag gaaccctggt ttcgctctgg ccgctgctgc tatcgcttgg 2460
ctgctgggaa gctccacctc ccagaaggtc atctacctgg tcatgatcct gctgatcgcc 2520
cctgcttaca gcatcagatg catcggcgtg agcaaccgtg acttcgtgga gggcatgtct 2580
ggcggaacct gggtggacgt ggtgctggaa cacggtggct gcgtgaccgt gatggctcag 2640
gacaagccaa ccgtcgacat cgagctggtg accaccaccg tgtctaacat ggccgaggtg 2700
cgcagctact gctacgaagc cagcatcagc gacatggcct ctgacagcag gtgcccaacc 2760
cagggcgaag cttacctgga caagcagtct gacacccagt acgtgtgcaa gagaaccctg 2820
gtggaccgtg gatggggtaa cggctgcgga ctgttcggca agggcagcct ggtgacctgc 2880
gctaagttcg cctgctccaa gaagatgacc ggcaagtcta tccagccaga gaacctggaa 2940
tacagaatca tgctgtctgt gcacggctcc cagcactctg gaatgatcgt gaacgacacc 3000
ggacacgaaa ccgacgaaaa cagagccaag gtggagatca cccctaactc tccacgtgcc 3060
gaagctaccc tgggaggttt cggcagcctg ggactggact gtgagcctcg taccggcctg 3120
gacttctccg acctgtacta cctgaccatg aacaacaagc actggctggt gcacaaggaa 3180
tggttccacg acatcccact gccatggcac gccggtgctg acactggaac cccacactgg 3240

FIG. 33C aacaacaagg aggctctggt ggagttcaag gacgcccacg ctaagagaca gactgtggtg 3300
gtgctgggtt cccaggaggg tgctgtgcac accgccctgg ctggagctct ggaggctgaa 3360
atggacggtg ccaagggccg tctgtctagc ggtcacctga agtgccgcct gaagatggac 3420
aagctgaggc tgaagggcgt gtcctactct ctgtgcaccg ccgctttcac cttcaccaag 3480
atccctgctg aaaccctgca cggcaccgtg accgtggaag tgcagtacgc tggaaccgat 3540
ggtccatgca aggtgcctgc tcagatggcc gtggacatgc agaccctgac ccctgtggga 3600
cgcctgatca ccgccaaccc agtgatcacc gagtctaccg aaaacagcaa gatgatgctg 3660
gagctggacc ctcccttcgg cgacagctac atcgtgatcg gagtgggtga aaagaagatc 3720
acccaccact ggcacaggag cggcagcacc atcggcaagg ctttcgaggc taccgtgcgc 3780
ggcgctaaga gaatggccgt gctgggcgac actgcttggg acttcggaag cgtgggcgga 3840
gccctgaact ccctgggcaa gggaatccac cagatcttcg gcgccgcttt caagtccctg 3900
ttcggtggca tgagctggtt ctcccagatc ctgatcggaa ccctgctgat gtggctgggt 3960
ctgaacacca agaacggctc tatcagcctg atgtgcctcg ctctcggtgg cgtgctgatt 4020
tttctctcta ccgcagtctc cgcatgagcc cctctccctc cccccccct aacgttactg 4080
gccgaagccg cttggaataa ggccggtgtg tgtttgtcta tatgtgattt tccaccatat 4140
tgccgtcttt tggcaatgtg agggcccgga aacctggccc tgtcttcttg acgagcattc 4200
ctaggggtct ttcccctctc gccaaaggaa tgcaaggtct gttgaatgtc gtgaaggaag 4260
cagttcctct ggaagcttct tgaagacaaa caacgtctgt agcgaccctt tgcaggcagc 4320
ggaacccccc acctggcgac aggtgcctct gcggccaaaa gccacgtgta taagatacac 4380
ctgcaaaggc ggcacaaccc cagtgccacg ttgtgagttg gatagttgtg gaaagagtca 4440
aatggctctc ctcaagcgta gtcaacaagg ggctgaagga tgcccagaag gtaccccatt 4500
gtatgggaat ctgatctggg gcctcggtgc acatgcttta catgtgttta gtcgaggtta 4560
aaaaagctct aggccccccg aaccacgggg acgtggtttt cctttgaaaa acacgatgat 4620
aagcttgcca caaatggaac tgagaccttg gctgctgtgg gtggtggctg ctactggcac 4680
cctggtgctg ctagcagctg acgcccaggg ccagaaggtg ttcaccaaca cctgggctgt 4740
gagaatcccc ggcggacctg ctgtggctaa cagcgtggct cgtaagcacg gcttcctgaa 4800
cctgggacag attttcggtg actactacca cttctggcac cgcggagtga ccaagaggag 4860
cctgtcccca cacagaccaa ggcactccag actgcagcgt gagccccagg tgcagtggct 4920
ggaacagcag gtggccaagc gcaggaccaa gagagacgtg taccaggagc ctaccgaccc 4980
aaagttcccc cagcagtggt atctgtccgg cgtgacccag cgtgacctga acgtgaaggc 5040
cgcttgggct cagggttaca ccggtcacgg catcgtggtg tccatcctgg acgacggcat 5100
cgagaagaac caccctgacc tggccggtaa ctacgaccca ggcgcttctt tcgacgtgaa 5160
cgaccaggac cccgaccctc agccaagata cacccagatg aacgacaaca gacatggaac 5220
cagatgtgct ggtgaagtgg ctgctgtggc taacaacggc gtgtgcggag tgggtgtggc 5280

FIG. 33D ctacaacgct agaatcggtg gcgtgcgtat gctggatgga gaagtgactg atgctgtgga 5340
agctagaagc ctgggactga acccaaacca catccacatc tactctgcca gctggggtcc 5400
agaggatgat ggaaagactg tggatggtcc tgctagactg gctgaggaag ccttcttccg 5460
cggcgtgagc cagggaaggg gaggtctggg aagcatcttc gtgtgggctt ctggtaacgg 5520
cggaagagag cacgactcct gcaactgcga cggatacacc aactctatct acaccctgag 5580
catcagctcc gctacccagt tcggtaacgt gccctggtac tccgaagcct gctctagcac 5640
cctggctacc acctactcct ctggcaacca gaacgagaag cagatcgtga ccaccgacct 5700
gcgtcagaag tgcaccgaat ctcacactgg cacctccgcc tctgctcctc tggctgctgg 5760
aatcatcgcc ctgaccctgg aggctaacaa gaacctgacc tggcgcgaca tgcagcacct 5820
ggtggtgcag acctccaagc cagctcacct gaacgccaac gactgggcta ccaacggcgt 5880
gggaaggaag gtgagccact cttacggtta cggtctgctg gatgctggtg ctatggtggc 5940
cctggctcag aactggacca ccgtggcccc tcagcgcaag tgcatcatcg acatcctgac 6000
cgagcctaag gacatcggaa agagactgga agtgcgtaag accgtgaccg cttgcctggg 6060
agagcccaac cacatcacca gactggaaca cgcccaggct cgtctgaccc tgtcttacaa 6120
cagacgtgga gacctggcca tccacctggt gtctccaatg ggcacccgca gcaccctgct 6180
ggctgctagg ccacacgact acagcgccga cggattcaac gactgggctt tcatgaccac 6240
ccactcctgg gacgaggacc cttctggtga atgggtgctg gagatcgaaa acaccagcga 6300
ggccaacaac tacggcaccc tgaccaagtt caccctggtg ctgtacggca ccgctcctga 6360
gggactgcca gtgccccctg aaagctccgg ttgcaagacc ctgacctcta gccaggcctg 6420
cgtggtgtgc gaggaaggct tctccctgca ccagaagtct tgcgtgcagc actgcccacc 6480
cggattcgct cctcaggtgc tggacaccca ctactctacc gagaacgacg tggaaaccat 6540
cagagccagc gtgtgcgctc cttgtcacgc ttcctgtgct acttgtcagg gaccagccct 6600
gactgactgc ctgtcctgcc catctcacgc cagcctggac cccgtggagc agacctgctc 6660
cagacagtct cagtcctctc gtgaaagccc tccacagcag cagcccccta gactgccacc 6720
cgaggtggaa gccggccaga gactgcgtgc tggactgctg ccttctcacc tgccagaggt 6780
ggtggctggt ctgagctgcg ctttcatcgt gctggtgttc gtgaccgtgt tcctggtgct 6840
gcagctgcgc agcggtttct ccttcagggg cgtgaaggtg tacaccatgg accgcggtct 6900
gatcagctac aagggtctgc ctccagaggc ttggcaggag gaatgcccat ctgacagcga 6960
agaggacgag ggacgtggag aacggactgc cttcatcaaa gatcagagcg cactgtaata 7020
aatcgattta attaatagca taaccccttg gggcctctaa acgggtcttg aggggttttt 7080
tggaattcac ccagctttct tgtacaaagt ggtgatagct tgtcgagaag tactagagga 7140
tcataatcag ccataccaca tttgtagagg ttttacttgc tttaaaaaac ctcccacacc 7200
tccccctgaa cctgaaacat aaaatgaatg caattgttgt tgttaacttg tttattgcag 7260
cttataatgg ttacaaataa agcaatagca tcacaaattt cacaaataaa gcattttttt 7320

FIG. 33E cactgcattc tagttgtggt ttgtccaaac tcatcaatgt atcttatcat gtctggatc 7379

FIG. 34A

SEQ ID NO: 8. Heterologous ZIKV del108C-prM-E & del108CDENV2-human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgct gctcggacac ggccctattc gtatggtgct 300
cgctatcctc gcctttctca ggtttaccgc tatcaagcct agtctgggtc tcatcaacag 360
atggggtagc gtgggcaaga aggaggctat ggaaatcatc aagaagttca agaaggacct 420
ggccgctatg ctgagaatca tcaacgctcg taaggagaag aagcgcaggg gtgccgacac 480
ctctgtggga atcgtgggtc tgctgctgac caccgctatg gctgctgagg tgaccagaag 540
aggctccgcc tactacatgt acctggacag gaacgacgct ggagaagcca tctctttccc 600
caccaccctg ggtatgaaca agtgctacat ccagatcatg gacctgggac acatgtgcga 660
cgccaccatg agctacgagt gcccaatgct ggacgagggt gtggaacccg acgacgtgga 720
ctgctggtgc aacaccacca gcacctgggt ggtgtacgga acctgccacc acaagaaggg 780
tgaagctcgc aggtccagac gtgccgtgac cctgccttcc cactctaccc gcaagctgca 840
gaccaggtcc cagacctggc tggagtctcg cgaatacacc aagcacctga tccgcgtgga 900
gaactggatc ttcaggaacc ctggtttcgc tctggccgct gctgctatcg cttggctgct 960
gggaagctcc acctcccaga aggtcatcta cctggtcatg atcctgctga tcgcccctgc 1020
ttacagcatc agatgcatcg gcgtgagcaa ccgtgacttc gtggagggca tgtctggcgg 1080
aacctgggtg gacgtggtgc tggaacacgg tggctgcgtg accgtgatgg ctcaggacaa 1140
gccaaccgtc gacatcgagc tggtgaccac caccgtgtct aacatggccg aggtgcgcag 1200
ctactgctac gaagccagca tcagcgacat ggcctctgac agcaggtgcc caacccaggg 1260
cgaagcttac ctggacaagc agtctgacac ccagtacgtg tgcaagagaa ccctggtgga 1320
ccgtggatgg ggtaacggct gcggactgtt cggcaagggc agcctggtga cctgcgctaa 1380
gttcgcctgc tccaagaaga tgaccggcaa gtctatccag ccagagaacc tggaatacag 1440
aatcatgctg tctgtgcacg gctcccagca ctctggaatg atcgtgaacg acaccggaca 1500
cgaaaccgac gaaaacagag ccaaggtgga gatcacccct aactctccac gtgccgaagc 1560
taccctggga ggtttcggca gcctgggact ggactgtgag cctcgtaccg gcctggactt 1620
ctccgacctg tactacctga ccatgaacaa caagcactgg ctggtgcaca aggaatggtt 1680
ccacgacatc ccactgccat ggcacgccgg tgctgacact ggaaccccac actggaacaa 1740

FIG. 34B caaggaggct ctggtggagt tcaaggacgc ccacgctaag agacagactg tggtggtgct 1800
gggttcccag gagggtgctg tgcacaccgc cctggctgga gctctggagg ctgaaatgga 1860
cggtgccaag ggccgtctgt ctagcggtca cctgaagtgc cgcctgaaga tggacaagct 1920
gaggctgaag ggcgtgtcct actctctgtg caccgccgct ttcaccttca ccaagatccc 1980
tgctgaaacc ctgcacggca ccgtgaccgt ggaagtgcag tacgctggaa ccgatggtcc 2040
atgcaaggtg cctgctcaga tggccgtgga catgcagacc ctgacccctg tgggacgcct 2100
gatcaccgcc aacccagtga tcaccgagtc taccgaaaac agcaagatga tgctggagct 2160
ggaccctccc ttcggcgaca gctacatcgt gatcggagtg ggtgaaaaga agatcaccca 2220
ccactggcac aggagcggca gcaccatcgg caaggctttc gaggctaccg tgcgcggcgc 2280
taagagaatg gccgtgctgg gcgacactgc ttgggacttc ggaagcgtgg gcggagccct 2340
gaactccctg ggcaagggaa tccaccagat cttcggcgcc gctttcaagt ccctgttcgg 2400
tggcatgagc tggttctccc agatcctgat cggaaccctg ctgatgtggc tgggtctgaa 2460
caccaagaac ggctctatca gcctgatgtg cctcgctctc ggtggcgtgc tgatttttct 2520
ctctaccgca gtctccgcat gagcccctct ccctccccc cccctaacgt tactggccga 2580
agccgcttgg aataaggccg gtgtgtgttt gtctatatgt gattttccac catattgccg 2640
tcttttggca atgtgagggc ccggaaacct ggccctgtct tcttgacgag cattcctagg 2700
ggtctttccc ctctcgccaa aggaatgcaa ggtctgttga atgtcgtgaa ggaagcagtt 2760
cctctggaag cttcttgaag acaaacaacg tctgtagcga ccctttgcag gcagcggaac 2820
cccccacctg gcgacaggtg cctctgcggc caaaagccac gtgtataaga tacacctgca 2880
aaggcggcac aaccccagtg ccacgttgtg agttggatag ttgtggaaag agtcaaatgg 2940
ctctcctcaa gcgtagtcaa caaggggctg aaggatgccc agaaggtacc ccattgtatg 3000
ggaatctgat ctggggcctc ggtgcacatg ctttacatgt gtttagtcga ggttaaaaaa 3060
gctctaggcc ccccgaacca cggggacgtg gttttccttt gaaaaacacg atgataagct 3120
tgccacaaat gctccagggt cgcggtccac tgaaactctt tatggctctc gtcgccttcc 3180
tgcggttcct cactattcct cctactgtcg gtattctgaa gaggtggggc accatcaaga 3240
agagcaaggc catcaacgtg ctgcgcggat tcaggaagga gatcggtagg atgctgaaca 3300
tcctgaaccg caggagacgt accgccggca tgatcatcat gctgatcccc accgtgatgg 3360
ctatggaact gagaccttgg ctgctgtggg tggtggctgc tactggcacc ctggtgctgc 3420
tagcagctga cgcccagggc cagaaggtgt tcaccaacac ctgggctgtg agaatccccg 3480
gcggacctgc tgtggctaac agcgtggctc gtaagcacgg cttcctgaac ctgggacaga 3540
ttttcggtga ctactaccac ttctggcacc gcggagtgac caagaggagc ctgtccccac 3600
acagaccaag gcactccaga ctgcagcgtg agccccaggt gcagtggctg gaacagcagg 3660
tggccaagcg caggaccaag agagacgtgt accaggagcc taccgaccca aagttccccc 3720
agcagtggta tctgtccggc gtgacccagc gtgacctgaa cgtgaaggcc gcttgggctc 3780

FIG. 34C agggttacac cggtcacggc atcgtggtgt ccatcctgga cgacggcatc gagaagaacc 3840
accctgacct ggccggtaac tacgacccag gcgcttcttt cgacgtgaac gaccaggacc 3900
ccgaccctca gccaagatac acccagatga acgacaacag acatggaacc agatgtgctg 3960
gtgaagtggc tgctgtggct aacaacggcg tgtgcggagt gggtgtggcc tacaacgcta 4020
gaatcggtgg cgtgcgtatg ctggatggag aagtgactga tgctgtggaa gctagaagcc 4080
tgggactgaa cccaaaccac atccacatct actctgccag ctggggtcca gaggatgatg 4140
gaaagactgt ggatggtcct gctagactgg ctgaggaagc cttcttccgc ggcgtgagcc 4200
agggaagggg aggtctggga agcatcttcg tgtgggcttc tggtaacggc ggaagagagc 4260
acgactcctg caactgcgac ggatacacca actctatcta caccctgagc atcagctccg 4320
ctacccagtt cggtaacgtg ccctggtact ccgaagcctg ctctagcacc ctggctacca 4380
cctactcctc tggcaaccag aacgagaagc agatcgtgac caccgacctg cgtcagaagt 4440
gcaccgaatc tcacactggc acctccgcct ctgctcctct ggctgctgga atcatcgccc 4500
tgaccctgga ggctaacaag aacctgacct ggcgcgacat gcagcacctg gtggtgcaga 4560
cctccaagcc agctcacctg aacgccaacg actgggctac caacggcgtg ggaaggaagg 4620
tgagccactc ttacggttac ggtctgctgg atgctggtgc tatggtggcc ctggctcaga 4680
actggaccac cgtggcccct cagcgcaagt gcatcatcga catcctgacc gagcctaagg 4740
acatcggaaa gagactggaa gtgcgtaaga ccgtgaccgc ttgcctggga gagcccaacc 4800
acatcaccag actggaacac gcccaggctc gtctgaccct gtcttacaac agacgtggag 4860
acctggccat ccacctggtg tctccaatgg gcacccgcag caccctgctg gctgctaggc 4920
cacacgacta cagcgccgac ggattcaacg actgggcttt catgaccacc cactcctggg 4980
acgaggaccc ttctggtgaa tgggtgctgg agatcgaaaa caccagcgag gccaacaact 5040
acggcaccct gaccaagttc accctggtgc tgtacggcac cgctcctgag ggactgccag 5100
tgccccctga aagctccggt tgcaagaccc tgacctctag ccaggcctgc gtggtgtgcg 5160
aggaaggctt ctccctgcac cagaagtctt gcgtgcagca ctgcccaccc ggattcgctc 5220
ctcaggtgct ggacacccac tactctaccg agaacgacgt ggaaaccatc agagccagcg 5280
tgtgcgctcc ttgtcacgct tcctgtgcta cttgtcaggg accagccctg actgactgcc 5340
tgtcctgccc atctcacgcc agcctggacc ccgtggagca gacctgctcc agacagtctc 5400
agtcctctcg tgaaagccct ccacagcagc agccccctag actgccaccc gaggtggaag 5460
ccggccagag actgcgtgct ggactgctgc cttctcacct gccagaggtg gtggctggtc 5520
tgagctgcgc tttcatcgtg ctggtgttcg tgaccgtgtt cctggtgctg cagctgcgca 5580
gcggtttctc cttcaggggc gtgaaggtgt acaccatgga ccgcggtctg atcagctaca 5640
agggtctgcc tccagaggct tggcaggagg aatgcccatc tgacagcgaa gaggacgagg 5700
gacgtggaga acggactgcc ttcatcaaag atcagagcgc actgtaataa atcgatttaa 5760
ttaatagcat aaccccttgg ggcctctaaa cgggtcttga ggggtttttt ggaattcacc 5820

FIG. 34D cagctttctt gtacaaagtg gtgatagctt gtcgagaagt actagaggat cataatcagc 5880
cataccacat ttgtagaggt tttacttgct ttaaaaaacc tcccacacct ccccctgaac 5940
ctgaaacata aaatgaatgc aattgttgtt gttaacttgt ttattgcagc ttataatggt 6000
tacaaataaa gcaatagcat cacaaatttc acaaataaag catttttttc actgcattct 6060
agttgtggtt tgtccaaact catcaatgta tcttatcatg tctggatc 6108

FIG. 35A

SEQ ID NO: 9. Homologous ZIKV del108C-prM-E & del108CZIKV-human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgct gctcggacac ggccctattc gtatggtgct 300
cgctatcctc gcctttctca ggtttaccgc tatcaagcct agtctgggtc tcatcaacag 360
atggggtagc gtgggcaaga aggaggctat ggaaatcatc aagaagttca agaaggacct 420
ggccgctatg ctgagaatca tcaacgctcg taaggagaag aagcgcaggg gtgccgacac 480
ctctgtggga atcgtgggtc tgctgctgac caccgctatg gctgctgagg tgaccagaag 540
aggctccgcc tactacatgt acctggacag gaacgacgct ggagaagcca tctctttccc 600
caccaccctg ggtatgaaca agtgctacat ccagatcatg gacctgggac acatgtgcga 660
cgccaccatg agctacgagt gcccaatgct ggacgagggt gtggaacccg acgacgtgga 720
ctgctggtgc aacaccacca gcacctgggt ggtgtacgga acctgccacc acaagaaggg 780
tgaagctcgc aggtccagac gtgccgtgac cctgccttcc cactctaccc gcaagctgca 840
gaccaggtcc cagacctggc tggagtctcg cgaatacacc aagcacctga tccgcgtgga 900
gaactggatc ttcaggaacc ctggtttcgc tctggccgct gctgctatcg cttggctgct 960
gggaagctcc acctcccaga aggtcatcta cctggtcatg atcctgctga tcgcccctgc 1020
ttacagcatc agatgcatcg gcgtgagcaa ccgtgacttc gtggagggca tgtctggcgg 1080
aacctgggtg gacgtggtgc tggaacacgg tggctgcgtg accgtgatgg ctcaggacaa 1140
gccaaccgtc gacatcgagc tggtgaccac caccgtgtct aacatggccg aggtgcgcag 1200
ctactgctac gaagccagca tcagcgacat ggcctctgac agcaggtgcc caacccaggg 1260
cgaagcttac ctggacaagc agtctgacac ccagtacgtg tgcaagagaa ccctggtgga 1320
ccgtggatgg ggtaacggct gcggactgtt cggcaagggc agcctggtga cctgcgctaa 1380
gttcgcctgc tccaagaaga tgaccggcaa gtctatccag ccagagaacc tggaatacag 1440
aatcatgctg tctgtgcacg gctcccagca ctctggaatg atcgtgaacg acaccggaca 1500

FIG. 35B cgaaaccgac gaaaacagag ccaaggtgga gatcacccct aactctccac gtgccgaagc 1560
taccctggga ggtttcggca gcctgggact ggactgtgag cctcgtaccg gcctggactt 1620
ctccgacctg tactacctga ccatgaacaa caagcactgg ctggtgcaca aggaatggtt 1680
ccacgacatc ccactgccat ggcacgccgg tgctgacact ggaaccccac actggaacaa 1740
caaggaggct ctggtggagt tcaaggacgc ccacgctaag agacagactg tggtggtgct 1800
gggttcccag gagggtgctg tgcacaccgc cctggctgga gctctggagg ctgaaatgga 1860
cggtgccaag ggccgtctgt ctagcggtca cctgaagtgc cgcctgaaga tggacaagct 1920
gaggctgaag ggcgtgtcct actctctgtg caccgccgct ttcaccttca ccaagatccc 1980
tgctgaaacc ctgcacggca ccgtgaccgt ggaagtgcag tacgctggaa ccgatggtcc 2040
atgcaaggtg cctgctcaga tggccgtgga catgcagacc ctgacccctg tgggacgcct 2100
gatcaccgcc aacccagtga tcaccgagtc taccgaaaac agcaagatga tgctggagct 2160
ggaccctccc ttcggcgaca gctacatcgt gatcggagtg ggtgaaaaga agatcaccca 2220
ccactggcac aggagcggca gcaccatcgg caaggctttc gaggctaccg tgcgcggcgc 2280
taagagaatg gccgtgctgg gcgacactgc ttgggacttc ggaagcgtgg gcggagccct 2340
gaactccctg ggcaagggaa tccaccagat cttcggcgcc gctttcaagt ccctgttcgg 2400
tggcatgagc tggttctccc agatcctgat cggaaccctg ctgatgtggc tgggtctgaa 2460
caccaagaac ggctctatca gcctgatgtg cctcgctctc ggtggcgtgc tgatttttct 2520
ctctaccgca gtctccgcat gagcccctct ccctcccccc cccctaacgt tactggccga 2580
agccgcttgg aataaggccg gtgtgtgttt gtctatatgt gattttccac catattgccg 2640
tcttttggca atgtgagggc ccggaaacct ggccctgtct tcttgacgag cattcctagg 2700
ggtctttccc ctctcgccaa aggaatgcaa ggtctgttga atgtcgtgaa ggaagcagtt 2760
cctctggaag cttcttgaag acaaacaacg tctgtagcga ccctttgcag gcagcggaac 2820
cccccacctg gcgacaggtg cctctgcggc caaaagccac gtgtataaga tacacctgca 2880
aaggcggcac aaccccagtg ccacgttgtg agttggatag ttgtggaaag agtcaaatgg 2940
ctctcctcaa gcgtagtcaa caaggggctg aaggatgccc agaaggtacc ccattgtatg 3000
ggaatctgat ctggggcctc ggtgcacatg ctttacatgt gtttagtcga ggttaaaaaa 3060
gctctaggcc ccccgaacca cggggacgtg gttttccttt gaaaaacacg atgataagct 3120
tgccacaaat gctgctcgga cacggcccta ttcgtatggt gctcgctatc ctcgcctttc 3180
tcaggtttac cgctatcaag cctagtctgg gtctcatcaa cagatggggt agcgtgggca 3240
agaaggaggc tatggaaatc atcaagaagt tcaagaagga cctggccgct atgctgagaa 3300
tcatcaacgc tcgtaaggag aagaagcgca ggggtgccga cacctctgtg ggaatcgtgg 3360
gtctgctgct gaccaccgct atggctatgg aactgagacc ttggctgctg tgggtggtgg 3420
ctgctactgg caccctggtg ctgctagcag ctgacgccca gggccagaag gtgttcacca 3480
acacctgggc tgtgagaatc cccggcggac ctgctgtggc taacagcgtg gctcgtaagc 3540

FIG. 35C acggcttcct gaacctggga cagattttcg gtgactacta ccacttctgg caccgcggag 3600
tgaccaagag gagcctgtcc ccacacagac caaggcactc cagactgcag cgtgagcccc 3660
aggtgcagtg gctggaacag caggtggcca agcgcaggac caagagagac gtgtaccagg 3720
agcctaccga cccaaagttc ccccagcagt ggtatctgtc cggcgtgacc cagcgtgacc 3780
tgaacgtgaa ggccgcttgg gctcagggtt acaccggtca cggcatcgtg gtgtccatcc 3840
tggacgacgg catcgagaag aaccaccctg acctggccgg taactacgac ccaggcgctt 3900
ctttcgacgt gaacgaccag gaccccgacc ctcagccaag atacacccag atgaacgaca 3960
acagacatgg aaccagatgt gctggtgaag tggctgctgt ggctaacaac ggcgtgtgcg 4020
gagtgggtgt ggcctacaac gctagaatcg gtggcgtgcg tatgctggat ggagaagtga 4080
ctgatgctgt ggaagctaga agcctgggac tgaacccaaa ccacatccac atctactctg 4140
ccagctgggg tccagaggat gatggaaaga ctgtggatgg tcctgctaga ctggctgagg 4200
aagccttctt ccgcggcgtg agccagggaa ggggaggtct gggaagcatc ttcgtgtggg 4260
cttctggtaa cggcggaaga gagcacgact cctgcaactg cgacggatac accaactcta 4320
tctacaccct gagcatcagc tccgctaccc agttcggtaa cgtgccctgg tactccgaag 4380
cctgctctag caccctggct accacctact cctctggcaa ccagaacgag aagcagatcg 4440
tgaccaccga cctgcgtcag aagtgcaccg aatctcacac tggcacctcc gcctctgctc 4500
ctctggctgc tggaatcatc gccctgaccc tggaggctaa caagaacctg acctggcgcg 4560
acatgcagca cctggtggtg cagacctcca agccagctca cctgaacgcc aacgactggg 4620
ctaccaacgg cgtgggaagg aaggtgagcc actcttacgg ttacggtctg ctggatgctg 4680
gtgctatggt ggccctggct cagaactgga ccaccgtggc ccctcagcgc aagtgcatca 4740
tcgacatcct gaccgagcct aaggacatcg gaaagagact ggaagtgcgt aagaccgtga 4800
ccgcttgcct gggagagccc aaccacatca ccagactgga acacgcccag gctcgtctga 4860
ccctgtctta caacagacgt ggagacctgg ccatccacct ggtgtctcca atgggcaccc 4920
gcagcaccct gctggctgct aggccacacg actacagcgc cgacggattc aacgactggg 4980
ctttcatgac cacccactcc tgggacgagg acccttctgg tgaatgggtg ctggagatcg 5040
aaaacaccag cgaggccaac aactacggca ccctgaccaa gttcaccctg gtgctgtacg 5100
gcaccgctcc tgagggactg ccagtgcccc ctgaaagctc cggttgcaag accctgacct 5160
ctagccaggc ctgcgtggtg tgcgaggaag gcttctccct gcaccagaag tcttgcgtgc 5220
agcactgccc acccggattc gctcctcagg tgctggacac ccactactct accgagaacg 5280
acgtggaaac catcagagcc agcgtgtgcg ctccttgtca cgcttcctgt gctacttgtc 5340
agggaccagc cctgactgac tgcctgtcct gcccatctca cgccagcctg gaccccgtgg 5400
agcagacctg ctccagacag tctcagtcct ctcgtgaaag ccctccacag cagcagcccc 5460
ctagactgcc acccgaggtg gaagccggcc agagactgcg tgctggactg ctgccttctc 5520
acctgccaga ggtggtggct ggtctgagct gcgctttcat cgtgctggtg ttcgtgaccg 5580

FIG. 35D tgttcctggt gctgcagctg cgcagcggtt tctccttcag gggcgtgaag gtgtacacca 5640
tggaccgcgg tctgatcagc tacaagggtc tgcctccaga ggcttggcag gaggaatgcc 5700
catctgacag cgaagaggac gagggacgtg gagaacggac tgccttcatc aaagatcaga 5760
gcgcactgta ataaatcgat ttaattaata gcataacccc ttggggcctc taaacgggtc 5820
ttgaggggtt ttttggaatt cacccagctt tcttgtacaa agtggtgata gcttgtcgag 5880
aagtactaga ggatcataat cagccatacc acatttgtag aggttttact tgctttaaaa 5940
aacctcccac acctccccct gaacctgaaa cataaaatga atgcaattgt tgttgttaac 6000
ttgtttattg cagcttataa tggttacaaa taaagcaata gcatcacaaa tttcacaaat 6060
aaagcatttt tttcactgca ttctagttgt ggtttgtcca aactcatcaa tgtatcttat 6120
catgtctgga tc 6132

FIG. 36A

SEQ ID NO: 10. ZIKV del108C-prM-E & human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgct gctcggacac ggccctattc gtatggtgct 300
cgctatcctc gcctttctca ggtttaccgc tatcaagcct agtctgggtc tcatcaacag 360
atggggtagc gtgggcaaga aggaggctat ggaaatcatc aagaagttca agaaggacct 420
ggccgctatg ctgagaatca tcaacgctcg taaggagaag aagcgcaggg gtgccgacac 480
ctctgtggga atcgtgggtc tgctgctgac caccgctatg gctgctgagg tgaccagaag 540
aggctccgcc tactacatgt acctggacag gaacgacgct ggagaagcca tctctttccc 600
caccaccctg ggtatgaaca agtgctacat ccagatcatg gacctgggac acatgtgcga 660
cgccaccatg agctacgagt gcccaatgct ggacgagggt gtggaacccg acgacgtgga 720
ctgctggtgc aacaccacca gcacctgggt ggtgtacgga acctgccacc acaagaaggg 780
tgaagctcgc aggtccagac gtgccgtgac cctgccttcc cactctaccc gcaagctgca 840
gaccaggtcc cagacctggc tggagtctcg cgaatacacc aagcacctga tccgcgtgga 900
gaactggatc ttcaggaacc ctggtttcgc tctggccgct gctgctatcg cttggctgct 960
gggaagctcc acctcccaga aggtcatcta cctggtcatg atcctgctga tcgcccctgc 1020
ttacagcatc agatgcatcg gcgtgagcaa ccgtgacttc gtggagggca tgtctggcgg 1080
aacctgggtg gacgtggtgc tggaacacgg tggctgcgtg accgtgatgg ctcaggacaa 1140
gccaaccgtc gacatcgagc tggtgaccac caccgtgtct aacatggccg aggtgcgcag 1200
ctactgctac gaagccagca tcagcgacat ggcctctgac agcaggtgcc caacccaggg 1260

FIG. 36B cgaagcttac ctggacaagc agtctgacac ccagtacgtg tgcaagagaa ccctggtgga 1320
ccgtggatgg ggtaacggct gcggactgtt cggcaagggc agcctggtga cctgcgctaa 1380
gttcgcctgc tccaagaaga tgaccggcaa gtctatccag ccagagaacc tggaatacag 1440
aatcatgctg tctgtgcacg gctcccagca ctctggaatg atcgtgaacg acaccggaca 1500
cgaaaccgac gaaaacagag ccaaggtgga gatcacccct aactctccac gtgccgaagc 1560
taccctggga ggtttcggca gcctgggact ggactgtgag cctcgtaccg gcctggactt 1620
ctccgacctg tactacctga ccatgaacaa caagcactgg ctggtgcaca aggaatggtt 1680
ccacgacatc ccactgccat ggcacgccgg tgctgacact ggaaccccac actggaacaa 1740
caaggaggct ctggtggagt tcaaggacgc ccacgctaag agacagactg tggtggtgct 1800
gggttcccag gagggtgctg tgcacaccgc cctggctgga gctctggagg ctgaaatgga 1860
cggtgccaag ggccgtctgt ctagcggtca cctgaagtgc cgcctgaaga tggacaagct 1920
gaggctgaag ggcgtgtcct actctctgtg caccgccgct ttcaccttca ccaagatccc 1980
tgctgaaacc ctgcacggca ccgtgaccgt ggaagtgcag tacgctggaa ccgatggtcc 2040
atgcaaggtg cctgctcaga tggccgtgga catgcagacc ctgacccctg tgggacgcct 2100
gatcaccgcc aacccagtga tcaccgagtc taccgaaaac agcaagatga tgctggagct 2160
ggaccctccc ttcggcgaca gctacatcgt gatcggagtg ggtgaaaaga agatcaccca 2220
ccactggcac aggagcggca gcaccatcgg caaggctttc gaggctaccg tgcgcggcgc 2280
taagagaatg gccgtgctgg gcgacactgc ttgggacttc ggaagcgtgg gcggagccct 2340
gaactccctg ggcaagggaa tccaccagat cttcggcgcc gctttcaagt ccctgttcgg 2400
tggcatgagc tggttctccc agatcctgat cggaaccctg ctgatgtggc tgggtctgaa 2460
caccaagaac ggctctatca gcctgatgtg cctcgctctc ggtggcgtgc tgatttttct 2520
ctctaccgca gtctccgcat gagcccctct ccctcccccc cccctaacgt tactggccga 2580
agccgcttgg aataaggccg gtgtgtgttt gtctatatgt gattttccac catattgccg 2640
tcttttggca atgtgagggc ccggaaacct ggccctgtct tcttgacgag cattcctagg 2700
ggtctttccc ctctcgccaa aggaatgcaa ggtctgttga atgtcgtgaa ggaagcagtt 2760
cctctggaag cttcttgaag acaaacaacg tctgtagcga ccctttgcag gcagcggaac 2820
cccccacctg gcgacaggtg cctctgcggc caaaagccac gtgtataaga tacacctgca 2880
aaggcggcac aaccccagtg ccacgttgtg agttggatag ttgtggaaag agtcaaatgg 2940
ctctcctcaa gcgtagtcaa caaggggctg aaggatgccc agaaggtacc ccattgtatg 3000
ggaatctgat ctggggcctc ggtgcacatg ctttacatgt gtttagtcga ggttaaaaaa 3060
gctctaggcc ccccgaacca cggggacgtg gttttccttt gaaaaacacg atgataagct 3120
tgccacaaat ggaactgaga ccttggctgc tgtgggtggt ggctgctact ggcaccctgg 3180
tgctgctagc agctgacgcc cagggccaga aggtgttcac caacacctgg gctgtgagaa 3240
tccccggcgg acctgctgtg gctaacagcg tggctcgtaa gcacggcttc ctgaacctgg 3300

FIG. 36C gacagatttt cggtgactac taccacttct ggcaccgcgg agtgaccaag aggagcctgt 3360
ccccacacag accaaggcac tccagactgc agcgtgagcc ccaggtgcag tggctggaac 3420
agcaggtggc caagcgcagg accaagagag acgtgtacca ggagcctacc gacccaaagt 3480
tcccccagca gtggtatctg tccggcgtga cccagcgtga cctgaacgtg aaggccgctt 3540
gggctcaggg ttacaccggt cacggcatcg tggtgtccat cctggacgac ggcatcgaga 3600
agaaccaccc tgacctggcc ggtaactacg acccaggcgc ttctttcgac gtgaacgacc 3660
aggaccccga ccctcagcca agatacaccc agatgaacga caacagacat ggaaccagat 3720
gtgctggtga agtggctgct gtggctaaca acggcgtgtg cggagtgggt gtggcctaca 3780
acgctagaat cggtggcgtg cgtatgctgg atggagaagt gactgatgct gtggaagcta 3840
gaagcctggg actgaaccca aaccacatcc acatctactc tgccagctgg ggtccagagg 3900
atgatggaaa gactgtggat ggtcctgcta gactggctga ggaagccttc ttccgcggcg 3960
tgagccaggg aaggggaggt ctgggaagca tcttcgtgtg ggcttctggt aacggcggaa 4020
gagagcacga ctcctgcaac tgcgacggat acaccaactc tatctacacc ctgagcatca 4080
gctccgctac ccagttcggt aacgtgccct ggtactccga agcctgctct agcaccctgg 4140
ctaccaccta ctcctctggc aaccagaacg agaagcagat cgtgaccacc gacctgcgtc 4200
agaagtgcac cgaatctcac actggcacct ccgcctctgc tcctctggct gctggaatca 4260
tcgccctgac cctggaggct aacaagaacc tgacctggcg cgacatgcag cacctggtgg 4320
tgcagacctc caagccagct cacctgaacg ccaacgactg ggctaccaac ggcgtgggaa 4380
ggaaggtgag ccactcttac ggttacggtc tgctggatgc tggtgctatg gtggccctgg 4440
ctcagaactg gaccaccgtg gcccctcagc gcaagtgcat catcgacatc ctgaccgagc 4500
ctaaggacat cggaaagaga ctggaagtgc gtaagaccgt gaccgcttgc ctgggagagc 4560
ccaaccacat caccagactg gaacacgccc aggctcgtct gaccctgtct tacaacagac 4620
gtggagacct ggccatccac ctggtgtctc caatgggcac ccgcagcacc ctgctggctg 4680
ctaggccaca cgactacagc gccgacggat tcaacgactg ggctttcatg accacccact 4740
cctgggacga ggacccttct ggtgaatggg tgctggagat cgaaaacacc agcgaggcca 4800
acaactacgg caccctgacc aagttcaccc tggtgctgta cggcaccgct cctgagggac 4860
tgccagtgcc ccctgaaagc tccggttgca agaccctgac ctctagccag gcctgcgtgg 4920
tgtgcgagga aggcttctcc ctgcaccaga agtcttgcgt gcagcactgc ccacccggat 4980
tcgctcctca ggtgctggac acccactact ctaccgagaa cgacgtggaa accatcagag 5040
ccagcgtgtg cgctccttgt cacgcttcct gtgctacttg tcagggacca gccctgactg 5100
actgcctgtc ctgcccatct cacgccagcc tggaccccgt ggagcagacc tgctccagac 5160
agtctcagtc ctctcgtgaa agccctccac agcagcagcc ccctagactg ccacccgagg 5220
tggaagccgg ccagagactg cgtgctggac tgctgccttc tcacctgcca gaggtggtgg 5280
ctggtctgag ctgcgctttc atcgtgctgg tgttcgtgac cgtgttcctg gtgctgcagc 5340

FIG. 36D tgcgcagcgg tttctccttc aggggcgtga aggtgtacac catggaccgc ggtctgatca 5400
gctacaaggg tctgcctcca gaggcttggc aggaggaatg cccatctgac agcgaagagg 5460
acgagggacg tggagaacgg actgccttca tcaaagatca gagcgcactg taataaatcg 5520
atttaattaa tagcataacc ccttggggcc tctaaacggg tcttgagggg ttttttggaa 5580
ttcacccagc tttcttgtac aaagtggtga tagcttgtcg agaagtacta gaggatcata 5640
atcagccata ccacatttgt agaggtttta cttgctttaa aaaacctccc acacctcccc 5700
ctgaacctga aacataaaat gaatgcaatt gttgttgtta acttgtttat tgcagcttat 5760
aatggttaca aataaagcaa tagcatcaca aatttcacaa ataaagcatt tttttcactg 5820
cattctagtt gtggtttgtc caaactcatc aatgtatctt atcatgtctg gatc 5874

FIG. 37A

SEQ ID NO: 11. YFV del108C-prM-E & del108CYFV-human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgag acctggacct tcaagaggtg ttcaaggatt 300
tatctttttc tttttgttca acattttgac tggaaaaaag atcacggccc acctaaagag 360
gttgtggaaa atgctggacc caagacaagg cttggctgtt ctaaggaaag ttaagagagt 420
ggtggccagt ttgatgagag gattgtcctc aaggaaacgc cgttcccatg atgttctgac 480
tgtgcaattc ctaattttgg gaatgctgtt gatgacgggt ggagtgacct tggtgcggaa 540
aaacagatgg ttgctcctaa atgtgacatc tgaggacctc gggaaaacat tctctgtggg 600
cacaggcaac tgcacaacaa acattttgga agccaagtac tggtgcccag actcaatgga 660
atacaactgt cccaatctca gtccaagaga ggagccagat gacattgatt gctggtgcta 720
tggggtggaa aacgttagag tcgcatatgg taagtgtgac tcagcaggca ggtctaggag 780
gtcaagaagg gccattgact tgcctacgca tgaaaaccat ggtttgaaga cccggcaaga 840
aaaatggatg actggaagaa tgggtgaaag gcaactccaa aagattgaga gatggctcgt 900
gaggaacccc ttttttgcag tgacagctct gaccattgcc taccttgtgg gaagcaacat 960
gacgcaacga gtcgtgattg ccctactggt cttggctgtt ggtccggcct actcagctca 1020
ctgcattgga attactgaca gggatttcat tgagggggtg catggaggaa cttgggtttc 1080
agctaccctg gagcaagaca agtgtgtcac tgttatggcc cctgacaagc cttcattgga 1140
catctcacta gagacagtag ccattgatgg acctgctgag gcgaggaaag tgtgttacaa 1200
tgcagttctc actcatgtga agattaatga caagtgcccc agcactggag aggcccacct 1260

FIG. 37B agctgaagag aacgaagggg acaatgcgtg caagcgcact tattctgata gaggctgggg 1320
caatggctgt ggcctatttg ggaaagggag cattgtggca tgcgccaaat tcacttgtgc 1380
caaatccatg agtttgtttg aggttgatca gaccaaaatt cagtatgtca tcagagcaca 1440
attgcatgta ggggccaagc aggaaaattg gaataccgac attaagactc tcaagtttga 1500
tgccctgtca ggctcccagg aagccgagtt cactgggtat ggaaaagcta cactggaatg 1560
ccaggtgcaa actgcggtgg actttggtaa cagttacatc gctgagatgg aaaaagagag 1620
ctggatagtg gacagacagt gggcccagga cttgaccctg ccatggcaga gtggaagtgg 1680
cggggtgtgg agagagatgc atcatcttgt cgaatttgaa cctccgcatg ccgccactat 1740
cagagtactg gccctgggaa accaggaagg ctccttgaaa acagctctta ccggcgcaat 1800
gagggttaca aaggacacaa atgacaacaa cctttacaaa ctacatggtg gacatgtttc 1860
ctgcagagtg aaattgtcag ctttgacact caaggggaca tcctacaaaa tgtgcactga 1920
caaaatgtct tttgtcaaga acccaactga cactggccat ggcactgttg tgatgcaggt 1980
gaaagtgcca aaaggagccc cctgcaggat tccagtgata gtagctgatg atcttacagc 2040
ggcaatcaat aaaggcattt tggttacagt taaccccatc gcctcaacca atgatgatga 2100
agtgctgatt gaggtgaacc caccttttgg agacagctac attatcgttg ggacaggaga 2160
ttcacgtctc acttaccagt ggcacaaaga gggaagctca ataggaaagt tgttcactca 2220
gaccatgaaa ggcgcggaac gcctggccgt catgggagac gccgcctggg atttcagctc 2280
cgctggaggg ttcttcactt cggttgggaa aggtattcat acggtgtttg gctctgcctt 2340
tcaggggcta tttggcggct tgaactggat aacaaaggtc atcatggggg cggtactcat 2400
atgggttggc atcaacacaa gaaacatgac aatgtccatg agcatgatct tggtaggagt 2460
gatcatgatg tttttgtctc taggagttgg ggcgtgagcc cctctccctc cccccccct 2520
aacgttactg gccgaagccg cttggaataa ggccggtgtg tgtttgtcta tatgtgattt 2580
tccaccatat tgccgtcttt tggcaatgtg agggcccgga aacctggccc tgtcttcttg 2640
acgagcattc ctaggggtct ttcccctctc gccaaaggaa tgcaaggtct gttgaatgtc 2700
gtgaaggaag cagttcctct ggaagcttct tgaagacaaa caacgtctgt agcgaccctt 2760
tgcaggcagc ggaacccccc acctggcgac aggtgcctct gcggccaaaa gccacgtgta 2820
taagatacac ctgcaaaggc ggcacaaccc cagtgccacg ttgtgagttg gatagttgtg 2880
gaaagagtca aatggctctc ctcaagcgta gtcaacaagg ggctgaagga tgcccagaag 2940
gtaccccatt gtatgggaat ctgatctggg gcctcggtgc acatgcttta catgtgttta 3000
gtcgaggtta aaaaagctct aggccccccg aaccacgggg acgtggtttt cctttgaaaa 3060
acacgatgat aagcttgcca caaatgagac ctggaccttc aagaggtgtt caaggattta 3120
tctttttctt tttgttcaac attttgactg gaaaaaagat cacggcccac ctaaagaggt 3180
tgtggaaaat gctggaccca agacaaggct tggctgttct aaggaaagtt aagagagtgg 3240
tggccagttt gatgagagga ttgtcctcaa ggaaacgccg ttcccatgat gttctgactg 3300

FIG. 37C tgcaattcct aattttggga atgctgttga tgacgggtgg aatggaactg agaccttggc 3360
tgctgtgggt ggtggctgct actggcaccc tggtgctgct agcagctgac gcccagggcc 3420
agaaggtgtt caccaacacc tgggctgtga gaatccccgg cggacctgct gtggctaaca 3480
gcgtggctcg taagcacggc ttcctgaacc tgggacagat tttcggtgac tactaccact 3540
tctggcaccg cggagtgacc aagaggagcc tgtccccaca cagaccaagg cactccagac 3600
tgcagcgtga gccccaggtg cagtggctgg aacagcaggt ggccaagcgc aggaccaaga 3660
gagacgtgta ccaggagcct accgacccaa agttccccca gcagtggtat ctgtccggcg 3720
tgacccagcg tgacctgaac gtgaaggccg cttgggctca gggttacacc ggtcacggca 3780
tcgtggtgtc catcctggac gacggcatcg agaagaacca ccctgacctg gccggtaact 3840
acgacccagg cgcttctttc gacgtgaacg accaggaccc cgaccctcag ccaagataca 3900
cccagatgaa cgacaacaga catggaacca gatgtgctgg tgaagtggct gctgtggcta 3960
acaacggcgt gtgcggagtg ggtgtggcct acaacgctag aatcggtggc gtgcgtatgc 4020
tggatggaga agtgactgat gctgtggaag ctagaagcct gggactgaac ccaaaccaca 4080
tccacatcta ctctgccagc tggggtccag aggatgatgg aaagactgtg gatggtcctg 4140
ctagactggc tgaggaagcc ttcttccgcg gcgtgagcca gggaagggga ggtctgggaa 4200
gcatcttcgt gtgggcttct ggtaacggcg gaagagagca cgactcctgc aactgcgacg 4260
gatacaccaa ctctatctac accctgagca tcagctccgc tacccagttc ggtaacgtgc 4320
cctggtactc cgaagcctgc tctagcaccc tggctaccac ctactcctct ggcaaccaga 4380
acgagaagca gatcgtgacc accgacctgc gtcagaagtg caccgaatct cacactggca 4440
cctccgcctc tgctcctctg gctgctggaa tcatcgccct gaccctggag gctaacaaga 4500
acctgacctg gcgcgacatg cagcacctgg tggtgcagac ctccaagcca gctcacctga 4560
acgccaacga ctgggctacc aacggcgtgg gaaggaaggt gagccactct tacggttacg 4620
gtctgctgga tgctggtgct atggtggccc tggctcagaa ctggaccacc gtggcccctc 4680
agcgcaagtg catcatcgac atcctgaccg agcctaagga catcggaaag agactggaag 4740
tgcgtaagac cgtgaccgct tgcctgggag agcccaacca catcaccaga ctggaacacg 4800
cccaggctcg tctgaccctg tcttacaaca gacgtggaga cctggccatc cacctggtgt 4860
ctccaatggg cacccgcagc accctgctgg ctgctaggcc acacgactac agcgccgacg 4920
gattcaacga ctgggctttc atgaccaccc actcctggga cgaggaccct tctggtgaat 4980
gggtgctgga gatcgaaaac accagcgagg ccaacaacta cggcaccctg accaagttca 5040
ccctggtgct gtacggcacc gctcctgagg gactgccagt gccccctgaa agctccggtt 5100
gcaagaccct gacctctagc caggcctgcg tggtgtgcga ggaaggcttc tccctgcacc 5160
agaagtcttg cgtgcagcac tgcccacccg gattcgctcc tcaggtgctg gacacccact 5220
actctaccga gaacgacgtg gaaaccatca gagccagcgt gtgcgctcct tgtcacgctt 5280
cctgtgctac ttgtcaggga ccagccctga ctgactgcct gtcctgccca tctcacgcca 5340

FIG. 37D gcctggaccc cgtggagcag acctgctcca gacagtctca gtcctctcgt gaaagccctc 5400
cacagcagca gccccctaga ctgccacccg aggtggaagc cggccagaga ctgcgtgctg 5460
gactgctgcc ttctcacctg ccagaggtgg tggctggtct gagctgcgct ttcatcgtgc 5520
tggtgttcgt gaccgtgttc ctggtgctgc agctgcgcag cggtttctcc ttcaggggcg 5580
tgaaggtgta caccatggac cgcggtctga tcagctacaa gggtctgcct ccagaggctt 5640
ggcaggagga atgcccatct gacagcgaag aggacgaggg acgtggagaa cggactgcct 5700
tcatcaaaga tcagagcgca ctgtaataaa tcgatttaat taatagcata accccttggg 5760
gcctctaaac gggtcttgag gggttttttg gaattcaccc agctttcttg tacaaagtgg 5820
tgatagcttg tcgagaagta ctagaggatc ataatcagcc ataccacatt tgtagaggtt 5880
ttacttgctt taaaaaacct cccacacctc cccctgaacc tgaaacataa aatgaatgca 5940
attgttgttg ttaacttgtt tattgcagct tataatggtt acaaataaag caatagcatc 6000
acaaatttca caaataaagc atttttttca ctgcattcta gttgtggttt gtccaaactc 6060
atcaatgtat cttatcatgt ctggatc 6087

FIG. 38A

SEQ ID NO: 12. HCV del108C-E1-E2 & del108CHCV-human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgct gccaagaagg ggtccaagac tcggagtgcg 300
tgccacccgc aagacctctg agcgtagcca gccaagaggc cgccgccagc caatccctaa 360
ggctcgcagg cctgaaggta gaacttgggc tcagccaggt tacccttggc cactgtacgg 420
aaacgaaggc tgcggatggg ctggatggct gctgagcccc aggggttcca gaccttcttg 480
gggtccaact gacccacgcc gccgcagccg caacctgggc aaggtcatcg acaccctgac 540
ctgcggattc gccgacctga tgggttacat cccactggtg ggagctcccc tgggcggagc 600
tgctagggcc ctggctcacg gtgtgagagt gctggaagac ggcgtgaact acgccaccgg 660
taacctgcca ggctgcagct tctccatctt cctgctggct ctgctgtcct gcctgactgg 720
accagcttct gcttaccagg tgaggaacag caccggtctg taccacgtga ccaacgactg 780
ccccaacagc tccatcgtgt tcgaagctgc tgatgctatc ctgcacaccc caggatgcgt 840
gccttgcgtg cgtgagggta acgcttccag atgctgggtg gctgtgaccc ctaccgtggc 900
caccagagac ggcaagctgc caaccaccca gctgaggaga cacatcgacc tgctggtggg 960
tagcgccacc ctgtgctccg ctctgtacgt gggcgacctg tgcggtagcg tgttcctggt 1020

FIG. 38B gggccagctg ttcaccttca gccctcgtcg ccactggacc acccaggact gcaactgctc 1080
catctaccca ggccacatct ctggacaccg tatggcttgg gacatgatga tgaactggag 1140
cccaactgcc gctctgctgg tggctcagct gctgagaatc ccacaggcca tcctggacat 1200
gatcgctggt gctcactggg gcgtgctggc tggaatggct tacttctcta tggtgggcaa 1260
ctgggccaag gtgctggtgg tgctgctgct gttcgccgga gtggacgctg aaacctacgt 1320
gaccggtggc agcgccgcta ggactactgc tggcctggct agtctgttct cccctggagc 1380
taagcagaac atccagctgg tgaacaccaa cggctcttgg cacatcaaca gcaccgccct 1440
gaactgcaac gactccctga acaccggttg gatcgctggc ctgttctacc accacaagtt 1500
caactctagc ggatgctccg aaaggctggc ttcttgcaga cctctgactg acttcgctca 1560
gggttggggt cctatcagcc acgctgatgg atctggtcca gaccagcgcc cctactgctg 1620
gcactaccct cccaagcctt gcggtatcgt gcctgctaag tccgtgtgcg gtcccgtgta 1680
ctgcttcacc ccctctcctg tggtggtggg aaccaccgac aggtctggtg ctccaaccta 1740
cagctgggga gccaacgaca ccgacgtgtt cgtgctgaac aacaccagac cacccctggg 1800
aaactggttc ggttgcacct ggatgaacag caccggcttc accaaggtgt gcggagcccc 1860
tccatgcgtg atcggaggtg tgggcaacaa caccctgcgt tgccccaccg actgcttccg 1920
caagcaccct gaggctacct actccagatg cggctctgga ccttggatca ccccaaggtg 1980
cctggtggac taccccctaca gactgtggca ctacccttgc accatcaact acaccgtgtt 2040
caaggtgcgt atgtacgtgg gcggagtgga gcacagactg gaagctgctt gtaactggac 2100
tcgcggcgac cgctgcaacc tggacgacag ggacagatct gagctgagcc ccctgctgct 2160
gtccaccacc cagtggcagg tgctgccatg cagcttcacc accctgcccg ccctgtccac 2220
tggcctgatc cacctgcacc agaacatcgt ggacgtgcag tacctgtacg gtgtgggctc 2280
ctctatcgca tcttgggcta tcaagtggga atacgtggtg ctgctgttcc tgctgctggc 2340
tgatgctcgc gtgtgctcct gcctgtggat gatgctgctg atctctcagg tggaggccgc 2400
tctggaaaac ctggtggtgc tgaacgctgc aagcctggct ggaacccacg gtctggtgtc 2460
cttcctggtg ttcttctgct tcgcttggta cctgaagggc aagtgggtgc ctggagccgt 2520
gtacgctctg tacggaatgt ggcctctgct gctgctgctg ctggccctgc cacagagagc 2580
ttacgctctg gacactgagg tggctgcttc ttgtggtggc gtggtgctgg tgggcctgat 2640
ggctctgacc ctgtctcctt actacaagag gtacatcagc tggtgcctgt ggtggctgca 2700
gtacttcctg accagaatcg aagcccagct gcacgtgtgg attcctcccc tgaacgtgcg 2760
cggcggcaga gatgccgtga tcctgctgat gtgcgtggtg caccccgctc tggtgttcga 2820
catcaccaag ctgctgctgg ccgctttcgg cccttaatct agagcccctc tccctccccc 2880
ccccctaacg ttactggccg aagccgcttg gaataaggcc ggtgtgtgtt tgtctatatg 2940
tgattttcca ccatattgcc gtcttttggc aatgtgaggg cccggaaacc tggccctgtc 3000
ttcttgacga gcattcctag gggtctttcc cctctcgcca aaggaatgca aggtctgttg 3060

FIG. 38C aatgtcgtga aggaagcagt tcctctggaa gcttcttgaa gacaaacaac gtctgtagcg 3120
accctttgca ggcagcggaa ccccccacct ggcgacaggt gcctctgcgg ccaaaagcca 3180
cgtgtataag atacacctgc aaaggcggca caaccccagt gccacgttgt gagttggata 3240
gttgtggaaa gagtcaaatg gctctcctca agcgtagtca acaaggggct gaaggatgcc 3300
cagaaggtac cccattgtat gggaatctga tctggggcct cggtgcacat gctttacatg 3360
tgtttagtcg aggttaaaaa agctctaggc cccccgaacc acggggacgt ggttttcctt 3420
tgaaaaacac gatgataagc ttgccacaaa tgctgcctag aaggggacct aggctgggtg 3480
tgagggccac cagaaagacc tctgagagga gccagcctag aggccgccgc cagccaatcc 3540
ctaaggctcg caggcccgag ggaagaacct gggctcagcc tggttaccca tggcccctgt 3600
acggcaacga aggttgcggc tgggctggtt ggctgctgtc tccacgtggt tcccgcccct 3660
cttggggtcc tactgaccca cgccgccgca gccgcaacct gggcaaggtc atcgacaccc 3720
tgacctgcgg attcgccgac ctgatgggtt acatccctct ggtgggagct ccactgggcg 3780
gagccgctcg tgccctggct cacggagtgc gcgtgctgga ggacggtgtg aactacgcca 3840
ccggcaacct gcccggatgc agcttctcca tcttcctgct ggctctgctg tcttgtctga 3900
ctggtccagc ttccgctatg gaactgcgcc cctggctgct gtgggtggtg gctgctactg 3960
gaaccctggt gctgctagca gctgacgccc agggccagaa ggtgttcacc aacacctggg 4020
ctgtgagaat ccccggcgga cctgctgtgg ctaacagcgt ggctcgtaag cacggcttcc 4080
tgaacctggg acagattttc ggtgactact accacttctg gcaccgcgga gtgaccaaga 4140
ggagcctgtc ccccacacaga ccaaggcact ccagactgca gcgtgagccc caggtgcagt 4200
ggctggaaca gcaggtggcc aagcgcagga ccaagagaga cgtgtaccag gagcctaccg 4260
acccaaagtt cccccagcag tggtatctgt ccggcgtgac ccagcgtgac ctgaacgtga 4320
aggccgcttg ggctcagggt tacaccggtc acggcatcgt ggtgtccatc ctggacgacg 4380
gcatcgagaa gaaccaccct gacctggccg gtaactacga cccaggcgct tctttcgacg 4440
tgaacgacca ggaccccgac cctcagccaa gatacaccca gatgaacgac aacagacatg 4500
gaaccagatg tgctggtgaa gtggctgctg tggctaacaa cggcgtgtgc ggagtgggtg 4560
tggcctacaa cgctagaatc ggtggcgtgc gtatgctgga tggagaagtg actgatgctg 4620
tggaagctag aagcctggga ctgaacccaa accacatcca catctactct gccagctggg 4680
gtccagagga tgatggaaag actgtggatg gtcctgctag actggctgag gaagccttct 4740
tccgcggcgt gagccaggga aggggaggtc tgggaagcat cttcgtgtgg gcttctggta 4800
acggcggaag agagcacgac tcctgcaact gcgacggata caccaactct atctacaccc 4860
tgagcatcag ctccgctacc cagttcggta acgtgccctg gtactccgaa gcctgctcta 4920
gcaccctggc taccacctac tcctctggca accagaacga gaagcagatc gtgaccaccg 4980
acctgcgtca gaagtgcacc gaatctcaca ctggcacctc cgcctctgct cctctggctg 5040
ctggaatcat cgccctgacc ctggaggcta acaagaacct gacctggcgc gacatgcagc 5100

FIG. 38D acctggtggt gcagacctcc aagccagctc acctgaacgc caacgactgg gctaccaacg 5160
gcgtgggaag gaaggtgagc cactcttacg gttacggtct gctggatgct ggtgctatgg 5220
tggccctggc tcagaactgg accaccgtgg cccctcagcg caagtgcatc atcgacatcc 5280
tgaccgagcc taaggacatc ggaaagagac tggaagtgcg taagaccgtg accgcttgcc 5340
tgggagagcc caaccacatc accagactgg aacacgccca ggctcgtctg accctgtctt 5400
acaacagacg tggagacctg gccatccacc tggtgtctcc aatgggcacc cgcagcaccc 5460
tgctggctgc taggccacac gactacagcg ccgacggatt caacgactgg gctttcatga 5520
ccacccactc ctgggacgag gacccttctg gtgaatgggt gctggagatc gaaaacacca 5580
gcgaggccaa caactacggc accctgacca agttcaccct ggtgctgtac ggcaccgctc 5640
ctgagggact gccagtgccc cctgaaagct ccggttgcaa gaccctgacc tctagccagg 5700
cctgcgtggt gtgcgaggaa ggcttctccc tgcaccagaa gtcttgcgtg cagcactgcc 5760
cacccggatt cgctcctcag gtgctggaca cccactactc taccgagaac gacgtggaaa 5820
ccatcagagc cagcgtgtgc gctccttgtc acgcttcctg tgctacttgt cagggaccag 5880
ccctgactga ctgcctgtcc tgcccatctc acgccagcct ggaccccgtg gagcagacct 5940
gctccagaca gtctcagtcc tctcgtgaaa gccctccaca gcagcagccc cctagactgc 6000
cacccgaggt ggaagccggc cagagactgc gtgctggact gctgccttct cacctgccag 6060
aggtggtggc tggtctgagc tgcgctttca tcgtgctggt gttcgtgacc gtgttcctgg 6120
tgctgcagct gcgcagcggt ttctccttca ggggcgtgaa ggtgtacacc atggaccgcg 6180
gtctgatcag ctacaagggt ctgcctccag aggcttggca ggaggaatgc ccatctgaca 6240
gcgaagagga cgagggacgt ggagaacgga ctgccttcat caaagatcag agcgcactgt 6300
aataaatcga tttaattaat agcataaccc cttggggcct ctaaacgggt cttgaggggt 6360
tttttggaat tcacccagct ttcttgtaca aagtggtgat agcttgtcga gaagtactag 6420
aggatcataa tcagccatac cacatttgta gaggttttac ttgctttaaa aaacctccca 6480
cacctccccc tgaacctgaa acataaaatg aatgcaattg ttgttgttaa cttgtttatt 6540
gcagcttata atggttacaa ataaagcaat agcatcacaa atttcacaaa taaagcattt 6600
ttttcactgc attctagttg tggtttgtcc aaactcatca atgtatctta tcatgtctgg 6660
atc 6663

FIG. 39A

SEQ ID NO: 13. YFV del108C-prM-E & human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240

FIG. 39B ttttttttt tggaatataa ataatatgag acctggacct tcaagaggtg ttcaaggatt 300
tatctttttc tttttgttca acattttgac tggaaaaaag atcacggccc acctaaagag 360
gttgtggaaa atgctggacc caagacaagg cttggctgtt ctaaggaaag ttaagagagt 420
ggtggccagt ttgatgagag gattgtcctc aaggaaacgc cgttcccatg atgttctgac 480
tgtgcaattc ctaattttgg gaatgctgtt gatgacgggt ggagtgacct tggtgcggaa 540
aaacagatgg ttgctcctaa atgtgacatc tgaggacctc gggaaaacat tctctgtggg 600
cacaggcaac tgcacaacaa acattttgga agccaagtac tggtgcccag actcaatgga 660
atacaactgt cccaatctca gtccaagaga ggagccagat gacattgatt gctggtgcta 720
tggggtggaa aacgttagag tcgcatatgg taagtgtgac tcagcaggca ggtctaggag 780
gtcaagaagg gccattgact tgcctacgca tgaaaaccat ggtttgaaga cccggcaaga 840
aaaatggatg actggaagaa tgggtgaaag gcaactccaa aagattgaga gatggctcgt 900
gaggaacccc ttttttgcag tgacagctct gaccattgcc taccttgtgg gaagcaacat 960
gacgcaacga gtcgtgattg ccctactggt cttggctgtt ggtccggcct actcagctca 1020
ctgcattgga attactgaca gggatttcat tgagggggtg catggaggaa cttgggtttc 1080
agctaccctg gagcaagaca agtgtgtcac tgttatggcc cctgacaagc cttcattgga 1140
catctcacta gagacagtag ccattgatgg acctgctgag gcgaggaaag tgtgttacaa 1200
tgcagttctc actcatgtga agattaatga caagtgcccc agcactggag aggcccacct 1260
agctgaagag aacgaagggg acaatgcgtg caagcgcact tattctgata gaggctgggg 1320
caatggctgt ggcctatttg ggaaagggag cattgtggca tgcgccaaat tcacttgtgc 1380
caaatccatg agtttgtttg aggttgatca gaccaaaatt cagtatgtca tcagagcaca 1440
attgcatgta ggggccaagc aggaaaattg gaataccgac attaagactc tcaagtttga 1500
tgccctgtca ggctcccagg aagccgagtt cactgggtat ggaaaagcta cactggaatg 1560
ccaggtgcaa actgcggtgg actttggtaa cagttacatc gctgagatgg aaaaagagag 1620
ctggatagtg gacagacagt gggcccagga cttgaccctg ccatggcaga gtggaagtgg 1680
cggggtgtgg agagagatgc atcatcttgt cgaatttgaa cctccgcatg ccgccactat 1740
cagagtactg gccctgggaa accaggaagg ctccttgaaa acagctctta ccggcgcaat 1800
gagggttaca aaggacacaa atgacaacaa cctttacaaa ctacatggtg gacatgtttc 1860
ctgcagagtg aaattgtcag ctttgacact caaggggaca tcctacaaaa tgtgcactga 1920
caaaatgtct tttgtcaaga acccaactga cactggccat ggcactgttg tgatgcaggt 1980
gaaagtgcca aaaggagccc cctgcaggat tccagtgata gtagctgatg atcttacagc 2040
ggcaatcaat aaaggcattt tggttacagt taaccccatc gcctcaacca atgatgatga 2100
agtgctgatt gaggtgaacc caccttttgg agacagctac attatcgttg ggacaggaga 2160
ttcacgtctc acttaccagt ggcacaaaga gggaagctca ataggaaagt tgttcactca 2220
gaccatgaaa ggcgcggaac gcctggccgt catgggagac gccgcctggg atttcagctc 2280

FIG. 39C cgctggaggg ttcttcactt cggttgggaa aggtattcat acggtgtttg gctctgcctt 2340
tcaggggcta tttggcggct tgaactggat aacaaaggtc atcatggggg cggtactcat 2400
atgggttggc atcaacacaa gaaacatgac aatgtccatg agcatgatct tggtaggagt 2460
gatcatgatg tttttgtctc taggagttgg ggcgtgagcc cctctccctc cccccccct 2520
aacgttactg gccgaagccg cttggaataa ggccggtgtg tgtttgtcta tatgtgattt 2580
tccaccatat tgccgtcttt tggcaatgtg agggcccgga aacctggccc tgtcttcttg 2640
acgagcattc ctaggggtct ttcccctctc gccaaaggaa tgcaaggtct gttgaatgtc 2700
gtgaaggaag cagttcctct ggaagcttct tgaagacaaa caacgtctgt agcgaccctt 2760
tgcaggcagc ggaacccccc acctggcgac aggtgcctct gcggccaaaa gccacgtgta 2820
taagatacac ctgcaaaggc ggcacaaccc cagtgccacg ttgtgagttg gatagttgtg 2880
gaaagagtca aatggctctc ctcaagcgta gtcaacaagg ggctgaagga tgcccagaag 2940
gtaccccatt gtatgggaat ctgatctggg gcctcggtgc acatgcttta catgtgttta 3000
gtcgaggtta aaaaagctct aggccccccg aaccacgggg acgtggtttt cctttgaaaa 3060
acacgatgat aagcttgcca caaatggaac tgagaccttg gctgctgtgg gtggtggctg 3120
ctactggcac cctggtgctg ctagcagctg acgcccaggg ccagaaggtg ttcaccaaca 3180
cctgggctgt gagaatcccc ggcggacctg ctgtggctaa cagcgtggct cgtaagcacg 3240
gcttcctgaa cctgggacag attttcggtg actactacca cttctggcac cgcggagtga 3300
ccaagaggag cctgtcccca cacagaccaa ggcactccag actgcagcgt gagccccagg 3360
tgcagtggct ggaacagcag gtggccaagc gcaggaccaa gagagacgtg taccaggagc 3420
ctaccgaccc aaagttcccc cagcagtggt atctgtccgg cgtgacccag cgtgacctga 3480
acgtgaaggc cgcttgggct cagggttaca ccggtcacgg catcgtggtg tccatcctgg 3540
acgacggcat cgagaagaac caccctgacc tggccggtaa ctacgaccca ggcgcttctt 3600
tcgacgtgaa cgaccaggac cccgaccctc agccaagata cacccagatg aacgacaaca 3660
gacatggaac cagatgtgct ggtgaagtgg ctgctgtggc taacaacggc gtgtgcggag 3720
tgggtgtggc ctacaacgct agaatcggtg gcgtgcgtat gctggatgga gaagtgactg 3780
atgctgtgga agctagaagc ctgggactga acccaaacca catccacatc tactctgcca 3840
gctggggtcc agaggatgat ggaaagactg tggatggtcc tgctagactg gctgaggaag 3900
ccttcttccg cggcgtgagc cagggaaggg gaggtctggg aagcatcttc gtgtgggctt 3960
ctggtaacgg cggaagagag cacgactcct gcaactgcga cggatacacc aactctatct 4020
acaccctgag catcagctcc gctacccagt tcggtaacgt gccctggtac tccgaagcct 4080
gctctagcac cctggctacc acctactcct ctggcaacca gaacgagaag cagatcgtga 4140
ccaccgacct gcgtcagaag tgcaccgaat ctcacactgg cacctccgcc tctgctcctc 4200
tggctgctgg aatcatcgcc ctgaccctgg aggctaacaa gaacctgacc tggcgcgaca 4260
tgcagcacct ggtggtgcag acctccaagc cagctcacct gaacgccaac gactgggcta 4320

FIG. 39D ccaacggcgt gggaaggaag gtgagccact cttacggtta cggtctgctg gatgctggtg 4380
ctatggtggc cctggctcag aactggacca ccgtggcccc tcagcgcaag tgcatcatcg 4440
acatcctgac cgagcctaag gacatcggaa agagactgga agtgcgtaag accgtgaccg 4500
cttgcctggg agagcccaac cacatcacca gactggaaca cgcccaggct cgtctgaccc 4560
tgtcttacaa cagacgtgga gacctggcca tccacctggt gtctccaatg ggcacccgca 4620
gcaccctgct ggctgctagg ccacacgact acagcgccga cggattcaac gactgggctt 4680
tcatgaccac ccactcctgg gacgaggacc cttctggtga atgggtgctg gagatcgaaa 4740
acaccagcga ggccaacaac tacggcaccc tgaccaagtt caccctggtg ctgtacggca 4800
ccgctcctga gggactgcca gtgccccctg aaagctccgg ttgcaagacc ctgacctcta 4860
gccaggcctg cgtggtgtgc gaggaaggct tctccctgca ccagaagtct tgcgtgcagc 4920
actgcccacc cggattcgct cctcaggtgc tggacaccca ctactctacc gagaacgacg 4980
tggaaaccat cagagccagc gtgtgcgctc cttgtcacgc ttcctgtgct acttgtcagg 5040
gaccagccct gactgactgc ctgtcctgcc catctcacgc cagcctggac cccgtggagc 5100
agacctgctc cagacagtct cagtcctctc gtgaaagccc tccacagcag cagcccccta 5160
gactgccacc cgaggtggaa gccggccaga gactgcgtgc tggactgctg ccttctcacc 5220
tgccagaggt ggtggctggt ctgagctgcg ctttcatcgt gctggtgttc gtgaccgtgt 5280
tcctggtgct gcagctgcgc agcggtttct ccttcagggg cgtgaaggtg tacaccatgg 5340
accgcggtct gatcagctac aagggtctgc ctccagaggc ttggcaggag gaatgcccat 5400
ctgacagcga agaggacgag ggacgtggag aacggactgc cttcatcaaa gatcagagcg 5460
cactgtaata aatcgattta attaatagca taaccccttg gggcctctaa acgggtcttg 5520
aggggttttt tggaattcac ccagctttct tgtacaaagt ggtgatagct tgtcgagaag 5580
tactagagga tcataatcag ccataccaca tttgtagagg ttttacttgc tttaaaaaac 5640
ctcccacacc tcccccctgaa cctgaaacat aaaatgaatg caattgttgt tgttaacttg 5700
tttattgcag cttataatgg ttacaaataa agcaatagca tcacaaattt cacaaataaa 5760
gcattttttt cactgcattc tagttgtggt ttgtccaaac tcatcaatgt atcttatcat 5820
gtctggatc 5829

FIG. 40A

SEQ ID NO: 14. HCV del108C-E1-E2-p7 & human furin proprotein bicistronic cassette cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240
ttttttttt tggaatataa ataatatgct gccaagaagg ggtccaagac tcggagtgcg 300

FIG. 40B tgccacccgc aagacctctg agcgtagcca gccaagaggc cgccgccagc caatccctaa 360
ggctcgcagg cctgaaggta gaacttgggc tcagccaggt tacccttggc cactgtacgg 420
aaacgaaggc tgcggatggg ctggatggct gctgagcccc aggggttcca gaccttcttg 480
gggtccaact gacccacgcc gccgcagccg caacctgggc aaggtcatcg acaccctgac 540
ctgcggattc gccgacctga tgggttacat cccactggtg ggagctcccc tgggcggagc 600
tgctagggcc ctggctcacg gtgtgagagt gctggaagac ggcgtgaact acgccaccgg 660
taacctgcca ggctgcagct tctccatctt cctgctggct ctgctgtcct gcctgactgg 720
accagcttct gcttaccagg tgaggaacag caccggtctg taccacgtga ccaacgactg 780
ccccaacagc tccatcgtgt tcgaagctgc tgatgctatc ctgcacaccc caggatgcgt 840
gccttgcgtg cgtgagggta acgcttccag atgctgggtg gctgtgaccc ctaccgtggc 900
caccagagac ggcaagctgc caaccaccca gctgaggaga cacatcgacc tgctggtggg 960
tagcgccacc ctgtgctccg ctctgtacgt gggcgacctg tgcggtagcg tgttcctggt 1020
gggccagctg ttcaccttca gccctcgtcg ccactggacc acccaggact gcaactgctc 1080
catctaccca ggccacatct ctggacaccg tatggcttgg gacatgatga tgaactggag 1140
cccaactgcc gctctgctgg tggctcagct gctgagaatc ccacaggcca tcctggacat 1200
gatcgctggt gctcactggg gcgtgctggc tggaatggct tacttctcta tggtgggcaa 1260
ctgggccaag gtgctggtgg tgctgctgct gttcgccgga gtggacgctg aaacctacgt 1320
gaccggtggc agcgccgcta ggactactgc tggcctggct agtctgttct cccctggagc 1380
taagcagaac atccagctgg tgaacaccaa cggctcttgg cacatcaaca gcaccgccct 1440
gaactgcaac gactccctga acaccggttg gatcgctggc ctgttctacc accacaagtt 1500
caactctagc ggatgctccg aaaggctggc ttcttgcaga cctctgactg acttcgctca 1560
gggttggggt cctatcagcc acgctgatgg atctggtcca gaccagcgcc cctactgctg 1620
gcactaccct cccaagcctt gcggtatcgt gcctgctaag tccgtgtgcg gtcccgtgta 1680
ctgcttcacc ccctctcctg tggtggtggg aaccaccgac aggtctggtg ctccaaccta 1740
cagctgggga gccaacgaca ccgacgtgtt cgtgctgaac aacaccagac cacccctggg 1800
aaactggttc ggttgcacct ggatgaacag caccggcttc accaaggtgt gcggagcccc 1860
tccatgcgtg atcggaggtg tgggcaacaa caccctgcgt tgccccaccg actgcttccg 1920
caagcaccct gaggctacct actccagatg cggctctgga ccttggatca ccccaaggtg 1980
cctggtggac taccccctaca gactgtggca ctacccttgc accatcaact acaccgtgtt 2040
caaggtgcgt atgtacgtgg gcggagtgga gcacagactg gaagctgctt gtaactggac 2100
tcgcggcgac cgctgcaacc tggacgacag ggacagatct gagctgagcc ccctgctgct 2160
gtccaccacc cagtggcagg tgctgccatg cagcttcacc accctgcccg ccctgtccac 2220
tggcctgatc cacctgcacc agaacatcgt ggacgtgcag tacctgtacg gtgtgggctc 2280
ctctatcgca tcttgggcta tcaagtggga atacgtggtg ctgctgttcc tgctgctggc 2340

FIG. 40C tgatgctcgc gtgtgctcct gcctgtggat gatgctgctg atctctcagg tggaggccgc 2400
tctggaaaac ctggtggtgc tgaacgctgc aagcctggct ggaacccacg gtctggtgtc 2460
cttcctggtg ttcttctgct tcgcttggta cctgaagggc aagtgggtgc ctggagccgt 2520
gtacgctctg tacggaatgt ggcctctgct gctgctgctg ctggccctgc cacagagagc 2580
ttacgctctg gacactgagg tggctgcttc ttgtggtggc gtggtgctgg tgggcctgat 2640
ggctctgacc ctgtctcctt actacaagag gtacatcagc tggtgcctgt ggtggctgca 2700
gtacttcctg accagaatcg aagcccagct gcacgtgtgg attcctcccc tgaacgtgcg 2760
cggcggcaga gatgccgtga tcctgctgat gtgcgtggtg caccccgctc tggtgttcga 2820
catcaccaag ctgctgctgg ccgctttcgg cccttaatct agagcccctc tccctccccc 2880
ccccctaacg ttactggccg aagccgcttg gaataaggcc ggtgtgtgtt tgtctatatg 2940
tgattttcca ccatattgcc gtcttttggc aatgtgaggg cccggaaacc tggccctgtc 3000
ttcttgacga gcattcctag gggtctttcc cctctcgcca aaggaatgca aggtctgttg 3060
aatgtcgtga aggaagcagt tcctctggaa gcttcttgaa gacaaacaac gtctgtagcg 3120
accctttgca ggcagcggaa ccccccacct ggcgacaggt gcctctgcgg ccaaaagcca 3180
cgtgtataag atacacctgc aaaggcggca caaccccagt gccacgttgt gagttggata 3240
gttgtggaaa gagtcaaatg gctctcctca agcgtagtca acaaggggct gaaggatgcc 3300
cagaaggtac cccattgtat gggaatctga tctggggcct cggtgcacat gctttacatg 3360
tgtttagtcg aggttaaaaa agctctaggc cccccgaacc acggggacgt ggttttcctt 3420
tgaaaaacac gatgataagc ttgccacaaa tggaactgcg cccctggctg ctgtgggtgg 3480
tggctgctac tggaaccctg gtgctgctag cagctgacgc ccagggccag aaggtgttca 3540
ccaacacctg ggctgtgaga atccccggcg gacctgctgt ggctaacagc gtggctcgta 3600
agcacggctt cctgaacctg ggacagattt tcggtgacta ctaccacttc tggcaccgcg 3660
gagtgaccaa gaggagcctg tccccacaca gaccaaggca ctccagactg cagcgtgagc 3720
cccaggtgca gtggctggaa cagcaggtgg ccaagcgcag gaccaagaga gacgtgtacc 3780
aggagcctac cgacccaaag ttcccccagc agtggtatct gtccggcgtg acccagcgtg 3840
acctgaacgt gaaggccgct tgggctcagg gttacaccgg tcacggcatc gtggtgtcca 3900
tcctggacga cggcatcgag aagaaccacc ctgacctggc cggtaactac gacccaggcg 3960
cttctttcga cgtgaacgac caggaccccg accctcagcc aagatacacc cagatgaacg 4020
acaacagaca tggaaccaga tgtgctggtg aagtggctgc tgtggctaac aacggcgtgt 4080
gcggagtggg tgtggcctac aacgctagaa tcggtggcgt gcgtatgctg gatggagaag 4140
tgactgatgc tgtggaagct agaagcctgg gactgaaccc aaaccacatc cacatctact 4200
ctgccagctg gggtccagag gatgatggaa agactgtgga tggtcctgct agactggctg 4260
aggaagcctt cttccgcggc gtgagccagg gaaggggagg tctgggaagc atcttcgtgt 4320
gggcttctgg taacggcgga agagagcacg actcctgcaa ctgcgacgga tacaccaact 4380

FIG. 40D ctatctacac cctgagcatc agctccgcta cccagttcgg taacgtgccc tggtactccg 4440
aagcctgctc tagcaccctg gctaccacct actcctctgg caaccagaac gagaagcaga 4500
tcgtgaccac cgacctgcgt cagaagtgca ccgaatctca cactggcacc tccgcctctg 4560
ctcctctggc tgctggaatc atcgccctga ccctggaggc taacaagaac ctgacctggc 4620
gcgacatgca gcacctggtg gtgcagacct ccaagccagc tcacctgaac gccaacgact 4680
gggctaccaa cggcgtggga aggaaggtga gccactctta cggttacggt ctgctggatg 4740
ctggtgctat ggtggccctg gctcagaact ggaccaccgt ggcccctcag cgcaagtgca 4800
tcatcgacat cctgaccgag cctaaggaca tcggaaagag actggaagtg cgtaagaccg 4860
tgaccgcttg cctgggagag cccaaccaca tcaccagact ggaacacgcc caggctcgtc 4920
tgaccctgtc ttacaacaga cgtggagacc tggccatcca cctggtgtct ccaatgggca 4980
cccgcagcac cctgctggct gctaggccac acgactacag cgccgacgga ttcaacgact 5040
gggctttcat gaccacccac tcctgggacg aggacccttc tggtgaatgg gtgctggaga 5100
tcgaaaacac cagcgaggcc aacaactacg gcaccctgac caagttcacc ctggtgctgt 5160
acggcaccgc tcctgaggga ctgccagtgc cccctgaaag ctccggttgc aagaccctga 5220
cctctagcca ggcctgcgtg gtgtgcgagg aaggcttctc cctgcaccag aagtcttgcg 5280
tgcagcactg cccacccgga ttcgctcctc aggtgctgga cacccactac tctaccgaga 5340
acgacgtgga aaccatcaga gccagcgtgt gcgctccttg tcacgcttcc tgtgctactt 5400
gtcagggacc agccctgact gactgcctgt cctgcccatc tcacgccagc ctggaccccg 5460
tggagcagac ctgctccaga cagtctcagt cctctcgtga aagccctcca cagcagcagc 5520
cccctagact gccacccgag gtggaagccg gccagagact gcgtgctgga ctgctgcctt 5580
ctcacctgcc agaggtggtg gctggtctga gctgcgcttt catcgtgctg gtgttcgtga 5640
ccgtgttcct ggtgctgcag ctgcgcagcg gtttctcctt caggggcgtg aaggtgtaca 5700
ccatggaccg cggtctgatc agctacaagg gtctgcctcc agaggcttgg caggaggaat 5760
gcccatctga cagcgaagag gacgagggac gtggagaacg gactgccttc atcaaagatc 5820
agagcgcact gtaataaatc gatttaatta atagcataac cccttggggc ctctaaacgg 5880
gtcttgaggg gtttttgga attcacccag ctttcttgta caaagtggtg atagcttgtc 5940
gagaagtact agaggatcat aatcagccat accacatttg tagaggtttt acttgcttta 6000
aaaaacctcc cacacctccc cctgaacctg aaacataaaa tgaatgcaat tgttgttgtt 6060
aacttgttta ttgcagctta taatggttac aaataaagca atagcatcac aaatttcaca 6120
aataaagcat ttttttcact gcattctagt tgtggtttgt ccaaactcat caatgtatct 6180
tatcatgtct ggatc 6195

METHOD FOR PRODUCING VIRUS LIKE PARTICLES

CROSS-REFERENCED TO RELATED APPLICATIONS

This application is a U.S. National Phase Application of PCT International Application No. PCT/US2017/028300, filed on Apr. 19, 2017, designating the United States of America, which is an International Application of and claims the benefit of priority to U.S. Provisional Patent Application No. 62/326,129, filed on Apr. 22, 2016.

SEQUENCE LISTING STATEMENT

The present application contains a Sequence Listing, which is being submitted via EFS-Web on even date herewith. The Sequence Listing is submitted in a file entitled "Sequence Listing 054342-505NO1US.txt," which was created on Oct. 18, 2018, and is approximately 124 kb in size. This Sequence Listing is hereby incorporated by reference.

FIELD OF THE INVENTION

The present invention relates to a platform technology to produce virus-like particles (VLPs). More particularly, the present invention relates to expression cassettes, for producing high yields of immunogenic flavivirus virus-like-particles (VLPs) for use in vaccines, vaccines comprising the VLPs and methods of prophylaxis or treatment of virus infection.

BACKGROUND

Dengue virus (DENV) and Zika virus (ZIKV) are enveloped, single-stranded positive-sense RNA viruses in the family Flaviviridae that cause significant morbidity and mortality in humans. Both viruses are transmitted by mosquitoes and DENV is endemic in most of the world's tropical and sub-tropical regions, whereas ZIKV has been endemic in Asia and Africa historically but is currently expanding its geographical range. Dengue virus (DENV) is a major public health problem worldwide with 50-100 million new infections each year [Pang T, Cardosa M J, Guzman M G, *Immunol Cell Biol* 85(1): 43-5 (2007)]. DENV is considered to be the most important arbo-viral (vector-borne) disease in the world and there are four closely related, yet antigenically distinct, serotypes, all of which can cause severe disease in humans. The majority of DENV-infected individuals present with a febrile illness that resolves after several days [Halstead S B, *Yale J Biol Med* 42(5): 350-62 (1970)]. Approximately 15 to 60% of patients suffer from classic dengue fever (DF) which is characterized by headaches, nausea, high fever and retro-orbital and bone pain. Leukopenia, thrombocytopenia and elevation in serum transaminases are common in symptomatic DF patients [Pang T, Cardosa M J, Guzman M G, *Immunol Cell Biol* 85(1): 43-5 (2007)]. A small percentage of patients also develop dengue hemorrhagic fever (DHF), a severe disease that can lead to dengue shock syndrome (DSS) and death. Fever, thrombocytopenia, hemorrhagic manifestations and evidence of increased vascular permeability and plasma leakage are common in DHF and DSS patients and viral loads are generally 10 to 100 fold higher as compared to DF patients [Pang T, Cardosa M J, Guzman M G, *Immunol Cell Biol* 85(1): 43-5 (2007)]. In total, there are more than 500,000 cases of DHF/DSS each year and depending on the country and clinician experience managing DHF/DSS, case fatality ranges but can be as high as 20% [Pang T, Cardosa M J, Guzman M G, *Immunol Cell Biol* 85(1): 43-5 (2007)]. DENV is transmitted mainly by *Aedes* mosquito species and although infection by one serotype can induce long-lasting immunity, no long-term cross protection to other (heterotypic) DENV serotypes is conferred. In fact, subsequent infection by a heterotypic serotype can result in immune-mediated enhancement of disease which significantly increases the risk of developing DHF [Pang T, Cardosa M J, Guzman M G, *Immunol Cell Biol* 85(1): 43-5 (2007)]. Globalization and modern transportation have facilitated the spread of DENV and consequently all four DENV serotypes are now found in most endemic regions increasing the risk of sequential serotype infections and the potential for severe disease [Gubler D J, *Ann N Y Acad Sci.* 951:13-24 (2001)]. The worldwide public health burden of DENV, DHF and DSS has led to classification of DENV as a category A priority pathogen by NIAID and currently, the only available treatment option for DENV is supportive care.

Zika virus (ZIKV) is another mosquito-borne flavivirus that has been shown to cause a febrile illness in humans that can resemble dengue fever with clinical symptoms including fever, headache, myalgia and rash. Since discovery of the virus in 1947 until recently, ZIKV appeared sporadically in Africa and Asia and a high seroprevalence of ZIKV antibodies in humans throughout Africa and Asia has been demonstrated [Haddow A D, et al., *PLoS Negl Trop Dis* 6(2): e1477 (2012)]. However, in 2007 the first large ZIKV epidemic occurred in Micronesia which was also the first time ZIKV was detected outside of Africa and Asia [Song, B.-H., et al., J. Neuroimmunol. (2017), doi.org/10.1016/j.jneuroim.2017.03.001]. Phylogenetic analysis of the isolate as well as another recent ZIKV isolate from a pediatric case in Cambodia demonstrated both recent strains were closely related to the Asian lineage of ZIKV and suggested the geographical range of the Asian ZIKV lineage was expanding [Haddow A D, et al. PLoS Negl Trop Dis 6(2): e1477 (2012)]. In 2013 the largest outbreak of ZIKV ever described was reported in French Polynesia, and for the first time clinical symptoms included severe autoimmune and neurological complications, including Guillain-BarrSyndrome and fetal abnormalities in pregnant women [Song, B.-H., et al., J. Neuroimmunol. (2017), doi.org/10.1016/j.jneuroim.2017.03.001]. The French Polynesian outbreak demonstrated for the first time the severe pathogenic potential of ZIKV. Further, phylogenetic analysis revealed the virus was most closely related to ZIKV isolates from Micronesia and Cambodia again demonstrating the expanding range of Asian lineage isolates with pathogenic potential [Song, B.-H., et al., J. Neuroimmunol. (2017), doi.org/10.1016/j.jneuroim.2017.03.001]. In 2013 and 2014, ZIKV appeared in New Caledonia, the Cook Islands, and Easter Island [Song, B.-H., et al., J. Neuroimmunol. (2017), doi.org/10.1016/j.jneuroim.2017.03.001] and an isolate from Easter Island was found to be most closely related to French Polynesian ZIKV [Song, B.-H., et al., J. Neuroimmunol. (2017), doi.org/10.1016/j.jneuroim.2017.03.001]. In May of the following year, the first ZIKV outbreak was reported in Northeastern Brazil and again the virus was determined to be most closely related to ZIKV from French Polynesia and the Cook islands [Song, B.-H., et al., J. Neuroimmunol. (2017), doi.org/10.1016/j.jneuroim.2017.03.001]. Unfortunately, by October 2015, autochthonous transmission of ZIKV had been demonstrated in 14 states in Brazil and in Columbia. Over the next 6 months, ZIKV spread rapidly across South America and the Caribbean with significant severe disease, including Guillain-Barre Syndrome, acute myelitis and severe birth defects, including over 4700 suspected cases of microcephaly [Song, B.-H., et al., J. Neuroimmunol. (2017), doi.org/10.1016/j.jneuroim.2017.03.001]. Further, infectious ZIKV has been isolated from breast milk and semen and sexual transmission has been documented in numerous incidences [Song, B.-H., et al., J. Neuroimmunol. (2017), doi.org/10.1016/j.jneuroim.2017.03.001]. Most recently, ZIKV has been associated with a rare neurological disorder in adults called acute disseminated encephalomyelitis (ADEM) which is characterized by autoimmune-mediated damage of the myelin in the brain and spinal cord. In February 2016 the World Health Organization declared a global health emergency of international concern related to ZIKV, and currently, the only available treatment option for ZIKV is supportive care.

As ZIKV exploded across the Americas in 2016, another mosquito-borne flavivirus, Yellow fever virus (YFV), was causing an epidemic in Africa [Bagcchi S. *The Lancet Infectious Diseases*, Volume 17, Issue 3, 269-270, (2017)]. Like DENV and ZIKV, YFV is found in tropical regions of Africa and the Americas and it can produce devastating outbreaks of disease. Most YFV infections are asymptomatic; however, some patients develop an acute illness characterized by one or two phases of disease. In the first phase symptoms include muscular pain, headache, chills, anorexia, nausea and/or vomiting, often with bradycardia. Patients who progress to the second phase (~15%) present with resurgence of fever, development of jaundice, abdominal pain, vomiting and haemorrhagic manifestations and approximately 50% of these patients die 10-14 days after the onset of disease. Mass vaccination is used to prevent and control YFV in the event of an outbreak. In response to the African outbreak in 2016, a mass YFV vaccination campaign was initiated and by September 2016 the outbreak had been contained [Bagcchi S. *The Lancet Infectious Diseases*, Volume 17, Issue 3, 269-270, (2017)]. In total, 961 cases of YFV and 137 deaths occurred. Importantly, although the YFV vaccine was effective, the global emergency YFV vaccine stockpile reserved for epidemic response was not enough to complete the African YFV vaccination campaign. Additional doses of vaccine had to be sourced from other nations and diluted prior to use to stretch supplies [Joseph T Wu, et al., *The Lancet*, Volume 388, Issue 10062, 10-16, Pages 2904-2911, 2016]. Beyond exhausting the world's emergency YFV vaccine stockpile, the epidemic revealed significant weaknesses in the emergency YFV vaccine supply pipeline. Just six months after the African YFV epidemic, a significant increase in YFV was reported in South America and to date, 234 cases and 80 deaths have been reported [Paules C I, Fauci A S. *N Engl J Med.* 2017 Mar. 8. doi: 10.1056/NEJMp1702172 (Epub ahead of print)]. The current lack of a global YFV vaccine stockpile and the long time needed to produce additional YFV vaccine is concerning given the ongoing YFV outbreak in Brazil.

In addition to YFV, hepatitis C virus (HCV) can cause a YFV-like disease and differential diagnosis of YFV and HCV based on acute symptoms can be difficult in endemic regions [Makiala-Mandanda S, et al., *J Clin Microbiol.* 2017 Feb. 15. pii: JCM.01847-16. doi: 10.1128/JCM.01847-16. (Epub ahead of print)]. Like YFV, HCV is a flavivirus and acute symptoms including fever, fatigue, decreased appetite, nausea, vomiting, abdominal pain, joint pain and jaundice. However, unlike YFV, HCV occurs worldwide and can cause chronic infection with a risk of cirrhosis of the liver within 20 years (15-30% of chronic patients). Globally, it is estimated that ~150 million people are chronically infected with HCV and that 25% of all liver cancer worldwide is caused by HCV [Thursz M, Fontanet A. *Nat Rev Gastroenterol Hepatol.* 2014; 11(1): 28-35. doi: 10.1038/nrgastro.2013.179. Epub 2013 Oct. 1]. Significant progress has been made in developing effective HCV therapeutics [Hull M W, Yoshida E M, Montaner J S. *Curr Infect Dis Rep.* 2016; 18(7): 22. doi: 10.1007/s11908-016-0527-8]; however, limited access to treatment largely due to cost has hampered efforts to reduce HCV burden globally. Further, there are six genotypes of HCV that demonstrate different sensitivities to therapeutic drugs and drug resistance HCV variants have also been documented [Jacobson I M. *Gastroenterol Hepatol* (NY). 2016; 12(10 Suppl 4): 1-11]. The lack of robust and reliable cell culture systems and lack of HCV animal models have slowed HCV drug development and significantly hampered vaccine research. Coinfection of HCV and DENV has also been demonstrated which may contribute to an increased susceptibility to hepatic damage in coinfected patients, complicating the symptoms of either DENV or HCV infection [Machain-Williams, Biomed Res Int. 2014; 321286. Doi: 10.1155/2014/321286].

DENV vaccine design and development have proven to be difficult due to antigenic differences between serotypes and enhancement of disease upon reinfection by a different serotype. Numerous monovalent and multivalent DENV vaccine candidates are currently in development including live attenuated DENV derived by passage in cell culture, engineering mutations in the 3' untranslated region or creating chimeric YFV expressing DENV prM or E, purified inactivated virus, purified recombinant DENV prM and E proteins and DNA molecules encoding DENV precursor membrane protein (prM) and E [Whitehead S S, et al., *Nature reviews Microbiology* 5(7): 518-28 (2007)]. All of these vaccine candidates have been evaluated for immunogenicity in rhesus macaques in monovalent or multivalent combinations and each has been shown to elicit high levels of neutralizing antibody and prevent viremia in vaccinated and then challenged animals [Whitehead S S, et al., *Nature reviews Microbiology* 5(7): 518-28 (2007)]. Based on these data, many of the monovalent, divalent and tetravalent vaccine candidates have transitioned to phase I and II safety trials. Unfortunately, the only tetravalent DENV vaccine candidate being evaluated in large efficacy trials in humans has returned disappointing results as DENV-mediated disease was exacerbated in vaccinated children under the age of 9 and no efficacy was demonstrated against DENV-2, the most common serotype in the region where the clinical trial was conducted [Halstead S B, *Lancet* 380(9853): 1535-6 (2012)]. Regardless, three countries, have approved the vaccine for use even though the efficacy against DENV-2 was low; however, vaccine use is restricted to individuals 9 and older. Interestingly, low vaccine efficacy did not correlate with the levels of neutralizing antibody, demonstrating that better models and more effective DENV vaccine candidates are needed.

In view of the above vaccine deficiencies, it is desirable to provide methods and constructs for more efficient production of recombinant secreted antigenic flavivirus proteins.

SUMMARY OF INVENTION

Accordingly, we have developed a novel virus-like-particle (VLP) expression cassette that features bicistronic transcription, simultaneous translation and synchronized intracellular trafficking of the flavivirus structural proteins and a host protease. Our underlying hypothesis is that the novel flavivirus VLP expression cassettes can be used to generate highly native flavivirus VLPs in sufficient yields to enable vaccine development. Results obtained using our novel DENV and ZIKV VLP expression cassettes support these claims.

According to a first aspect of the invention, there is provided an expression cassette comprising;

i. a flavivirus structural gene, and ii. a furin gene.

The presence of the furin gene advantageously produces furin protein within the same cell as the virus proteins, which provides enhanced processing of the recombinant flavivirus proteins which increases yield of secreted mature virus-like particles containing neutralizing epitopes for vaccine use. Advantageously, co-expression of two genes may be achieved by inserting an element between the genes that allows bicistronic expression.

In a preferred embodiment the expression cassette comprises;

i. a flavivirus structural gene, ii. a furin gene, and iii. a bicistronic expression element positioned between the flavivirus structural gene and the furin gene.

A suitable bicistronic expression element is an internal ribosome entry site (IRES). It would be understood that the IRES in the cassette between the virus protein and furin protein may be replaced by other elements suitable for multicistronic expression. For example, the IRES could potentially be replaced with DNA encoding the 2A peptide from the foot-and-mouth disease virus (FDMV) (F2A) for bicistronic or polycistronic expression [Chan H Y, et al., *PLoS ONE* 6.12 (2011)].

In another preferred embodiment the expression cassette comprises;

i. a flavivirus structural gene, ii. a furin gene, and iii. IRES positioned between the flavivirus structural gene and the furin gene.

In a preferred embodiment, the flavivirus structural gene comprises a partial capsid protein (delC), and either a complete membrane precursor (prM) protein coding sequence and a complete envelope (E) protein coding sequence or a complete membrane protein (p7) coding sequence and complete E protein coding sequences (E1 and E2).

The partial capsid protein (delC) is preferably one that functions to anchor the flavivirus structural protein in the cellular endoplasmic reticulum (ER) membrane In another preferred embodiment, the furin gene comprises a furin signal peptide (fsp) and a furin proprotein coding sequence. Preferably the furin coding sequence is full length.

In another preferred embodiment, the expression cassette further comprises a partial capsid protein (delC) fused in frame to the 5' end of the furin signal peptide.

The partial capsid protein (delC) is preferably one that functions to anchor the flavivirus structural protein and/or the furin proprotein in the cellular ER membrane. More preferably, when the same delC protein is used for the flavivirus structural protein and the furin proprotein, it co-localizes both proteins to the same site in the ER membrane and provide a temporal balance that is optimal for flavivirus processing. Co-localisation has the advantage of increasing the efficiency of the furin protein processing of the flavivirus structural proteins and increases the yield of mature secreted structural proteins and VLPs.

In a preferred embodiment the delC protein spans the cellular ER membrane and does not contain the first 108 nucleotides of the capsid protein coding sequence. An example is the del108C ZIKA, DENV, YFV and HCV sequences used in the Examples.

In a preferred embodiment, expression cassettes comprising p7 are fused in frame to the 5' end of a partial nonstructural 2 protein (NS2del).

The partial NS2 (NS2del) is preferably one that contains a furin cleavage site that regulates cleavage of flavivirus structural proteins. Inclusion of delNS2 has the advantage of increasing the efficiency of the furin protein processing of the flavivirus structural proteins.

In a preferred embodiment the NS2del protein spans a putative furin cleavage site and contains the first 267 nucleotides of the NS2 coding sequence. An example is the NS2del384 HCV sequence used in the Examples.

In another preferred embodiment, the expression cassette further comprises a promoter to drive transcription of the expression cassette.

The promoter initiates the transcription and is therefore the point of control for the expression of the cloned genes in the expression cassette. The promoters used in expression vectors are normally inducible, meaning that protein synthesis is only initiated when required by the introduction of an inducer such as IPTG. Gene expression however may also be constitutive. Several types of promoters could be selected from to drive expression of the genes in the expression cassette. For example, constitutive promoters may include the simian virus 40 early promoter (SV40), cytomegalovirus immediate-early promoter (CMV), human Ubiquitin C promoter (UBC), human elongation factor 1a promoter (EF1A), mouse phosphoglycerate kinase 1 promoter (PGK), and chicken β-Actin promoter coupled with CMV early enhancer (CAGG), and copia transposon promoter (COPIA) and actin 5C promoter (ACTSC) for *Drosophila* systems). For expression in insect cells, the baculovirus *Autographa californica* multiple nuclear polyhedrosis virus (AcMNPV) Polyhedrin promoter may be used, as disclosed in the Examples herein. It would be understood by the person skilled in the art that the choice of promoter may depend on the type of cell intended to express the viral proteins and host protease and the level of expression desired.

In a preferred embodiment, the expression cassette comprises a baculovirus *Autographa californica* multiple nuclear polyhedrosis virus (AcMNPV) Polyhedrin promoter to drive transcription of the expression cassette.

In another preferred embodiment, the expression cassette further comprises a polyA signal sequence positioned at the 3' end of the furin gene.

In a preferred embodiment, the polyA signal sequence is a SV40 late polyA signal sequence.

In another preferred embodiment, the furin gene is selected from the group comprising human, non-human mammal or insect furin gene. In a preferred embodiment, the furin gene is human.

An example of two expression cassettes according to the invention is shown in FIG. 1.

It would be understood by a skilled person in the art that the expression cassette could be designed to express virus proteins in various types of cells in vitro. In another preferred embodiment, the flavivirus structural gene and the furin gene are codon-optimised for expression in insect cells.

In a preferred embodiment the expression cassette according to the invention has the structure shown in FIGS. 2A-E with positions of elements described in FIGS. 2F-J, respectively. More preferably, the cassette represented in FIG. 2A has a nucleotide sequence comprising SEQ ID NO: 1; the cassette represented in FIG. 2B has a nucleotide sequence comprising SEQ ID NO: 9; the cassette represented in FIG. 2C has a nucleotide sequence comprising SEQ ID NO: 8; the cassette represented in FIG. 2D has a nucleotide sequence comprising SEQ ID NO: 11 and the cassette represented in FIG. 2E has a nucleotide sequence comprising SEQ ID NO: 12.

Another example of two expression cassettes according to the invention is shown in FIG. 3. In preferred embodiments the expression cassette has the structure represented in FIG. 4A, 4B, 4C or 4D with positions of elements described in FIGS. 4E-4H, respectively, having, respectively, a nucleotide sequence comprising SEQ ID Nos: 2, 10, 13 and 14.

In another preferred embodiment, the expression cassette further comprises a promoter, a flavivirus NS1 gene and a polyA signal sequence on the complementary DNA strand upstream of the flavivirus structural gene-IRES-furin proprotein sequences.

In a preferred embodiment, the promoter for the flavivirus NS1 gene is baculovirus AcMNPV p10 promoter.

In a preferred embodiment, the polyA signal sequence for the flavivirus NS1 gene is Herpes Simplex virus thymidine kinase (HSV tk) polyA signal sequence.

Preferred examples of an expression cassette according to the invention are shown in FIGS. 9 and 11. In a preferred embodiment, the expression cassette may have the structure shown in FIG. 10A, 10B or 10C with positions of elements described in FIGS. 10D-10F, respectively. More preferably, the cassette of FIG. 10A has a nucleotide sequence represented by SEQ ID NO: 3; the cassette of FIG. 10B has a nucleotide sequence represented by SEQ ID NO: 6 and the cassette of FIG. 100 has a nucleotide sequence represented by SEQ ID NO: 5.

Another example of an expression cassette according to the invention is shown in FIG. 12A-B with positions of elements described in FIGS. 12C-D, respectively. More preferably, the cassette of FIG. 12A has a nucleotide sequence represented by SEQ ID NO: 4 and the cassette of FIG. 12B has a nucleotide sequence represented by SEQ ID NO: 7.

In another preferred embodiment, the flavivirus is selected from at least one of the group comprising Dengue virus, Zika virus, Yellow fever virus, West Nile virus and Japanese encephalitis virus and serotypes thereof.

In another preferred embodiment, the flavivirus is Hepatitis C virus.

In a preferred embodiment, the flavivirus is selected from at least one of the group comprising Dengue virus serotype 1, Dengue virus serotype 2, Dengue virus serotype 3, Dengue virus serotype 4 and Zika virus.

In a preferred embodiment, the Dengue virus serotype is DENV2.

In another preferred embodiment, the cassette is homologous or heterologous with respect to the partial capsid protein delC.

In a preferred embodiment, the cassette is heterologous and comprises a Dengue virus delC and/or a Zika virus delC.

Preferred embodiments of the expression cassettes of the invention are shown in the Figures and Sequence Listing.

According to another aspect of the invention there is provided the use of an expression cassette according to any aspect of the invention described herein for the recombinant production of secreted virus proteins.

According to a preferred embodiment there is provided the use of an expression cassette according to any aspect of the invention described herein for the recombinant production of virus-like particles (VLPs).

According to another aspect of the invention there is provided a method for the production of recombinant secreted flavivirus structural proteins and/or VLPs comprising the steps: cultivating a eukaryotic cell that has been transfected with a plasmid containing an expression cassette as defined according to any aspect of the invention, and recovering the recombinant secreted virus structural proteins and/or VLPs from the cell or the cultivation medium.

In a preferred embodiment, the eukaryotic cell is a mammalian cell. More preferably the mammalian cell is Chinese hamster ovary of human kidney.

In a preferred embodiment the method of production comprises the steps: cultivating a eukaryotic cell that has been infected with a recombinant baculovirus expressing the novel VLP expression cassette as defined herein, and recovering recombinant secreted flavivirus structural proteins and/or VLPs from the cell or the cultivation medium.

In a preferred embodiment, the eukaryotic cell is an insect cell. Preferably the insect cell is Sf9 from *Spodoptera frugiperda*.

It would be understood by the person skilled in the art that the choice of cell type and cell-specific promoter may depend on the type of cell intended to express the secreted viral proteins and host protease and the level of expression desired.

According to another aspect of the invention there is provided at least one isolated recombinant secreted flavivirus structural protein and/or VLP produced by the method of the invention herein defined.

According to another aspect of the invention there is provided a vaccine comprising at least one recombinant secreted flavivirus structural protein and/or VLP produced by the method of the invention herein defined.

In a preferred embodiment, the at least one recombinant secreted flavivirus structural protein and/or VLP comprises neutralizing epitopes from Dengue virus serotypes 1, 2, 3 and/or 4.

In a preferred embodiment, the at least one recombinant secreted flavivirus structural protein and/or VLP comprises Zika virus neutralizing epitopes.

In a preferred embodiment, at least one recombinant secreted flavivirus structural protein and/or VLP comprises Yellow fever virus neutralizing epitopes.

In a preferred embodiment, at least one recombinant secreted flavivirus structural protein and/or VLP comprises Hepatitis C virus neutralizing epitopes.

According to another aspect of the invention there is provided a method of treatment or prophylaxis comprising administering to a subject in need of such treatment or prophylaxis an efficacious amount of vaccine according to any aspect of the invention.

According to another aspect of the invention there is provided the use of at least one isolated recombinant secreted flavivirus structural protein and/or VLP as herein defined or a vaccine as herein defined for the manufacture of a medicament for the treatment or prophylaxis of a flavivirus infection. Preferably, the flavivirus infection is selected from at least one of the group comprising Dengue virus infection and Zika virus infection.

BRIEF DESCRIPTION OF THE FIGURES

FIGS. 1A-1D show general flavivirus structural gene bicistronic human furin proprotein expression cassettes. The flavivirus structural gene includes a partial flavivirus capsid protein coding sequence (delC) and the complete membrane precursor (prM) and envelope (E) protein coding sequences (FIG. 1A, FIG. 10) or complete membrane (p7) and E (E1 and E2) protein coding sequences (FIG. 1B, FIG. 1D). For cassettes containing p7, a partial 5'-NS2 fragment has been fused in frame downstream (*). An Internal Ribosome Entry Site (IRES) sequence is located downstream of the flavivirus structural gene and upstream of a novel fusion protein sequence that encodes flavivirus deIC fused in frame to the human furin signal peptide (hfsp) and the entire coding sequence of the human furin proprotein gene. Transcription of the bicistronic expression cassette is dependent on the baculovirus *Autographa californica* multiple nuclear polyhedrosis virus (AcMNPV) Polyhedrin promoter and mRNA is stabilized by the Simian virus 40 (SV40) late polyA signal.

FIGS. 2A-2J show specific flavivirus structural gene bicistronic human furin proprotein expression cassettes. The flavivirus structural gene includes a partial dengue 2 (DENV2, FIGS. 2A and 2F) or Zika virus (ZIKV, FIGS. 2B-C and 2G-H), Yellow fever virus (YFV, FIGS. 2D and 2I) or Hepatitis C virus (HCV, FIGS. 2E and 2J) capsid protein coding sequence (del108CDENV2, del108CZIKV, del108CYFV or del108CHCV) and the complete DENV2, ZIKV, YFV membrane precursor (prM) and envelope (E) protein coding sequences or the complete HCV membrane (p7) and envelope coding sequences (HCV E1 and HCV E2). For all, del108C does not contain the first 108 nucleotides of the capsid protein coding sequence. An Internal Ribosome Entry Site (IRES) sequence is located downstream of the DENV2, ZIKV, YFV or HCV structural gene and upstream of a novel fusion protein sequence that encodes DENV2, ZIKV, YFV or HCV del108C fused in frame to the human furin signal peptide (hfsp) and the entire coding sequence of the human furin proprotein gene. Transcription of the bicistronic expression cassette is dependent on the baculovirus AcMNPV Polyhedrin promoter and mRNA is stabilized by the SV40 late polyA signal. The overall size of the expression cassette in nucleotides is indicated by the number after the SV40 late polyA signal box.

FIGS. 3A-3D show general flavivirus structural gene bicistronic human furin proprotein expression cassettes without del108C upstream of the human furin proprotein. The flavivirus structural gene includes a partial flavivirus capsid protein coding sequence (delC) and either the complete membrane precursor (prM) and envelope (E) protein coding sequences (FIGS. 3A and 3C) or complete membrane (p7) and E (E1 and E2) protein coding sequences (FIGS. 3B and 3D). For cassettes containing p7, a partial 5'-NS2 fragment has been fused in frame downstream (*). An Internal Ribosome Entry Site (IRES) sequence is located downstream of the flavivirus structural gene and upstream of the human furin signal peptide (hfsp) and the entire coding sequence of the human furin proprotein gene. Transcription of the bicistronic expression cassette is dependent on the baculovirus AcMNPV Polyhedrin promoter and mRNA is stabilized by the SV40 late polyA signal.

FIGS. 4A-4H show specific flavivirus structural gene bicistronic human furin proprotein expression cassette without del108C upstream of the human furin proprotein. The flavivirus structural gene includes a partial DENV2 (FIGS. 4A and 4E), ZIKV (FIGS. 4B and 4F), YFV (FIGS. 4C and 4G) or HCV (FIGS. 4D and 4H) capsid protein coding sequence (del108CDENV2, del108CZIKV, del108CYFV or del108CHCV) and the complete DENV2, ZIKV, YFV membrane precursor (prM) and envelope (E) protein coding sequences or the complete HCV membrane (p7) and envelope coding sequences (HCV E1 and HCV E2). For all, del108C does not contain the first 108 nucleotides of the capsid protein coding sequence. An Internal Ribosome Entry Site (IRES) sequence is located downstream of the DENV2, ZIKV, YFV or HCV structural gene and upstream of the human furin signal peptide (hfsp) and the entire coding sequence of the human furin proprotein gene. Transcription of the bicistronic expression cassette is dependent on the baculovirus AcMNPV Polyhedrin promoter and mRNA is stabilized by the SV40 late polyA signal. The overall size of the expression cassette in nucleotides is indicated by the number after the SV40 late polyA signal box.

FIGS. 5A-5C show codon Optimization of DENV2 del108C-prM-E for expression in insect cells. The Codon Adaptation Index (CAI, FIG. 5A) and Frequency of Optimal Codons (FOP, FIG. 5B) are shown. In addition, GC Content Adjustment (FIG. 5C) is also shown.

FIGS. 6A-6C show codon Optimization of ZIKV del108C-prM-E for expression in insect cells. The Codon Adaptation Index (CAI, FIG. 6A) and Frequency of Optimal Codons (FOP, FIG. 6B) are shown. In addition, GC Content Adjustment (FIG. 6C) is also shown.

FIGS. 7A-7C show codon Optimization of HCV del108C-E1-E2-p7-delNS2 for expression in insect cells. The Codon Adaptation Index (CAI, FIG. 7A) and Frequency of Optimal Codons (FOP, FIG. 7B) are shown. In addition, GC Content Adjustment (FIG. 7C) is also shown.

FIGS. 8A-8C show codon Optimization of del108CDENV2-hfsp-human furin proprotein for expression in insect cells. The Codon Adaptation Index (CAI, FIG. 8A) and Frequency of Optimal Codons (FOP, FIG. 8B) are shown. In addition, GC Content Adjustment (FIG. 8C) is also shown.

FIGS. 10A-10F show specific flavivirus structural gene bicistronic human furin proprotein dual promoter nonstructural protein 1 (NS1) expression cassettes. The flavivirus structural gene includes a partial DENV2 (FIGS. 10A and 10D) or ZIKV (FIGS. 10B, 100, 10E and 10F) capsid protein coding sequence (del108CDENV2 or del108CZIKV) and the complete DENV2 or ZIKV membrane precursor (prM) and envelope (E) protein coding sequences. For DENV2 and ZIKV, del108C does not contain the first 108 nucleotides of the capsid protein coding sequence. An Internal Ribosome Entry Site (IRES) sequence is located downstream of the DENV2 or ZIKV structural gene and upstream of a novel fusion protein sequence that encodes del108CDENV2 (FIGS. 10A, 10C, 10D and 10F) or del108CZIKV (FIGS. 10B and 10E) fused in frame to the human furin signal peptide (hfsp) and the entire coding sequence of the human furin proprotein gene. Transcription of the bicistronic mRNA is dependent on the baculovirus AcMNPV Polyhedrin promoter and mRNA is stabilized by the SV40 late polyA signal. Transcription of the DENV2 or ZIKV nonstructural protein 1 (NS1) coding sequence is dependent on the baculovirus AcMNPV p10 promoter and both p10 and NS1 are encoded on the complement DNA strand upstream of the bicistronic flavivirus structural gene-IRES-human furin proprotein sequences. The DENV2 or ZIKV NS1 mRNA is stabilized by the HSV tk polyA signal. The overall size of the dual promoter expression cassette in nucleotides is indicated by the number after the SV40 late polyA signal box.

FIGS. 12A-12D show specific flavivirus structural gene bicistronic human furin proprotein dual promoter nonstructural protein 1 (NS1) expression cassettes without del108C upstream of the human furin proprotein. The flavivirus structural gene includes a partial DENV2 (FIGS. 12A and 12C) or ZIKV (FIGS. 12B and 12D) capsid protein coding sequence (del108CDENV2 or del108CZIKV) and the complete DENV2 or ZIKV membrane precursor (prM) and envelope (E) protein coding sequences. For DENV2 and ZIKV, del108C does not contain the first 108 nucleotides of the capsid protein coding sequence. An Internal Ribosome Entry Site (IRES) sequence is located downstream of the DENV2 or ZIKV structural gene and upstream of the human furin signal peptide (hfsp) and the entire coding sequence of the human furin proprotein gene. Transcription of the bicistronic mRNA is dependent on the baculovirus AcMNPV Polyhedrin promoter and mRNA is stabilized by the SV40 late polyA signal. Transcription of the DENV2 or ZIKV nonstructural protein 1 (NS1) coding sequence is dependent on the baculovirus AcMNPV p10 promoter and both p10 and NS1 are encoded on the complement DNA strand upstream of the bicistronic flavivirus structural gene-IRES-human furin proprotein sequences. The DENV2 or ZIKV NS1 mRNA is stabilized by the HSV tk polyA signal. The overall size of the dual promoter expression cassette in nucleotides is indicated by the number after the SV40 late polyA signal box.

FIGS. 13A-13C show codon Optimization of DENV2 NS1 for expression in insect cells. The Codon Adaptation Index (CAI, FIG. 13A) and Frequency of Optimal Codons (FOP, FIG. 13B) are shown. In addition, GC Content Adjustment (FIG. 13C is also shown.

FIGS. 15A-15B show characterization of secreted DENV2 E expressed using a recombinant baculovirus containing the DENV2 structural gene and del108CDENV2-human furin proprotein bicistronic expression cassette. Insect Sf9 cells were infected with recombinant baculovirus containing the DENV2 structural gene and del108CDENV2-human furin proprotein bicistronic expression cassette. Cell culture supernatants and cell pellets were harvested as described in the methods and, following ultrafiltration (membrane cutoff size of 750 kDa), permeate and retentate were collected. All materials were analyzed using SDS-PAGE under non-reducing (FIG. 15A) or reducing (FIG. 15B) conditions and Western blot. Western blots were probed with the flavivirus envelope (E)-specific monoclonal antibody FE1. Abbreviations: FGUS=negative baculovirus control; LYS=cell lysate; VS=viral supernatant; VS (1)=freeze-thawed viral supernatant; VS (1) SF=sterile filtered viral supernatant; VS (1) UF-P1=sterile filtered viral supernatant ultrafiltration permeate; VS (1) UF-R1=sterile filtered viral supernatant ultrafiltration retentate.

FIGS. 27A-27D show nucleotide sequence of DENV2 del108C-prM-E & del108CDENV2-human furin proprotein bicistronic cassette shown in FIG. 2A; SEQ ID NO: 1.

FIGS. 28A-28C show nucleotide sequence of DENV2 del108C-prM-E & human furin proprotein bicistronic cassette shown in FIG. 4A; SEQ ID NO: 2.

FIGS. 29A-29D show nucleotide sequence of Dual Promoter-DENV2 del108C-prM-E & del108CDENV2-human furin proprotein bicistronic cassette+DENV2 NS1 shown in FIG. 10A; SEQ ID NO: 3.

FIGS. 30A-30E show nucleotide sequence of Dual Promoter-DENV2 del108C-prM-E & human furin proprotein bicistronic cassette+DENV2 NS1 shown in FIG. 11A; SEQ ID NO: 4.

FIGS. 31A-31E show nucleotide sequence of Dual Promoter-Heterologous ZIKV del108C-prM-E & del108CDENV2-human furin proprotein bicistronic cassette+ZIKV NS1 shown in FIG. 100; SEQ ID NO: 5.

FIGS. 32A-32E show nucleotide sequence of Dual Promoter-Homologous ZIKV del108C-prM-E & del108CZIKV-human furin proprotein bicistronic cassette+ ZIKV NS1 shown in FIG. 10B; SEQ ID NO: 6.

FIGS. 33A-33E show nucleotide sequence of Dual Promoter-ZIKV del108C-prM-E & human furin proprotein bicistronic cassette+ZIKV NS1 shown in FIG. 11B; SEQ ID NO: 7.

FIGS. 34A-34D show nucleotide sequence of Heterologous ZIKV del108C-prM-E & del108CDENV2-human furin proprotein bicistronic cassette shown in FIG. 2C; SEQ ID NO: 8.

FIGS. 35A-35D show nucleotide sequence of Homologous ZIKV del108C-prM-E & del108CZIKV-human furin proprotein bicistronic cassette shown in FIG. 2B; SEQ ID NO: 9.

FIGS. 36A-36D show nucleotide sequence of ZIKV del108C-prM-E & human furin proprotein bicistronic cassette shown in FIG. 4B; SEQ ID NO: 10.

FIGS. 37A-37D show nucleotide sequence of YFV del108C-prM-E & del108CYFV-human furin proprotein bicistronic cassette shown in FIG. 2D; SEQ ID NO: 11.

FIGS. 38A-38D show nucleotide sequence of HCV del108C-E1-E2 & del108CHCV-human furin proprotein bicistronic cassette shown in FIG. 2E; SEQ ID NO: 12.

FIGS. 39A-39D show nucleotide sequence of YFV del108C-prM-E & human furin proprotein bicistronic cassette shown in FIG. 4C; SEQ ID NO: 13.

FIGS. 40A-40D show nucleotide sequence of HCV del108C-E1-E2-p7 & human furin proprotein bicistronic cassette shown in FIG. 4D; SEQ ID NO: 14.

DETAILED DESCRIPTION OF PREFERRED EMBODIMENTS

Figure 9:
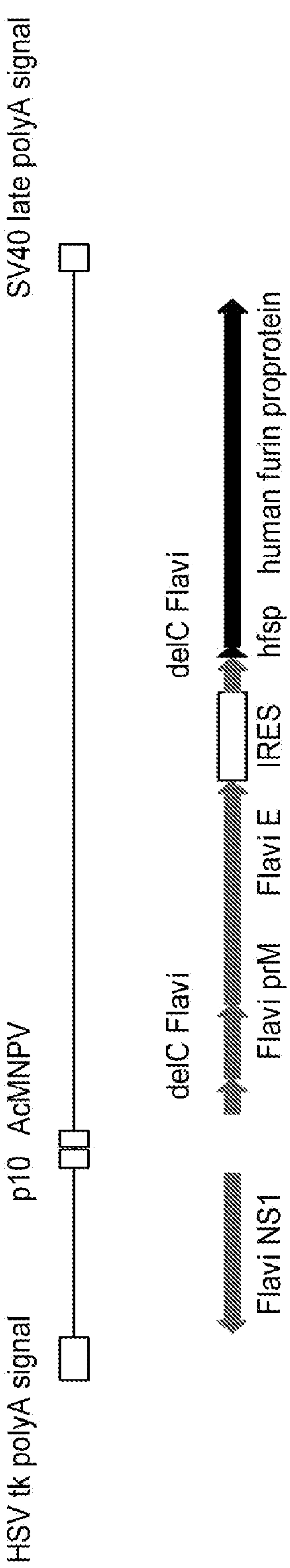
FIG. 9 shows general flavivirus structural gene bicistronic human furin proprotein dual promoter nonstructural protein 1 (NS1) expression cassette. The flavivirus structural gene includes a partial flavivirus capsid protein coding sequence (delC) and the complete membrane precursor (prM) and envelope (E) protein coding sequences. An Internal Ribosome Entry Site (IRES) sequence is located downstream of the flavivirus structural gene and upstream of a novel fusion protein sequence that encodes flavivirus delC fused in frame to the human furin signal peptide (hfsp) and the entire coding sequence of the human furin proprotein gene. Transcription of the bicistronic mRNA is dependent on the baculovirus AcMNPV Polyhedrin promoter and mRNA is stabilized by the SV40 late polyA signal. Transcription of the flavivirus nonstructural protein 1 (NS1) coding sequence is dependent on the baculovirus AcMNPV p10 promoter and both p10 and NS1 are encoded on the complement DNA strand upstream of the bicistronic flavivirus structural gene-IRES-human furin proprotein sequences. The NS1 mRNA is stabilized by the Herpes Simplex virus thymidine kinase (HSV tk) polyA signal.
Figure 10A:
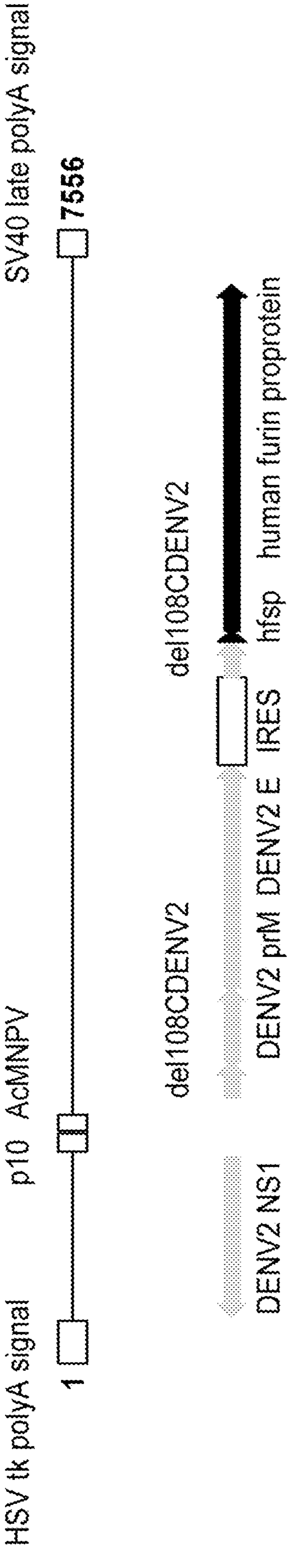
Figure 10B:
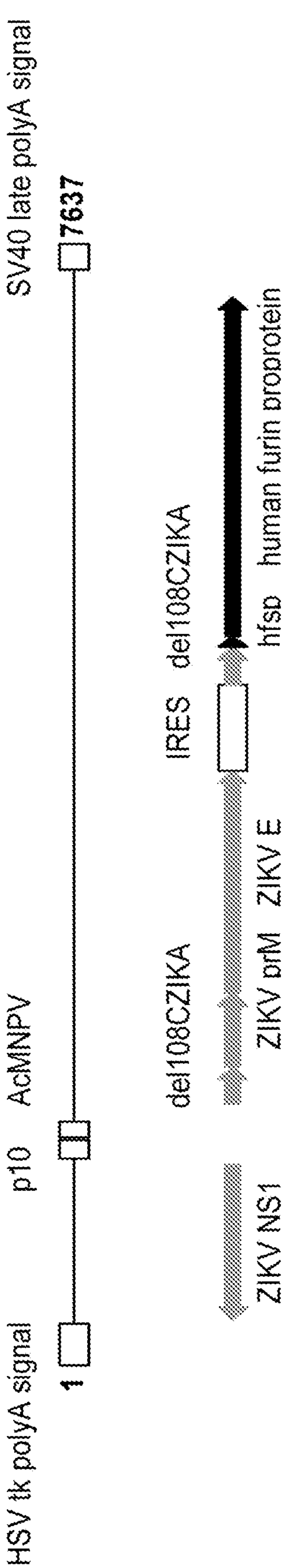
Figure 10C:
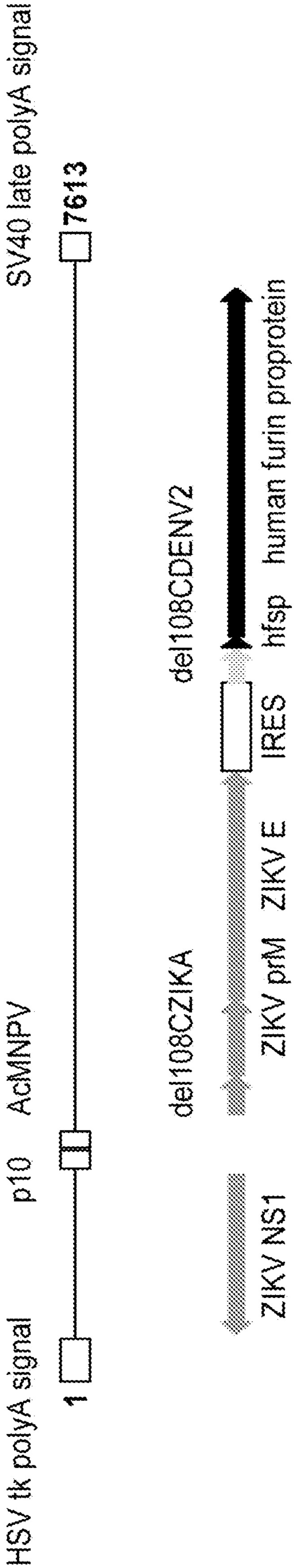
Figure 11:
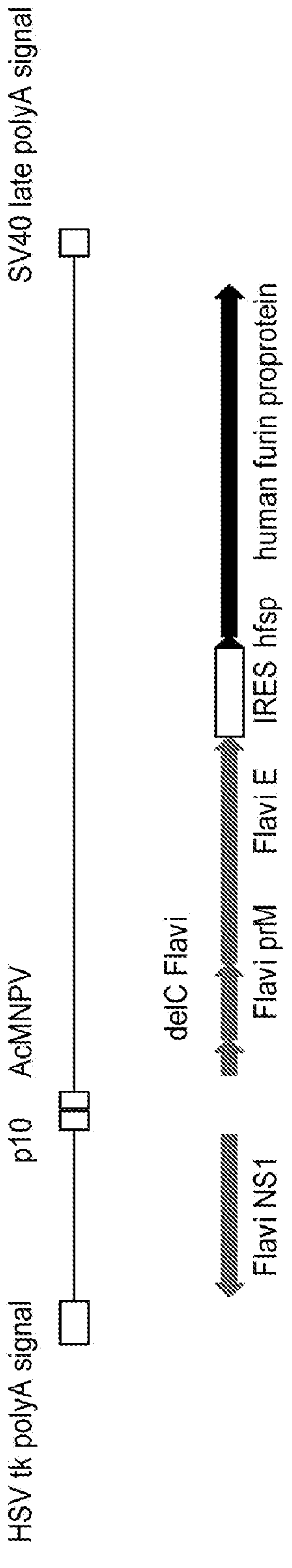
FIG. 11 shows a general flavivirus structural gene bicistronic human furin proprotein-dual promoter nonstructural protein 1 (NS1) expression cassette without del108C upstream of the human furin proprotein. The flavivirus structural gene includes a partial flavivirus capsid protein coding sequence (delC) and the complete membrane precursor (prM) and envelope (E) protein coding sequences. An Internal Ribosome Entry Site (IRES) sequence is located downstream of the flavivirus structural gene and upstream of the human furin signal peptide (hfsp) and the entire coding sequence of the human furin proprotein gene. Transcription of the bicistronic mRNA is dependent on the baculovirus AcMNPV Polyhedrin promoter and mRNA is stabilized by the SV40 late polyA signal. Transcription of the flavivirus nonstructural protein 1 (NS1) coding sequence is dependent on the baculovirus AcMNPV p10 promoter and both p10 and NS1 are encoded on the complement DNA strand upstream of the bicistronic flavivirus structural gene-IRES-human furin proprotein sequences. The NS1 mRNA is stabilized by the HSV tk polyA signal.
Figure 12A:
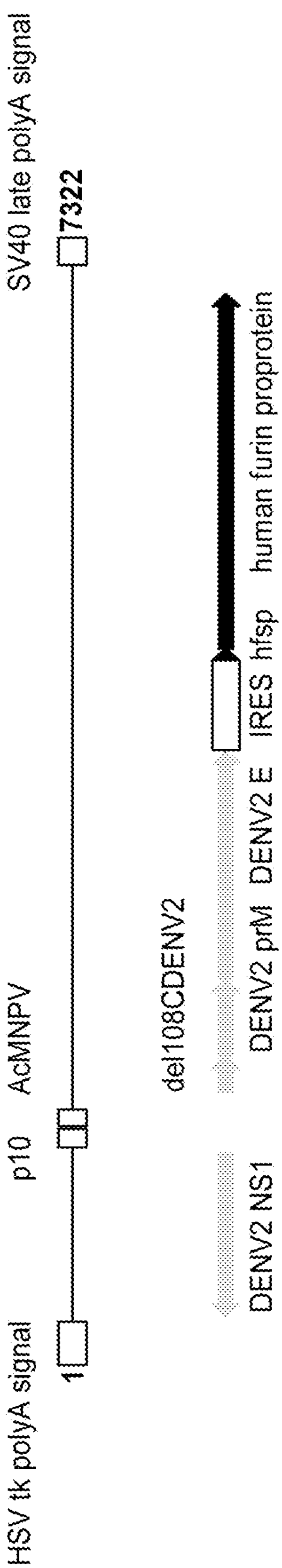
Figure 12B:
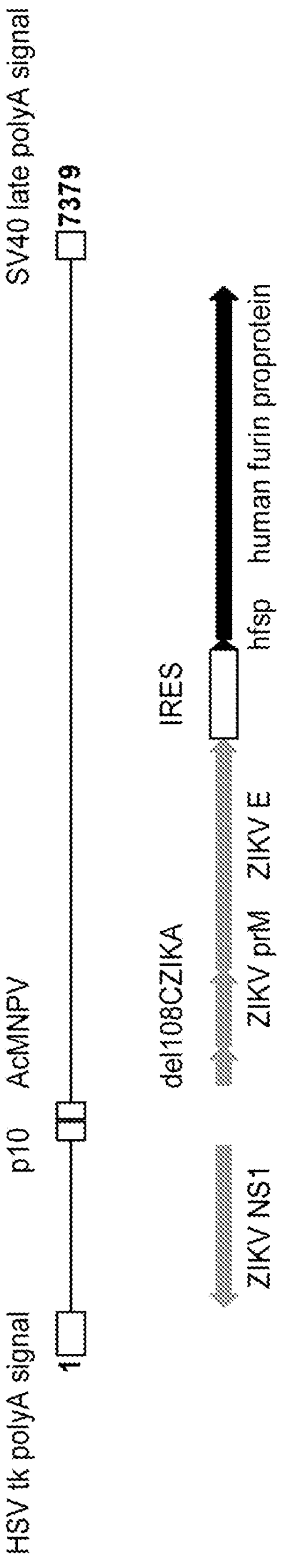

Vaccine candidates based on DENV VLPs have not been attempted because of insufficient VLP yields due to improper processing of DENV E and/or insufficient secretion of E. In general, flavivirus VLPs have proven to be difficult to make for similar reasons, although some, like Japanese encephalitis virus (JEV), work better than others [Kuwahara M and Konishi E, *Clinical and vaccine immunology*: CVI 17(10): 1560-6 (2010)]. For these reasons, the VLP platform was mostly abandoned for DENV vaccines and other flaviviruses; however, over the years different groups have tried to optimize DENV VLP expression cassettes to increase yields. Most recently, a new DENV VLP cassette was constructed that included a defensin A signal sequence, DENV prM and DENV E containing a JEV E transmembrane domain. Unfortunately, when analyzed in insect cells, yields were either still low or an E fusion loop mutation was needed to stabilize VLP production limiting vaccine potential [Charoensria N, et al., *Journal of virological methods* 205C: 116-23 (2014)]. Flaviviruses require furin to cleave prM which occurs in the low pH environment of the Golgi in both insect cells and mammalian cells [Lindenbach B D, et al., *Flaviviridae*: The viruses and their replication. In: Knipe D M, Howley P M, editors. *Fields Virology*. 5 ed. Philadelphia: Lippincott Williams & Wilkins; p. 1101-52 (2007); Gubler D J. Flaviviruses. In: Knipe D M, Howley P M, editors. *Fields Virology*, Fifth Edition. Philadelphia, Pa.: Lippincott Williams & Wilkins; p. 1153-252 (2007)]. More specifically, low pH induces conformational changes in prM-E that expose the furin cleavage site within prM and cleavage is one of the final steps of virion maturation prior to budding [Pierson T C and Diamond M S, Current opinion in virology 2(2): 168-75 (2012)]. The exact factors that control the extent of virion maturation remain poorly understood and unfortunately for DENV VLPs produced using over expression systems, VLP maturation and budding are highly inefficient. Although slightly different than DENV, ZIKV and YFV, HCV E1-E2-p7 also require cleavage by host proteases and numerous furin sites are present in the HCV structural gene. Although mature HCV virions are resistant to pH, the sensitivity of immature HCV particles to pH remains largely unknown as do the exact factors that control virion maturation [Falcón V., et al., *Virus Genes,* 53(2):15-164 (2017)]. Historically, like DENV, for HCV VLPs produced using over expression systems, VLP maturation and budding is highly inefficient [Baumert T F, et al., *J Virol.* 1998; 72(5): 3827-36].

We hypothesized that if we could somehow synchronize DENV prM-E or HCV E1-E2-p7 and furin expression and assure furin would always accompany DENV prM-E of HCV E1-E2-p7 as it traffics through the endoplasmic reticulum (ER) and Golgi, cleavage and maturation of DENV prM-E or HCV E1-E2-p7 and secretion of DENV E or HCV E1-E2 could be significantly improved. Further, we believed that maintaining DENV prM-E or HCV E1-E2-p7 and furin in close proximity would not just improve but would also maximize cleavage.

Definitions

Certain terms employed in the specification, examples and appended claims are collected here for convenience.

The term "subject" is herein defined as vertebrate, particularly mammal, more particularly human. For purposes of research, the subject may particularly be at least one animal model, e.g., a mouse, rat and the like. In particular, for treatment or prophylaxis of flavivirus infection and/or flavivirus-linked diseases, the subject may be a human.

The term "treatment", as used in the context of the invention refers to ameliorating, therapeutic or curative treatment.

The term "comprising" is herein defined to be that where the various components, ingredients, or steps, can be conjointly employed in practicing the present invention. Accordingly, the term "comprising" encompasses the more restrictive terms "consisting essentially of" and "consisting of."

A person skilled in the art will appreciate that the present invention may be practiced without undue experimentation according to the methods given herein. The methods, techniques and chemicals are as described in the references given or from protocols in standard biotechnology and molecular biology text books.

EXAMPLES

Materials and Methods

Tissue Culture

Sf9 cells were purchased from Gibco (Grand Island, N.Y.)) and maintained in Sf-900 II SFM (1×) supplemented with Gentamicin (Gibco) in a 28° C. incubator.

SDS-PAGE and Immunoblotting

Cell lysates, clarified supernatants, permeates and partially purified DENV2 and ZIKV VLP retentates were analyzed using SDS-PAGE and Western blot. Samples were separated (10-12% acrylamide gels), transferred to nitrocellulose membranes and probed with DENV and ZIKV E-specific mouse monoclonal antibodies or polyclonal human DENV or ZIKV patient serum. Bound mouse or human IgG was detected using horseradish peroxidase (HRP) conjugated anti-mouse or anti-human antibodies and TMB Membrane peroxidase substrates (KPL, Gaithersburg, Md., USA).

Electron Microscopy

Partially purified DENV2 VLPS or clarified culture supernatants containing ZIKV VLPs were sent to Nanoimaging Services (San Diego, Calif.) for cryo-transmission electron microscopy (TEM). The DENV sample was imaged undiluted whereas the clarified supernatant containing ZIKV VLPs was pelleted using 35% sucrose and ultracentrifugation prior to imaging. The samples were preserved in vitrified ice supported by holey carbon films on 400-mesh copper grids. The samples were prepared by applying a 3p1 drop of sample suspension to a cleaned grid, blotting away with filter paper, and immediately proceeding with vitrification in liquid ethane. Grids were stored under liquid nitrogen until transferred to the electron microscope for imaging. Electron microscopy was performed using an FEI Tecnai T12 electron microscope (serial number D1100), operating at 120 keV equipped with an FEI Eagle 4k×4k CCD camera. Vitreous ice grids were transferred into the electron microscope using a cryostage that maintains the grids at a temperature below −170° C. Images of each grid were acquired at multiple scales to assess the overall distribution of the specimen.

Flavivirus Virus-Like Particle (VLP) Expression Cassette Design:

Generation of Novel Bicistronic DENV and ZIKV VLP Expression Cassettes

We opted to examine DENV VLP feasibility using DENV2 due to low DENV2 vaccine performance in recent clinical trials [Halstead S B. Lancet 380(9853): 1535-6 (2012)]. The DENV2 polyprotein sequence (C-prM-E) used to make the bicistronic VLP expression cassette was a consensus sequence derived from patient isolate sequences and is most closely related to a 1996 isolate (GenBank: KF744405.1). For ZIKV, the French Polynesian polyprotein sequence was used to construct the bicistronic VLP expression cassette and C-prM-E is identical in amino acid sequence to ZIKV recently isolated in Brazil [Song, B.-H., et al., J. Neuroimmunol. (2017), doi.org/10.1016/j.jneuroim.2017.03.001]. For YFV, the Asibi polyprotein sequence was used to construct the bicistronic VLP expression cassette (GenBank: KF769016.1). For HCV, HC-TN was used to construct the bicistronic VLP expression cassette containing capsid-E1-E2-p7 (GenBank: EF621489).

General schematics of novel bicistronic flavivirus VLP expression cassettes are shown in FIGS. 1 and 3. Specific examples of the novel bicistronic DENV2, ZIKV, YFV and HVC VLP expression cassette are shown in FIGS. 2 and 4. Source materials for the DENV VLP cassette (DENV2 del108C-prM-E ORF-IRES and IRES-DENV2 del108C ORF-human furin signal peptide-human furin proprotein ORF) were synthesized by GenScript (Piscataway, N.J., USA) using DENV 2 structural protein coding sequences (capsid=C; membrane precursor=prM; envelope glycoprotein=E), an Encephalomyocarditis virus (EMCV) internal ribosome binding site (IRES) sequence and human furin signal peptide (hfsp) and human furin proprotein coding sequences. The DENV2 del108C ORF-hfsp-human furin proprotein ORF genetic fusion created during synthesis represents a highly novel feature of the bicistronic VLP cassette. The ORFs were codon optimized (FIGS. 5 and 7) for expression in insect cells prior to synthesis and each IRES contained an overlapping unique BglI restriction site to facilitate cloning. The DENV2 del108C-prM-E ORF-IRES synthesized DNA had a unique BamHI site upstream of the DENV2 del108C-prM-E ORF. The IRES-DENV2 del108C ORF-hfsp-human furin proprotein ORF synthesized DNA had a unique EcoR1 site downstream of the human furin proprotein ORF. Each piece of synthesized DNA was cloned sequentially into a Gateway® entry vector (Invitrogen, Carlsbad, Calif., USA) using BamHI/BgII and then BgII/EcorRI giving rise to the novel bicistronic DENV2 VLP expression cassette (DENV2 del108C-prM-E ORF-IRES-DENV2 del108C ORF-hfsp-human furin proprotein ORF). Expression clones containing the novel bicistronic DENV2 VLP expression cassette inserted downstream of the polyhedrin promoter were made from the entry clone and the destination vector pDEST8 according to the instructions in the Invitrogen Gateway Technology® manual (pIRA1). An example of the novel bicistronic DENV2 VLP expression cassette is shown in FIG. 2A. The novel bicistronic ZIKV VLP expression cassettes were made similarly. The ZIKV del108C-prM-E ORF-IRES sequence was codon optimized for expression in insect cells (FIG. 6) and synthesized by GenScript using ZIKV structural protein coding sequences (capsid=C; membrane precursor=prM; envelope glycoprotein=E) and the EMCV IRES sequence. Synthesized DNA had a unique BamHI site upstream of the ZIKV del108C-prM-E ORF and an overlapping unique KpnI site within the IRES. The synthesized ZIKV del108C-prM-E ORF-IRES DNA was cloned into the expression clone containing the novel bicistronic DENV2 VLP expression cassette, replacing DENV2 del108C-prM-E ORF-IRES with ZIKV del108C-prM-E ORF-IRES; giving rise to pIRA3. An example of the first ZIKV VLP expression cassette is shown in FIG. 2C. An IRES-ZIKV del108C-hfsp ORF genetic fusion was also synthesized by GenScript which contained an overlapping unique KpnI site within the IRES and an overlapping unique NheI site within hfsp. This fragment was cloned into the first bicistronic ZIKV VLP expression cassette using KpnI and NheI, replacing DENV2 del108C-hfsp with a ZIKV del108C-hfsp. The ZIKV del108C-hfsp-human furin proprotein ORF genetic fusion represents a highly novel feature of the second novel bicistronic ZIKV VLP expression cassette (pIRA5). An example of the second ZIKV VLP expression cassette is shown in FIG. 2B. Similarly, an IRES-hfsp ORF genetic fusion was also synthesized by GenScript which contained an overlapping unique KpnI site within the IRES and an overlapping unique NheI site within hfsp. This fragment has been cloned into the bicistronic DENV2 or ZIKV VLP expression cassette using KpnI and NheI, replacing DENV2 or ZIKV del108C-hfsp with simply hfsp (pIRA2 and pIRA4, respectively). General and specific examples are shown in FIGS. 3 and 4.

Recombinant bacmids containing the novel bicistronic DENV2 and ZIKV VLP expression cassettes bacIRA1, bacIRA3, bacIRA4 and bacIRA5 were made from individual expression clones according to the instructions in the Invitrogen BAC-TO-BAC® manual.

Production and Purification of DENV and ZIKV VLP

One µg of each recombinant bacmid (bacIRA1, bacIRA3, bacIRA4 or bacIRA5) was transfected into a T25 flask containing $2\times10^6$ Sf9 cells using Effectene® Transfection Reagent kit (Qiagen) as per manufacturer's instructions to generate recombinant baculovirus stocks (passage 1). The passage 1 stocks were amplified to generate master virus stocks (passage 2) and working virus stocks (passage 3) with a titre of $>10^9$ plaque forming units (pfu)/ml. Virus titre for recombinant baculovirus was determined by plaque assay on Sf9 cells. Briefly, $8\times10^5$ Sf9 cells were seeded into each well of a 6-well plate and incubated overnight at 28° C. Medium was removed from the well and 1 ml of virus inoculum in 10-fold serial dilution was added to the wells. After 1 h incubation at 28° C., 2 ml per well of overlay medium (Sf-900 II SFM (1×) supplemented with 1% HI-FBS, Gentamicin, and 1% SeaPlaque agarose (Lonza)) was added to the wells. After 6-10 days incubation at 28° C., wells were stained with neutral red and plaque numbers were manually counted after 1 day incubation at 28° C.

DENV2 and ZIKV recombinant secreted flavivirus structural proteins and/or VLPs were produced by infecting Sf9 cell suspension with recombinant baculoviruses (passage 3) at a multiplicity of infection (MOI) of 0.1-3. Cell pellets and virus supernatant were harvested on day 3 or 4, cell pellets were lysed and supernatants were clarified by centrifugation at 3,200×g for 10 min. Clarified supernatant was concentrated approximately 10-fold using 750, 500, 300 or 100 KDa MWCO Hollow Fiber Ultrafiltration Cartridge (GE Healthcare Life Sciences) and the retentate was subjected to further diafiltration.

Retentates containing DENV or ZIKV VLPs were centrifuged at 21,000×g for 3 hours. Supernatant was collected and stored at −86° C. Pellets containing VLPs were resuspended in NTE buffer (10 mM Tris, 100 mM NaCl, 1 mM EDTA; pH=8.0) overnight. Pellets were overlaid on top of 15-60% discontinuous sucrose gradients and gradients were centrifuged at 17,000 rpm for 18 hours at 4C. Following centrifugation, 2 ml fractions were collected from the top of the gradient and analyzed by Western blot. Fractions containing DENV or ZIKV VLPs were pooled, diluted 1:10 with NTE (<10% sucrose final) and further buffer exchanged/concentrated using 100 kDA Centricon spin columns and centrifugation. Concentrated purified DENV or ZIKV VLPs were quantitated using BCA kits (Thermofisher) following the manufacturer's instructions.

DENV or ZIKV In Vitro VLP Potency ELISA

Potent vaccine candidates are known to contain antigenic epitopes that can elicit neutralizing antibodies in the host. In an effort to estimate the potency of the DENV and ZIKV VLP vaccine candidates in vitro, an ELISA was established to measure the presence of neutralizing epitopes within DENV and ZIKV VLPs. The indirect potency ELISA was based on standard methods [Hickey A C, et al., *Am J Trop Med Hyg.* 89(6): 1043-57 (2013)] with slight modification. Specifically, anti-human IgG was used to capture DENV or ZIKV-specific antibody from DENV or ZIKV patient sera. Subsequently, retentates containing DENV or ZIKV VLPs or purified VLPs, infectious ZIKV, inactivated DENV2 or an irrelevant insect cell antigen (C636) were added and plates were incubated overnight at 4° C. After washing, 1 non-neutralizing and 7 different DENV- or ZIKV-neutralizing monoclonal mouse antibodies were added individually and plates were incubated for 1 hr at room temperature. Following 3 washes, rabbit anti-mouse-HRP was added and plates were incubated for 1 hr at room temperature. Plates were washed and developed with TMB following standard protocols. Optical density was measured at 450 nm.

DENV and ZIKV VLP Immunogenicity Assessment

The hallmark of any vaccine candidate, including VLPs, is the ability to elicit neutralizing antibodies in vivo. Further, the use of adjuvant can greatly increase immune responses in vivo. To determine if DENV and ZIKV VLPs are immunogenic in vivo, purified VLPs were used to immunize mice. Antigen was prepared by infecting Sf9 cells with recombinant baculovirus expressing DENV2 or ZIKV-VLPs and harvesting culture supernatant on day 4 or 5. Supernatant was clarified by centrifugation and concentrated approximately 10-fold using 500, 300 or 100 kDa MWCO Hollow Fiber Ultrafiltration Cartridges (GE Healthcare Life Sciences) and retentates were subjected to further diafiltration. Following diafiltration, retentates were centrifuged at 21,000×g and pellets containing VLPs were resuspended and overlaid onto discontinuous sucrose gradients (15-60%). Following centrifugation, fractions containing VLPs were pooled, diluted, buffer exchanged and concentrated and VLPs were quantitated using BCA kits and assessed in vitro using the VLP potency ELISA.

Two groups of C57BL/6 mice were immunized with 1 or 2.5 µg ZIKV VLPs, respectively, and VLPs were premixed with adjuvant prior to immunizations (0.1% Alhydrogel (aluminum hydroxide); Brenntag Biosector, Denmark). An additional group of control mice received adjuvant alone. Each group of mice contained 10 animals and mice were immunized intramuscularly with 100 ul VLP containing adjuvant. Animals were boosted with an identical dose of VLPs containing adjuvant 3 weeks later (100 μl/animal administered intramuscularly). Blood was collected on day 0, day 21 and day 42 for analysis of antibody responses in mice.

The strength and specificity of the antibody response in vaccinated animals was evaluated using indirect ELISA according to standard methods with slight modification [Hickey A C, et al., *Am J Trop Med Hyg.* 89(6): 1043-57 (2013)]. Plates were coated with anti-human IgG and ZIKV patient sera was used to capture infectious ZIKV. Mouse sera were diluted 1:100 to 1:12800 for the assay.

Plaque assay and plaque reduction neutralization tests (PRNT) were done as previously described [Hickey A C, et al., *Am J Trop Med Hyg.* 89(6): 1043-57 (2013)]. For PRNT, the level of serum neutralizing antibody against ZIKV was determined for individual animals in each group and an average was also determined for each group.

ZIKV VLP Efficacy Assessment

Recently, a new highly lethal mouse model of ZIKV neuropathogenesis has been described [Smith D R, et al., *PLoS Negl Trop Dis* 11(1): e0005296. doi:10.1371/journal.pntd.0005296 (2017)] and this new mouse model was used to evaluate the efficacy of ZIKV-VLP vaccine candidates. All mice immunized with two doses of 1 or 2.5 μg ZIKV VLP-adjuvant or adjuvant alone, as described above, were inoculated with a lethal dose of ZIKV three weeks after boost. Animals were monitored for disease following challenge and percent weight change and survival curves were generated for each group of immunized mice.

Brief Description of Expression Cassettes:

Single Promoter Bicistronic Expression Cassette a. Bicistronic containing flavivirus structural genes and human furin proprotein. Both open reading frames (ORF) are in close proximity and transcribed simultaneously (FIGS. 1A-D, 2A-J, 3A-D, 4A-H)
b. polyA signal sequence for RNA stabilization
c. Internal Ribosome Entry Site (IRES) for enhanced translation of the second ORF (human furin proprotein); (FIGS. 1A-D, 2A-J, 3A-D, 4A-H).
d. Partial flavivirus capsid sequence fused in-frame upstream of flavivirus prM-Envelope (E) or E1-E2-p7 and human furin proprotein to serve as a signal sequence for protein trafficking and ER membrane anchor. The identical signal sequence will target both translated proteins to the same location, again keeping the viral structural proteins in close proximity to the protease, human furin (FIGS. 1 and 2).
   I. These constructs also contain the natural human furin proprotein signal peptide (hfsp) upstream of the human furin proprotein sequence for in case it is important for cleavage of the human furin proprotein to the active form of the furin protein.
   II. Some constructs have been designed with only the hfsp for simplicity (FIGS. 3 and 4).
e. Flavivirus structural genes and the human furin proprotein sequence were codon optimized for insect cell expression (FIGS. 5A-C, 6A-C, 7A-C, 8A-C). As optimization was extensive, protein translation should be significantly increased.

Figure 13A:
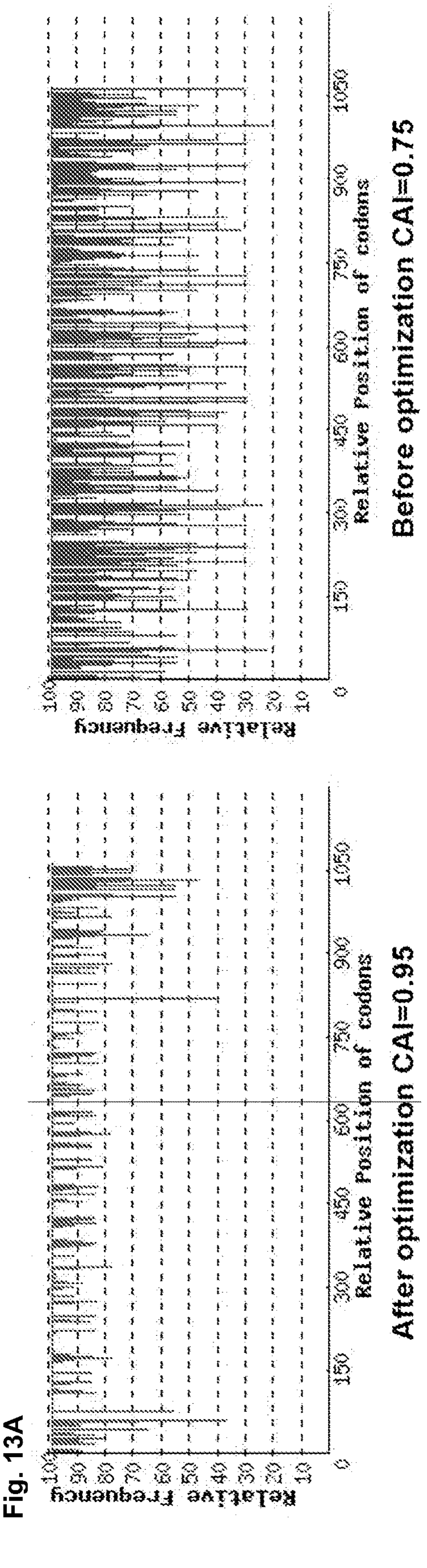
Figure 13B:
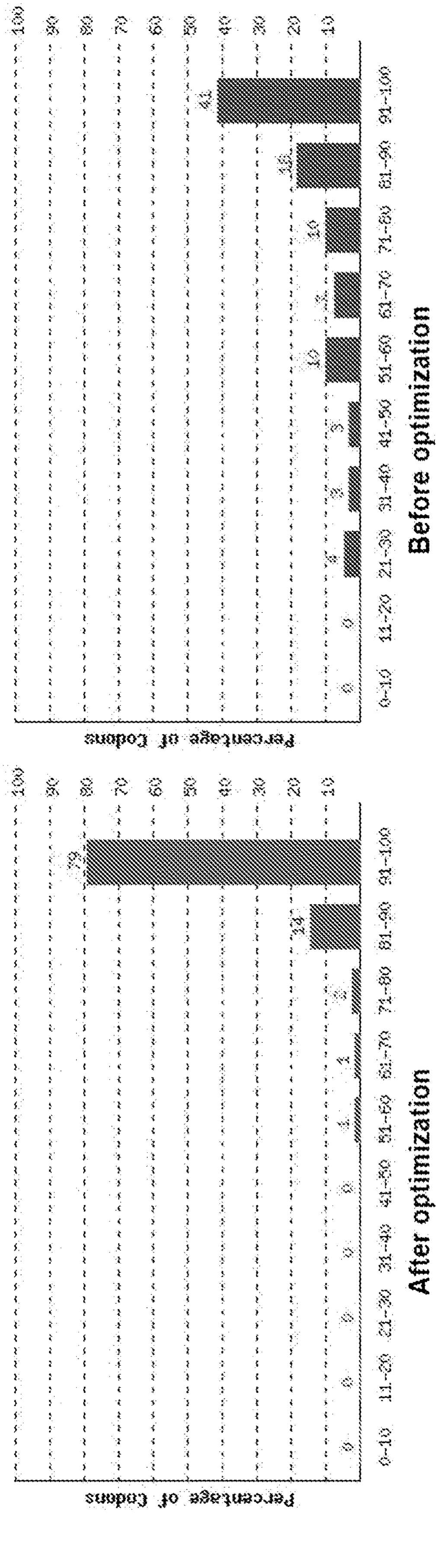

Dual Promoter a. Contains the bicistronic cassette described above as well as a second promoter upstream of a flavivirus nonstructural protein 1 (NS1) sequence (FIGS. 9-12).
b. A second polyA signal sequence downstream of the NS-1 sequence for RNA stabilization
c. The flavivirus NS-1 gene was codon optimized for insect cell expression (FIGS. 13A-C). As optimization was extensive, protein translation should be significantly increased.

Results

A recombinant baculovirus containing the DENV2 Single Promoter Bicistronic VLP Expression Cassette (FIG. 2) was made and rescued. The recombinant virus was used to infect insect cells and the culture supernatants or cell lysates were collected at various time points post-infection and analyzed using SDS-PAGE and Western blot. Blots from non-reduced samples were probed with human seronegative or seropositive DENV reference serum or with DENV-specific monoclonal antibodies (mAbs).

As demonstrated in FIG. 14A, pooled convalescent serum from DENV patients (PCS) and pooled high positive human DENV reference serum (HPR) both recognized a protein identical in size to DENV envelope (E). Moreover, a doublet was apparent which is consistent with non-reduced DENV2 E analyzed from infectious virus and suggests that DENV2 delC-prM-E was processed properly.

Of the 4 DENV-mAbs assayed, only the two specific for DENV E (DE8 and FE1) gave signal, confirming the presence of DENV E doublet (FIG. 14B).

Figure 14:
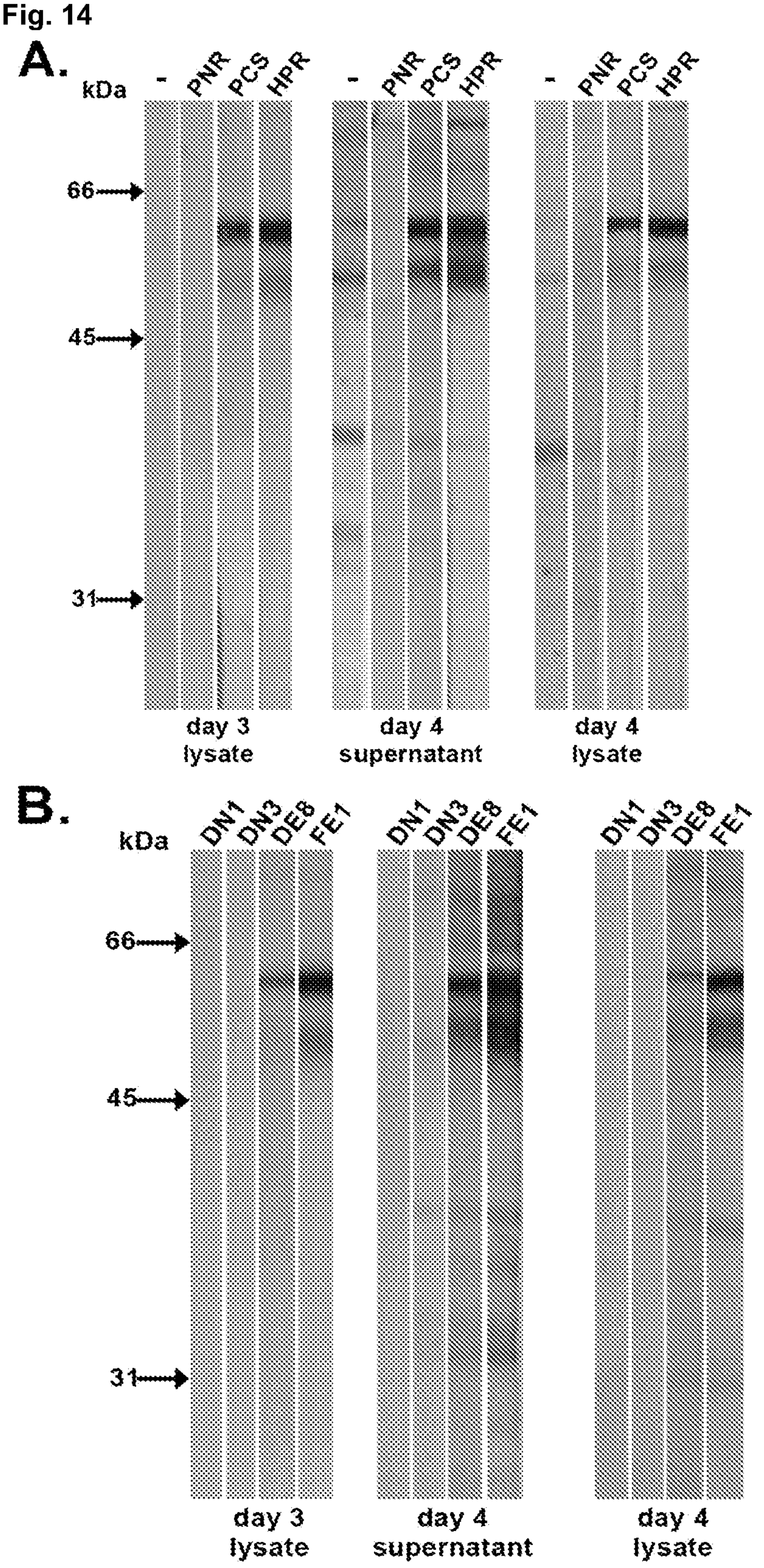
FIGS. 14A-14B show expression of secreted DENV2 E using a recombinant baculovirus containing the DENV2 structural gene and del108CDENV2-human furin proprotein bicistronic expression cassette. Insect Sf9 cells were infected with recombinant baculovirus containing the DENV2 structural gene and del108CDENV2-human furin proprotein bicistronic expression cassette. Insect cell culture supernatants and cell pellets were harvested as described in the methods and all materials were analyzed using non-reducing SDS-PAGE and Western blot. Nitrocellulose membranes were cut into strips for Western blotting and each strip was probed with either human sera (FIG. 14A) or DENV-specific mouse monoclonal antibodies (FIG. 14B) as indicated. Abbreviations: −=negative human serum; PNR=pooled negative DENV reference sera; PCS=pooled convalescent DENV sera; HPR=pooled high positive DENV reference sera; DN=DENV NS1-specific monoclonal antibody; DE=DENV envelope (E)-specific monoclonal antibody; FE=flavivirus envelope (E)-specific monoclonal antibody.

Importantly, FIG. 14 also demonstrated that significant amounts of the DENV2 E were present in the culture supernatant, demonstrating the presence of secreted properly processed DENV2 E.

In an effort to determine if a virus-like particle was secreted into the culture supernatant, a large 1 liter culture of insect cells was infected with the recombinant baculovirus containing the DENV2 Single Promoter Bicistronic VLP Expression Cassette. The cell lysate and culture supernatant were harvested and the supernatant was processed using a 750 kDa ultrafiltration step. All materials were then analyzed by SDS-PAGE and Western as described above; however, both reduced and non-reduced samples were analyzed but only human HPR and mAb FE1 were used to probe blots.

As demonstrated in FIG. 15, mAb FE1 detected the DENV2 E doublet in non-reduced samples in the lysate, supernatant and ultrafiltration retentate; however amounts appeared quite low in the retentate (A). DENV2 E was only faintly detected in reduced supernatant samples (B); however, significant DENV2 E was present in the ultrafiltration retentate.

Figure 16:
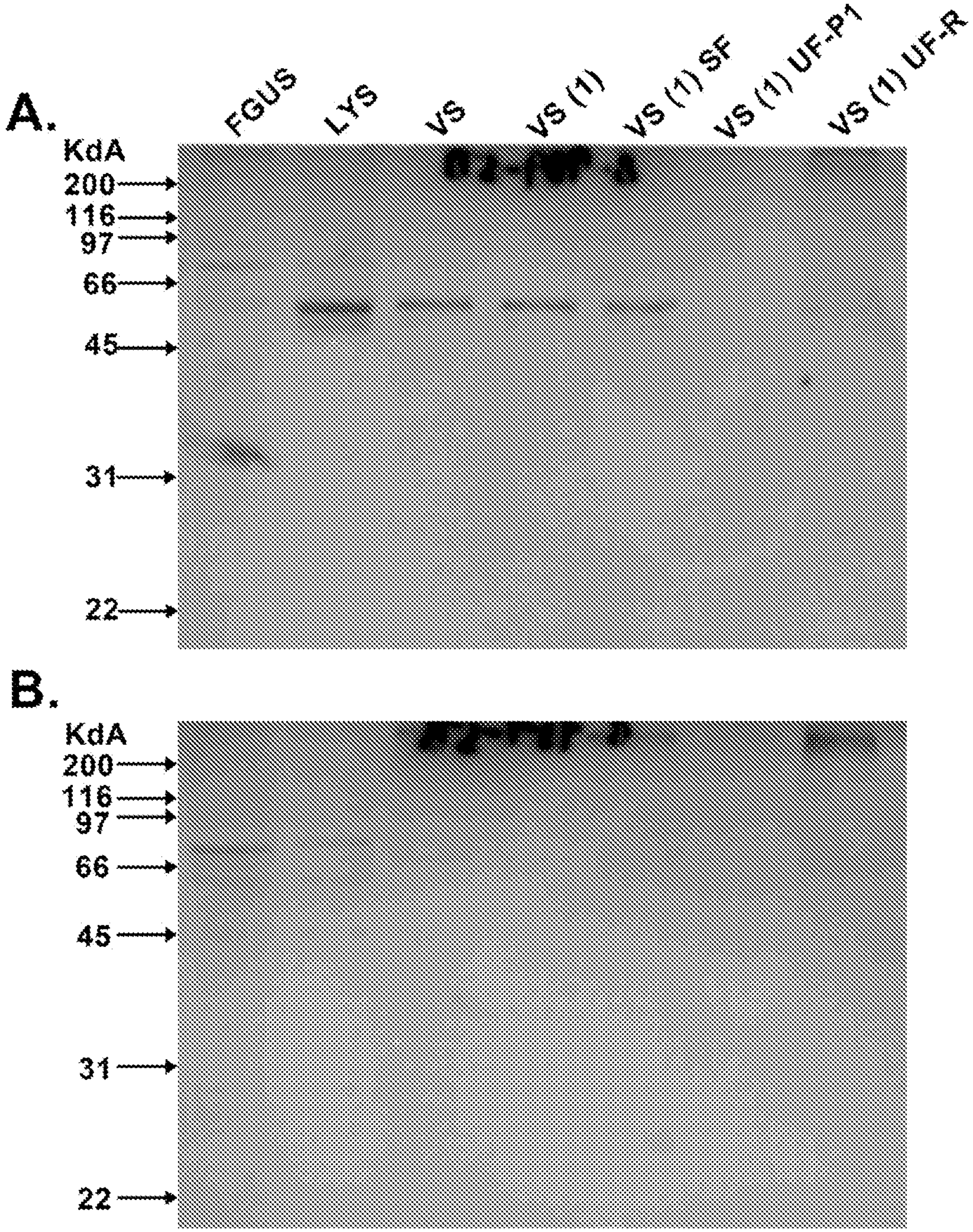
FIGS. 16A-16B show further characterization of secreted DENV2 E expressed using a recombinant baculovirus containing the DENV2 structural gene and del108CDENV2-human furin proprotein bicistronic expression cassette. Insect Sf9 cells were infected with recombinant baculovirus containing the DENV2 structural gene amd del108CDENV2-human furin proprotein bicistronic expression cassette. Cell culture supernatants and cell pellets were harvested as described in the methods. Following ultrafiltration (membrane cutoff size of 750 kDa), permeate and retentate were collected. All materials were analyzed using SDS-PAGE under non-reducing (FIG. 16A) or reducing (FIG. 16B) conditions and Western blot. Western blots were probed with pooled high positive DENV reference sera. Abbreviations: FGUS=negative baculovirus control; LYS=cell lysate; VS=viral supernatant; VS (1)=freeze-thawed viral supernatant; VS (1) SF=sterile filtered viral supernatant; VS (1) UF-P1=sterile filtered viral supernatant ultrafiltration permeate; VS (1) UF-R1=sterile filtered viral supernatant ultrafiltration retentate.

As demonstrated in FIG. 16, DENV HPR detected the DENV2 E doublet in non-reduced samples in the lysate, supernatant and ultrafiltration retentate; and although amounts of secreted E appear to be low in the retentate, a high molecular weight secreted DENV2 E species is present at the very top of the blot (A). DENV2 E was only faintly detected in reduced supernatant samples (B); however, significantly, a high molecular weight secreted DENV2 E species was present in the ultrafiltration retentate.

Together the data in FIGS. 15 and 16 suggest a large molecule weight species of secreted E is generated by the DENV2 Single Promoter Bicistronic VLP Expression Cassette.

Figure 17:
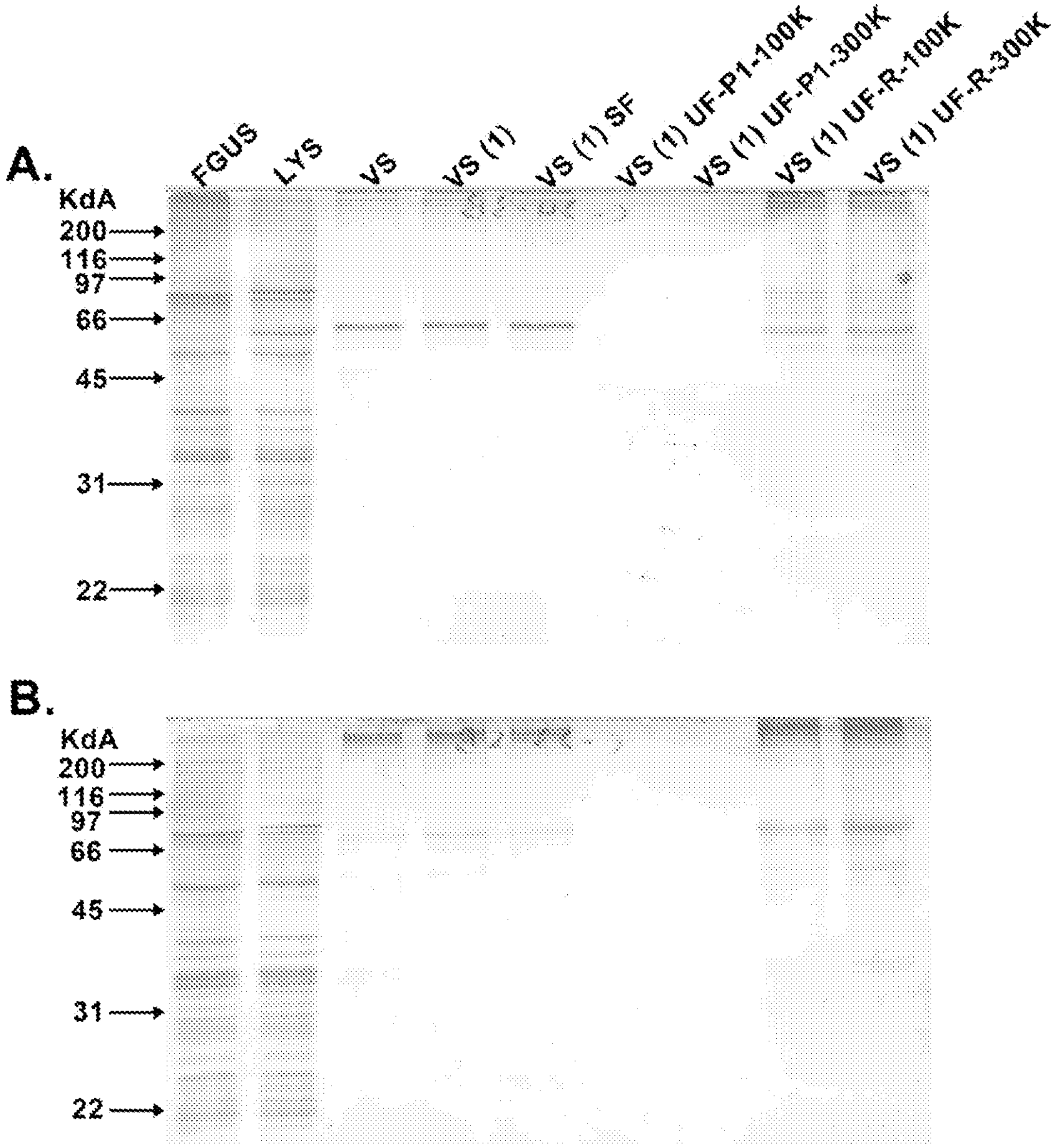
FIGS. 17A-17B show additional characterization of secreted DENV2 E expressed using a recombinant baculovirus containing the DENV2 structural gene and del108CDENV2-human furin proprotein bicistronic expression cassette. Insect Sf9 cells were infected with recombinant baculovirus containing the DENV2 structural gene and del108CDENV2-human furin proprotein expression cassette. Cell culture supernatants and cell pellets were harvested as described in the methods. Following ultrafiltration (membrane cutoff sizes of 100 or 300 kDa), permeate and retentate were collected. All materials were analyzed using SDS-PAGE under non-reducing (FIG. 17A) or reducing (FIG. 17B) conditions and Western blot. Western blots were probed with pooled high positive DENV reference sera. Abbreviations: FGUS=negative baculovirus control; LYS=cell lysate; VS=viral supernatant; VS (1)=freeze-thawed viral supernatant; VS (1) SF=sterile filtered viral supernatant; VS (1) UF-P1=sterile filtered viral supernatant ultrafiltration permeate; VS (1) UF-R1=sterile filtered viral supernatant ultrafiltration retentate.

The experiment was repeated and the cell lysate and culture supernatant were harvested and the supernatant was processed using either a 100 or 300 kDa ultrafiltration step. All materials were then analyzed by SDS-PAGE and Western as described above; however, both reduced and non-reduced samples were analyzed but only human HPR was used to probe blots. Results are shown in FIGS. 17A-B and demonstrate a large molecular weight species of secreted DENV2 E, suggesting a virus-like-particle.

Figure 18:
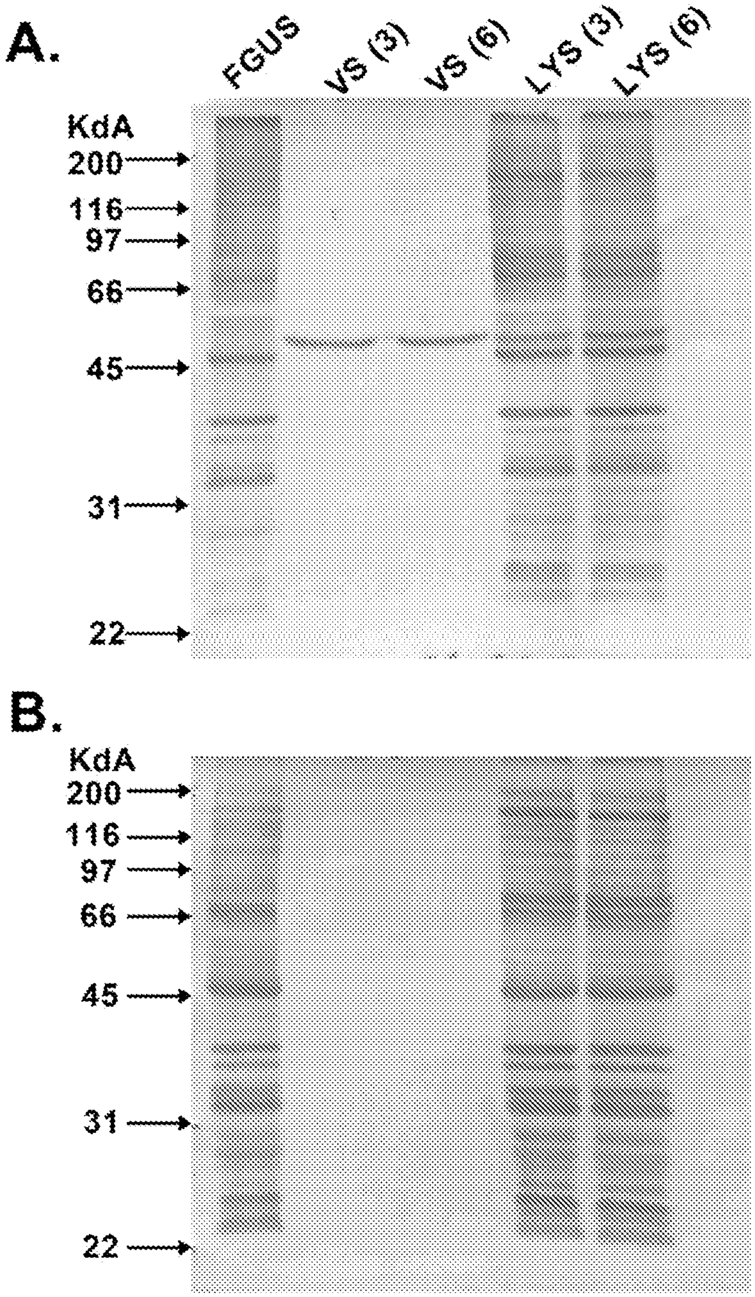
FIGS. 18A-18B show characterization of secreted ZIKV E expressed using a recombinant baculovirus containing the ZIKV structural gene and del108CDENV2-human furin proprotein bicistronic expression cassette. Insect Sf9 cells were infected with recombinant baculovirus containing the ZIKV structural gene and del108CDENV2-human furin proprotein bicistronic expression cassette. Cell culture supernatants and cell pellets were harvested as described in the methods and all materials were analyzed using SDS-PAGE under non-reducing (FIG. 18A) or reducing (FIG. 18B) conditions and Western blot. Western blots were probed with the flavivirus envelope (E)-specific monoclonal antibody FE5. Abbreviations: FGUS=negative baculovirus control; LYS=cell lysate; VS=viral supernatant. Results from two recombinant baculoviruses derived from two independent clones (3 and 6) are shown.
Figure 19:
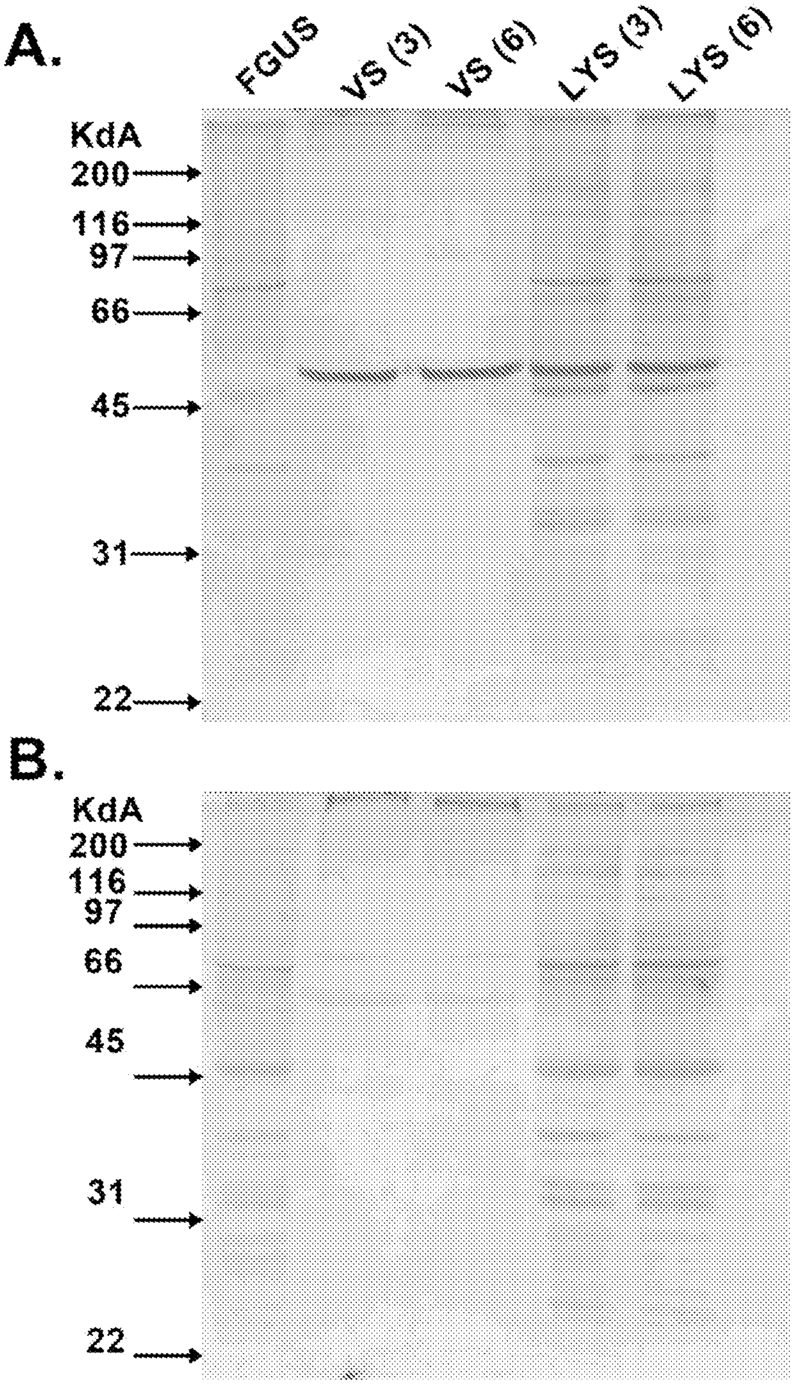
FIGS. 19A-19B show further characterization of secreted ZIKV E expressed using a recombinant baculovirus containing the ZIKV structural gene and del108CDENV2-human furin proprotein bicistronic expression cassette. Insect Sf9 cells were infected with recombinant baculovirus containing the ZIKV structural gene and del108CDENV2-human furin proprotein bicistronic expression cassette. Cell culture supernatants and cell pellets were harvested as described in the methods, and all materials were analyzed using SDS-PAGE under non-reducing (FIG. 19A) or reducing (FIG. 19B) conditions and Western blot. Western blots were probed with pooled high positive DENV reference sera. Abbreviations: FGUS=negative baculovirus control; LYS=cell lysate; VS=viral supernatant. Results from two recombinant baculoviruses derived from two independent clones (3 and 6) are shown.

Similar experiments were done with the ZIKV VLP cassette. The recombinant baculovirus was used to infect insect cells and the culture supernatants or cell lysates were collected at day 4 post-infection and analyzed using SDS-PAGE and Western blot. Blots from non-reduced samples were probed seropositive DENV reference serum or with FE5, a flavivirus E-specific monoclonal antibody (mAb). Results are shown in FIGS. 18 (mAb) and FIG. 19 (DENV reference serum). As demonstrated in FIG. 18, FE5 mAb detected fully processed ZIKV E in non-reduced samples in the lysate and supernatant and the majority of E was in the supernatant (A). ZIKV E was only faintly detected in reduced supernatant samples (B). As demonstrated in FIG. 19, DENV HPR recognized fully processed ZIKV E in non-reduced samples in the lysate and supernatant and the majority of processed ZIKV E was in the supernatant (A). Importantly, a high molecular weight secreted ZIKV E species was present at the very top of the blot. Secreted ZIKV E was only faintly detected in reduced supernatant samples (B); however, significantly, a high molecular weight species of secreted ZIKV E was present.

Figure 20:
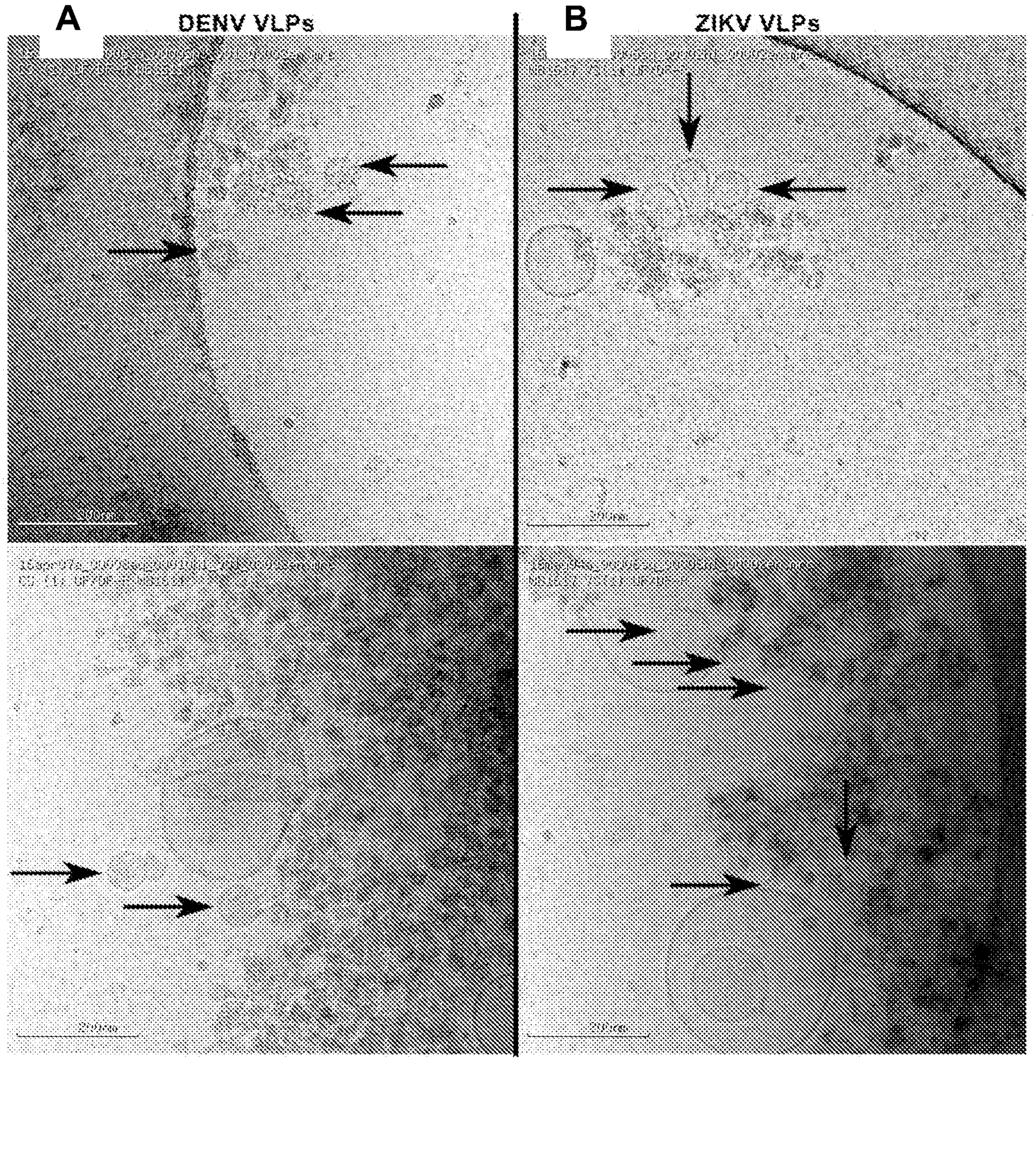
FIGS. 20A-20B show additional characterization of secreted DENV2 or ZIKV E expressed using a recombinant baculovirus containing the DENV2 or ZIKV structural gene bicistronic human furin proprotein expression cassette. Insect Sf9 cells were infected with recombinant baculovirus containing the DENV2 (A, left panels) or ZIKV (B, right panels) structural gene and del108C-DENV2-human furin proprotein expression cassette. Cell culture supernatants and cell pellets were harvested as described in the methods. Following ultrafiltration and diafiltration (membrane cutoff sizes of 300 or 100 kDa), retentate was collected and imaged using electron microscopy. Electron micrographs of two different grids showing DENV2 VLPs (A; left) or two different grids showing ZIKV VLPs (B; right). Magnification was 52000× scale bars are shown. Baculovirus particles (rod shaped ~45 nm in diameter and ~250 nm in length) as well as enveloped virus-like-particles similar in size to DENV (~40-50 nm, black arrows) were present in the material imaged.

In further efforts to determine if a virus-like particle was secreted into the culture supernatant, 1 liter and 0.4 liter cultures of insect cells were infected with the recombinant baculoviruses containing the DENV2 and ZIKV Single Promoter Bicistronic VLP Expression Cassettes, respectively. The cell lysates and culture supernatants were harvested and the supernatant was clarified by centrifugation and further processed using 300 or 100 kDa ultrafiltration and diafiltration, respectively. The retentates were initially analyzed by Western blot to verify that secreted DENV2 and ZIKV E were present (data not shown) and subsequently analyzed using cryo transmission electron microscopy (cryoTEM). Importantly, as demonstrated in FIG. 20, baculovirus particles as well as enveloped virus-like-particles the approximate size of DENV2 (A, upper and lower panels) and ZIKV (B, upper and lower panels) (40-50 nm) were evident in electron micrographs of the retentates.

Figure 21:
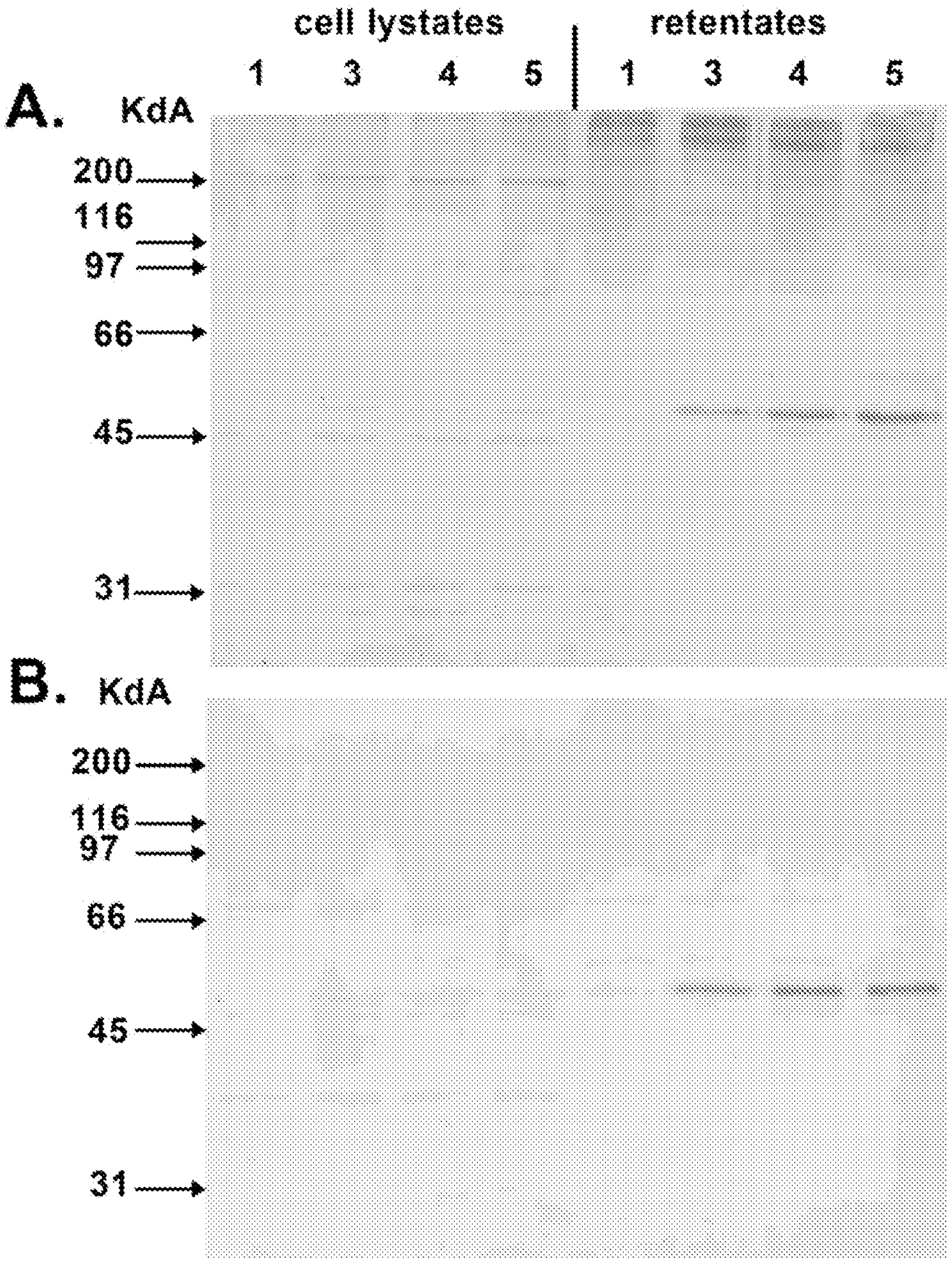
FIGS. 21A-21B show additional characterization of secreted ZIKV E expressed using three different ZIKV structural gene and human furin proprotein bicistronic expression cassettes: bacIRA3 (ZIKV del108C-prM-E and del108CDENV2-human furin proprotein), bacIRA4 (ZIKV del108C-prM-E and human furin proprotein) and bacIRA5 (ZIKV del108C-prM-E and del108CZIKV-human furin proprotein). Insect Sf9 cells were infected with recombinant baculovirus bacIRA3, bacIRA4 or bacIRA5. Cell culture supernatants and cell pellets were harvested as described in the methods. Following ultrafiltration and diafiltration (membrane cutoff size of 300 kDa), retentate was collected. Cell lysates and retentates were analyzed using SDS-PAGE and Western blot. Western blots were probed with ZIKV patient serum (FIG. 21A) or mouse monoclonal antibody FE5 (FIG. 21B); for both blots 1: baculovirus control; 3: bacIRA3; 4: bacIRA4; 5: bacIRA5.

To further characterize VLP expression cassettes, a head-to-head comparison was undertaken using the three different ZIKV VLP expression cassettes (bacIRA3, bacIRA4 and bacIRA5). Each cassette has the same ZIKV del108C-prM-E upstream of the IRES, but bacIRA3 has the del108C from DENV2 genetically fused to the human furin signal peptide (hfsp), bacIRA4 has no del108C upstream of hfsp and bacIRA5 has the homologous del108C from ZIKV fused to the hfsp. For each, a 0.4 liter culture of insect cells was infected with the corresponding recombinant baculovirus. The cell lysates and culture supernatants were harvested and the supernatants were clarified by centrifugation and further processed using 300 kDa ultrafiltration and diafiltration. The cell lysates and retentates were analyzed by Western blot to compare the amounts of secreted ZIKV E generated by each ZIKV VLP expression cassette. As shown in FIG. 21A-B, significant amounts of ZIKV E were present in the retentates for all three expression cassettes (lanes 3, 4 and 5). Importantly, as 300 kDa MWCO cartridges were used for ultrafiltration, the ZIKV E detected in retentates reflects a high molecular weight species of E and, together with the electron microscopy data, suggest significant amounts of ZIKV VLPs are present in all 3 retentates. Additionally, the ZIKV VLP expression cassette containing homologous ZIKV del108C upstream of human furin demonstrated the highest amounts of ZIKV E expression (lane 5).

Figure 22A:
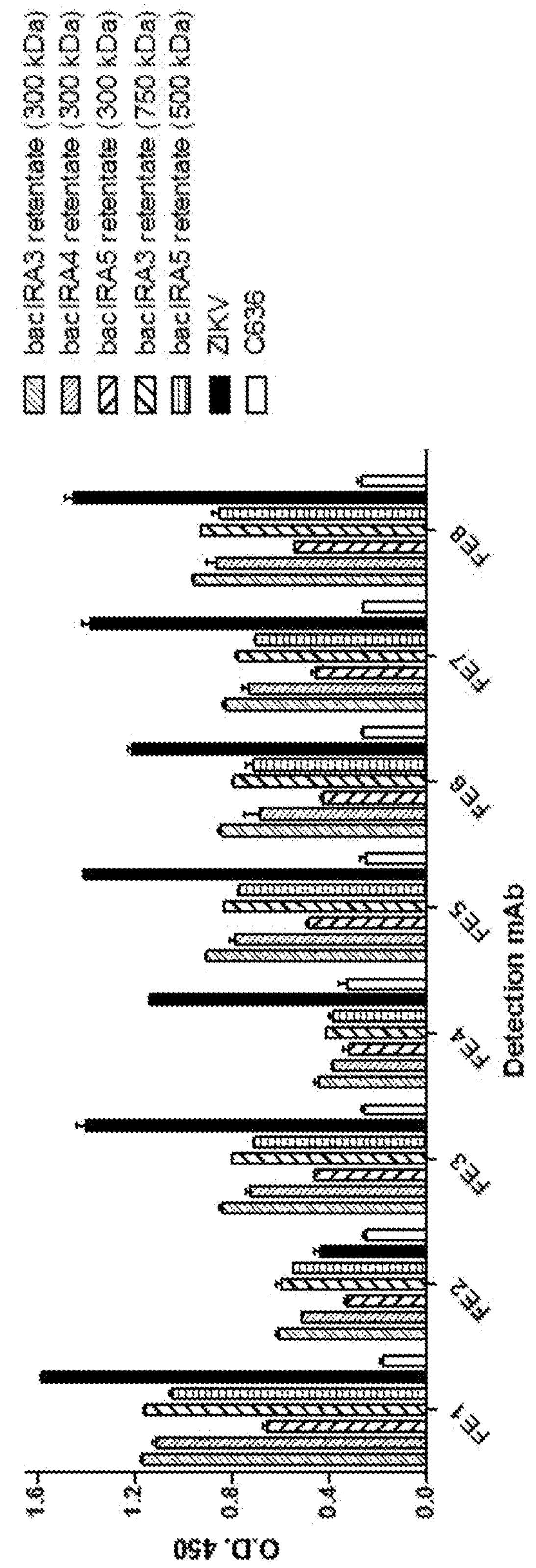
FIG. 22A-22B shows binding of neutralizing monoclonal antibodies to secreted ZIKV or DENV2 E present in retentates generated using 3 different ZIKV VLP expression cassettes (FIG. 22A) or a single DENV2 VLP expression cassette (FIG. 22B). The specific VLP expression cassette used to make the retentate and the membrane cutoff size used for ultrafiltration and diafiltration are shown in the legend. ELISA plates were coated with human anti-IgG, blocked, and incubated with ZIKV or DENV patient serum. Retentate, infectious ZIKV, DENV2 or a nonspecific insect antigen (C636 and C6362) was added to appropriate wells. Subsequently, 8 cross-reactive mouse monoclonal antibodies (FE1-FE8; shown on the x-axis) were added followed by rabbit anti-mouse-HRP. Plates were developed using TMB using standard protocols and the optical density (O.D.) at 450 nm was measured (y-axis). Of the mouse monoclonal antibodies used, all neutralize both ZIKV and DENV2 except FE2, which does not neutralize ZIKV or DENV2. All 7 ZIKV-neutralizing antibodies bound ZIKV and DENV2 secreted E except FE4, which did not bind well to ZIKV or DENV2 secreted E captured from retentates.
Figure 22B:
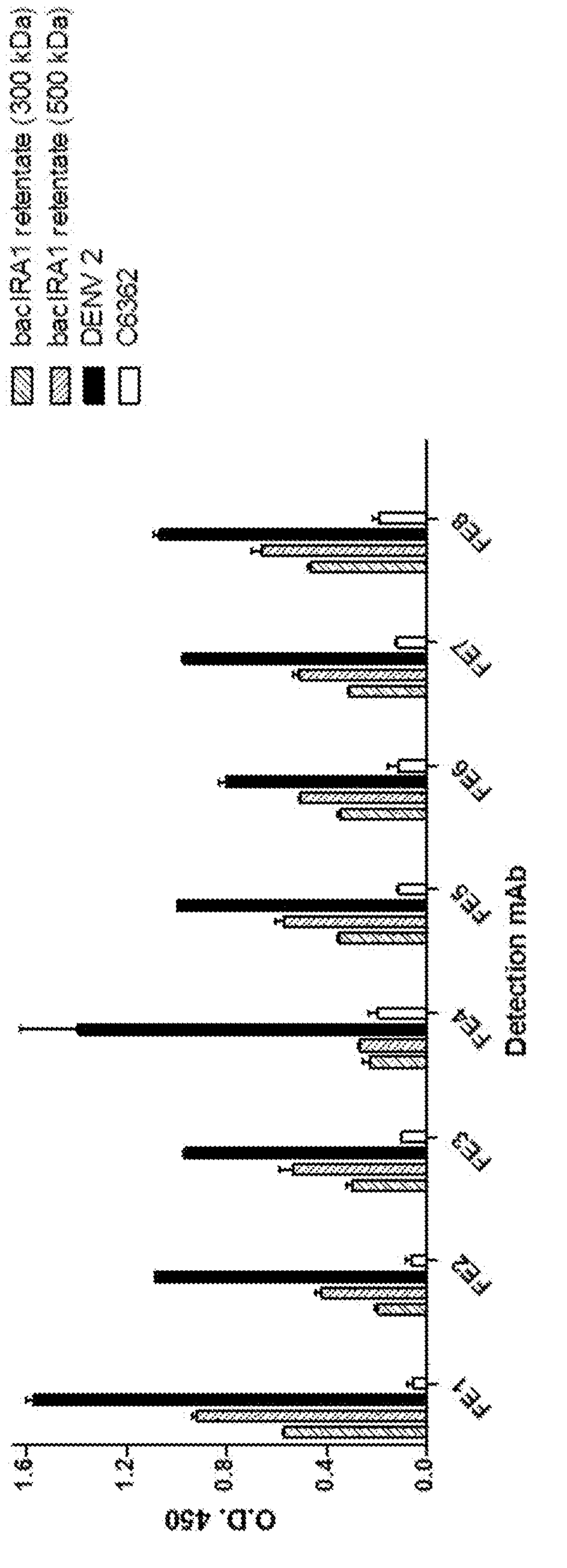

To assess the antigenic potential of the high molecular weight species of ZIKV and DENV2 E generated using the ZIKV and DENV2 VLP expression cassettes, retentates from studies described above were assayed using an in vitro VLP potency ELISA as described in the methods. For these studies, three additional 1 liter cultures of insect cells were infected with bacIRA1, bacIRA3 or bacIRA5 and cell lysates and culture supernatants were harvested as described above. However, following clarification by centrifugation, supernatants were processed using 500 or 750 kDa ultrafiltration and diafiltration and retentates were then assayed using the in vitro VLP potency ELISA. Eight E-specific mouse monoclonal antibodies are used in the VLP potency assay of which 7 neutralize ZIKV and DENV2 and one (FE2) is non-neutralizing. Importantly, as shown in FIG. 22A, for all 5 retentates generated using ZIKV VLP expression cassettes, captured high molecular weight ZIKV E was bound by 6 of 7 E-specific neutralizing antibodies, demonstrating the presence of ZIKV E-specific neutralizing epitopes in the high molecular weight species of ZIKV E. Similarly, as shown in FIG. 22B, for retentates generated using a DENV2 VLP expression cassette, captured high molecular weight DENV2 E was bound by all E-specific neutralizing antibodies, demonstrating the presence of DENV2 E-specific neutralizing epitopes in the high molecular weight species of DENV2 E.

Figure 23A:
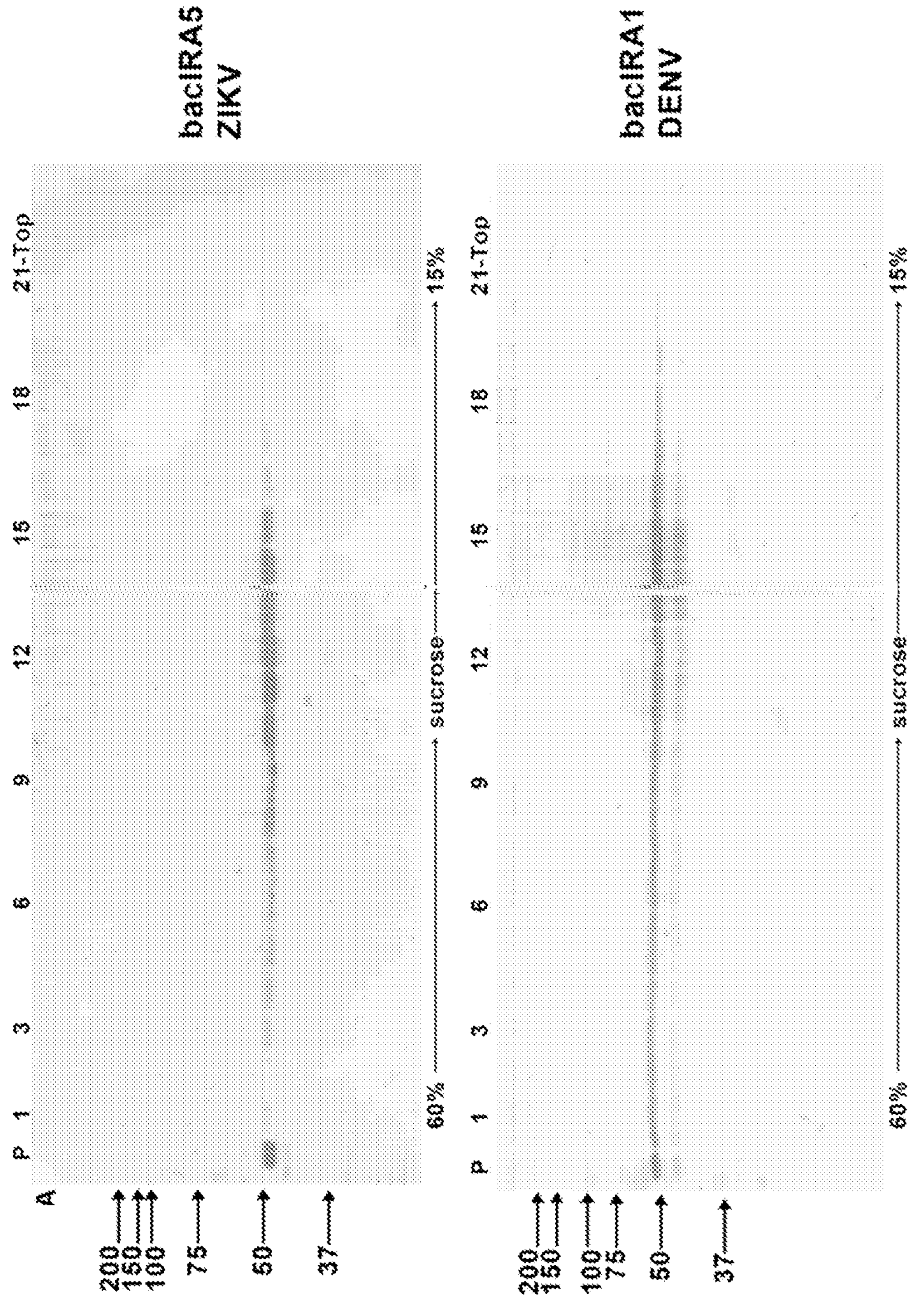
FIGS. 23A-23B show the results of sucrose gradient sedimentation experiments. Retentates (described in FIG. 22) were centrifuged at 21,000×g. Supernatants were removed and pellets were resuspended in NTE buffer and overlaid onto discontinuous sucrose gradients (15-60%). Gradients were centrifuged at 17,000 rpm for 18 hours and 2 ml fractions were collected from each gradient. Fractions were analyzed using SDS-PAGE and Western blot and blots were probed with ZIKV or DENV patient serum. Sucrose gradient fractions from bacIRA5 retentate (500 kDA) and bacIRA1 retentate (500 kDA) are shown as representative examples (FIG. 23A). For each gradient, fractions containing ZIKV or DENV2 VLPs were pooled, diluted, buffer exchanged and concentrated. For each, retentate starting material, diluted fractions containing ZIKV or DENV2 VLPs, concentrator flow through and purified ZIKV or DENV2 VLPS were analyzed using SDS-PAGE and Western blot and blots were probed with ZIKV or DENV patient serum (FIG. 23B). The specific ZIKV or DENV2 VLP expression cassette used to make the retentate and the membrane used for ultrafiltration and diafiltration are shown above the blots. Samples were loaded in the following order: retentate starting material, diluted fractions containing ZIKV or DENV2 VLPs, concentrator flow through and purified ZIKV or DENV2 VLPs. Purified ZIKV or DENV2 VLPs are further indicated by the arrows.
Figure 23B:
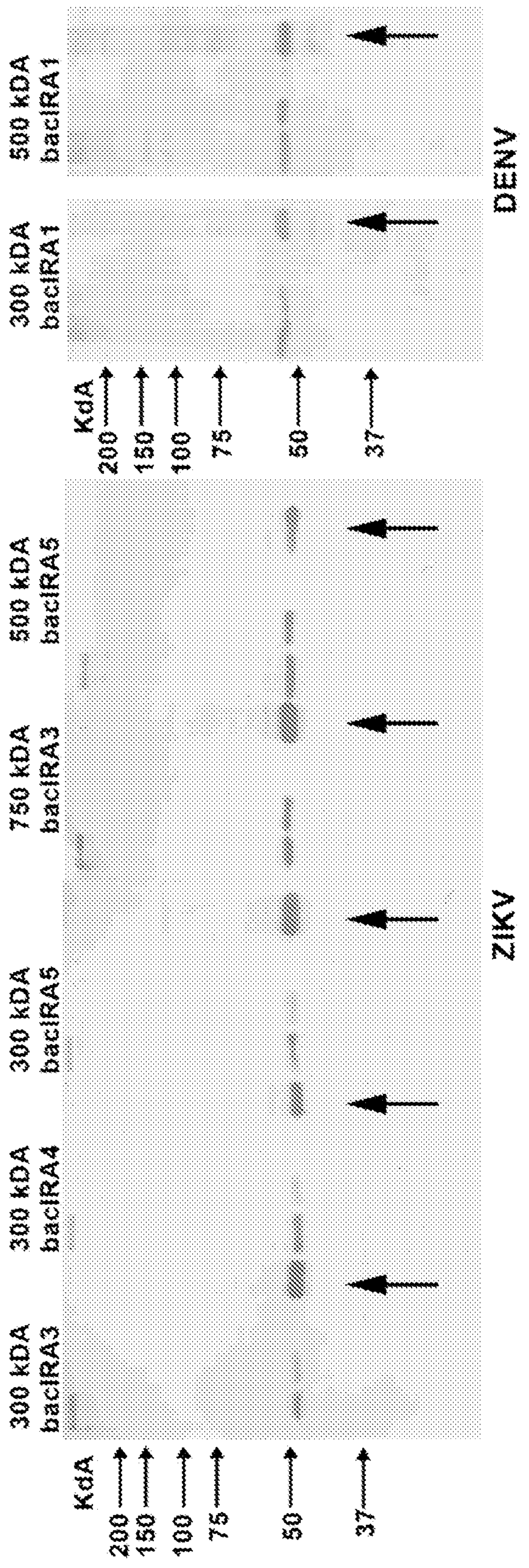
Figure 24:
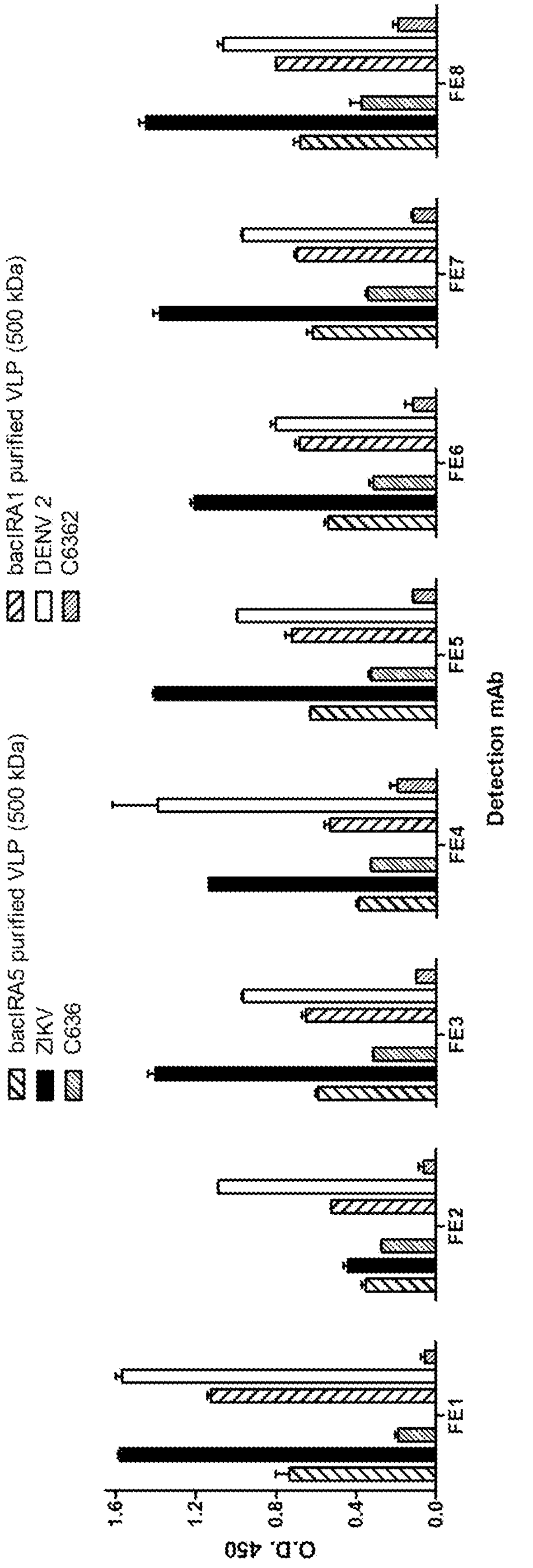
FIG. 24 shows binding of neutralizing monoclonal antibodies to purified ZIKV or DENV2 VLPs. Plates were coated with human anti-IgG, blocked and incubated with ZIKV or DENV patient serum (1:1000). Purified ZIKV VLPs, infectious ZIKV or nonspecific insect cell antigen (C636), purified DENV2 VLPs, DENV2 or nonspecific insect cell antigen (C6362) was added to appropriate wells. Subsequently, 8 cross-reactive mouse monoclonal antibodies (FE1-FE8; shown on the x-axis) were added followed by rabbit anti-mouse-HRP (1:8000). Plates were developed using TMB using standard protocols and the optical density (O.D.) at 450 nm was measured (y-axis). Of the mouse monoclonal antibodies used, all neutralize both ZIKV and DENV2 except FE2, which does not neutralize ZIKV or DENV2. All 7 ZIKV-neutralizing antibodies bound ZIKV and DENV2 secreted E except FE4, which did not bind well to purified ZIKV VLPs.

To further determine if the high molecular weight species of ZIKV or DENV E seen in retentates was a VLP, classical sucrose gradient sedimentation studies were undertaken. The 7 retentates described in FIG. 22 were used for these studies. Each was centrifuged at 21,000×g, supernatant was removed and the pellet was resuspended in NTE overnight and then overlaid on a discontinuous sucrose gradient (15-60%). After centrifugation, 2 ml fractions were collected from the top of the gradient to the bottom and fractions were analysed by Western blot. Results from retentates made using bacIRA5 (ZIKV) and bacIRA1 (DENV2) and 500 kDa ultrafiltration and diafiltration are shown in FIG. 23A. Importantly, ZIKV and DENV2 VLPs were predominantly detected in fractions 9-16, a distribution nearly identical to those published previously for flavivirus viral particles [Putnak R, et al., *J Infect Dis*. December; 174(6): 1176-84, 1996]. Further, although only two representative gradients are shown for ZIKV and DENV E, all 7 retentates gave nearly identical results, suggesting that all VLP expression cassettes generated secreted ZIKV or DENV2 VLPs with a density similar to that seen for flavivirus particles. For each sucrose gradient, fractions containing ZIKV or DENV2 VLPs were pooled, diluted, buffer exchanged and then concentrated. Western blot analysis of pooled fractions and purified concentrated ZIKV or DENV2 VLPs are shown in FIG. 23B. The highest yield of purified ZIKV VLPs was from the retentate generated using bacIRA5 (contains del108CZIKV upstream of human furin) and processed using 500 kDa ultrafiltration and diafiltration. The retentate generated using bacIRA1 (contains del108CDENV2 upstream of human furin) and processed using 500 kDa ultrafiltration and diafiltration demonstrated DENV2 VLP yields similar to the high ZIKV VLP yields generated using bacIRA5. The ZIKV VLPs generated with bacIRA5 were chosen for immunogenicity and efficacy studies. Prior to starting in vivo studies, the purified ZIKV VLPs as well as the purified DENV2 VLPs were analysed using the in vitro VLP potency ELISA. As shown in FIG. 24, purified ZIKV VLPs were bound by 6 or 7 E-specific mouse neutralizing monoclonal antibodies and purified DENV2 VLPs were bound by all E-specific mouse neutralizing monoclonal antibodies.

Figure 25:
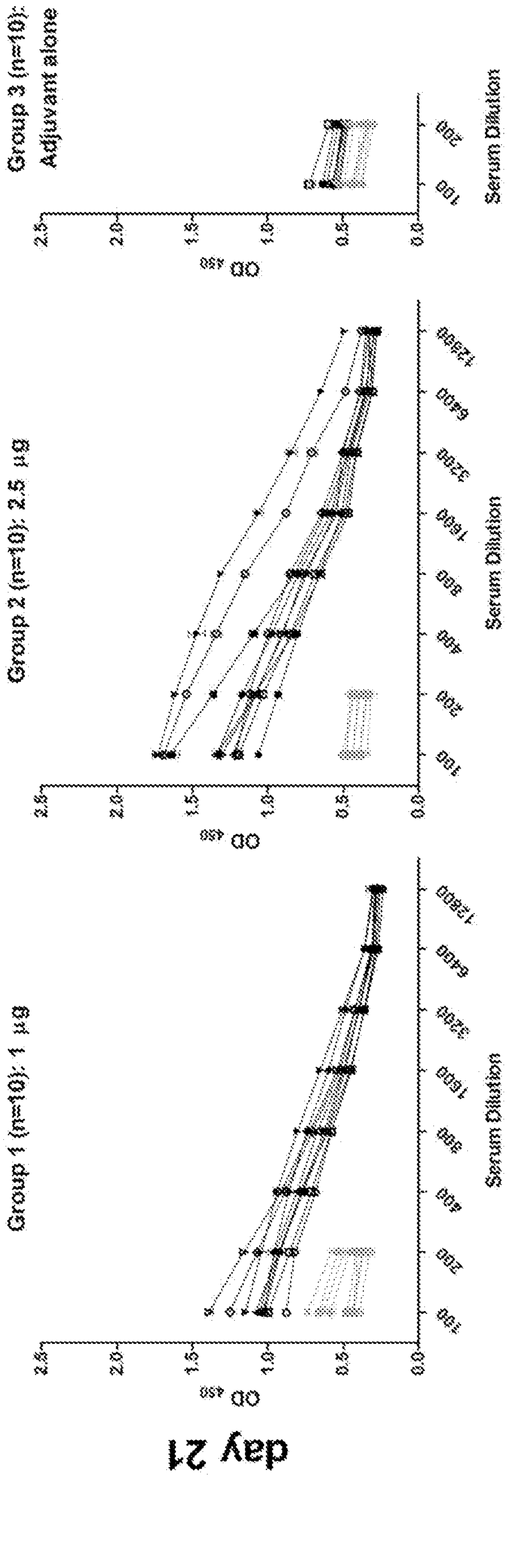
FIG. 25 shows total ZIKV-specific immunoglobulins (Ig) in mice immunized with purified ZIKV VLPs. Plates were coated with human anti-IgG. After blocking, ZIKV patient serum (1:1000) was added followed by infectious ZIKV or nonspecific insect cell antigen (C636). Subsequently, serum samples from ZIKV VLP-immunized mice were added to followed by rabbit anti-mouse-HRP (1:8000). Plates were developed using TMB using standard protocols and the optical density (O.D.) at 450 nm was measured (y-axis). Serum dilution is shown on the x-axis and each line represents one animal. Group number and ZIKV VLP dose are shown above the graphs and sample day is shown to the left of the graphs. Serum samples from day 0 for each group are shown in gray on day 21 and day 42 graphs.
Figure 25:
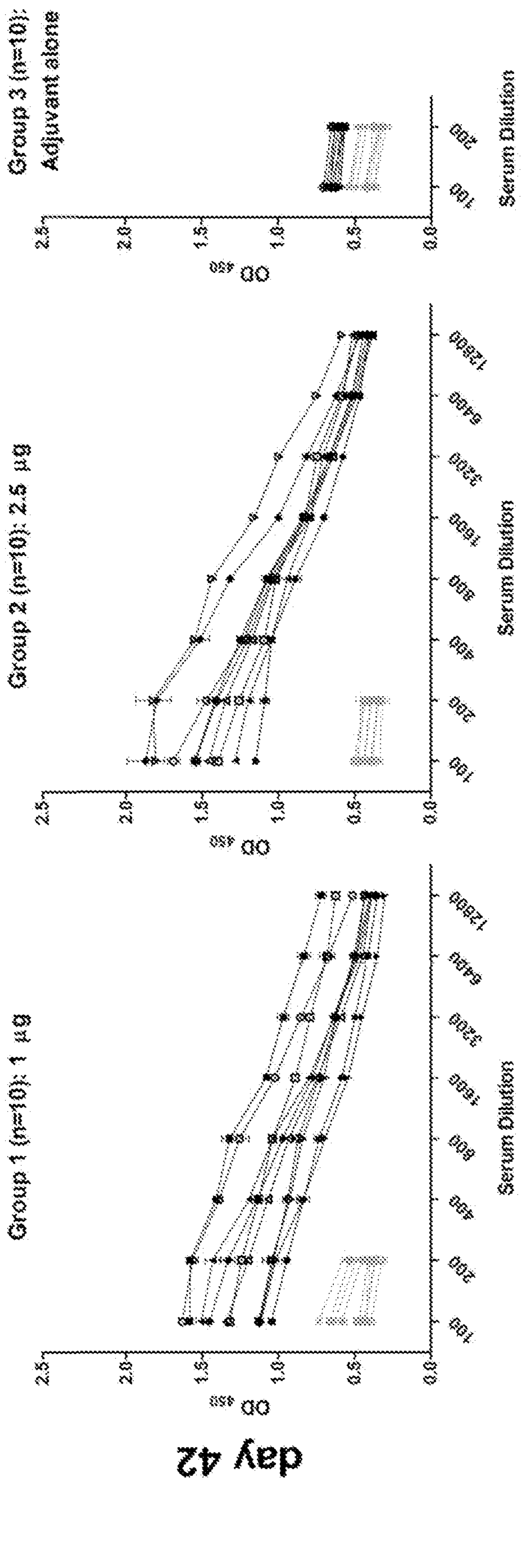

To assess VLP immunogenicity, purified ZIKV VLPs were used to immunize wildtype C57BL/6 mice. Two groups of mice (n=10 per group) were immunized with ZIKV VLPs. Group 1 animals received 1 μg ZIKV VLPs twice administered intramuscularly. Animals in Group 2 received 2.5 μg ZIKV VLPs twice i administered intramuscularly. For both groups, prime and boost were done 21 days apart and VLPs were mixed with adjuvant (0.1% Alhydrogel) just prior to immunization. A third group of animals (n=10) received adjuvant alone on the same schedule. Serum was collected from all animals prior to prime (day 0), prior to boost (day 21) and 3 weeks after boost (day 42). ZIKV-specific immunoglobulins (Ig) in sera from immunized mice were measured using an indirect ELISA as described in the methods and results are shown in FIG. 25. Importantly, all animals that were immunized with ZIKV VLPs had detectable ZIKV-specific Ig in serum on day 21 and levels increased with dose and following boost (day 42). By comparison, ZIKV-specific Ig was not found in animals that received adjuvant alone. Mouse serum samples were also assayed in PRNT and ZIKV neutralizing antibodies were detected in all animals except one in Group 1 (Table 1) and adjuvant alone animals (data not shown).

TABLE 1

ZIKV-specific neutralizing antibody responses in mice immunized with ZIKV VLP[1]

| Mouse # | Group 1 day 21 | Group 1 day 42 | Group 2 day 21 | Group 2 day 42 |
|---|---|---|---|---|
| 1 | 28.6 | 10.8 | 34.9 | 13.8 |
| 2 | −4.6 | 15.3 | 60.7 | 47.0 |
| 3 | 44.7 | 7.1 | 43.7 | 53.1 |
| 4 | 23.1 | 7.4 | 53.0 | ND |
| 5 | 36.9 | 59.2 | 42.9 | 100* |
| 6 | 29.6 | 50.8 | 73.9 | 51.8 |
| 7 | 8.5 | 45.6 | 67.4 | 39.2 |
| 8 | 12.4 | 10.6 | 27.3 | 78.4 |
| 9 | 36.1 | 30.3 | 19.0 | 74.8 |
| 10 | 7.6 | 11.4 | 49.4 | 42.3 |
| Average | 22.3 | 24.9 | 47.2 | 55.6 |

[1]Percent ZIKV neutralization at 1:16 serum dilution

Individual serum samples from group 1 animals demonstrated a range of ZIKV neutralization (7-59%) and as an averaged group demonstrated 22% neutralization on day 21 and 25% neutralization on day 42. Individual serum samples from group 2 animals also demonstrated a range of ZIKV neutralization (27-100%) and as an averaged group demonstrated 47% neutralization on day 21 and 56% neutralization on day 42. Importantly these data demonstrate that the purified ZIKV VLPs are immunogenic and elicit ZIKV-neutralizing antibodies in vivo.

Recently, a new highly lethal mouse model of ZIKV neuropathogenesis was described [Smith D R, et al., *PLoS Negl Trop Dis* 11(1): e0005296. doi:10.1371/journal.pntd.0005296 (2017)] that used immunocompetent wildtype C57BL/6 mice. This highly relevant mouse model was used to evaluate the efficacy of the new ZIKV VLP vaccine candidates. All mice from the ZIKV VLP immunogenicity studies (Groups 1, 2 and 3 described above) were inoculated with a lethal dose of ZIKV three weeks after boost (day 42). Animals were monitored for disease following challenge and survival curves were generated for each group of mice. As demonstrated in FIG. 26, none of the mice in the adjuvant alone group survived. Conversely, 50% of the animals in Group 1 and 80% of the animals in Group 2 survived ZIKV challenge and survival seemed to correlate to neutralization activity higher than 15% (Table 1). Importantly, although the two doses of ZIKV VLP used were considered suboptimal, performance was significant even in the lowest dose group (1 μg). Most importantly, the data demonstrate that ZIKV VLP immunizations afford protection against lethal ZIKV challenge highlighting their exceptional vaccine potential.

Discussion

A new bicistronic expression cassette for DENV VLP production that included both DENV prM-E and furin was designed. The new cassette also included key transcriptional and translational regulatory elements as well as a novel signal sequence strategy in an attempt to co-locate DENV prM-E and furin during cell trafficking. FIG. 2 details the features of the new DENV VLP expression cassette and includes two similar ZIKV VLP expression cassettes. After comparing the furin amino acid sequence from Sf9 cells to the human furin proprotein sequence, significant discrepancies, including whole domain differences were noted. As this could possibly account for the low cleavage of DENV prM in Sf9 cells, we opted to use the human furin proprotein sequence in the new VLP expression cassette. Further, human furin may have less toxic effects in Sf9 cells given the differences between the Sf9 and human furin sequences which should benefit VLP production. The open reading frames (ORFs) for DENV or ZIKV prM-E and human furin proprotein were codon optimized for insect cell expression and cloned downstream of a single promoter sequentially with an Internal Ribosome Entry Site (IRES) between the two ORFs. Such an approach allows DENV or ZIKV prM-E and furin to be transcribed on one mRNA, in temporal sync, but translated independently. Also, as excess furin could cause detrimental cleavage effects in the cell, the human furin proprotein ORF was inserted downstream of the IRES to dampen expression slightly. As DENV capsid (C) protein anchors in the membrane of the ER and contains the bonafide DENV signal sequence for prM-E, a partial fragment of DENV C (del108C) was used as an ER membrane anchor and signal sequence for both DENV prM-E and human furin. By targeting both proteins to the same region of the ER membrane normally targeted by DENV prM-E we hypothesized furin and prM-E would remain in close proximity. Further, the cellular signal peptidase that cleaves the membrane anchored DENV C will be the same for both proteins as the signal sequences were identical, eliminating another potential idiosyncrasy. A similar approach was used for the ZIKV VLP expression cassette; however, in addition to the ZIKA del108C-prM-E-IRES-ZIKA del108C-human furin, cassette an additional ZIKV VLP expression cassette was made with DENV2 del108C upstream of human furin. For comparison, DENV2 and ZIKV VLP expression cassettes that lack del108C sequences upstream of human furin have also been made. For YFV and HCV, expression cassettes were made that contained the viral del108C upstream of the flavivirus structural gene and human furin as well as expression cassettes that did not contain the viral del108C upstream of human furin. All cassettes have been designed so that the region between the IRES and furin can be changed easily. Further, all cassettes contain the normal human furin signal sequence (hfsp) in case it is important for cleavage of human furin proprotein to the active human furin protein.

For other medically important arboviruses, including some flaviviruses, baculovirus-insect cell expression systems have emerged as an ideal platform for producing recombinant antigens and VLPs [Metz S W, Pijlman G P. *J Invertebr Pathol* 107 Suppl: S16-30 (2011)]. Indeed this is not too surprising as all arboviruses actively replicate in arthropod cells. For these reasons we opted to pilot expression of our new DENV and ZIKV VLP expression cassettes using recombinant baculovirus and chose the polyhedrin promoter to drive bicistronic transcription (FIG. 2). In initial experiments, Sf9 cells were infected with recombinant baculovirus expressing the bicistronic DENV VLP cassette. On day 3 and 4 post-infection cells and culture supernatants were harvested and analyzed using SDS-PAGE and Western blot and results are shown in FIG. 14A-B. Two species of DENV E with approximate molecular weights between 50 and 60 kDa were present in cell lysates and culture supernantants, consistent with previous reports of properly processed DENV E analyzed under non-reducing conditions. Importantly, the supernatant contained the highest amount of both forms of DENV E.

To further assess secreted DENV E, a 1 L Sf9 culture was employed and cells were infected with the recombinant baculovirus expressing the biscistronic DENV VLP cassette. On day 4 cells and culture supernatant were harvested and culture supernatants (VS) were freeze/thawed once (VS (1)), sterile filtered (VS (1) SF) and subjected to ultrafiltration using two different molecular weight cutoffs (100K and 300K kDA). The permeates (UF-P1) and retentates (UF-R) were collected and all materials were analyzed using SDS-PAGE under non-reduced (A) or reduced (B) conditions and Western blot using DENV HPR. Results are shown in FIG. 17A-B. Interestingly, under reduced conditions, significant amounts of a high molecular weight species of secreted DENV E was found in the culture supernatants and ultrafiltration retentates but was not present in the lysate. The high molecular weight species of secreted DENV E was also present in the non-reduced culture supernatants and ultrafiltration retentates (at the very top of the blot). Importantly, electron microscopy studies using a ultrafiltration retentate containing secreted DENV E revealed the presence of virus-like-particles similar in size to DENV. Although further characterization needs to be done, we were excited by the data as significant amounts of secreted DENV E was produced using the recombinant baculovirus platform and secreted E appears to be processed properly and form high molecular weight virus-like-particles which could represent the first scalable recombinant DENV VLP. We have also rescued the recombinant baculovirus expressing the bicistronic ZIKV VLP cassette. Importantly, in initial experiments, the majority of ZIKV E was also secreted into the culture supernatant, processed properly and forms high molecular weight species analogous to DENV VS results (FIG. 19A-B). Electron microscopy studies using a ultrafiltration retentate containing secreted ZIKV E revealed the presence of virus-like-particles similar in size to ZIKV (FIG. 20B) which optimistically suggested a recombinant ZIKV VLP vaccine may be possible, which would be ideal for pregnant women.

Figure 26:
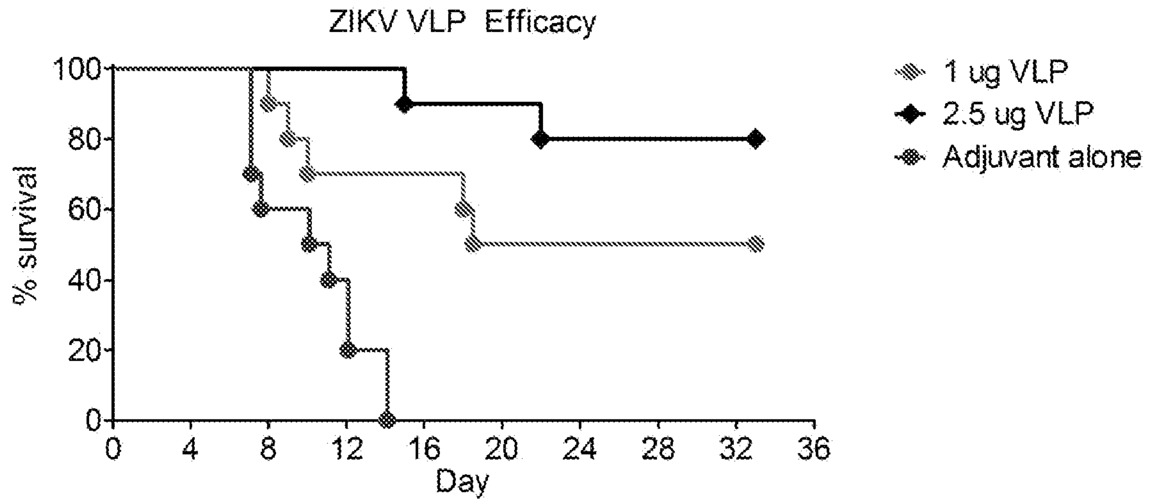
FIG. 26 shows survival of mice immunized with purified ZIKV VLPs and then challenged with a lethal dose of ZIKV. As detailed in the methods, all ZIKV VLP-immunized mice with challenged with a lethal dose of ZIKV. Animals were monitored for 5 weeks post-challenge and survival percentage on relevant days is shown for each group. All animals in the adjuvant alone group did not survive ZIKV challenge; whereas 50% of animals in Group 1 (1 μg) and 80% of animals in Group 2 (2.5 μg) survived ZIKV challenge.

We have continued to evaluate the novel VLP platform and have compared ZIKV VLP cassettes that contain heterologous, homologous or no del108C sequences upstream of human furin and have confirmed that the homologous combination leads to the highest levels of secreted ZIKV E in culture supernatants (FIG. 21A-B). We have also determined that the homologous del108C combination in the DENV2 VLP cassette leads to maximum yields of secreted DENV2 E in culture supernatants. Further, we have demonstrated that the secreted ZIKV and DENV2 E in retentates are recognized by cross-reactive neutralizing monoclonal antibodies (FIG. 22) and secreted ZIKV and DENV2 E densities are similar to flavivirus particle density (FIG. 23A). Importantly, we have shown that purified ZIKV or DENV2 VLPs retain important neutralizing epitopes (FIG. 24) and ZIKV VLPs can elicit neutralizing antibodies in the host (FIG. 25). Of most significance, we have shown that ZIKV VLP immunizations protect animals from lethal ZIKV challenge (FIG. 26).

In order to advance our understanding of potential flavivirus VLP vaccines, we believe it is essential to compare and contrast different viruses using our new flavivirus VLP expression cassette. We have prioritized DENV and ZIKV in our initial studies as recent large DENV2 vaccine trials have not produced desirable outcomes, opening the door for new vaccine ideas and ZIKV because a VLP vaccine would be ideal for pregnant women. Moreover, DENV and ZIKV co-circulate in many parts of the world and by studying the viruses and VLPs side by side we hope to determine the extent of serological cross-reactivity between the two.

BIBLIOGRAPHY

Bagcchi S. Looking back at yellow fever in Angola. *The Lancet Infectious Diseases*, Volume 17, Issue 3, 269-270, 2017.

Baumert T F, Ito S, Wong D T, Liang T J. Hepatitis C virus structural proteins assemble into viruslike particles in insect cells. *J Virol.* 1998; 72(5): 3827-36.

Butler D. First Zika-linked birth defects detected in Colombia. *Nature.* 2016; 531(7593):153.

Chan H Y, et al. "Comparison of IRES and F2A-Based Locus-Specific Multicistronic Expression in Stable Mouse Lines." *PLoS ONE* 6.12 (2011)

Charoensria N, Suphatrakul A, Sriburi R, Yasanga T, Junjhon J, Keelapang P, et al. An optimized expression vector for improving the yield of dengue virus-like particles from transfected insect cells. Journal of virological methods. 205C:116-23 (2014).

Falcón V, Acosta-Rivero N, González S, Dueñas-Carrera S, Martinez-Donato G, Menéndez I, Garateix R, Silva J A, Acosta E, Kouri J. Ultrastructural and biochemical basis for hepatitis C virus morphogenesis. *Virus Genes.* 53(2): 151-164 2017. doi: 10.1007/s11262-017-1426-2. Epub 2017 Feb. 23.

Gubler D J. Human arbovirus infections worldwide. Ann N Y Acad Sci. 2001; 951:13-24.

Gubler D J, Kuno G, Markoff L. Flaviviruses. In: Knipe D M, Howley P M, editors. Fields Virology, Fifth Edition. Philadelphia, Pa.: Lippincott Williams & Wilkins; 2007. p. 1153-252.

Haddow A D, Schuh A J, Yasuda C Y, Kasper M R, Heang V, Huy R, et al. Genetic characterization of Zika virus strains: geographic expansion of the Asian lineage. PLoS Negl Trop Dis. 2012; 6(2):e1477. PMCID: 3289602.

Halstead S B. Observations related to pathogensis of dengue hemorrhagic fever. V I. Hypotheses and discussion. Yale J Biol Med. 1970; 42(5):350-62. PMCID: 2591710.

Halstead S B. Dengue vaccine development: a 75% solution? Lancet. 2012; 380(9853):1535-6.

Hickey A C, et al., Serotype-specific host responses in rhesus macaques after primary dengue challenge. *Am J Trop Med Hyg.* 89(6): 1043-57 (2013)

Hull M W, Yoshida E M, Montaner J S. Update on Current Evidence for Hepatitis C Therapeutic Options in HCV Mono-infected Patients. *Curr Infect Dis Rep.* 2016; 18(7): 22. doi: 10.1007/s11908-016-0527-8.

Jacobson I M. The HCV Treatment Revolution Continues: Resistance Considerations, Pangenotypic Efficacy, and Advances in Challenging Populations. *Gastroenterol Hepatol* (NY). 2016; 12(10 Suppl 4): 1-11.

Kuwahara M, Konishi E. Evaluation of extracellular subviral particles of dengue virus type 2 and Japanese encephalitis virus produced by *Spodoptera frugiperda* cells for use as vaccine and diagnostic antigens. Clinical and vaccine immunology: CVI.17(10):1560-6. PMCID: 2952984 (2010).

Lindenbach B D, Theil H J, Rice C M. *Flaviviridae*: The viruses and their replication. In: Knipe D M, Howley P M, editors. Fields Virology. 5 ed. Philadelphia: Lippincott Williams & Wilkins; 2007. p. 1101-52.

Makiala-Mandanda S, Le Gal F, et al., High prevalence and diversity of hepatitis viruses in suspected cases of yellow fever in the Democratic Republic of Congo. *J Clin Microbiol.* 2017 Feb. 15. pii: JCM.01847-16. doi: 10.1128/JCM.01847-16. [Epub ahead of print].

Marcyniuk B, Mann D M A, Yates P O. J Neurol Sci. 1986; 76: 335.

Metz S W, Pijlman G P. Arbovirus vaccines; opportunities for the baculovirus-insect cell expression system. J Invertebr Pathol. 107 Suppl:S16-30 (2011).

Pang T, Cardosa M J, Guzman M G. Of cascades and perfect storms: the immunopathogenesis of dengue haemorrhagic fever-dengue shock syndrome (DHF/DSS). Immunol Cell Biol. 2007; 85(1):43-5.

Paules C I, Fauci A S. Yellow Fever—Once Again on the Radar Screen in the Americas. *N Engl J Med.* 2017 Mar. 8. doi: 10.1056/NEJMp1702172. [Epub ahead of print].

Pierson T C, Diamond M S. Degrees of maturity: the complex structure and biology of flaviviruses. Current opinion in virology. 2(2):168-75. PMCID: 3715965 (2012).

Putnak R, Barvir D A, Burrous J M, Dubois D R, D'Andrea V M, Hoke C H, Sadoff J C, Eckels K H. Development of a purified, inactivated, dengue-2 virus vaccine prototype in Vero cells: immunogenicity and protection in mice and rhesus monkeys. *J Infect Dis*. December; 174(6): 1176-84, 1996.

Smith D R, Hollidge B, Daye S, Zeng X, Blancett C, Kuszpit K, et al. (2017) Neuropathogenesis of Zika Virus in a Highly Susceptible Immunocompetent Mouse Model after Antibody Blockade of Type I Interferon. *PLoS Neg/Trop Dis* 11(1): e0005296. doi:10.1371/journal.pntd.0005296.

Song, B.-H., et al., Zika virus: History, epidemiology, transmission, and clinical presentation, *J. Neuroimmunol.* (2017), http://dx.doi.org/10.1016/j.jneuroim.2017.03.001.

Thursz M, Fontanet A. HCV transmission in industrialized countries and resource-constrained areas. *Nat Rev Gastroenterol Hepatol.* 2014; 11(1): 28-35. doi: 10.1038/nrgastro.2013.179. Epub 2013 Oct. 1.

Whitehead S S, Blaney J E, Durbin A P, Murphy B R. Prospects for a dengue virus vaccine. Nature reviews Microbiology. 2007; 5(7):518-28.

Joseph T Wu, Corey M Peak, Gabriel M Leung, Marc Lipsitch. Fractional dosing of yellow fever vaccine to extend supply: a modelling study. *The Lancet*, Volume 388, Issue 10062, 10-16, Pages 2904-2911, 2016.

The invention claimed is:

1. An expression cassette comprising;

i. a flavivirus structural gene, ii. a furin gene, and iii. a bicistronic expression element positioned between the flavivirus structural gene and the furin gene, wherein:

i) the flavivirus structural gene comprises a partial capsid protein (delC) coding sequence, a complete membrane precursor (prM) protein coding sequence, and a complete envelope (Env) protein coding sequence, wherein the delC coding sequence comprises the C-terminal anchor containing the signal sequence for prM; or ii) the flavivirus structural gene comprises a partial capsid protein (delC) coding sequence, a membrane (p7) protein coding sequence, and complete envelope (E1 and E2) protein coding sequences, wherein the delC protein coding sequence comprises the C-terminal anchor containing the signal sequence to E1.

2. The expression cassette of claim 1, wherein the bicistronic expression element is selected from the group comprising an internal ribosome entry site (IRES) and F2A.

3. The expression cassette of claim 1, wherein the furin gene comprises a furin signal peptide (fsp) coding sequence and a furin proprotein coding sequence.

4. The expression cassette of claim 1, further comprising a partial capsid protein (delC) coding sequence, wherein the delC protein coding sequence comprises the C-terminal anchor sequence containing the signal sequence for prM or E1, fused in frame to the 5' end of a furin signal peptide coding sequence.

5. The expression cassette of claim 4, wherein the delC protein coding sequence does not contain the first 108 nucleotides of the capsid protein coding sequence.

6. The expression cassette of claim 1, comprising a promoter to drive transcription of the expression cassette.

7. The expression cassette of claim 1, comprising a polyA signal sequence positioned at the 3' end of the furin gene.

8. The expression cassette of claim 7, wherein the polyA signal sequence is a SV40 late polyA signal sequence.

9. The expression cassette of claim 1, wherein the furin gene is selected from the group comprising human, non-human mammal or insect furin gene.

10. The expression cassette of claim 9, wherein the furin gene is human.

11. The expression cassette of claim 1, wherein the flavivirus structural gene and the furin gene are codon-optimized for expression in insect cells.

12. The expression cassette of claim 1, wherein the flavivirus is selected from at least one of the group comprising Dengue virus, Zika virus, Yellow fever virus, West Nile virus and Japanese encephalitis virus and serotypes thereof.

13. The expression cassette of claim 1, wherein the flavivirus is Hepatitis C virus.

14. The expression cassette of claim 12, wherein the flavivirus is selected from at least one of the group comprising Dengue virus serotype 1, Dengue virus serotype 2, Dengue virus serotype 3, Dengue virus serotype 4 and Zika virus.

15. The expression cassette of claim 14, wherein the Dengue virus serotype is DENV2.

16. The expression cassette of claim 4, wherein the cassette is homologous or heterologous with respect to the partial capsid protein delC coding sequence.

17. The expression cassette of claim 16, wherein the cassette is heterologous and comprises a Dengue virus delC coding sequence and a ZIKA virus delC coding sequence.

18. The expression cassette of claim 1, comprising a nucleic acid sequence selected from the group comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 SEQ ID NO: 10, SEQ ID NO: 11, SEQ ID NO: 12, SEQ ID NO: 13 and SEQ ID NO: 14.

19. A method for the production of recombinant secreted flavivirus structural proteins and/or VLPs comprising the steps:

cultivating a eukaryotic cell that has been transfected with a plasmid containing an expression cassette of claim 1, and recovering the recombinant secreted virus structural proteins and/or VLPs from the cell or the cultivation medium.

20. The method of claim 19, wherein the eukaryotic cell has been infected with a recombinant baculovirus expressing said expression cassette.

21. The method of claim 19, wherein the eukaryotic cell is selected from:

i) a mammalian cell;

ii) a Chinese hamster ovary cell or human kidney cell;

iii) an insect cell, or iv) a Sf9 insect cell from *Spodoptera frugiperda*.

* * * * *

SEQUENCE LISTING

```
<160> NUMBER OF SEQ ID NOS: 14

<210> SEQ ID NO 1
<211> LENGTH: 6051
<212> TYPE: DNA
<213> ORGANISM: Artificial Sequence
<220> FEATURE:
<223> OTHER INFORMATION: DENV2 del108C-prM-E-IRES-del108CDENV2-human
      furin proprotein cassette

<400> SEQUENCE: 1

cgtatactcc ggaatattaa tagatcatgg agataattaa aatgataacc atctcgcaaa      60

taaataagta ttttactgtt ttcgtaacag ttttgtaata aaaaaaccta taaatattcc     120

ggattattca taccgtccca ccatcgggcg cggatcatca caagtttgta caaaaaagca     180

ggctagatct taatacgact cactatatta attaaggatc ccaaaaaatt gaaattttat     240

ttttttttt tggaatataa ataatatgct ccagggcaga ggaccactca agctgttcat     300

ggcactcgtc gcctttctcc ggtttctcac tatcccaccc actgtcggta tcctgaagag     360

atggggcacc atcaagaaga gcaaggctat caacgtgctg cgcggattca ggaaggagat     420

cggtcgtatg ctgaacatcc tgaaccgcag gagacgtacc gctggaatga tcatcatgct     480

gatcccaacc gtgatggcct tccacctgac caccagaaac ggagagcccc acatgatcgt     540

gtctcgtcag gaaaagggca agagcctgct gttcaagacc gaggacggcg tgaacatgtg     600

caccctgatg gctatggacc tgggcgagct gtgcgaagac accatcacct acaagtgccc     660

actgctgaga cagaacgagc ccgaagacat cgactgctgg tgcaactcta ccagcacctg     720

ggtgacctac ggcacctgta ccaccactgg agagcacaga agggaaaaga gatctgtggc     780
```

-continued

```
cctggtgccc cacgtgggta tgggactgga gacccgtacc gaaacctgga tgagctccga    840
gggagcctgg aagcacgctc agagaatcga aacctggatt ctgcgtcacc ctggattcac    900
cctgatggcc gctatcctgg cttacaccat cggcaccacc aacttccagc gtgccctgat    960
cttcatcctg ctgaccgccg tggctccaag catgaccatg cgctgcatcg gcatctccaa   1020
cagggacttc gtggagggag tgtccggcgg atcttgggtg gacatcgtgc tggaacacgg   1080
ttcctgcgtg actaccatgg ccaagaacaa gcctaccctg gacttcgagc tgatcaagac   1140
cgaagccaag cagccagcta ccctgcgcaa gtactgcatc gaggccaagc tgaccaacac   1200
cactactgag tctaggtgcc caacccaggg tgaacctagc ctgaacgagg aacaggacaa   1260
gaggttcgtg tgcaagcact ctatggtgga caggggttgg ggcaacggat gcggcctgtt   1320
cggaaagggc ggcatcgtga cctgcgccat gttcacctgc aagaagaaca tggagggcaa   1380
gatcgtgcag cccgagaacc tggaatacac catcgtgatc acccctcact ctggagagga   1440
acacgctgtg ggcaacgaca ccggaaagca cggcaaggag atcaagatca cccctcagtc   1500
tagcatcacc gaggccgaac tgaccggcta cggaaccgtg accatggaat gcagccctcg   1560
caccggcctg gacttcaacg agatggtgct gctgcagatg gaaaacaagg cttggctggt   1620
gcacaggcag tggttcctgg acctgcctct gccttggctg ccaggtgctg acacccaggg   1680
cagcaactgg attcagaagg agaccctggt gaccttcaag aacccccacg ctaagaagca   1740
ggacgtggtg gtgctgggct cccaggaggg agctatgcac accgctctga ccggagccac   1800
cgaaatccag atgtcctctg gaaacctgct gttcaccggt cacctgaagt gcagactgcg   1860
tatggacaag ctgcagctga agggaatgtc ctactctatg tgcaccggca agttcaaggt   1920
ggtgaaggag atcgccgaaa cccagcacgg caccatcgtg gtgagagtgc agtacgaggg   1980
tgacggcagc ccttgcaaga tcccattcga gatcatggac ctggaaaagc gccacgtgct   2040
gggcaggctg atcaccgtga accctatcgt gaccgaaaag gactccccag tgaacatcga   2100
ggctgaaccc cctttcggag actcttacgt gatcatcggt gtggagcctg gccagctgaa   2160
gctgaactgg ttcaagaagg gaagctccat cggtcagatg ttcgaaacca ccatgagagg   2220
cgctaagcgt atggccatcc tgggcgacac tgcttgggac ttcggctccc tgggcggcgt   2280
gttcacctct atcggcaagg ctctgcacca ggtgttcggc gccatctacg gagccgcttt   2340
cagcggagtg tcctggacca tgaagatcct gatcggtgtg atcatcacct ggatcggcat   2400
gaacagcagg tccacctctc tgagcgtctc tctggtcctc gtgggcgtcg tgactctcta   2460
tctcggtgtg gtcgtgcagg catgagcccc tctccctccc ccccccctaa cgttactggc   2520
cgaagccgct tggaataagg ccggtgtgtg tttgtctata tgtgattttc caccatattg   2580
ccgtcttttg gcaatgtgag ggcccggaaa cctggccctg tcttcttgac gagcattcct   2640
aggggtcttt cccctctcgc caaaggaatg caaggtctgt tgaatgtcgt gaaggaagca   2700
gttcctctgg aagcttcttg aagacaaaca acgtctgtag cgaccctttg caggcagcgg   2760
aaccccccac ctggcgacag gtgcctctgc ggccaaaagc cacgtgtata agatacacct   2820
gcaaaggcgg cacaacccca gtgccacgtt gtgagttgga tagttgtgga aagagtcaaa   2880
tggctctcct caagcgtagt caacaagggg ctgaaggatg cccagaaggt accccattgt   2940
atgggaatct gatctggggc ctcggtgcac atgctttaca tgtgtttagt cgaggttaaa   3000
aaagctctag gccccccgaa ccacggggac gtggttttcc tttgaaaaac acgatgataa   3060
gcttgccaca aatgctccag ggtcgcggtc cactgaaact ctttatggct ctcgtcgcct   3120
tcctgcggtt cctcactatt cctcctactg tcggtattct gaagaggtgg ggcaccatca   3180
```

-continued

```
agaagagcaa ggccatcaac gtgctgcgcg gattcaggaa ggagatcggt aggatgctga   3240
acatcctgaa ccgcaggaga cgtaccgccg gcatgatcat catgctgatc cccaccgtga   3300
tggctatgga actgagacct tggctgctgt gggtggtggc tgctactggc accctggtgc   3360
tgctagcagc tgacgcccag ggccagaagg tgttcaccaa cacctgggct gtgagaatcc   3420
ccggcggacc tgctgtggct aacagcgtgg ctcgtaagca cggcttcctg aacctgggac   3480
agattttcgg tgactactac cacttctggc accgcggagt gaccaagagg agcctgtccc   3540
cacacagacc aaggcactcc agactgcagc gtgagcccca ggtgcagtgg ctggaacagc   3600
aggtggccaa gcgcaggacc aagagagacg tgtaccagga gcctaccgac ccaaagttcc   3660
cccagcagtg gtatctgtcc ggcgtgaccc agcgtgacct gaacgtgaag gccgcttggg   3720
ctcagggtta caccggtcac ggcatcgtgg tgtccatcct ggacgacggc atcgagaaga   3780
accaccctga cctggccggt aactacgacc caggcgcttc tttcgacgtg aacgaccagg   3840
accccgaccc tcagccaaga tacacccaga tgaacgacaa cagacatgga accagatgtg   3900
ctggtgaagt ggctgctgtg gctaacaacg gcgtgtgcgg agtgggtgtg gcctacaacg   3960
ctagaatcgg tggcgtgcgt atgctggatg gagaagtgac tgatgctgtg gaagctagaa   4020
gcctgggact gaacccaaac cacatccaca tctactctgc cagctggggt ccagaggatg   4080
atggaaagac tgtggatggt cctgctagac tggctgagga agccttcttc cgcggcgtga   4140
gccagggaag gggaggtctg ggaagcatct tcgtgtgggc ttctggtaac ggcggaagag   4200
agcacgactc ctgcaactgc gacggataca ccaactctat ctacaccctg agcatcagct   4260
ccgctaccca gttcggtaac gtgccctggt actccgaagc ctgctctagc accctggcta   4320
ccacctactc ctctggcaac cagaacgaga agcagatcgt gaccaccgac ctgcgtcaga   4380
agtgcaccga atctcacact ggcacctccg cctctgctcc tctggctgct ggaatcatcg   4440
ccctgaccct ggaggctaac aagaacctga cctggcgcga catgcagcac ctggtggtgc   4500
agacctccaa gccagctcac ctgaacgcca acgactgggc taccaacggc gtgggaagga   4560
aggtgagcca ctcttacggt tacggtctgc tggatgctgg tgctatggtg gccctggctc   4620
agaactggac caccgtggcc cctcagcgca agtgcatcat cgacatcctg accgagccta   4680
aggacatcgg aaagagactg gaagtgcgta agaccgtgac cgcttgcctg ggagagccca   4740
accacatcac cagactggaa cacgcccagg ctcgtctgac cctgtcttac aacagacgtg   4800
gagacctggc catccacctg gtgtctccaa tgggcacccg cagcaccctg ctggctgcta   4860
ggccacacga ctacagcgcc gacggattca acgactgggc tttcatgacc acccactcct   4920
gggacgagga ccccttctggt gaatgggtgc tggagatcga aaacaccagc gaggccaaca   4980
actacggcac cctgaccaag ttcaccctgg tgctgtacgg caccgctcct gagggactgc   5040
cagtgccccc tgaaagctcc ggttgcaaga ccctgacctc tagccaggcc tgcgtggtgt   5100
gcgaggaagg cttctccctg caccagaagt cttgcgtgca gcactgccca cccggattcg   5160
ctcctcaggt gctggacacc cactactcta ccgagaacga cgtggaaacc atcagagcca   5220
gcgtgtgcgc tccttgtcac gcttcctgtg ctacttgtca gggaccagcc ctgactgact   5280
gcctgtcctg cccatctcac gccagcctgg accccgtgga gcagacctgc tccagacagt   5340
ctcagtcctc tcgtgaaagc cctccacagc agcagccccc tagactgcca cccgaggtgg   5400
aagccggcca gagactgcgt gctggactgc tgccttctca cctgccagag gtggtggctg   5460
gtctgagctg cgctttcatc gtgctggtgt tcgtgaccgt gttcctggtg ctgcagctgc   5520
gcagcggttt ctccttcagg ggcgtgaagg tgtacaccat ggaccgcggt ctgatcagct   5580
```

-continued acaagggtct gcctccagag gcttggcagg aggaatgccc atctgacagc gaagaggacg 5640
agggacgtgg agaacggact gccttcatca aagatcagag cgcactgtaa taaatcgatt 5700
taattaatag cataacccct tggggcctct aaacgggtct tgaggggttt tttggaattc 5760
acccagcttt cttgtacaaa gtggtgatag cttgtcgaga agtactagag gatcataatc 5820
agccatacca catttgtaga ggttttactt gctttaaaaa acctcccaca cctccccctg 5880
aacctgaaac ataaaatgaa tgcaattgtt gttgttaact tgtttattgc agcttataat 5940
ggttacaaat aaagcaatag catcacaaat ttcacaaata aagcattttt ttcactgcat 6000
tctagttgtg gtttgtccaa actcatcaat gtatcttatc atgtctggat c 6051

<210> SEQ ID NO 2
<211> LENGTH: 5817
<212> TYPE: DNA
<213> ORGANISM: Artificial Sequence
<220> FEATURE:
<223> OTHER INFORMATION: DENV2 del108C-prM-E-IRES-human furin proprotein cassette

<400> SEQUENCE: 2
cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagca 180
ggctagatct taatacgact cactatatta attaaggatc ccaaaaaatt gaaattttat 240 ttttttttt tggaatataa ataatatgct ccagggcaga ggaccactca agctgttcat 300
ggcactcgtc gcctttctcc ggtttctcac tatcccaccc actgtcggta tcctgaagag 360
atggggcacc atcaagaaga gcaaggctat caacgtgctg cgcggattca ggaaggagat 420
cggtcgtatg ctgaacatcc tgaaccgcag gagacgtacc gctggaatga tcatcatgct 480
gatcccaacc gtgatggcct tccacctgac caccagaaac ggagagcccc acatgatcgt 540
gtctcgtcag gaaaagggca agagcctgct gttcaagacc gaggacggcg tgaacatgtg 600
caccctgatg gctatggacc tgggcgagct gtgcgaagac accatcacct acaagtgccc 660
actgctgaga cagaacgagc ccgaagacat cgactgctgg tgcaactcta ccagcacctg 720
ggtgacctac ggcacctgta ccaccactgg agagcacaga agggaaaaga gatctgtggc 780
cctggtgccc cacgtgggta tgggactgga gacccgtacc gaaacctgga tgagctccga 840
gggagcctgg aagcacgctc agagaatcga aacctggatt ctgcgtcacc ctggattcac 900
cctgatggcc gctatcctgg cttacaccat cggcaccacc aacttccagc gtgccctgat 960
cttcatcctg ctgaccgccg tggctccaag catgaccatg cgctgcatcg gcatctccaa 1020
cagggacttc gtggagggag tgtccggcgg atcttgggtg gacatcgtgc tggaacacgg 1080
ttcctgcgtg actaccatgg ccaagaacaa gcctaccctg gacttcgagc tgatcaagac 1140
cgaagccaag cagccagcta ccctgcgcaa gtactgcatc gaggccaagc tgaccaacac 1200
cactactgag tctaggtgcc caacccaggg tgaacctagc ctgaacgagg aacaggacaa 1260
gaggttcgtg tgcaagcact ctatggtgga caggggttgg ggcaacggat gcggcctgtt 1320
cggaaagggc ggcatcgtga cctgcgccat gttcacctgc aagaagaaca tggagggcaa 1380
gatcgtgcag cccgagaacc tggaatacac catcgtgatc acccctcact ctggagagga 1440
acacgctgtg ggcaacgaca ccggaaagca cggcaaggag atcaagatca cccctcagtc 1500
tagcatcacc gaggccgaac tgaccggcta cggaaccgtg accatggaat gcagccctcg 1560

-continued

```
caccggcctg gacttcaacg agatggtgct gctgcagatg gaaaacaagg cttggctggt   1620
gcacaggcag tggttcctgg acctgcctct gccttggctg ccaggtgctg acacccaggg   1680
cagcaactgg attcagaagg agaccctggt gaccttcaag aacccccacg ctaagaagca   1740
ggacgtggtg gtgctgggct cccaggaggg agctatgcac accgctctga ccggagccac   1800
cgaaatccag atgtcctctg gaaacctgct gttcaccggt cacctgaagt gcagactgcg   1860
tatggacaag ctgcagctga agggaatgtc ctactctatg tgcaccggca agttcaaggt   1920
ggtgaaggag atcgccgaaa cccagcacgg caccatcgtg gtgagagtgc agtacgaggg   1980
tgacggcagc ccttgcaaga tcccattcga gatcatggac ctggaaaagc gccacgtgct   2040
gggcaggctg atcaccgtga accctatcgt gaccgaaaag gactccccag tgaacatcga   2100
ggctgaaccc cctttcggag actcttacgt gatcatcggt gtggagcctg gccagctgaa   2160
gctgaactgg ttcaagaagg gaagctccat cggtcagatg ttcgaaacca ccatgagagg   2220
cgctaagcgt atggccatcc tgggcgacac tgcttgggac ttcggctccc tgggcggcgt   2280
gttcacctct atcggcaagg ctctgcacca ggtgttcggc gccatctacg gagccgcttt   2340
cagcggagtg tcctggacca tgaagatcct gatcggtgtg atcatcacct ggatcggcat   2400
gaacagcagg tccacctctc tgagcgtctc tctggtcctc gtgggcgtcg tgactctcta   2460
tctcggtgtg gtcgtgcagg catgagcccc tctccctccc ccccccctaa cgttactggc   2520
cgaagccgct tggaataagg ccggtgtgtg tttgtctata tgtgattttc caccatattg   2580
ccgtcttttg gcaatgtgag ggcccggaaa cctggccctg tcttcttgac gagcattcct   2640
aggggtcttt cccctctcgc caaaggaatg caaggtctgt tgaatgtcgt gaaggaagca   2700
gttcctctgg aagcttcttg aagacaaaca acgtctgtag cgaccctttg caggcagcgg   2760
aaccccccac ctggcgacag gtgcctctgc ggccaaaagc cacgtgtata agatacacct   2820
gcaaaggcgg cacaacccca gtgccacgtt gtgagttgga tagttgtgga aagagtcaaa   2880
tggctctcct caagcgtagt caacaagggg ctgaaggatg cccagaaggt accccattgt   2940
atgggaatct gatctggggc ctcggtgcac atgctttaca tgtgtttagt cgaggttaaa   3000
aaagctctag gccccccgaa ccacggggac gtggttttcc tttgaaaaac acgatgataa   3060
gcttgccaca aatggaactg agaccttggc tgctgtgggt ggtggctgct actggcaccc   3120
tggtgctgct agcagctgac gcccagggcc agaaggtgtt caccaacacc tgggctgtga   3180
gaatccccgg cggacctgct gtggctaaca gcgtggctcg taagcacggc ttcctgaacc   3240
tgggacagat tttcggtgac tactaccact tctggcaccg cggagtgacc aagaggagcc   3300
tgtccccaca cagaccaagg cactccagac tgcagcgtga gccccaggtg cagtggctgg   3360
aacagcaggt ggccaagcgc aggaccaaga gagacgtgta ccaggagcct accgacccaa   3420
agttccccca gcagtggtat ctgtccggcg tgacccagcg tgacctgaac gtgaaggccg   3480
cttgggctca gggttacacc ggtcacggca tcgtggtgtc catcctggac gacggcatcg   3540
agaagaacca ccctgacctg gccggtaact acgacccagg cgcttctttc gacgtgaacg   3600
accaggaccc cgaccctcag ccaagataca cccagatgaa cgacaacaga catggaacca   3660
gatgtgctgg tgaagtggct gctgtggcta acaacggcgt gtgcggagtg ggtgtggcct   3720
acaacgctag aatcggtggc gtgcgtatgc tggatggaga agtgactgat gctgtggaag   3780
ctagaagcct gggactgaac ccaaaccaca tccacatcta ctctgccagc tggggtccag   3840
aggatgatgg aaagactgtg gatggtcctg ctagactggc tgaggaagcc ttcttccgcg   3900
gcgtgagcca gggaagggga ggtctgggaa gcatcttcgt gtgggcttct ggtaacggcg   3960
```

```
gaagagagca cgactcctgc aactgcgacg gatacaccaa ctctatctac accctgagca   4020

tcagctccgc tacccagttc ggtaacgtgc cctggtactc cgaagcctgc tctagcaccc   4080

tggctaccac ctactcctct ggcaaccaga acgagaagca gatcgtgacc accgacctgc   4140

gtcagaagtg caccgaatct cacactggca cctccgcctc tgctcctctg gctgctggaa   4200

tcatcgccct gaccctggag gctaacaaga acctgacctg gcgcgacatg cagcacctgg   4260

tggtgcagac ctccaagcca gctcacctga acgccaacga ctgggctacc aacggcgtgg   4320

gaaggaaggt gagccactct tacggttacg gtctgctgga tgctggtgct atggtggccc   4380

tggctcagaa ctggaccacc gtggcccctc agcgcaagtg catcatcgac atcctgaccg   4440

agcctaagga catcggaaag agactggaag tgcgtaagac cgtgaccgct tgcctgggag   4500

agcccaacca catcaccaga ctggaacacg cccaggctcg tctgaccctg tcttacaaca   4560

gacgtggaga cctggccatc cacctggtgt ctccaatggg cacccgcagc accctgctgg   4620

ctgctaggcc acacgactac agcgccgacg gattcaacga ctgggctttc atgaccaccc   4680

actcctggga cgaggaccct tctggtgaat gggtgctgga gatcgaaaac accagcgagg   4740

ccaacaacta cggcaccctg accaagttca ccctggtgct gtacggcacc gctcctgagg   4800

gactgccagt gccccctgaa agctccggtt gcaagaccct gacctctagc caggcctgcg   4860

tggtgtgcga ggaaggcttc tccctgcacc agaagtcttg cgtgcagcac tgcccacccg   4920

gattcgctcc tcaggtgctg gacacccact actctaccga gaacgacgtg gaaaccatca   4980

gagccagcgt gtgcgctcct tgtcacgctt cctgtgctac ttgtcaggga ccagccctga   5040

ctgactgcct gtcctgccca tctcacgcca gcctggaccc cgtggagcag acctgctcca   5100

gacagtctca gtcctctcgt gaaagccctc cacagcagca gcccccctaga ctgccacccg   5160

aggtggaagc cggccagaga ctgcgtgctg gactgctgcc ttctcacctg ccagaggtgg   5220

tggctggtct gagctgcgct ttcatcgtgc tggtgttcgt gaccgtgttc ctggtgctgc   5280

agctgcgcag cggtttctcc ttcaggggcg tgaaggtgta caccatggac cgcggtctga   5340

tcagctacaa gggtctgcct ccagaggctt ggcaggagga atgcccatct gacagcgaag   5400

aggacgaggg acgtggagaa cggactgcct tcatcaaaga tcagagcgca ctgtaataaa   5460

tcgatttaat taatagcata accccttggg gcctctaaac gggtcttgag gggtttttttg   5520

gaattcaccc agctttcttg tacaaagtgg tgatagcttg tcgagaagta ctagaggatc   5580

ataatcagcc ataccacatt tgtagaggtt ttacttgctt taaaaaacct cccacacctc   5640

cccctgaacc tgaaacataa aatgaatgca attgttgttg ttaacttgtt tattgcagct   5700

tataatggtt acaaataaag caatagcatc acaaatttca caaataaagc atttttttca   5760

ctgcattcta gttgtggttt gtccaaactc atcaatgtat cttatcatgt ctggatc      5817
```

```
<210> SEQ ID NO 3
<211> LENGTH: 7556
<212> TYPE: DNA
<213> ORGANISM: Artificial Sequence
<220> FEATURE:
<223> OTHER INFORMATION: Dual Promoter-DENV2 del108C-prM-E-IRES-
      del108CDENV2-human furin proprotein cassette + DENV2 NS1

<400> SEQUENCE: 3

gtggctatgg cagggcttgc cgccccgacg ttggctgcga gccctgggcc ttcacccgaa     60

cttgggggtt ggggtgggga aaaggaagaa acgcgggcgt attggtccca atggggtctc    120

ggtggggtat cgacagagtg ccagccctgg gaccgaaccc cgcgtttatg aacaaacgac    180
```

-continued

```
ccaacacccg tgcgttttat tctgtctttt tattgccgtc atagcgcggg ttccttccgg    240
tattgtctcc ttccgtgttt cagttagcct cccccatctc ccggtagcgc atgctctaga    300
ggcgcgcctt attaggctgt cacgagagag gacacgagat tttcttcttt ttctttcaga    360
ggacgaattt ccatgccgta ccagcatccg tcctcgccac ggtatctcag agggggcagg    420
gtgcaggacc tgcaacacca ttcggtgatc agcttgccag aagcggtggt ggtcctcagg    480
gaaggacctc tgtttccgca gtcttcggtc accaccacgg tggttccctt gcagaagtcg    540
aagtccatct caagcttgcc caggtgccat ggtccagcgg tctgggtgtg gtatccaggg    600
cggtagttgt gctggctcac ggggccagcg aagttctttg ggatgatcat ttcagactcc    660
agcactccgt tggaccacag ggtgtggctc ttgggccagt ggcagctctt cacttcgatg    720
aaagaagcct tctcgatctt ccaggtgtcg ttcagggcgg attcgatcca gtagcccatg    780
tcagcgtgca cggctctgtt gtccttgata gcggcagaca tcagcttgga gtcgcagaag    840
gcgtcctgct tctccctcag gcgcagccag atgttggtgg tgaacactcc gaagccgtag    900
tcttccacct ccaggctgtt ccaagcacgg ttggtgttag ggcattcggc ggtttcgggg    960
ccgtcgatca ggaaggtctg gttgtggctt tcggtagaca ggatcttagc cttgccccag   1020
gtcttccagg agtatctcag ctcggtgggc tgggggcgca ggctgcgctt gccagcgtgc   1080
atgatgccct tgatgtctcc ggtcatgatg gtcagcttca cttcgttctc agacaggatg   1140
tggttcagtt cgggggtgat ctgcttccac atcaggttct ccagacgggt cacagatctg   1200
atgccgcaga taccctcctg gtgggccttc tggatagcgg aggccagctt ggatgggctt   1260
tcaggctgga acttgtactg ctcggtccag gtatgcacgt tgtcggtgat aaagatgccg   1320
ctaccacact tcagttcctt gttcctccag ctgaccacgc agccgctgtc catgcggccg   1380
cctcgagatc ccgggtgatc aagtcttcgt cgagtgattg taaataaaat gtaatttaca   1440
gtatagtatt ttaattaata tacaaatgat ttgataataa ttcttattta actataaatat   1500
attgtgttgg gttgaattaa aggtccgtat catggagata attaaaatga taaccatctc   1560
gcaaataaat aagtatttta ctgttttcgt aacagttttg taataaaaaa acctataaat   1620
attccggatt attcataccg tcccaccatc gggcgcggat catcacaagt ttgtacaaaa   1680
aagcaggcta gatcttaata cgactcacta tattaattaa ggatcccaaa aaattgaaat   1740
tttatttttt tttttggaa tataaataat atgctccagg gcagaggacc actcaagctg   1800
ttcatggcac tcgtcgcctt tctccggttt ctcactatcc cacccactgt cggtatcctg   1860
aagagatggg gcaccatcaa gaagagcaag gctatcaacg tgctgcgcgg attcaggaag   1920
gagatcggtc gtatgctgaa catcctgaac cgcaggagac gtaccgctgg aatgatcatc   1980
atgctgatcc caaccgtgat ggccttccac ctgaccacca gaaacggaga gccccacatg   2040
atcgtgtctc gtcaggaaaa gggcaagagc ctgctgttca agaccgagga cggcgtgaac   2100
atgtgcaccc tgatggctat ggacctgggc gagctgtgcg aagacaccat cacctacaag   2160
tgcccactgc tgagacagaa cgagcccgaa gacatcgact gctggtgcaa ctctaccagc   2220
acctgggtga cctacggcac ctgtaccacc actggagagc acagaaggga aaagagatct   2280
gtggccctgg tgccccacgt gggtatggga ctggagaccc gtaccgaaac ctggatgagc   2340
tccgagggag cctggaagca cgctcagaga atcgaaacct ggattctgcg tcaccctgga   2400
ttcaccctga tggccgctat cctggcttac accatcggca ccaccaactt ccagcgtgcc   2460
ctgatcttca tcctgctgac cgccgtggct ccaagcatga ccatgcgctg catcggcatc   2520
tccaacaggg acttcgtgga gggagtgtcc ggcggatctt gggtggacat cgtgctggaa   2580
```

-continued

```
cacggttcct gcgtgactac catggccaag aacaagccta ccctggactt cgagctgatc   2640
aagaccgaag ccaagcagcc agctaccctg cgcaagtact gcatcgaggc caagctgacc   2700
aacaccacta ctgagtctag gtgcccaacc cagggtgaac ctagcctgaa cgaggaacag   2760
gacaagaggt tcgtgtgcaa gcactctatg gtggacaggg gttggggcaa cggatgcggc   2820
ctgttcggaa agggcggcat cgtgacctgc gccatgttca cctgcaagaa gaacatggag   2880
ggcaagatcg tgcagcccga gaacctggaa tacaccatcg tgatcacccc tcactctgga   2940
gaggaacacg ctgtgggcaa cgacaccgga aagcacggca aggagatcaa gatcacccct   3000
cagtctagca tcaccgaggc cgaactgacc ggctacggaa ccgtgaccat ggaatgcagc   3060
cctcgcaccg gcctggactt caacgagatg gtgctgctgc agatggaaaa caaggcttgg   3120
ctggtgcaca ggcagtggtt cctggacctg cctctgcctt ggctgccagg tgctgacacc   3180
cagggcagca actggattca gaaggagacc ctggtgacct tcaagaaccc ccacgctaag   3240
aagcaggacg tggtggtgct gggctcccag gagggagcta tgcacaccgc tctgaccgga   3300
gccaccgaaa tccagatgtc ctctggaaac ctgctgttca ccggtcacct gaagtgcaga   3360
ctgcgtatgg acaagctgca gctgaaggga atgtcctact ctatgtgcac cggcaagttc   3420
aaggtggtga aggagatcgc cgaaacccag cacggcacca tcgtggtgag agtgcagtac   3480
gagggtgacg gcagcccttg caagatccca ttcgagatca tggacctgga aaagcgccac   3540
gtgctgggca ggctgatcac cgtgaaccct atcgtgaccg aaaaggactc cccagtgaac   3600
atcgaggctg aacccccttt cggagactct tacgtgatca tcggtgtgga gcctggccag   3660
ctgaagctga actggttcaa gaagggaagc tccatcggtc agatgttcga aaccaccatg   3720
agaggcgcta agcgtatggc catcctgggc gacactgctt gggacttcgg ctccctgggc   3780
ggcgtgttca cctctatcgg caaggctctg caccaggtgt tcggcgccat ctacggagcc   3840
gctttcagcg gagtgtcctg gaccatgaag atcctgatcg gtgtgatcat cacctggatc   3900
ggcatgaaca gcaggtccac ctctctgagc gtctctctgg tcctcgtggg cgtcgtgact   3960
ctctatctcg gtgtggtcgt gcaggcatga gcccctctcc ctcccccccc cctaacgtta   4020
ctggccgaag ccgcttggaa taaggccggt gtgtgtttgt ctatatgtga ttttccacca   4080
tattgccgtc ttttggcaat gtgagggccc ggaaacctgg ccctgtcttc ttgacgagca   4140
ttcctagggg tctttcccct ctcgccaaag gaatgcaagg tctgttgaat gtcgtgaagg   4200
aagcagttcc tctggaagct tcttgaagac aaacaacgtc tgtagcgacc ctttgcaggc   4260
agcggaaccc cccacctggc gacaggtgcc tctgcggcca aaagccacgt gtataagata   4320
cacctgcaaa ggcggcacaa ccccagtgcc acgttgtgag ttggatagtt gtggaaagag   4380
tcaaatggct ctcctcaagc gtagtcaaca aggggctgaa ggatgcccag aaggtacccc   4440
attgtatggg aatctgatct ggggcctcgg tgcacatgct ttacatgtgt ttagtcgagg   4500
ttaaaaaagc tctaggcccc ccgaaccacg gggacgtggt tttcctttga aaaacacgat   4560
gataagcttg ccacaaatgc tccagggtcg cggtccactg aaactcttta tggctctcgt   4620
cgccttcctg cggttcctca ctattcctcc tactgtcggt attctgaaga ggtggggcac   4680
catcaagaag agcaaggcca tcaacgtgct gcgcggattc aggaaggaga tcggtaggat   4740
gctgaacatc ctgaaccgca ggagacgtac cgccggcatg atcatcatgc tgatccccac   4800
cgtgatggct atggaactga gaccttggct gctgtgggtg gtggctgcta ctggcaccct   4860
ggtgctgcta gcagctgacg cccagggcca gaaggtgttc accaacacct gggctgtgag   4920
aatccccggc ggacctgctg tggctaacag cgtggctcgt aagcacggct tcctgaacct   4980
```

gggacagatt ttcggtgact actaccactt ctggcaccgc ggagtgacca agaggagcct 5040
gtccccacac agaccaaggc actccagact gcagcgtgag ccccaggtgc agtggctgga 5100
acagcaggtg gccaagcgca ggaccaagag agacgtgtac caggagccta ccgacccaaa 5160
gttcccccag cagtggtatc tgtccggcgt gacccagcgt gacctgaacg tgaaggccgc 5220
ttgggctcag ggttacaccg gtcacggcat cgtggtgtcc atcctggacg acggcatcga 5280
gaagaaccac cctgacctgg ccggtaacta cgacccaggc gcttctttcg acgtgaacga 5340
ccaggacccc gaccctcagc caagatacac ccagatgaac gacaacagac atggaaccag 5400
atgtgctggt gaagtggctg ctgtggctaa caacggcgtg tgcggagtgg gtgtggccta 5460
caacgctaga atcggtggcg tgcgtatgct ggatggagaa gtgactgatg ctgtggaagc 5520
tagaagcctg ggactgaacc caaaccacat ccacatctac tctgccagct ggggtccaga 5580
ggatgatgga aagactgtgg atggtcctgc tagactggct gaggaagcct tcttccgcgg 5640
cgtgagccag ggaaggggag gtctgggaag catcttcgtg tgggcttctg gtaacggcgg 5700
aagagagcac gactcctgca actgcgacgg atacaccaac tctatctaca ccctgagcat 5760
cagctccgct acccagttcg gtaacgtgcc ctggtactcc gaagcctgct ctagcaccct 5820
ggctaccacc tactcctctg gcaaccagaa cgagaagcag atcgtgacca ccgacctgcg 5880
tcagaagtgc accgaatctc acactggcac ctccgcctct gctcctctgg ctgctggaat 5940
catcgccctg accctggagg ctaacaagaa cctgacctgg cgcgacatgc agcacctggt 6000
ggtgcagacc tccaagccag ctcacctgaa cgccaacgac tgggctacca acggcgtggg 6060
aaggaaggtg agccactctt acggttacgg tctgctggat gctggtgcta tggtggccct 6120
ggctcagaac tggaccaccg tggcccctca gcgcaagtgc atcatcgaca tcctgaccga 6180
gcctaaggac atcggaaaga gactggaagt gcgtaagacc gtgaccgctt gcctgggaga 6240
gcccaaccac atcaccagac tggaacacgc ccaggctcgt ctgaccctgt cttacaacag 6300
acgtggagac ctggccatcc acctggtgtc tccaatgggc acccgcagca ccctgctggc 6360
tgctaggcca cacgactaca gcgccgacgg attcaacgac tgggctttca tgaccaccca 6420
ctcctgggac gaggaccctt ctggtgaatg ggtgctggag atcgaaaaca ccagcgaggc 6480
caacaactac ggcaccctga ccaagttcac cctggtgctg tacggcaccg ctcctgaggg 6540
actgccagtg ccccctgaaa gctccggttg caagaccctg acctctagcc aggcctgcgt 6600
ggtgtgcgag gaaggcttct ccctgcacca gaagtcttgc gtgcagcact gcccacccgg 6660
attcgctcct caggtgctgg acacccacta ctctaccgag aacgacgtgg aaaccatcag 6720
agccagcgtg tgcgctcctt gtcacgcttc ctgtgctact tgtcagggac cagccctgac 6780
tgactgcctg tcctgcccat ctcacgccag cctggacccc gtggagcaga cctgctccag 6840
acagtctcag tcctctcgtg aaagccctcc acagcagcag cccccctagac tgccacccga 6900
ggtggaagcc ggccagagac tgcgtgctgg actgctgcct tctcacctgc cagaggtggt 6960
ggctggtctg agctgcgctt tcatcgtgct ggtgttcgtg accgtgttcc tggtgctgca 7020
gctgcgcagc ggtttctcct tcaggggcgt gaaggtgtac accatggacc gcggtctgat 7080
cagctacaag ggtctgcctc cagaggcttg gcaggaggaa tgcccatctg acagcgaaga 7140
ggacgaggga cgtggagaac ggactgcctt catcaaagat cagagcgcac tgtaataaat 7200
cgatttaatt aatagcataa cccccttgggg cctctaaacg ggtcttgagg ggttttttgg 7260
aattcaccca gctttcttgt acaaagtggt gatagcttgt cgagaagtac tagaggatca 7320
taatcagcca taccacattt gtagaggttt tacttgcttt aaaaaacctc ccacacctcc 7380
ccctgaacct gaaacataaa atgaatgcaa ttgttgttgt taacttgttt attgcagctt 7440
ataatggtta caaataaagc aatagcatca caaatttcac aaataaagca tttttttcac 7500
tgcattctag ttgtggtttg tccaaactca tcaatgtatc ttatcatgtc tggatc 7556

<210> SEQ ID NO 4
<211> LENGTH: 7322
<212> TYPE: DNA
<213> ORGANISM: Artificial Sequence
<220> FEATURE:
<223> OTHER INFORMATION: Dual Promoter-DENV2 del108C-prM-E-IRES-human furin proprotein cassette

<400> SEQUENCE: 4
gtggctatgg cagggcttgc cgccccgacg ttggctgcga gccctgggcc ttcacccgaa 60
cttgggggtt ggggtgggga aaaggaagaa acgcgggcgt attggtccca atggggtctc 120
ggtggggtat cgacagagtg ccagccctgg gaccgaaccc cgcgtttatg aacaaacgac 180
ccaacacccg tgcgttttat tctgtctttt tattgccgtc atagcgcggg ttccttccgg 240
tattgtctcc ttccgtgttt cagttagcct cccccatctc ccggtagcgc atgctctaga 300
ggcgcgcctt attaggctgt cacgagagag gacacgagat ttcttctttt ttctttcaga 360
ggacgaattt ccatgccgta ccagcatccg tcctcgccac ggtatctcag agggggcagg 420
gtgcaggacc tgcaacacca ttcggtgatc agcttgccag aagcggtggt ggtcctcagg 480
gaaggacctc tgtttccgca gtcttcggtc accaccacgg tggttccctt gcagaagtcg 540
aagtccatct caagcttgcc caggtgccat ggtccagcgg tctgggtgtg gtatccaggg 600
cggtagttgt gctggctcac ggggccagcg aagttctttg ggatgatcat ttcagactcc 660
agcactccgt tggaccacag ggtgtggctc ttgggccagt ggcagctctt cacttcgatg 720
aaagaagcct tctcgatctt ccaggtgtcg ttcagggcgg attcgatcca gtagcccatg 780
tcagcgtgca cggctctgtt gtccttgata gcggcagaca tcagcttgga gtcgcagaag 840
gcgtcctgct tctccctcag gcgcagccag atgttggtgg tgaacactcc gaagccgtag 900
tcttccacct ccaggctgtt ccaagcacgg ttggtgttag ggcattcggc ggtttcgggg 960
ccgtcgatca ggaaggtctg gttgtggctt tcggtagaca ggatcttagc cttgccccag 1020
gtcttccagg agtatctcag ctcggtgggc tgggggcgca ggctgcgctt gccagcgtgc 1080
atgatgccct tgatgtctcc ggtcatgatg gtcagcttca cttcgttctc agacaggatg 1140
tggttcagtt cgggggtgat ctgcttccac atcaggttct ccagacgggt cacagatctg 1200
atgccgcaga taccctcctg gtgggccttc tggatagcgg aggccagctt ggatgggctt 1260
tcaggctgga acttgtactg ctcggtccag gtatgcacgt tgtcggtgat aaagatgccg 1320
ctaccacact tcagttcctt gttcctccag ctgaccacgc agccgctgtc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt ttttttggaa tataaataat atgctccagg gcagaggacc actcaagctg 1800
ttcatggcac tcgtcgcctt tctccggttt ctcactatcc cacccactgt cggtatcctg 1860

-continued

```
aagagatggg gcaccatcaa gaagagcaag gctatcaacg tgctgcgcgg attcaggaag   1920
gagatcggtc gtatgctgaa catcctgaac cgcaggagac gtaccgctgg aatgatcatc   1980
atgctgatcc caaccgtgat ggccttccac ctgaccacca gaaacggaga gccccacatg   2040
atcgtgtctc gtcaggaaaa gggcaagagc ctgctgttca agaccgagga cggcgtgaac   2100
atgtgcaccc tgatggctat ggacctgggc gagctgtgcg aagacaccat cacctacaag   2160
tgcccactgc tgagacagaa cgagcccgaa gacatcgact gctggtgcaa ctctaccagc   2220
acctgggtga cctacggcac ctgtaccacc actggagagc acagaaggga aaagagatct   2280
gtggccctgg tgccccacgt gggtatggga ctggagaccc gtaccgaaac ctggatgagc   2340
tccgagggag cctggaagca cgctcagaga atcgaaacct ggattctgcg tcaccctgga   2400
ttcaccctga tggccgctat cctggcttac accatcggca ccaccaactt ccagcgtgcc   2460
ctgatcttca tcctgctgac cgccgtggct ccaagcatga ccatgcgctg catcggcatc   2520
tccaacaggg acttcgtgga gggagtgtcc ggcggatctt gggtggacat cgtgctggaa   2580
cacggttcct gcgtgactac catggccaag aacaagccta ccctggactt cgagctgatc   2640
aagaccgaag ccaagcagcc agctaccctg cgcaagtact gcatcgaggc caagctgacc   2700
aacaccacta ctgagtctag gtgcccaacc cagggtgaac ctagcctgaa cgaggaacag   2760
gacaagaggt tcgtgtgcaa gcactctatg gtggacaggg gttggggcaa cggatgcggc   2820
ctgttcggaa agggcggcat cgtgacctgc gccatgttca cctgcaagaa gaacatggag   2880
ggcaagatcg tgcagcccga gaacctggaa tacaccatcg tgatcacccc tcactctgga   2940
gaggaacacg ctgtgggcaa cgacaccgga aagcacggca aggagatcaa gatcacccct   3000
cagtctagca tcaccgaggc cgaactgacc ggctacggaa ccgtgaccat ggaatgcagc   3060
cctcgcaccg gcctggactt caacgagatg gtgctgctgc agatggaaaa caaggcttgg   3120
ctggtgcaca ggcagtggtt cctggacctg cctctgcctt ggctgccagg tgctgacacc   3180
cagggcagca actggattca gaaggagacc ctggtgacct tcaagaaccc ccacgctaag   3240
aagcaggacg tggtggtgct gggctcccag gagggagcta tgcacaccgc tctgaccgga   3300
gccaccgaaa tccagatgtc ctctggaaac ctgctgttca ccggtcacct gaagtgcaga   3360
ctgcgtatgg acaagctgca gctgaaggga atgtcctact ctatgtgcac cggcaagttc   3420
aaggtggtga aggagatcgc cgaaacccag cacggcacca tcgtggtgag agtgcagtac   3480
gagggtgacg gcagcccttg caagatccca ttcgagatca tggacctgga aaagcgccac   3540
gtgctgggca ggctgatcac cgtgaaccct atcgtgaccg aaaaggactc cccagtgaac   3600
atcgaggctg aacccccttt cggagactct tacgtgatca tcggtgtgga gcctggccag   3660
ctgaagctga actggttcaa gaagggaagc tccatcggtc agatgttcga aaccaccatg   3720
agaggcgcta agcgtatggc catcctgggc gacactgctt gggacttcgg ctccctgggc   3780
ggcgtgttca cctctatcgg caaggctctg caccaggtgt tcggcgccat ctacggagcc   3840
gctttcagcg gagtgtcctg gaccatgaag atcctgatcg gtgtgatcat cacctggatc   3900
ggcatgaaca gcaggtccac ctctctgagc gtctctctgg tcctcgtggg cgtcgtgact   3960
ctctatctcg gtgtggtcgt gcaggcatga gcccctctcc ctcccccccc cctaacgtta   4020
ctggccgaag ccgcttggaa taaggccggt gtgtgtttgt ctatatgtga ttttccacca   4080
tattgccgtc ttttggcaat gtgagggccc ggaaacctgg ccctgtcttc ttgacgagca   4140
ttcctagggg tctttcccct ctcgccaaag gaatgcaagg tctgttgaat gtcgtgaagg   4200
aagcagttcc tctggaagct tcttgaagac aaacaacgtc tgtagcgacc ctttgcaggc   4260
```

-continued

```
agcggaaccc cccacctggc gacaggtgcc tctgcggcca aaagccacgt gtataagata   4320
cacctgcaaa ggcggcacaa ccccagtgcc acgttgtgag ttggatagtt gtggaaagag   4380
tcaaatggct ctcctcaagc gtagtcaaca aggggctgaa ggatgcccag aaggtacccc   4440
attgtatggg aatctgatct ggggcctcgg tgcacatgct ttacatgtgt ttagtcgagg   4500
ttaaaaaagc tctaggcccc ccgaaccacg gggacgtggt tttcctttga aaaacacgat   4560
gataagcttg ccacaaatgg aactgagacc ttggctgctg tgggtggtgg ctgctactgg   4620
caccctggtg ctgctagcag ctgacgccca gggccagaag gtgttcacca acacctgggc   4680
tgtgagaatc cccggcggac ctgctgtggc taacagcgtg gctcgtaagc acggcttcct   4740
gaacctggga cagattttcg gtgactacta ccacttctgg caccgcggag tgaccaagag   4800
gagcctgtcc ccacacagac caaggcactc cagactgcag cgtgagcccc aggtgcagtg   4860
gctggaacag caggtggcca agcgcaggac caagagagac gtgtaccagg agcctaccga   4920
cccaaagttc cccagcagt ggtatctgtc cggcgtgacc cagcgtgacc tgaacgtgaa   4980
ggccgcttgg gctcagggtt acaccggtca cggcatcgtg gtgtccatcc tggacgacgg   5040
catcgagaag aaccaccctg acctggccgg taactacgac ccaggcgctt ctttcgacgt   5100
gaacgaccag gaccccgacc ctcagccaag atacacccag atgaacgaca acagacatgg   5160
aaccagatgt gctggtgaag tggctgctgt ggctaacaac ggcgtgtgcg gagtgggtgt   5220
ggcctacaac gctagaatcg gtggcgtgcg tatgctggat ggagaagtga ctgatgctgt   5280
ggaagctaga agcctgggac tgaacccaaa ccacatccac atctactctg ccagctgggg   5340
tccagaggat gatggaaaga ctgtggatgg tcctgctaga ctggctgagg aagccttctt   5400
ccgcggcgtg agccagggaa ggggaggtct gggaagcatc ttcgtgtggg cttctggtaa   5460
cggcggaaga gagcacgact cctgcaactg cgacggatac accaactcta tctacaccct   5520
gagcatcagc tccgctaccc agttcggtaa cgtgccctgg tactccgaag cctgctctag   5580
caccctggct accacctact cctctggcaa ccagaacgag aagcagatcg tgaccaccga   5640
cctgcgtcag aagtgcaccg aatctcacac tggcacctcc gcctctgctc ctctggctgc   5700
tggaatcatc gccctgaccc tggaggctaa caagaacctg acctggcgcg acatgcagca   5760
cctggtggtg cagacctcca agccagctca cctgaacgcc aacgactggg ctaccaacgg   5820
cgtgggaagg aaggtgagcc actcttacgg ttacggtctg ctggatgctg gtgctatggt   5880
ggccctggct cagaactgga ccaccgtggc ccctcagcgc aagtgcatca tcgacatcct   5940
gaccgagcct aaggacatcg gaaagagact ggaagtgcgt aagaccgtga ccgcttgcct   6000
gggagagccc aaccacatca ccagactgga acacgcccag gctcgtctga ccctgtctta   6060
caacagacgt ggagacctgg ccatccacct ggtgtctcca atgggcaccc gcagcaccct   6120
gctggctgct aggccacacg actacagcgc cgacggattc aacgactggg ctttcatgac   6180
caccccactcc tgggacgagg acccttctgg tgaatgggtg ctggagatcg aaaacaccag   6240
cgaggccaac aactacggca ccctgaccaa gttcaccctg gtgctgtacg gcaccgctcc   6300
tgagggactg ccagtgcccc ctgaaagctc cggttgcaag accctgacct ctagccaggc   6360
ctgcgtggtg tgcgaggaag gcttctccct gcaccagaag tcttgcgtgc agcactgccc   6420
acccggattc gctcctcagg tgctggacac ccactactct accgagaacg acgtggaaac   6480
catcagagcc agcgtgtgcg ctccttgtca cgcttcctgt gctacttgtc agggaccagc   6540
cctgactgac tgcctgtcct gcccatctca cgccagcctg gaccccgtgg agcagacctg   6600
ctccagacag tctcagtcct ctcgtgaaag ccctccacag cagcagcccc ctagactgcc   6660
```

```
acccgaggtg gaagccggcc agagactgcg tgctggactg ctgccttctc acctgccaga   6720

ggtggtggct ggtctgagct gcgctttcat cgtgctggtg ttcgtgaccg tgttcctggt   6780

gctgcagctg cgcagcggtt tctccttcag gggcgtgaag gtgtacacca tggaccgcgg   6840

tctgatcagc tacaagggtc tgcctccaga ggcttggcag gaggaatgcc catctgacag   6900

cgaagaggac gagggacgtg gagaacggac tgccttcatc aaagatcaga gcgcactgta   6960

ataaatcgat ttaattaata gcataacccc ttggggcctc taaacgggtc ttgaggggtt   7020

ttttggaatt cacccagctt tcttgtacaa agtggtgata gcttgtcgag aagtactaga   7080

ggatcataat cagccatacc acatttgtag aggttttact tgctttaaaa aacctcccac   7140

acctccccct gaacctgaaa cataaaatga atgcaattgt tgttgttaac ttgtttattg   7200

cagcttataa tggttacaaa taaagcaata gcatcacaaa tttcacaaat aaagcatttt   7260

tttcactgca ttctagttgt ggtttgtcca aactcatcaa tgtatcttat catgtctgga   7320

tc                                                                  7322
```

<210> SEQ ID NO 5
<211> LENGTH: 7613
<212> TYPE: DNA
<213> ORGANISM: Artificial Sequence
<220> FEATURE:
<223> OTHER INFORMATION: Dual Promoter-Heterologous ZIKV del108C-prM-E-
      IRES-del108CDENV2-human furin proprotein cassette + ZIKV NS1

<400> SEQUENCE: 5

```
gtggctatgg cagggcttgc cgccccgacg ttggctgcga gccctgggcc ttcacccgaa     60

cttgggggtt ggggtgggga aaaggaagaa acgcgggcgt attggtccca atggggtctc    120

ggtggggtat cgacagagtg ccagccctgg gaccgaaccc cgcgtttatg aacaaacgac    180

ccaacacccg tgcgttttat tctgtctttt tattgccgtc atagcgcggg ttccttccgg    240

tattgtctcc ttccgtgttt cagttagcct cccccatctc ccggtagcgc atgctctaga    300

ggcgcgcctt attatgcagt caccattgac cttactaagt tactttctgg ttctttcctg    360

ggccttatct ccattccata ccaacagcca tctttagccc ggaacgacag tgggggcatt    420

gtgcactccc tgcagcacca ttcctcgatc acccttccgc ttgcagtggt tgatctcaga    480

gatggtcctc ttgttccaca tgtttcctcc acgtggacct tagtgcctgg gcattcctca    540

aaccgaattt caagctcttc actgtgccat ggccctttca tttgggtcct gtagccctct    600

ctggtattgt gatggctgag tggcccagct aaagacttgg gtatgatcag atcactctct    660

tctattccat ctgtccacaa tgtgtgggac tttggccatt cacatgtttt catctcgatc    720

agatgggccc tcttcagcct ccatgtgtca ttcttctcac tctcaatcca gtagcctaga    780

tcactgtgta cagcctcctt tcccttaaca gctgttccaa taacggctgg atcacactct    840

aatgaataat cttctctaac cttgagccag acactagtgt gaaatacccc gaacccatga    900

tcctccacaa gaaagctgtt ccatgctcta tgtttgagtg ggcattcctt cagtgtgtca    960

ccatccacga caaagctgtt atttgtcttt gctgctctga cgaagtacga tttcccccaa   1020

gccttccagc cgtggggcag ctcgttcaca ggcacgggca atctctgtgg acctctccac   1080

atggggtttt ttacagatcc cacaacgacc gtcagttgaa ctccattctc ttccaggatt   1140

gcgttgagct ccccttctac tgatctccac atgatgtttt ccattcttga aacagaggag   1200

atcccacaga taccatcttc ccaggcttgc ttgactgctg ctgccaatct acggggggag   1260

tcaggatggt acttgtacct gtccctccag gcttcaacgt cgttatagac gaacacccct   1320
```

-continued gtaccgcatc tcgtctcctt ctttgagaag tccaccgagc accccacatc catgcggccg 1380
cctcgagatc ccgggtgatc aagtcttcgt cgagtgattg taaataaaat gtaatttaca 1440
gtatagtatt ttaattaata tacaaatgat ttgataataa ttcttattta actataatat 1500
attgtgttgg gttgaattaa aggtccgtat catggagata attaaaatga taaccatctc 1560
gcaaataaat aagtatttta ctgttttcgt aacagttttg taataaaaaa acctataaat 1620
attccggatt attcataccg tcccaccatc gggcgcggat catcacaagt ttgtacaaaa 1680
aagcaggcta gatcttaata cgactcacta tattaattaa ggatcccaaa aaattgaaat 1740
tttatttttt tttttggaa tataaataat atgctgctcg gacacggccc tattcgtatg 1800
gtgctcgcta tcctcgcctt tctcaggttt accgctatca agcctagtct gggtctcatc 1860
aacagatggg gtagcgtggg caagaaggag gctatggaaa tcatcaagaa gttcaagaag 1920
gacctggccg ctatgctgag aatcatcaac gctcgtaagg agaagaagcg caggggtgcc 1980
gacacctctg tgggaatcgt gggtctgctg ctgaccaccg ctatggctgc tgaggtgacc 2040
agaagaggct ccgcctacta catgtacctg gacaggaacg acgctggaga agccatctct 2100
ttccccacca ccctgggtat gaacaagtgc tacatccaga tcatggacct gggacacatg 2160
tgcgacgcca ccatgagcta cgagtgccca atgctggacg agggtgtgga acccgacgac 2220
gtggactgct ggtgcaacac caccagcacc tgggtggtgt acggaacctg ccaccacaag 2280
aagggtgaag ctcgcaggtc cagacgtgcc gtgaccctgc cttcccactc tacccgcaag 2340
ctgcagacca ggtcccagac ctggctggag tctcgcgaat acaccaagca cctgatccgc 2400
gtggagaact ggatcttcag gaaccctggt ttcgctctgg ccgctgctgc tatcgcttgg 2460
ctgctgggaa gctccacctc ccagaaggtc atctacctgg tcatgatcct gctgatcgcc 2520
cctgcttaca gcatcagatg catcggcgtg agcaaccgtg acttcgtgga gggcatgtct 2580
ggcggaacct gggtggacgt ggtgctggaa cacggtggct gcgtgaccgt gatggctcag 2640
gacaagccaa ccgtcgacat cgagctggtg accaccaccg tgtctaacat ggccgaggtg 2700
cgcagctact gctacgaagc cagcatcagc gacatggcct ctgacagcag gtgcccaacc 2760
cagggcgaag cttacctgga caagcagtct gacacccagt acgtgtgcaa gagaaccctg 2820
gtggaccgtg gatggggtaa cggctgcgga ctgttcggca agggcagcct ggtgacctgc 2880
gctaagttcg cctgctccaa gaagatgacc ggcaagtcta tccagccaga gaacctggaa 2940
tacagaatca tgctgtctgt gcacggctcc cagcactctg gaatgatcgt gaacgacacc 3000
ggacacgaaa ccgacgaaaa cagagccaag gtggagatca cccctaactc tccacgtgcc 3060
gaagctaccc tgggaggttt cggcagcctg ggactggact gtgagcctcg taccggcctg 3120
gacttctccg acctgtacta cctgaccatg aacaacaagc actggctggt gcacaaggaa 3180
tggttccacg acatcccact gccatggcac gccggtgctg acactggaac cccacactgg 3240
aacaacaagg aggctctggt ggagttcaag gacgcccacg ctaagagaca gactgtggtg 3300
gtgctgggtt cccaggaggg tgctgtgcac accgccctgg ctggagctct ggaggctgaa 3360
atggacggtg ccaagggccg tctgtctagc ggtcacctga agtgccgcct gaagatggac 3420
aagctgaggc tgaagggcgt gtcctactct ctgtgcaccg ccgctttcac cttcaccaag 3480
atccctgctg aaaccctgca cggcaccgtg accgtggaag tgcagtacgc tggaaccgat 3540
ggtccatgca aggtgcctgc tcagatggcc gtggacatgc agaccctgac ccctgtggga 3600
cgcctgatca ccgccaaccc agtgatcacc gagtctaccg aaaacagcaa gatgatgctg 3660
gagctggacc ctcccttcgg cgacagctac atcgtgatcg gagtgggtga aaagaagatc 3720

-continued

```
acccaccact ggcacaggag cggcagcacc atcggcaagg ctttcgaggc taccgtgcgc   3780
ggcgctaaga gaatggccgt gctgggcgac actgcttggg acttcggaag cgtgggcgga   3840
gccctgaact ccctgggcaa gggaatccac cagatcttcg gcgccgcttt caagtccctg   3900
ttcggtggca tgagctggtt ctcccagatc ctgatcggaa ccctgctgat gtggctgggt   3960
ctgaacacca agaacggctc tatcagcctg atgtgcctcg ctctcggtgg cgtgctgatt   4020
tttctctcta ccgcagtctc cgcatgagcc cctctccctc cccccccct aacgttactg   4080
gccgaagccg cttggaataa ggccggtgtg tgtttgtcta tatgtgattt tccaccatat   4140
tgccgtcttt tggcaatgtg agggcccgga aacctggccc tgtcttcttg acgagcattc   4200
ctaggggtct ttcccctctc gccaaaggaa tgcaaggtct gttgaatgtc gtgaaggaag   4260
cagttcctct ggaagcttct tgaagacaaa caacgtctgt agcgaccctt tgcaggcagc   4320
ggaacccccc acctggcgac aggtgcctct gcggccaaaa gccacgtgta taagatacac   4380
ctgcaaaggc ggcacaaccc cagtgccacg ttgtgagttg gatagttgtg gaaagagtca   4440
aatggctctc ctcaagcgta gtcaacaagg ggctgaagga tgcccagaag gtaccccatt   4500
gtatgggaat ctgatctggg gcctcggtgc acatgcttta catgtgttta gtcgaggtta   4560
aaaaagctct aggccccccg aaccacgggg acgtggtttt cctttgaaaa acacgatgat   4620
aagcttgcca caaatgctcc agggtcgcgg tccactgaaa ctctttatgg ctctcgtcgc   4680
cttcctgcgg ttcctcacta ttcctcctac tgtcggtatt ctgaagaggt ggggcaccat   4740
caagaagagc aaggccatca acgtgctgcg cggattcagg aaggagatcg gtaggatgct   4800
gaacatcctg aaccgcagga gacgtaccgc cggcatgatc atcatgctga tccccaccgt   4860
gatggctatg gaactgagac cttggctgct gtgggtggtg gctgctactg gcaccctggt   4920
gctgctagca gctgacgccc agggccagaa ggtgttcacc aacacctggg ctgtgagaat   4980
ccccggcgga cctgctgtgg ctaacagcgt ggctcgtaag cacggcttcc tgaacctggg   5040
acagattttc ggtgactact accacttctg gcaccgcgga gtgaccaaga ggagcctgtc   5100
cccacacaga ccaaggcact ccagactgca gcgtgagccc caggtgcagt ggctggaaca   5160
gcaggtggcc aagcgcagga ccaagagaga cgtgtaccag gagcctaccg acccaaagtt   5220
cccccagcag tggtatctgt ccggcgtgac ccagcgtgac ctgaacgtga aggccgcttg   5280
ggctcagggt tacaccggtc acggcatcgt ggtgtccatc ctggacgacg gcatcgagaa   5340
gaaccaccct gacctggccg gtaactacga cccaggcgct tctttcgacg tgaacgacca   5400
ggaccccgac cctcagccaa gatacaccca gatgaacgac aacagacatg gaaccagatg   5460
tgctggtgaa gtggctgctg tggctaacaa cggcgtgtgc ggagtgggtg tggcctacaa   5520
cgctagaatc ggtggcgtgc gtatgctgga tggagaagtg actgatgctg tggaagctag   5580
aagcctggga ctgaacccaa accacatcca catctactct gccagctggg gtccagagga   5640
tgatggaaag actgtggatg gtcctgctag actggctgag gaagccttct tccgcggcgt   5700
gagccaggga aggggaggtc tgggaagcat cttcgtgtgg gcttctggta acggcggaag   5760
agagcacgac tcctgcaact gcgacggata caccaactct atctacaccc tgagcatcag   5820
ctccgctacc cagttcggta acgtgccctg gtactccgaa gcctgctcta gcaccctggc   5880
taccacctac tcctctggca accagaacga gaagcagatc gtgaccaccg acctgcgtca   5940
gaagtgcacc gaatctcaca ctggcacctc cgcctctgct cctctggctg ctggaatcat   6000
cgccctgacc ctggaggcta acaagaacct gacctggcgc gacatgcagc acctggtggt   6060
gcagacctcc aagccagctc acctgaacgc caacgactgg gctaccaacg gcgtgggaag   6120
```

```
gaaggtgagc cactcttacg gttacggtct gctggatgct ggtgctatgg tggccctggc   6180

tcagaactgg accaccgtgg cccctcagcg caagtgcatc atcgacatcc tgaccgagcc   6240

taaggacatc ggaaagagac tggaagtgcg taagaccgtg accgcttgcc tgggagagcc   6300

caaccacatc accagactgg aacacgccca ggctcgtctg accctgtctt acaacagacg   6360

tggagacctg gccatccacc tggtgtctcc aatgggcacc cgcagcaccc tgctggctgc   6420

taggccacac gactacagcg ccgacggatt caacgactgg gctttcatga ccacccactc   6480

ctgggacgag gacccttctg gtgaatgggt gctggagatc gaaaacacca gcgaggccaa   6540

caactacggc accctgacca agttcaccct ggtgctgtac ggcaccgctc ctgagggact   6600

gccagtgccc cctgaaagct ccggttgcaa gaccctgacc tctagccagg cctgcgtggt   6660

gtgcgaggaa ggcttctccc tgcaccagaa gtcttgcgtg cagcactgcc cacccggatt   6720

cgctcctcag gtgctggaca cccactactc taccgagaac gacgtggaaa ccatcagagc   6780

cagcgtgtgc gctccttgtc acgcttcctg tgctacttgt cagggaccag ccctgactga   6840

ctgcctgtcc tgcccatctc acgccagcct ggaccccgtg gagcagacct gctccagaca   6900

gtctcagtcc tctcgtgaaa gccctccaca gcagcagccc cctagactgc cacccgaggt   6960

ggaagccggc cagagactgc gtgctggact gctgccttct cacctgccag aggtggtggc   7020

tggtctgagc tgcgctttca tcgtgctggt gttcgtgacc gtgttcctgg tgctgcagct   7080

gcgcagcggt ttctccttca ggggcgtgaa ggtgtacacc atggaccgcg gtctgatcag   7140

ctacaagggt ctgcctccag aggcttggca ggaggaatgc ccatctgaca gcgaagagga   7200

cgagggacgt ggagaacgga ctgccttcat caaagatcag agcgcactgt aataaatcga   7260

tttaattaat agcataaccc cttggggcct ctaaacgggt cttgaggggt tttttggaat   7320

tcacccagct ttcttgtaca aagtggtgat agcttgtcga gaagtactag aggatcataa   7380

tcagccatac cacatttgta gaggttttac ttgctttaaa aaacctccca cacctccccc   7440

tgaacctgaa acataaaatg aatgcaattg ttgttgttaa cttgtttatt gcagcttata   7500

atggttacaa ataaagcaat agcatcacaa atttcacaaa taaagcattt ttttcactgc   7560

attctagttg tggtttgtcc aaactcatca atgtatctta tcatgtctgg atc          7613
```

<210> SEQ ID NO 6
<211> LENGTH: 7637
<212> TYPE: DNA
<213> ORGANISM: Artificial Sequence
<220> FEATURE:
<223> OTHER INFORMATION: Dual Promoter-Homologous ZIKV del108C-prM-E-IRES-del108CZIKV-human furin proprotein cassette + ZIKV NS1

<400> SEQUENCE: 6

```
gtggctatgg cagggcttgc cgccccgacg ttggctgcga gccctgggcc ttcacccgaa     60

cttgggggtt ggggtgggga aaaggaagaa acgcgggcgt attggtccca atggggtctc    120

ggtggggtat cgacagagtg ccagccctgg gaccgaaccc cgcgtttatg aacaaacgac    180

ccaacacccg tgcgttttat tctgtctttt tattgccgtc atagcgcggg ttccttccgg    240

tattgtctcc ttccgtgttt cagttagcct cccccatctc ccggtagcgc atgctctaga    300

ggcgcgcctt attatgcagt caccattgac cttactaagt tactttctgg ttctttcctg    360

ggccttatct ccattccata ccaacagcca tctttagccc ggaacgacag tgggggcatt    420

gtgcactccc tgcagcacca ttcctcgatc acccttccgc ttgcagtggt tgatctcaga    480

gatggtcctc ttgttccaca tgtttcctcc acgtggacct tagtgcctgg gcattcctca    540
```

-continued

```
aaccgaattt caagctcttc actgtgccat ggccctttca tttgggtcct gtagccctct    600
ctggtattgt gatggctgag tggcccagct aaagacttgg gtatgatcag atcactctct    660
tctattccat ctgtccacaa tgtgtgggac tttggccatt cacatgtttt catctcgatc    720
agatgggccc tcttcagcct ccatgtgtca ttcttctcac tctcaatcca gtagcctaga    780
tcactgtgta cagcctcctt tcccttaaca gctgttccaa taacggctgg atcacactct    840
aatgaataat cttctctaac cttgagccag acactagtgt gaaatacccc gaacccatga    900
tcctccacaa gaaagctgtt ccatgctcta tgtttgagtg ggcattcctt cagtgtgtca    960
ccatccacga caaagctgtt atttgtcttt gctgctctga cgaagtacga tttcccccaa   1020
gccttccagc cgtggggcag ctcgttcaca ggcacgggca atctctgtgg acctctccac   1080
atggggtttt ttacagatcc cacaacgacc gtcagttgaa ctccattctc ttccaggatt   1140
gcgttgagct ccccttctac tgatctccac atgatgtttt ccattcttga aacagaggag   1200
atcccacaga taccatcttc ccaggcttgc ttgactgctg ctgccaatct acggggggag   1260
tcaggatggt acttgtacct gtccctccag gcttcaacgt cgttatagac gaacacccct   1320
gtaccgcatc tcgtctcctt ctttgagaag tccaccgagc accccacatc catgcggccg   1380
cctcgagatc ccgggtgatc aagtcttcgt cgagtgattg taaataaaat gtaatttaca   1440
gtatagtatt ttaattaata tacaaatgat ttgataataa ttcttattta actataatat   1500
attgtgttgg gttgaattaa aggtccgtat catggagata attaaaatga taaccatctc   1560
gcaaataaat aagtatttta ctgttttcgt aacagttttg taataaaaaa acctataaat   1620
attccggatt attcataccg tcccaccatc gggcgcggat catcacaagt ttgtacaaaa   1680
aagcaggcta gatcttaata cgactcacta tattaattaa ggatcccaaa aaattgaaat   1740
tttatttttt ttttttggaa tataaataat atgctgctcg gacacggccc tattcgtatg   1800
gtgctcgcta tcctcgcctt tctcaggttt accgctatca agcctagtct gggtctcatc   1860
aacagatggg gtagcgtggg caagaaggag gctatggaaa tcatcaagaa gttcaagaag   1920
gacctggccg ctatgctgag aatcatcaac gctcgtaagg agaagaagcg caggggtgcc   1980
gacacctctg tgggaatcgt gggtctgctg ctgaccaccg ctatggctgc tgaggtgacc   2040
agaagaggct ccgcctacta catgtacctg gacaggaacg acgctggaga agccatctct   2100
ttccccacca ccctgggtat gaacaagtgc tacatccaga tcatggacct gggacacatg   2160
tgcgacgcca ccatgagcta cgagtgccca atgctggacg agggtgtgga acccgacgac   2220
gtggactgct ggtgcaacac caccagcacc tgggtggtgt acggaacctg ccaccacaag   2280
aagggtgaag ctcgcaggtc cagacgtgcc gtgaccctgc cttcccactc tacccgcaag   2340
ctgcagacca ggtcccagac ctggctggag tctcgcgaat acaccaagca cctgatccgc   2400
gtggagaact ggatcttcag gaaccctggt ttcgctctgg ccgctgctgc tatcgcttgg   2460
ctgctgggaa gctccacctc ccagaaggtc atctacctgg tcatgatcct gctgatcgcc   2520
cctgcttaca gcatcagatg catcggcgtg agcaaccgtg acttcgtgga gggcatgtct   2580
ggcggaacct gggtggacgt ggtgctggaa cacggtggct gcgtgaccgt gatggctcag   2640
gacaagccaa ccgtcgacat cgagctggtg accaccaccg tgtctaacat ggccgaggtg   2700
cgcagctact gctacgaagc cagcatcagc gacatggcct ctgacagcag gtgcccaacc   2760
cagggcgaag cttacctgga caagcagtct gacacccagt acgtgtgcaa gagaaccctg   2820
gtggaccgtg gatggggtaa cggctgcgga ctgttcggca agggcagcct ggtgacctgc   2880
gctaagttcg cctgctccaa gaagatgacc ggcaagtcta tccagccaga gaacctggaa   2940
```

-continued

```
tacagaatca tgctgtctgt gcacggctcc cagcactctg gaatgatcgt gaacgacacc   3000
ggacacgaaa ccgacgaaaa cagagccaag gtggagatca cccctaactc tccacgtgcc   3060
gaagctaccc tgggaggttt cggcagcctg ggactggact gtgagcctcg taccggcctg   3120
gacttctccg acctgtacta cctgaccatg aacaacaagc actggctggt gcacaaggaa   3180
tggttccacg acatcccact gccatggcac gccggtgctg acactggaac cccacactgg   3240
aacaacaagg aggctctggt ggagttcaag gacgcccacg ctaagagaca gactgtggtg   3300
gtgctgggtt cccaggaggg tgctgtgcac accgccctgg ctggagctct ggaggctgaa   3360
atggacggtg ccaagggccg tctgtctagc ggtcacctga agtgccgcct gaagatggac   3420
aagctgaggc tgaagggcgt gtcctactct ctgtgcaccg ccgctttcac cttcaccaag   3480
atccctgctg aaaccctgca cggcaccgtg accgtggaag tgcagtacgc tggaaccgat   3540
ggtccatgca aggtgcctgc tcagatggcc gtggacatgc agaccctgac ccctgtggga   3600
cgcctgatca ccgccaaccc agtgatcacc gagtctaccg aaaacagcaa gatgatgctg   3660
gagctggacc ctcccttcgg cgacagctac atcgtgatcg gagtgggtga aaagaagatc   3720
acccaccact ggcacaggag cggcagcacc atcggcaagg ctttcgaggc taccgtgcgc   3780
ggcgctaaga gaatggccgt gctgggcgac actgcttggg acttcggaag cgtgggcgga   3840
gccctgaact ccctgggcaa gggaatccac cagatcttcg gcgccgcttt caagtccctg   3900
ttcggtggca tgagctggtt ctcccagatc ctgatcggaa ccctgctgat gtggctgggt   3960
ctgaacacca agaacggctc tatcagcctg atgtgcctcg ctctcggtgg cgtgctgatt   4020
tttctctcta ccgcagtctc cgcatgagcc cctctccctc cccccccct aacgttactg   4080
gccgaagccg cttggaataa ggccggtgtg tgtttgtcta tatgtgattt tccaccatat   4140
tgccgtcttt tggcaatgtg agggcccgga aacctggccc tgtcttcttg acgagcattc   4200
ctaggggtct ttcccctctc gccaaaggaa tgcaaggtct gttgaatgtc gtgaaggaag   4260
cagttcctct ggaagcttct tgaagacaaa caacgtctgt agcgaccctt tgcaggcagc   4320
ggaacccccc acctggcgac aggtgcctct gcggccaaaa gccacgtgta taagatacac   4380
ctgcaaaggc ggcacaaccc cagtgccacg ttgtgagttg gatagttgtg gaaagagtca   4440
aatggctctc ctcaagcgta gtcaacaagg ggctgaagga tgcccagaag gtaccccatt   4500
gtatgggaat ctgatctggg gcctcggtgc acatgcttta catgtgttta gtcgaggtta   4560
aaaaagctct aggccccccg aaccacgggg acgtggtttt cctttgaaaa acacgatgat   4620
aagcttgcca caaatgctgc tcggacacgg ccctattcgt atggtgctcg ctatcctcgc   4680
ctttctcagg tttaccgcta tcaagcctag tctgggtctc atcaacagat ggggtagcgt   4740
gggcaagaag gaggctatgg aaatcatcaa gaagttcaag aaggacctgg ccgctatgct   4800
gagaatcatc aacgctcgta aggagaagaa gcgcaggggt gccgacacct ctgtgggaat   4860
cgtgggtctg ctgctgacca ccgctatggc tatggaactg agaccttggc tgctgtgggt   4920
ggtggctgct actggcaccc tggtgctgct agcagctgac gcccagggcc agaaggtgtt   4980
caccaacacc tgggctgtga gaatccccgg cggacctgct gtggctaaca gcgtggctcg   5040
taagcacggc ttcctgaacc tgggacagat tttcggtgac tactaccact tctggcaccg   5100
cggagtgacc aagaggagcc tgtccccaca cagaccaagg cactccagac tgcagcgtga   5160
gccccaggtg cagtggctgg aacagcaggt ggccaagcgc aggaccaaga gagacgtgta   5220
ccaggagcct accgacccaa agttccccca gcagtggtat ctgtccggcg tgacccagcg   5280
tgacctgaac gtgaaggccg cttgggctca gggttacacc ggtcacggca tcgtggtgtc   5340
```

-continued

```
catcctggac gacggcatcg agaagaacca ccctgacctg gccggtaact acgacccagg   5400
cgcttctttc gacgtgaacg accaggaccc cgaccctcag ccaagataca cccagatgaa   5460
cgacaacaga catggaacca gatgtgctgg tgaagtggct gctgtggcta acaacggcgt   5520
gtgcggagtg ggtgtggcct acaacgctag aatcggtggc gtgcgtatgc tggatggaga   5580
agtgactgat gctgtggaag ctagaagcct gggactgaac ccaaaccaca tccacatcta   5640
ctctgccagc tggggtccag aggatgatgg aaagactgtg gatggtcctg ctagactggc   5700
tgaggaagcc ttcttccgcg gcgtgagcca gggaagggga ggtctgggaa gcatcttcgt   5760
gtgggcttct ggtaacggcg gaagagagca cgactcctgc aactgcgacg gatacaccaa   5820
ctctatctac accctgagca tcagctccgc tacccagttc ggtaacgtgc cctggtactc   5880
cgaagcctgc tctagcaccc tggctaccac ctactcctct ggcaaccaga acgagaagca   5940
gatcgtgacc accgacctgc gtcagaagtg caccgaatct cacactggca cctccgcctc   6000
tgctcctctg gctgctggaa tcatcgccct gaccctggag gctaacaaga acctgacctg   6060
gcgcgacatg cagcacctgg tggtgcagac ctccaagcca gctcacctga acgccaacga   6120
ctgggctacc aacggcgtgg gaaggaaggt gagccactct tacggttacg gtctgctgga   6180
tgctggtgct atggtggccc tggctcagaa ctggaccacc gtggcccctc agcgcaagtg   6240
catcatcgac atcctgaccg agcctaagga catcggaaag agactggaag tgcgtaagac   6300
cgtgaccgct tgcctgggag agcccaacca catcaccaga ctggaacacg cccaggctcg   6360
tctgaccctg tcttacaaca gacgtggaga cctggccatc cacctggtgt ctccaatggg   6420
cacccgcagc accctgctgg ctgctaggcc acacgactac agcgccgacg gattcaacga   6480
ctgggctttc atgaccaccc actcctggga cgaggaccct tctggtgaat gggtgctgga   6540
gatcgaaaac accagcgagg ccaacaacta cggcaccctg accaagttca ccctggtgct   6600
gtacggcacc gctcctgagg gactgccagt gccccctgaa agctccggtt gcaagaccct   6660
gacctctagc caggcctgcg tggtgtgcga ggaaggcttc tccctgcacc agaagtcttg   6720
cgtgcagcac tgcccacccg gattcgctcc tcaggtgctg gacacccact actctaccga   6780
gaacgacgtg gaaaccatca gagccagcgt gtgcgctcct tgtcacgctt cctgtgctac   6840
ttgtcaggga ccagccctga ctgactgcct gtcctgccca tctcacgcca gcctggaccc   6900
cgtggagcag acctgctcca gacagtctca gtcctctcgt gaaagccctc cacagcagca   6960
gcccccctaga ctgccacccg aggtggaagc cggccagaga ctgcgtgctg gactgctgcc   7020
ttctcacctg ccagaggtgg tggctggtct gagctgcgct ttcatcgtgc tggtgttcgt   7080
gaccgtgttc ctggtgctgc agctgcgcag cggtttctcc ttcaggggcg tgaaggtgta   7140
caccatggac cgcggtctga tcagctacaa gggtctgcct ccagaggctt ggcaggagga   7200
atgcccatct gacagcgaag aggacgaggg acgtggagaa cggactgcct tcatcaaaga   7260
tcagagcgca ctgtaataaa tcgatttaat taatagcata accccttggg gcctctaaac   7320
gggtcttgag ggtttttttg gaattcaccc agctttcttg tacaaagtgg tgatagcttg   7380
tcgagaagta ctagaggatc ataatcagcc ataccacatt tgtagaggtt ttacttgctt   7440
taaaaaacct cccacacctc cccctgaacc tgaaacataa aatgaatgca attgttgttg   7500
ttaacttgtt tattgcagct tataatggtt acaaataaag caatagcatc acaaatttca   7560
caaataaagc atttttttca ctgcattcta gttgtggttt gtccaaactc atcaatgtat   7620
cttatcatgt ctggatc                                                 7637
```

```
<210> SEQ ID NO 7
<211> LENGTH: 7379
<212> TYPE: DNA
<213> ORGANISM: Artificial Sequence
<220> FEATURE:
<223> OTHER INFORMATION: Dual Promoter-ZIKV del108C-prM-E-IRES-human
      furin proprotein cassette + ZIKV NS1

<400> SEQUENCE: 7

gtggctatgg cagggcttgc cgccccgacg ttggctgcga gccctgggcc ttcacccgaa     60

cttgggggtt ggggtgggga aaaggaagaa acgcgggcgt attggtccca atggggtctc    120

ggtggggtat cgacagagtg ccagccctgg gaccgaaccc cgcgtttatg aacaaacgac    180

ccaacacccg tgcgttttat tctgtctttt tattgccgtc atagcgcggg ttccttccgg    240

tattgtctcc ttccgtgttt cagttagcct cccccatctc ccggtagcgc atgctctaga    300

ggcgcgcctt attatgcagt caccattgac cttactaagt tactttctgg ttctttcctg    360

ggccttatct ccattccata ccaacagcca tctttagccc ggaacgacag tgggggcatt    420

gtgcactccc tgcagcacca ttcctcgatc acccttccgc ttgcagtggt tgatctcaga    480

gatggtcctc ttgttccaca tgtttcctcc acgtggacct tagtgcctgg gcattcctca    540

aaccgaattt caagctcttc actgtgccat ggccctttca tttgggtcct gtagccctct    600

ctggtattgt gatggctgag tggcccagct aaagacttgg gtatgatcag atcactctct    660

tctattccat ctgtccacaa tgtgtgggac tttggccatt cacatgtttt catctcgatc    720

agatgggccc tcttcagcct ccatgtgtca ttcttctcac tctcaatcca gtagcctaga    780

tcactgtgta cagcctcctt tcccttaaca gctgttccaa taacggctgg atcacactct    840

aatgaataat cttctctaac cttgagccag acactagtgt gaaatacccc gaacccatga    900

tcctccacaa gaaagctgtt ccatgctcta tgtttgagtg ggcattcctt cagtgtgtca    960

ccatccacga caaagctgtt atttgtcttt gctgctctga cgaagtacga tttcccccaa   1020

gccttccagc cgtggggcag ctcgttcaca ggcacgggca atctctgtgg acctctccac   1080

atggggtttt ttacagatcc cacaacgacc gtcagttgaa ctccattctc ttccaggatt   1140

gcgttgagct cccccttctac tgatctccac atgatgtttt ccattcttga aacagaggag   1200

atcccacaga taccatcttc ccaggcttgc ttgactgctg ctgccaatct acggggggag   1260

tcaggatggt acttgtacct gtccctccag gcttcaacgt cgttatagac gaacacccct   1320

gtaccgcatc tcgtctcctt ctttgagaag tccaccgagc accccacatc catgcggccg   1380

cctcgagatc ccgggtgatc aagtcttcgt cgagtgattg taaataaaat gtaatttaca   1440

gtatagtatt ttaattaata tacaaatgat ttgataataa ttcttattta actataatat   1500

attgtgttgg gttgaattaa aggtccgtat catggagata attaaaatga taaccatctc   1560

gcaaataaat aagtatttta ctgttttcgt aacagttttg taataaaaaa acctataaat   1620

attccggatt attcataccg tcccaccatc gggcgcggat catcacaagt ttgtacaaaa   1680

aagcaggcta gatcttaata cgactcacta tattaattaa ggatcccaaa aaattgaaat   1740

tttatttttt ttttttggaa tataaataat atgctgctcg gacacggccc tattcgtatg   1800

gtgctcgcta tcctcgcctt tctcaggttt accgctatca agcctagtct gggtctcatc   1860

aacagatggg gtagcgtggg caagaaggag gctatggaaa tcatcaagaa gttcaagaag   1920

gacctggccg ctatgctgag aatcatcaac gctcgtaagg agaagaagcg caggggtgcc   1980

gacacctctg tgggaatcgt gggtctgctg ctgaccaccg ctatggctgc tgaggtgacc   2040

agaagaggct ccgcctacta catgtacctg gacaggaacg acgctggaga agccatctct   2100
```

ttccccacca ccctgggtat gaacaagtgc tacatccaga tcatggacct gggacacatg 2160
tgcgacgcca ccatgagcta cgagtgccca atgctggacg agggtgtgga acccgacgac 2220
gtggactgct ggtgcaacac caccagcacc tgggtggtgt acggaacctg ccaccacaag 2280
aagggtgaag ctcgcaggtc cagacgtgcc gtgaccctgc cttcccactc tacccgcaag 2340
ctgcagacca ggtcccagac ctggctggag tctcgcgaat acaccaagca cctgatccgc 2400
gtggagaact ggatcttcag gaaccctggt ttcgctctgg ccgctgctgc tatcgcttgg 2460
ctgctgggaa gctccacctc ccagaaggtc atctacctgg tcatgatcct gctgatcgcc 2520
cctgcttaca gcatcagatg catcggcgtg agcaaccgtg acttcgtgga gggcatgtct 2580
ggcggaacct gggtggacgt ggtgctggaa cacggtggct gcgtgaccgt gatggctcag 2640
gacaagccaa ccgtcgacat cgagctggtg accaccaccg tgtctaacat ggccgaggtg 2700
cgcagctact gctacgaagc cagcatcagc gacatggcct ctgacagcag gtgcccaacc 2760
cagggcgaag cttacctgga caagcagtct gacacccagt acgtgtgcaa gagaaccctg 2820
gtggaccgtg gatggggtaa cggctgcgga ctgttcggca agggcagcct ggtgacctgc 2880
gctaagttcg cctgctccaa gaagatgacc ggcaagtcta tccagccaga gaacctggaa 2940
tacagaatca tgctgtctgt gcacggctcc cagcactctg gaatgatcgt gaacgacacc 3000
ggacacgaaa ccgacgaaaa cagagccaag gtggagatca cccctaactc tccacgtgcc 3060
gaagctaccc tgggaggttt cggcagcctg ggactggact gtgagcctcg taccggcctg 3120
gacttctccg acctgtacta cctgaccatg aacaacaagc actggctggt gcacaaggaa 3180
tggttccacg acatcccact gccatggcac gccggtgctg acactggaac ccccacactgg 3240
aacaacaagg aggctctggt ggagttcaag gacgcccacg ctaagagaca gactgtggtg 3300
gtgctgggtt cccaggaggg tgctgtgcac accgccctgg ctggagctct ggaggctgaa 3360
atggacggtg ccaagggccg tctgtctagc ggtcacctga agtgccgcct gaagatggac 3420
aagctgaggc tgaagggcgt gtcctactct ctgtgcaccg ccgctttcac cttcaccaag 3480
atccctgctg aaaccctgca cggcaccgtg accgtggaag tgcagtacgc tggaaccgat 3540
ggtccatgca aggtgcctgc tcagatggcc gtggacatgc agaccctgac ccctgtggga 3600
cgcctgatca ccgccaaccc agtgatcacc gagtctaccg aaaacagcaa gatgatgctg 3660
gagctggacc ctcccttcgg cgacagctac atcgtgatcg gagtgggtga aaagaagatc 3720
acccaccact ggcacaggag cggcagcacc atcggcaagg ctttcgaggc taccgtgcgc 3780
ggcgctaaga gaatggccgt gctgggcgac actgcttggg acttcggaag cgtgggcgga 3840
gccctgaact ccctgggcaa gggaatccac cagatcttcg gcgccgcttt caagtccctg 3900
ttcggtggca tgagctggtt ctcccagatc ctgatcggaa ccctgctgat gtggctgggt 3960
ctgaacacca agaacggctc tatcagcctg atgtgcctcg ctctcggtgg cgtgctgatt 4020
tttctctcta ccgcagtctc cgcatgagcc cctctccctc cccccccct aacgttactg 4080
gccgaagccg cttggaataa ggccggtgtg tgtttgtcta tatgtgattt tccaccatat 4140
tgccgtcttt tggcaatgtg agggcccgga aacctggccc tgtcttcttg acgagcattc 4200
ctaggggtct ttcccctctc gccaaaggaa tgcaaggtct gttgaatgtc gtgaaggaag 4260
cagttcctct ggaagcttct tgaagacaaa caacgtctgt agcgaccctt tgcaggcagc 4320
ggaacccccc acctggcgac aggtgcctct gcggccaaaa gccacgtgta taagatacac 4380
ctgcaaaggc ggcacaaccc cagtgccacg ttgtgagttg gatagttgtg gaaagagtca 4440
aatggctctc ctcaagcgta gtcaacaagg ggctgaagga tgcccagaag gtaccccatt 4500

-continued

```
gtatgggaat ctgatctggg gcctcggtgc acatgcttta catgtgttta gtcgaggtta   4560
aaaaagctct aggccccccg aaccacgggg acgtggtttt cctttgaaaa acacgatgat   4620
aagcttgcca caaatggaac tgagaccttg gctgctgtgg gtggtggctg ctactggcac   4680
cctggtgctg ctagcagctg acgcccaggg ccagaaggtg ttcaccaaca cctgggctgt   4740
gagaatcccc ggcggacctg ctgtggctaa cagcgtggct cgtaagcacg gcttcctgaa   4800
cctgggacag attttcggtg actactacca cttctggcac cgcggagtga ccaagaggag   4860
cctgtcccca cacagaccaa ggcactccag actgcagcgt gagccccagg tgcagtggct   4920
ggaacagcag gtggccaagc gcaggaccaa gagagacgtg taccaggagc ctaccgaccc   4980
aaagttcccc cagcagtggt atctgtccgg cgtgacccag cgtgacctga acgtgaaggc   5040
cgcttgggct cagggttaca ccggtcacgg catcgtggtg tccatcctgg acgacggcat   5100
cgagaagaac caccctgacc tggccggtaa ctacgaccca ggcgcttctt tcgacgtgaa   5160
cgaccaggac cccgaccctc agccaagata cacccagatg aacgacaaca gacatggaac   5220
cagatgtgct ggtgaagtgg ctgctgtggc taacaacggc gtgtgcggag tgggtgtggc   5280
ctacaacgct agaatcggtg gcgtgcgtat gctggatgga gaagtgactg atgctgtgga   5340
agctagaagc ctgggactga acccaaacca catccacatc tactctgcca gctggggtcc   5400
agaggatgat ggaaagactg tggatggtcc tgctagactg gctgaggaag ccttcttccg   5460
cggcgtgagc cagggaaggg gaggtctggg aagcatcttc gtgtgggctt ctggtaacgg   5520
cggaagagag cacgactcct gcaactgcga cggatacacc aactctatct acaccctgag   5580
catcagctcc gctacccagt tcggtaacgt gccctggtac tccgaagcct gctctagcac   5640
cctggctacc acctactcct ctggcaacca gaacgagaag cagatcgtga ccaccgacct   5700
gcgtcagaag tgcaccgaat ctcacactgg cacctccgcc tctgctcctc tggctgctgg   5760
aatcatcgcc ctgaccctgg aggctaacaa gaacctgacc tggcgcgaca tgcagcacct   5820
ggtggtgcag acctccaagc cagctcacct gaacgccaac gactgggcta ccaacggcgt   5880
gggaaggaag gtgagccact cttacggtta cggtctgctg gatgctggtg ctatggtggc   5940
cctggctcag aactggacca ccgtggcccc tcagcgcaag tgcatcatcg acatcctgac   6000
cgagcctaag gacatcggaa agagactgga agtgcgtaag accgtgaccg cttgcctggg   6060
agagcccaac cacatcacca gactggaaca cgcccaggct cgtctgaccc tgtcttacaa   6120
cagacgtgga gacctggcca tccacctggt gtctccaatg ggcacccgca gcaccctgct   6180
ggctgctagg ccacacgact acagcgccga cggattcaac gactgggctt tcatgaccac   6240
ccactcctgg gacgaggacc cttctggtga atgggtgctg gagatcgaaa acaccagcga   6300
ggccaacaac tacggcaccc tgaccaagtt caccctggtg ctgtacggca ccgctcctga   6360
gggactgcca gtgccccctg aaagctccgg ttgcaagacc ctgacctcta gccaggcctg   6420
cgtggtgtgc gaggaaggct tctccctgca ccagaagtct tgcgtgcagc actgcccacc   6480
cggattcgct cctcaggtgc tggacaccca ctactctacc gagaacgacg tggaaaccat   6540
cagagccagc gtgtgcgctc cttgtcacgc ttcctgtgct acttgtcagg gaccagccct   6600
gactgactgc ctgtcctgcc catctcacgc cagcctggac cccgtggagc agacctgctc   6660
cagacagtct cagtcctctc gtgaaagccc tccacagcag cagcccccta gactgccacc   6720
cgaggtggaa gccggccaga gactgcgtgc tggactgctg ccttctcacc tgccagaggt   6780
ggtggctggt ctgagctgcg ctttcatcgt gctggtgttc gtgaccgtgt tcctggtgct   6840
gcagctgcgc agcggtttct ccttcagggg cgtgaaggtg tacaccatgg accgcggtct   6900
```

-continued

```
gatcagctac aagggtctgc ctccagaggc ttggcaggag gaatgcccat ctgacagcga   6960

agaggacgag ggacgtggag aacggactgc cttcatcaaa gatcagagcg cactgtaata   7020

aatcgattta attaatagca taaccccttg gggcctctaa acgggtcttg aggggttttt   7080

tggaattcac ccagctttct tgtacaaagt ggtgatagct tgtcgagaag tactagagga   7140

tcataatcag ccataccaca tttgtagagg ttttacttgc tttaaaaaac ctcccacacc   7200

tcccccctgaa cctgaaacat aaaatgaatg caattgttgt tgttaacttg tttattgcag   7260

cttataatgg ttacaaataa agcaatagca tcacaaattt cacaaataaa gcattttttt   7320

cactgcattc tagttgtggt ttgtccaaac tcatcaatgt atcttatcat gtctggatc    7379
```

<210> SEQ ID NO 8
<211> LENGTH: 6108
<212> TYPE: DNA
<213> ORGANISM: Artificial Sequence
<220> FEATURE:
<223> OTHER INFORMATION: Heterologous ZIKV del108C-prM-E-IRES-
      del108CDENV2-human furin proprotein cassette

<400> SEQUENCE: 8

```
cgtatactcc ggaatattaa tagatcatgg agataattaa aatgataacc atctcgcaaa     60

taaataagta ttttactgtt ttcgtaacag ttttgtaata aaaaaaccta taaatattcc    120

ggattattca taccgtccca ccatcgggcg cggatcatca caagtttgta caaaaaagca    180

ggctagatct taatacgact cactatatta attaaggatc ccaaaaaatt gaaattttat    240

ttttttttt tggaatataa ataatatgct gctcggacac ggccctattc gtatggtgct    300

cgctatcctc gcctttctca ggtttaccgc tatcaagcct agtctgggtc tcatcaacag    360

atggggtagc gtgggcaaga aggaggctat ggaaatcatc aagaagttca agaaggacct    420

ggccgctatg ctgagaatca tcaacgctcg taaggagaag aagcgcaggg gtgccgacac    480

ctctgtggga atcgtgggtc tgctgctgac caccgctatg gctgctgagg tgaccagaag    540

aggctccgcc tactacatgt acctggacag gaacgacgct ggagaagcca tctctttccc    600

caccaccctg ggtatgaaca agtgctacat ccagatcatg gacctgggac acatgtgcga    660

cgccaccatg agctacgagt gcccaatgct ggacgagggt gtggaacccg acgacgtgga    720

ctgctggtgc aacaccacca gcacctgggt ggtgtacgga acctgccacc acaagaaggg    780

tgaagctcgc aggtccagac gtgccgtgac cctgccttcc cactctaccc gcaagctgca    840

gaccaggtcc cagacctggc tggagtctcg cgaatacacc aagcacctga tccgcgtgga    900

gaactggatc ttcaggaacc ctggtttcgc tctggccgct gctgctatcg cttggctgct    960

gggaagctcc acctcccaga aggtcatcta cctggtcatg atcctgctga tcgcccctgc   1020

ttacagcatc agatgcatcg gcgtgagcaa ccgtgacttc gtggagggca tgtctggcgg   1080

aacctgggtg gacgtggtgc tggaacacgg tggctgcgtg accgtgatgg ctcaggacaa   1140

gccaaccgtc gacatcgagc tggtgaccac caccgtgtct aacatggccg aggtgcgcag   1200

ctactgctac gaagccagca tcagcgacat ggcctctgac agcaggtgcc caacccaggg   1260

cgaagcttac ctggacaagc agtctgacac ccagtacgtg tgcaagagaa ccctggtgga   1320

ccgtggatgg ggtaacggct gcggactgtt cggcaagggc agcctggtga cctgcgctaa   1380

gttcgcctgc tccaagaaga tgaccggcaa gtctatccag ccagagaacc tggaatacag   1440

aatcatgctg tctgtgcacg gctcccagca ctctggaatg atcgtgaacg acaccggaca   1500

cgaaaccgac gaaaacagag ccaaggtgga gatcacccct aactctccac gtgccgaagc   1560
```

-continued

```
taccctggga ggtttcggca gcctgggact ggactgtgag cctcgtaccg gcctggactt   1620
ctccgacctg tactacctga ccatgaacaa caagcactgg ctggtgcaca aggaatggtt   1680
ccacgacatc ccactgccat ggcacgccgg tgctgacact ggaaccccac actggaacaa   1740
caaggaggct ctggtggagt tcaaggacgc ccacgctaag agacagactg tggtggtgct   1800
gggttcccag gagggtgctg tgcacaccgc cctggctgga gctctggagg ctgaaatgga   1860
cggtgccaag ggccgtctgt ctagcggtca cctgaagtgc cgcctgaaga tggacaagct   1920
gaggctgaag ggcgtgtcct actctctgtg caccgccgct ttcaccttca ccaagatccc   1980
tgctgaaacc ctgcacggca ccgtgaccgt ggaagtgcag tacgctggaa ccgatggtcc   2040
atgcaaggtg cctgctcaga tggccgtgga catgcagacc ctgacccctg tgggacgcct   2100
gatcaccgcc aacccagtga tcaccgagtc taccgaaaac agcaagatga tgctggagct   2160
ggaccctccc ttcggcgaca gctacatcgt gatcggagtg ggtgaaaaga agatcaccca   2220
ccactggcac aggagcggca gcaccatcgg caaggctttc gaggctaccg tgcgcggcgc   2280
taagagaatg gccgtgctgg gcgacactgc ttgggacttc ggaagcgtgg gcggagccct   2340
gaactccctg ggcaagggaa tccaccagat cttcggcgcc gctttcaagt ccctgttcgg   2400
tggcatgagc tggttctccc agatcctgat cggaaccctg ctgatgtggc tgggtctgaa   2460
caccaagaac ggctctatca gcctgatgtg cctcgctctc ggtggcgtgc tgatttttct   2520
ctctaccgca gtctccgcat gagcccctct ccctcccccc cccctaacgt tactggccga   2580
agccgcttgg aataaggccg gtgtgtgttt gtctatatgt gattttccac catattgccg   2640
tcttttggca atgtgagggc ccggaaacct ggccctgtct tcttgacgag cattcctagg   2700
ggtctttccc ctctcgccaa aggaatgcaa ggtctgttga atgtcgtgaa ggaagcagtt   2760
cctctggaag cttcttgaag acaaacaacg tctgtagcga ccctttgcag gcagcggaac   2820
cccccacctg gcgacaggtg cctctgcggc caaaagccac gtgtataaga tacacctgca   2880
aaggcggcac aaccccagtg ccacgttgtg agttggatag ttgtggaaag agtcaaatgg   2940
ctctcctcaa gcgtagtcaa caaggggctg aaggatgccc agaaggtacc ccattgtatg   3000
ggaatctgat ctggggcctc ggtgcacatg ctttacatgt gtttagtcga ggttaaaaaa   3060
gctctaggcc ccccgaacca cggggacgtg gttttccttt gaaaaacacg atgataagct   3120
tgccacaaat gctccagggt cgcggtccac tgaaactctt tatggctctc gtcgccttcc   3180
tgcggttcct cactattcct cctactgtcg gtattctgaa gaggtggggc accatcaaga   3240
agagcaaggc catcaacgtg ctgcgcggat tcaggaagga gatcggtagg atgctgaaca   3300
tcctgaaccg caggagacgt accgccggca tgatcatcat gctgatcccc accgtgatgg   3360
ctatggaact gagaccttgg ctgctgtggg tggtggctgc tactggcacc ctggtgctgc   3420
tagcagctga cgcccagggc cagaaggtgt tcaccaacac ctgggctgtg agaatccccg   3480
gcggacctgc tgtggctaac agcgtggctc gtaagcacgg cttcctgaac ctgggacaga   3540
ttttcggtga ctactaccac ttctggcacc gcggagtgac caagaggagc ctgtccccac   3600
acagaccaag gcactccaga ctgcagcgtg agccccaggt gcagtggctg gaacagcagg   3660
tggccaagcg caggaccaag agagacgtgt accaggagcc taccgaccca aagttccccc   3720
agcagtggta tctgtccggc gtgacccagc gtgacctgaa cgtgaaggcc gcttgggctc   3780
agggttacac cggtcacggc atcgtggtgt ccatcctgga cgacggcatc gagaagaacc   3840
accctgacct ggccggtaac tacgacccag gcgcttcttt cgacgtgaac gaccaggacc   3900
ccgaccctca gccaagatac acccagatga acgacaacag acatggaacc agatgtgctg   3960
```

-continued

```
gtgaagtggc tgctgtggct aacaacggcg tgtgcggagt gggtgtggcc tacaacgcta   4020

gaatcggtgg cgtgcgtatg ctggatggag aagtgactga tgctgtggaa gctagaagcc   4080

tgggactgaa cccaaaccac atccacatct actctgccag ctggggtcca gaggatgatg   4140

gaaagactgt ggatggtcct gctagactgg ctgaggaagc cttcttccgc ggcgtgagcc   4200

agggaagggg aggtctggga agcatcttcg tgtgggcttc tggtaacggc ggaagagagc   4260

acgactcctg caactgcgac ggatacacca actctatcta caccctgagc atcagctccg   4320

ctacccagtt cggtaacgtg ccctggtact ccgaagcctg ctctagcacc ctggctacca   4380

cctactcctc tggcaaccag aacgagaagc agatcgtgac caccgacctg cgtcagaagt   4440

gcaccgaatc tcacactggc acctccgcct ctgctcctct ggctgctgga atcatcgccc   4500

tgaccctgga ggctaacaag aacctgacct ggcgcgacat gcagcacctg gtggtgcaga   4560

cctccaagcc agctcacctg aacgccaacg actgggctac caacggcgtg ggaaggaagg   4620

tgagccactc ttacggttac ggtctgctgg atgctggtgc tatggtggcc ctggctcaga   4680

actggaccac cgtggcccct cagcgcaagt gcatcatcga catcctgacc gagcctaagg   4740

acatcggaaa gagactggaa gtgcgtaaga ccgtgaccgc ttgcctggga gagcccaacc   4800

acatcaccag actggaacac gcccaggctc gtctgaccct gtcttacaac agacgtggag   4860

acctggccat ccacctggtg tctccaatgg gcacccgcag caccctgctg gctgctaggc   4920

cacacgacta cagcgccgac ggattcaacg actgggcttt catgaccacc cactcctggg   4980

acgaggaccc ttctggtgaa tgggtgctgg agatcgaaaa caccagcgag gccaacaact   5040

acggcaccct gaccaagttc accctggtgc tgtacggcac cgctcctgag ggactgccag   5100

tgccccctga aagctccggt tgcaagaccc tgacctctag ccaggcctgc gtggtgtgcg   5160

aggaaggctt ctccctgcac cagaagtctt gcgtgcagca ctgcccaccc ggattcgctc   5220

ctcaggtgct ggacacccac tactctaccg agaacgacgt ggaaaccatc agagccagcg   5280

tgtgcgctcc ttgtcacgct tcctgtgcta cttgtcaggg accagccctg actgactgcc   5340

tgtcctgccc atctcacgcc agcctggacc ccgtggagca gacctgctcc agacagtctc   5400

agtcctctcg tgaaagccct ccacagcagc agccccctag actgccaccc gaggtggaag   5460

ccggccagag actgcgtgct ggactgctgc cttctcacct gccagaggtg gtggctggtc   5520

tgagctgcgc tttcatcgtg ctggtgttcg tgaccgtgtt cctggtgctg cagctgcgca   5580

gcggtttctc cttcaggggc gtgaaggtgt acaccatgga ccgcggtctg atcagctaca   5640

agggtctgcc tccagaggct tggcaggagg aatgcccatc tgacagcgaa gaggacgagg   5700

gacgtggaga acggactgcc ttcatcaaag atcagagcgc actgtaataa atcgatttaa   5760

ttaatagcat aaccccttgg ggcctctaaa cgggtcttga ggggtttttt ggaattcacc   5820

cagctttctt gtacaaagtg gtgatagctt gtcgagaagt actagaggat cataatcagc   5880

cataccacat ttgtagaggt tttacttgct ttaaaaaacc tcccacacct ccccctgaac   5940

ctgaaacata aaatgaatgc aattgttgtt gttaacttgt ttattgcagc ttataatggt   6000

tacaaataaa gcaatagcat cacaaatttc acaaataaag catttttttc actgcattct   6060

agttgtggtt tgtccaaact catcaatgta tcttatcatg tctggatc                6108
```

<210> SEQ ID NO 9
<211> LENGTH: 6132
<212> TYPE: DNA
<213> ORGANISM: Artificial Sequence
<220> FEATURE:
<223> OTHER INFORMATION: Homologous ZIKV del108C-prM-E-IRES-del108CZIKV-
human furin proprotein cassette

<400> SEQUENCE: 9

```
cgtatactcc ggaatattaa tagatcatgg agataattaa aatgataacc atctcgcaaa     60
taaataagta ttttactgtt ttcgtaacag ttttgtaata aaaaaaccta taaatattcc    120
ggattattca taccgtccca ccatcgggcg cggatcatca caagtttgta caaaaaagca    180
ggctagatct taatacgact cactatatta attaaggatc ccaaaaaatt gaaattttat    240
tttttttttt tggaatataa ataatatgct gctcggacac ggccctattc gtatggtgct    300
cgctatcctc gcctttctca ggtttaccgc tatcaagcct agtctgggtc tcatcaacag    360
atggggtagc gtgggcaaga aggaggctat ggaaatcatc aagaagttca agaaggacct    420
ggccgctatg ctgagaatca tcaacgctcg taaggagaag aagcgcaggg gtgccgacac    480
ctctgtggga atcgtgggtc tgctgctgac caccgctatg gctgctgagg tgaccagaag    540
aggctccgcc tactacatgt acctggacag gaacgacgct ggagaagcca tctctttccc    600
caccaccctg ggtatgaaca agtgctacat ccagatcatg gacctgggac acatgtgcga    660
cgccaccatg agctacgagt gcccaatgct ggacgagggt gtggaacccg acgacgtgga    720
ctgctggtgc aacaccacca gcacctgggt ggtgtacgga acctgccacc acaagaaggg    780
tgaagctcgc aggtccagac gtgccgtgac cctgccttcc cactctaccc gcaagctgca    840
gaccaggtcc cagacctggc tggagtctcg cgaatacacc aagcacctga tccgcgtgga    900
gaactggatc ttcaggaacc ctggtttcgc tctggccgct gctgctatcg cttggctgct    960
gggaagctcc acctcccaga aggtcatcta cctggtcatg atcctgctga tcgcccctgc   1020
ttacagcatc agatgcatcg gcgtgagcaa ccgtgacttc gtggagggca tgtctggcgg   1080
aacctgggtg gacgtggtgc tggaacacgg tggctgcgtg accgtgatgg ctcaggacaa   1140
gccaaccgtc gacatcgagc tggtgaccac caccgtgtct aacatggccg aggtgcgcag   1200
ctactgctac gaagccagca tcagcgacat ggcctctgac agcaggtgcc caacccaggg   1260
cgaagcttac ctggacaagc agtctgacac ccagtacgtg tgcaagagaa ccctggtgga   1320
ccgtggatgg ggtaacggct gcggactgtt cggcaagggc agcctggtga cctgcgctaa   1380
gttcgcctgc tccaagaaga tgaccggcaa gtctatccag ccagagaacc tggaatacag   1440
aatcatgctg tctgtgcacg gctcccagca ctctggaatg atcgtgaacg acaccggaca   1500
cgaaaccgac gaaaacagag ccaaggtgga gatcacccct aactctccac gtgccgaagc   1560
taccctggga ggtttcggca gcctgggact ggactgtgag cctcgtaccg gcctggactt   1620
ctccgacctg tactacctga ccatgaacaa caagcactgg ctggtgcaca aggaatggtt   1680
ccacgacatc ccactgccat ggcacgccgg tgctgacact ggaaccccac actggaacaa   1740
caaggaggct ctggtggagt tcaaggacgc ccacgctaag agacagactg tggtggtgct   1800
gggttcccag gagggtgctg tgcacaccgc cctggctgga gctctggagg ctgaaatgga   1860
cggtgccaag ggccgtctgt ctagcggtca cctgaagtgc cgcctgaaga tggacaagct   1920
gaggctgaag ggcgtgtcct actctctgtg caccgccgct ttcaccttca ccaagatccc   1980
tgctgaaacc ctgcacggca ccgtgaccgt ggaagtgcag tacgctggaa ccgatggtcc   2040
atgcaaggtg cctgctcaga tggccgtgga catgcagacc ctgacccctg tgggacgcct   2100
gatcaccgcc aacccagtga tcaccgagtc taccgaaaac agcaagatga tgctggagct   2160
ggaccctccc ttcggcgaca gctacatcgt gatcggagtg ggtgaaaaga agatcaccca   2220
```

-continued

```
ccactggcac aggagcggca gcaccatcgg caaggctttc gaggctaccg tgcgcggcgc   2280
taagagaatg gccgtgctgg gcgacactgc ttgggacttc ggaagcgtgg gcggagccct   2340
gaactccctg ggcaagggaa tccaccagat cttcggcgcc gctttcaagt ccctgttcgg   2400
tggcatgagc tggttctccc agatcctgat cggaaccctg ctgatgtggc tgggtctgaa   2460
caccaagaac ggctctatca gcctgatgtg cctcgctctc ggtggcgtgc tgatttttct   2520
ctctaccgca gtctccgcat gagcccctct ccctcccccc cccctaacgt tactggccga   2580
agccgcttgg aataaggccg gtgtgtgttt gtctatatgt gattttccac catattgccg   2640
tcttttggca atgtgagggc ccggaaacct ggccctgtct tcttgacgag cattcctagg   2700
ggtctttccc ctctcgccaa aggaatgcaa ggtctgttga atgtcgtgaa ggaagcagtt   2760
cctctggaag cttcttgaag acaaacaacg tctgtagcga ccctttgcag gcagcggaac   2820
cccccacctg gcgacaggtg cctctgcggc caaaagccac gtgtataaga tacacctgca   2880
aaggcggcac aaccccagtg ccacgttgtg agttggatag ttgtggaaag agtcaaatgg   2940
ctctcctcaa gcgtagtcaa caaggggctg aaggatgccc agaaggtacc ccattgtatg   3000
ggaatctgat ctggggcctc ggtgcacatg ctttacatgt gtttagtcga ggttaaaaaa   3060
gctctaggcc ccccgaacca cggggacgtg gttttccttt gaaaaacacg atgataagct   3120
tgccacaaat gctgctcgga cacggcccta ttcgtatggt gctcgctatc ctcgcctttc   3180
tcaggtttac cgctatcaag cctagtctgg gtctcatcaa cagatggggt agcgtgggca   3240
agaaggaggc tatggaaatc atcaagaagt tcaagaagga cctggccgct atgctgagaa   3300
tcatcaacgc tcgtaaggag aagaagcgca ggggtgccga cacctctgtg ggaatcgtgg   3360
gtctgctgct gaccaccgct atggctatgg aactgagacc ttggctgctg tgggtggtgg   3420
ctgctactgg caccctggtg ctgctagcag ctgacgccca gggccagaag gtgttcacca   3480
acacctgggc tgtgagaatc cccggcggac ctgctgtggc taacagcgtg gctcgtaagc   3540
acggcttcct gaacctggga cagattttcg gtgactacta ccacttctgg caccgcggag   3600
tgaccaagag gagcctgtcc ccacacagac caaggcactc cagactgcag cgtgagcccc   3660
aggtgcagtg gctggaacag caggtggcca agcgcaggac caagagagac gtgtaccagg   3720
agcctaccga cccaaagttc cccagcagt ggtatctgtc cggcgtgacc cagcgtgacc   3780
tgaacgtgaa ggccgcttgg gctcagggtt acaccggtca cggcatcgtg gtgtccatcc   3840
tggacgacgg catcgagaag aaccaccctg acctggccgg taactacgac ccaggcgctt   3900
ctttcgacgt gaacgaccag gaccccgacc ctcagccaag atacacccag atgaacgaca   3960
acagacatgg aaccagatgt gctggtgaag tggctgctgt ggctaacaac ggcgtgtgcg   4020
gagtgggtgt ggcctacaac gctagaatcg gtggcgtgcg tatgctggat ggagaagtga   4080
ctgatgctgt ggaagctaga agcctgggac tgaacccaaa ccacatccac atctactctg   4140
ccagctgggg tccagaggat gatggaaaga ctgtggatgg tcctgctaga ctggctgagg   4200
aagccttctt ccgcggcgtg agccagggaa ggggaggtct gggaagcatc ttcgtgtggg   4260
cttctggtaa cggcggaaga gagcacgact cctgcaactg cgacggatac accaactcta   4320
tctacaccct gagcatcagc tccgctaccc agttcggtaa cgtgccctgg tactccgaag   4380
cctgctctag caccctggct accacctact cctctggcaa ccagaacgag aagcagatcg   4440
tgaccaccga cctgcgtcag aagtgcaccg aatctcacac tggcacctcc gcctctgctc   4500
ctctggctgc tggaatcatc gccctgaccc tggaggctaa caagaacctg acctggcgcg   4560
acatgcagca cctggtggtg cagacctcca agccagctca cctgaacgcc aacgactggg   4620
```

-continued

```
ctaccaacgg cgtgggaagg aaggtgagcc actcttacgg ttacggtctg ctggatgctg   4680
gtgctatggt ggccctggct cagaactgga ccaccgtggc ccctcagcgc aagtgcatca   4740
tcgacatcct gaccgagcct aaggacatcg gaaagagact ggaagtgcgt aagaccgtga   4800
ccgcttgcct gggagagccc aaccacatca ccagactgga acacgcccag gctcgtctga   4860
ccctgtctta caacagacgt ggagacctgg ccatccacct ggtgtctcca atgggcaccc   4920
gcagcaccct gctggctgct aggccacacg actacagcgc cgacggattc aacgactggg   4980
ctttcatgac cacccactcc tgggacgagg acccttctgg tgaatgggtg ctggagatcg   5040
aaaacaccag cgaggccaac aactacggca ccctgaccaa gttcaccctg gtgctgtacg   5100
gcaccgctcc tgagggactg ccagtgcccc ctgaaagctc cggttgcaag accctgacct   5160
ctagccaggc ctgcgtggtg tgcgaggaag gcttctccct gcaccagaag tcttgcgtgc   5220
agcactgccc acccggattc gctcctcagg tgctggacac ccactactct accgagaacg   5280
acgtggaaac catcagagcc agcgtgtgcg ctccttgtca cgcttcctgt gctacttgtc   5340
agggaccagc cctgactgac tgcctgtcct gcccatctca cgccagcctg gaccccgtgg   5400
agcagacctg ctccagacag tctcagtcct ctcgtgaaag ccctccacag cagcagcccc   5460
ctagactgcc acccgaggtg gaagccggcc agagactgcg tgctggactg ctgccttctc   5520
acctgccaga ggtggtggct ggtctgagct gcgctttcat cgtgctggtg ttcgtgaccg   5580
tgttcctggt gctgcagctg cgcagcggtt tctccttcag gggcgtgaag gtgtacacca   5640
tggaccgcgg tctgatcagc tacaagggtc tgcctccaga ggcttggcag gaggaatgcc   5700
catctgacag cgaagaggac gagggacgtg gagaacggac tgccttcatc aaagatcaga   5760
gcgcactgta ataaatcgat ttaattaata gcataacccc ttggggcctc taaacgggtc   5820
ttgaggggtt ttttggaatt cacccagctt tcttgtacaa agtggtgata gcttgtcgag   5880
aagtactaga ggatcataat cagccatacc acatttgtag aggttttact tgctttaaaa   5940
aacctcccac acctcccct gaacctgaaa cataaaatga atgcaattgt tgttgttaac   6000
ttgtttattg cagcttataa tggttacaaa taaagcaata gcatcacaaa tttcacaaat   6060
aaagcatttt tttcactgca ttctagttgt ggtttgtcca aactcatcaa tgtatcttat   6120
catgtctgga tc                                                        6132
```

<210> SEQ ID NO 10
<211> LENGTH: 5874
<212> TYPE: DNA
<213> ORGANISM: Artificial Sequence
<220> FEATURE:
<223> OTHER INFORMATION: ZIKV del108C-prM-E-IRES-human furin proprotein cassette

<400> SEQUENCE: 10

```
cgtatactcc ggaatattaa tagatcatgg agataattaa aatgataacc atctcgcaaa     60
taaataagta ttttactgtt ttcgtaacag ttttgtaata aaaaaaccta taaatattcc    120
ggattattca taccgtccca ccatcgggcg cggatcatca caagtttgta caaaaaagca    180
ggctagatct taatacgact cactatatta attaaggatc ccaaaaaatt gaaattttat    240
ttttttttt tggaatataa ataatatgct gctcggacac ggccctattc gtatggtgct    300
cgctatcctc gcctttctca ggtttaccgc tatcaagcct agtctgggtc tcatcaacag    360
atggggtagc gtgggcaaga aggaggctat ggaaatcatc aagaagttca agaaggacct    420
ggccgctatg ctgagaatca tcaacgctcg taaggagaag aagcgcaggg gtgccgacac    480
```

-continued

```
ctctgtggga atcgtgggtc tgctgctgac caccgctatg gctgctgagg tgaccagaag    540
aggctccgcc tactacatgt acctggacag gaacgacgct ggagaagcca tctctttccc    600
caccaccctg ggtatgaaca agtgctacat ccagatcatg gacctgggac acatgtgcga    660
cgccaccatg agctacgagt gcccaatgct ggacgagggt gtggaacccg acgacgtgga    720
ctgctggtgc aacaccacca gcacctgggt ggtgtacgga acctgccacc acaagaaggg    780
tgaagctcgc aggtccagac gtgccgtgac cctgccttcc cactctaccc gcaagctgca    840
gaccaggtcc cagacctggc tggagtctcg cgaatacacc aagcacctga tccgcgtgga    900
gaactggatc ttcaggaacc ctggtttcgc tctggccgct gctgctatcg cttggctgct    960
gggaagctcc acctcccaga aggtcatcta cctggtcatg atcctgctga tcgcccctgc   1020
ttacagcatc agatgcatcg gcgtgagcaa ccgtgacttc gtggagggca tgtctggcgg   1080
aacctgggtg gacgtggtgc tggaacacgg tggctgcgtg accgtgatgg ctcaggacaa   1140
gccaaccgtc gacatcgagc tggtgaccac caccgtgtct aacatggccg aggtgcgcag   1200
ctactgctac gaagccagca tcagcgacat ggcctctgac agcaggtgcc caacccaggg   1260
cgaagcttac ctggacaagc agtctgacac ccagtacgtg tgcaagagaa ccctggtgga   1320
ccgtggatgg ggtaacggct gcggactgtt cggcaagggc agcctggtga cctgcgctaa   1380
gttcgcctgc tccaagaaga tgaccggcaa gtctatccag ccagagaacc tggaatacag   1440
aatcatgctg tctgtgcacg gctcccagca ctctggaatg atcgtgaacg acaccggaca   1500
cgaaaccgac gaaaacagag ccaaggtgga gatcacccct aactctccac gtgccgaagc   1560
taccctggga ggtttcggca gcctgggact ggactgtgag cctcgtaccg gcctggactt   1620
ctccgacctg tactacctga ccatgaacaa caagcactgg ctggtgcaca aggaatggtt   1680
ccacgacatc ccactgccat ggcacgccgg tgctgacact ggaaccccac actggaacaa   1740
caaggaggct ctggtggagt tcaaggacgc ccacgctaag agacagactg tggtggtgct   1800
gggttcccag gagggtgctg tgcacaccgc cctggctgga gctctggagg ctgaaatgga   1860
cggtgccaag ggccgtctgt ctagcggtca cctgaagtgc cgcctgaaga tggacaagct   1920
gaggctgaag ggcgtgtcct actctctgtg caccgccgct ttcaccttca ccaagatccc   1980
tgctgaaacc ctgcacggca ccgtgaccgt ggaagtgcag tacgctggaa ccgatggtcc   2040
atgcaaggtg cctgctcaga tggccgtgga catgcagacc ctgacccctg tgggacgcct   2100
gatcaccgcc aacccagtga tcaccgagtc taccgaaaac agcaagatga tgctggagct   2160
ggaccctccc ttcggcgaca gctacatcgt gatcggagtg ggtgaaaaga agatcaccca   2220
ccactggcac aggagcggca gcaccatcgg caaggctttc gaggctaccg tgcgcggcgc   2280
taagagaatg gccgtgctgg gcgacactgc ttgggacttc ggaagcgtgg gcggagccct   2340
gaactccctg ggcaagggaa tccaccagat cttcggcgcc gctttcaagt ccctgttcgg   2400
tggcatgagc tggttctccc agatcctgat cggaaccctg ctgatgtggc tgggtctgaa   2460
caccaagaac ggctctatca gcctgatgtg cctcgctctc ggtggcgtgc tgatttttct   2520
ctctaccgca gtctccgcat gagcccctct ccctcccccc cccctaacgt tactggccga   2580
agccgcttgg aataaggccg gtgtgtgttt gtctatatgt gattttccac catattgccg   2640
tcttttggca atgtgagggc ccggaaacct ggccctgtct tcttgacgag cattcctagg   2700
ggtctttccc ctctcgccaa aggaatgcaa ggtctgttga atgtcgtgaa ggaagcagtt   2760
cctctggaag cttcttgaag acaaacaacg tctgtagcga ccctttgcag gcagcggaac   2820
cccccacctg gcgacaggtg cctctgcggc caaaagccac gtgtataaga tacacctgca   2880
```

-continued

```
aaggcggcac aaccccagtg ccacgttgtg agttggatag ttgtggaaag agtcaaatgg   2940
ctctcctcaa gcgtagtcaa caaggggctg aaggatgccc agaaggtacc ccattgtatg   3000
ggaatctgat ctggggcctc ggtgcacatg ctttacatgt gtttagtcga ggttaaaaaa   3060
gctctaggcc ccccgaacca cggggacgtg gttttccttt gaaaaacacg atgataagct   3120
tgccacaaat ggaactgaga ccttggctgc tgtgggtggt ggctgctact ggcaccctgg   3180
tgctgctagc agctgacgcc cagggccaga aggtgttcac caacacctgg gctgtgagaa   3240
tccccggcgg acctgctgtg gctaacagcg tggctcgtaa gcacggcttc ctgaacctgg   3300
gacagatttt cggtgactac taccacttct ggcaccgcgg agtgaccaag aggagcctgt   3360
ccccacacag accaaggcac tccagactgc agcgtgagcc ccaggtgcag tggctggaac   3420
agcaggtggc caagcgcagg accaagagag acgtgtacca ggagcctacc gacccaaagt   3480
tcccccagca gtggtatctg tccggcgtga cccagcgtga cctgaacgtg aaggccgctt   3540
gggctcaggg ttacaccggt cacggcatcg tggtgtccat cctggacgac ggcatcgaga   3600
agaaccaccc tgacctggcc ggtaactacg acccaggcgc ttctttcgac gtgaacgacc   3660
aggaccccga ccctcagcca agatacaccc agatgaacga caacagacat ggaaccagat   3720
gtgctggtga agtggctgct gtggctaaca acggcgtgtg cggagtgggt gtggcctaca   3780
acgctagaat cggtggcgtg cgtatgctgg atggagaagt gactgatgct gtggaagcta   3840
gaagcctggg actgaaccca aaccacatcc acatctactc tgccagctgg ggtccagagg   3900
atgatggaaa gactgtggat ggtcctgcta gactggctga ggaagccttc ttccgcggcg   3960
tgagccaggg aaggggaggt ctgggaagca tcttcgtgtg ggcttctggt aacggcggaa   4020
gagagcacga ctcctgcaac tgcgacggat acaccaactc tatctacacc ctgagcatca   4080
gctccgctac ccagttcggt aacgtgccct ggtactccga agcctgctct agcaccctgg   4140
ctaccaccta ctcctctggc aaccagaacg agaagcagat cgtgaccacc gacctgcgtc   4200
agaagtgcac cgaatctcac actggcacct ccgcctctgc tcctctggct gctggaatca   4260
tcgccctgac cctggaggct aacaagaacc tgacctggcg cgacatgcag cacctggtgg   4320
tgcagacctc caagccagct cacctgaacg ccaacgactg ggctaccaac ggcgtgggaa   4380
ggaaggtgag ccactcttac ggttacggtc tgctggatgc tggtgctatg gtggccctgg   4440
ctcagaactg gaccaccgtg gcccctcagc gcaagtgcat catcgacatc ctgaccgagc   4500
ctaaggacat cggaaagaga ctggaagtgc gtaagaccgt gaccgcttgc ctgggagagc   4560
ccaaccacat caccagactg gaacacgccc aggctcgtct gaccctgtct tacaacagac   4620
gtggagacct ggccatccac ctggtgtctc caatgggcac ccgcagcacc ctgctggctg   4680
ctaggccaca cgactacagc gccgacggat tcaacgactg ggctttcatg accacccact   4740
cctgggacga ggacccttct ggtgaatggg tgctggagat cgaaaacacc agcgaggcca   4800
acaactacgg caccctgacc aagttcaccc tggtgctgta cggcaccgct cctgagggac   4860
tgccagtgcc ccctgaaagc tccggttgca agaccctgac ctctagccag gcctgcgtgg   4920
tgtgcgagga aggcttctcc ctgcaccaga agtcttgcgt gcagcactgc ccacccggat   4980
tcgctcctca ggtgctggac acccactact ctaccgagaa cgacgtggaa accatcagag   5040
ccagcgtgtg cgctccttgt cacgcttcct gtgctacttg tcagggacca gccctgactg   5100
actgcctgtc ctgcccatct cacgccagcc tggaccccgt ggagcagacc tgctccagac   5160
agtctcagtc ctctcgtgaa agccctccac agcagcagcc ccctagactg ccacccgagg   5220
tggaagccgg ccagagactg cgtgctggac tgctgccttc tcacctgcca gaggtggtgg   5280
```

-continued

```
ctggtctgag ctgcgctttc atcgtgctgg tgttcgtgac cgtgttcctg gtgctgcagc   5340

tgcgcagcgg tttctccttc aggggcgtga aggtgtacac catggaccgc ggtctgatca   5400

gctacaaggg tctgcctcca gaggcttggc aggaggaatg cccatctgac agcgaagagg   5460

acgagggacg tggagaacgg actgccttca tcaaagatca gagcgcactg taataaatcg   5520

atttaattaa tagcataacc ccttggggcc tctaaacggg tcttgagggg tttttggaa    5580

ttcacccagc tttcttgtac aaagtggtga tagcttgtcg agaagtacta gaggatcata   5640

atcagccata ccacatttgt agaggtttta cttgctttaa aaaacctccc acacctcccc   5700

ctgaacctga aacataaaat gaatgcaatt gttgttgtta acttgtttat tgcagcttat   5760

aatggttaca aataaagcaa tagcatcaca aatttcacaa ataaagcatt tttttcactg   5820

cattctagtt gtggtttgtc caaactcatc aatgtatctt atcatgtctg gatc         5874
```

```
<210> SEQ ID NO 11
<211> LENGTH: 6087
<212> TYPE: DNA
<213> ORGANISM: Artificial Sequence
<220> FEATURE:
<223> OTHER INFORMATION: YFV del108C-prM-E-IRES-del108CYFV-human furin
      proprotein cassette

<400> SEQUENCE: 11

cgtatactcc ggaatattaa tagatcatgg agataattaa aatgataacc atctcgcaaa     60

taaataagta ttttactgtt ttcgtaacag ttttgtaata aaaaaaccta taaatattcc    120

ggattattca taccgtccca ccatcgggcg cggatcatca caagtttgta caaaaaagca    180

ggctagatct taatacgact cactatatta attaaggatc ccaaaaaatt gaaattttat    240

ttttttttt tggaatataa ataatatgag acctggacct tcaagaggtg ttcaaggatt    300

tatctttttc tttttgttca acattttgac tggaaaaaag atcacggccc acctaaagag    360

gttgtggaaa atgctggacc caagacaagg cttggctgtt ctaaggaaag ttaagagagt    420

ggtggccagt ttgatgagag gattgtcctc aaggaaacgc cgttcccatg atgttctgac    480

tgtgcaattc ctaattttgg gaatgctgtt gatgacgggt ggagtgacct tggtgcggaa    540

aaacagatgg ttgctcctaa atgtgacatc tgaggacctc gggaaaacat tctctgtggg    600

cacaggcaac tgcacaacaa acattttgga agccaagtac tggtgcccag actcaatgga    660

atacaactgt cccaatctca gtccaagaga ggagccagat gacattgatt gctggtgcta    720

tggggtggaa aacgttagag tcgcatatgg taagtgtgac tcagcaggca ggtctaggag    780

gtcaagaagg gccattgact tgcctacgca tgaaaaccat ggtttgaaga cccggcaaga    840

aaaatggatg actggaagaa tgggtgaaag gcaactccaa aagattgaga gatggctcgt    900

gaggaacccc tttttgcag tgacagctct gaccattgcc taccttgtgg gaagcaacat    960

gacgcaacga gtcgtgattg ccctactggt cttggctgtt ggtccggcct actcagctca   1020

ctgcattgga attactgaca gggatttcat tgagggggtg catggaggaa cttgggtttc   1080

agctaccctg gagcaagaca agtgtgtcac tgttatggcc cctgacaagc cttcattgga   1140

catctcacta gagacagtag ccattgatgg acctgctgag gcgaggaaag tgtgttacaa   1200

tgcagttctc actcatgtga agattaatga caagtgcccc agcactggag aggcccacct   1260

agctgaagag aacgaagggg acaatgcgtg caagcgcact tattctgata gaggctgggg   1320

caatggctgt ggcctatttg ggaaagggag cattgtggca tgcgccaaat tcacttgtgc   1380

caaatccatg agtttgtttg aggttgatca gaccaaaatt cagtatgtca tcagagcaca   1440
```

-continued

```
attgcatgta ggggccaagc aggaaaattg gaataccgac attaagactc tcaagtttga   1500
tgccctgtca ggctcccagg aagccgagtt cactgggtat ggaaaagcta cactggaatg   1560
ccaggtgcaa actgcggtgg actttggtaa cagttacatc gctgagatgg aaaaagagag   1620
ctggatagtg gacagacagt gggcccagga cttgaccctg ccatggcaga gtggaagtgg   1680
cggggtgtgg agagagatgc atcatcttgt cgaatttgaa cctccgcatg ccgccactat   1740
cagagtactg gccctgggaa accaggaagg ctccttgaaa acagctctta ccggcgcaat   1800
gagggttaca aaggacacaa atgacaacaa cctttacaaa ctacatggtg gacatgtttc   1860
ctgcagagtg aaattgtcag ctttgacact caaggggaca tcctacaaaa tgtgcactga   1920
caaaatgtct tttgtcaaga acccaactga cactggccat ggcactgttg tgatgcaggt   1980
gaaagtgcca aaaggagccc cctgcaggat tccagtgata gtagctgatg atcttacagc   2040
ggcaatcaat aaaggcattt tggttacagt taaccccatc gcctcaacca atgatgatga   2100
agtgctgatt gaggtgaacc caccttttgg agacagctac attatcgttg ggacaggaga   2160
ttcacgtctc acttaccagt ggcacaaaga gggaagctca ataggaaagt tgttcactca   2220
gaccatgaaa ggcgcggaac gcctggccgt catgggagac gccgcctggg atttcagctc   2280
cgctggaggg ttcttcactt cggttgggaa aggtattcat acggtgtttg gctctgcctt   2340
tcaggggcta tttggcggct tgaactggat aacaaaggtc atcatggggg cggtactcat   2400
atgggttggc atcaacacaa gaaacatgac aatgtccatg agcatgatct tggtaggagt   2460
gatcatgatg tttttgtctc taggagttgg ggcgtgagcc cctctccctc ccccccccct   2520
aacgttactg gccgaagccg cttggaataa ggccggtgtg tgtttgtcta tatgtgattt   2580
tccaccatat tgccgtcttt tggcaatgtg agggcccgga aacctggccc tgtcttcttg   2640
acgagcattc ctaggggtct ttcccctctc gccaaaggaa tgcaaggtct gttgaatgtc   2700
gtgaaggaag cagttcctct ggaagcttct tgaagacaaa caacgtctgt agcgaccctt   2760
tgcaggcagc ggaacccccc acctggcgac aggtgcctct gcggccaaaa gccacgtgta   2820
taagatacac ctgcaaaggc ggcacaaccc cagtgccacg ttgtgagttg gatagttgtg   2880
gaaagagtca aatggctctc ctcaagcgta gtcaacaagg ggctgaagga tgcccagaag   2940
gtaccccatt gtatgggaat ctgatctggg gcctcggtgc acatgcttta catgtgttta   3000
gtcgaggtta aaaaagctct aggccccccg aaccacgggg acgtggtttt cctttgaaaa   3060
acacgatgat aagcttgcca caaatgagac ctggaccttc aagaggtgtt caaggattta   3120
tctttttctt tttgttcaac attttgactg gaaaaaagat cacggcccac ctaaagaggt   3180
tgtggaaaat gctggaccca agacaaggct tggctgttct aaggaaagtt aagagagtgg   3240
tggccagttt gatgagagga ttgtcctcaa ggaaacgccg ttcccatgat gttctgactg   3300
tgcaattcct aattttggga atgctgttga tgacgggtgg aatggaactg agaccttggc   3360
tgctgtgggt ggtggctgct actggcaccc tggtgctgct agcagctgac gcccagggcc   3420
agaaggtgtt caccaacacc tgggctgtga gaatccccgg cggacctgct gtggctaaca   3480
gcgtggctcg taagcacggc ttcctgaacc tgggacagat tttcggtgac tactaccact   3540
tctggcaccg cggagtgacc aagaggagcc tgtccccaca cagaccaagg cactccagac   3600
tgcagcgtga gccccaggtg cagtggctgg aacagcaggt ggccaagcgc aggaccaaga   3660
gagacgtgta ccaggagcct accgacccaa agttccccca gcagtggtat ctgtccggcg   3720
tgacccagcg tgacctgaac gtgaaggccg cttgggctca gggttacacc ggtcacggca   3780
tcgtggtgtc catcctggac gacggcatcg agaagaacca ccctgacctg gccggtaact   3840
```

-continued

```
acgacccagg cgcttctttc gacgtgaacg accaggaccc cgaccctcag ccaagataca   3900
cccagatgaa cgacaacaga catggaacca gatgtgctgg tgaagtggct gctgtggcta   3960
acaacggcgt gtgcggagtg ggtgtggcct acaacgctag aatcggtggc gtgcgtatgc   4020
tggatggaga agtgactgat gctgtggaag ctagaagcct gggactgaac ccaaaccaca   4080
tccacatcta ctctgccagc tggggtccag aggatgatgg aaagactgtg gatggtcctg   4140
ctagactggc tgaggaagcc ttcttccgcg gcgtgagcca gggaagggga ggtctgggaa   4200
gcatcttcgt gtgggcttct ggtaacggcg gaagagagca cgactcctgc aactgcgacg   4260
gatacaccaa ctctatctac accctgagca tcagctccgc tacccagttc ggtaacgtgc   4320
cctggtactc cgaagcctgc tctagcaccc tggctaccac ctactcctct ggcaaccaga   4380
acgagaagca gatcgtgacc accgacctgc gtcagaagtg caccgaatct cacactggca   4440
cctccgcctc tgctcctctg gctgctggaa tcatcgccct gaccctggag gctaacaaga   4500
acctgacctg gcgcgacatg cagcacctgg tggtgcagac ctccaagcca gctcacctga   4560
acgccaacga ctgggctacc aacggcgtgg gaaggaaggt gagccactct tacggttacg   4620
gtctgctgga tgctggtgct atggtggccc tggctcagaa ctggaccacc gtggcccctc   4680
agcgcaagtg catcatcgac atcctgaccg agcctaagga catcggaaag agactggaag   4740
tgcgtaagac cgtgaccgct tgcctgggag agcccaacca catcaccaga ctggaacacg   4800
cccaggctcg tctgaccctg tcttacaaca gacgtggaga cctggccatc cacctggtgt   4860
ctccaatggg cacccgcagc accctgctgg ctgctaggcc acacgactac agcgccgacg   4920
gattcaacga ctgggctttc atgaccaccc actcctggga cgaggaccct tctggtgaat   4980
gggtgctgga gatcgaaaac accagcgagg ccaacaacta cggcaccctg accaagttca   5040
ccctggtgct gtacggcacc gctcctgagg gactgccagt gccccctgaa agctccggtt   5100
gcaagaccct gacctctagc caggcctgcg tggtgtgcga ggaaggcttc tccctgcacc   5160
agaagtcttg cgtgcagcac tgcccacccg gattcgctcc tcaggtgctg gacacccact   5220
actctaccga gaacgacgtg gaaaccatca gagccagcgt gtgcgctcct tgtcacgctt   5280
cctgtgctac ttgtcaggga ccagccctga ctgactgcct gtcctgccca tctcacgcca   5340
gcctggaccc cgtggagcag acctgctcca gacagtctca gtcctctcgt gaaagccctc   5400
cacagcagca gcccccctaga ctgccacccg aggtggaagc cggccagaga ctgcgtgctg   5460
gactgctgcc ttctcacctg ccagaggtgg tggctggtct gagctgcgct ttcatcgtgc   5520
tggtgttcgt gaccgtgttc ctggtgctgc agctgcgcag cggtttctcc ttcaggggcg   5580
tgaaggtgta caccatggac cgcggtctga tcagctacaa gggtctgcct ccagaggctt   5640
ggcaggagga atgcccatct gacagcgaag aggacgaggg acgtggagaa cggactgcct   5700
tcatcaaaga tcagagcgca ctgtaataaa tcgatttaat taatagcata accccttggg   5760
gcctctaaac gggtcttgag gggttttttg gaattcaccc agctttcttg tacaaagtgg   5820
tgatagcttg tcgagaagta ctagaggatc ataatcagcc ataccacatt tgtagaggtt   5880
ttacttgctt taaaaaacct cccacacctc cccctgaacc tgaaacataa aatgaatgca   5940
attgttgttg ttaacttgtt tattgcagct tataatggtt acaaataaag caatagcatc   6000
acaaatttca caaataaagc atttttttca ctgcattcta gttgtggttt gtccaaactc   6060
atcaatgtat cttatcatgt ctggatc                                       6087
```

<210> SEQ ID NO 12
<211> LENGTH: 6663
<212> TYPE: DNA
<213> ORGANISM: Artificial Sequence
<220> FEATURE:
<223> OTHER INFORMATION: HCV del108C-E1-E2-IRES-del108CHCV-human furin proprotein cassette

<400> SEQUENCE: 12

```
cgtatactcc ggaatattaa tagatcatgg agataattaa aatgataacc atctcgcaaa     60
taaataagta ttttactgtt ttcgtaacag ttttgtaata aaaaaaccta taaatattcc    120
ggattattca taccgtccca ccatcgggcg cggatcatca caagtttgta caaaaaagca    180
ggctagatct taatacgact cactatatta attaaggatc ccaaaaaatt gaaattttat    240
ttttttttt tggaatataa ataatatgct gccaagaagg ggtccaagac tcggagtgcg    300
tgccacccgc aagacctctg agcgtagcca gccaagaggc cgccgccagc caatccctaa    360
ggctcgcagg cctgaaggta gaacttgggc tcagccaggt tacccttggc cactgtacgg    420
aaacgaaggc tgcggatggg ctggatggct gctgagcccc aggggttcca gaccttcttg    480
gggtccaact gacccacgcc gccgcagccg caacctgggc aaggtcatcg acaccctgac    540
ctgcggattc gccgacctga tgggttacat cccactggtg ggagctcccc tgggcggagc    600
tgctagggcc ctggctcacg gtgtgagagt gctggaagac ggcgtgaact acgccaccgg    660
taacctgcca ggctgcagct tctccatctt cctgctggct ctgctgtcct gcctgactgg    720
accagcttct gcttaccagg tgaggaacag caccggtctg taccacgtga ccaacgactg    780
ccccaacagc tccatcgtgt tcgaagctgc tgatgctatc ctgcacaccc caggatgcgt    840
gccttgcgtg cgtgagggta acgcttccag atgctgggtg gctgtgaccc ctaccgtggc    900
caccagagac ggcaagctgc caaccaccca gctgaggaga cacatcgacc tgctggtggg    960
tagcgccacc ctgtgctccg ctctgtacgt gggcgacctg tgcggtagcg tgttcctggt   1020
gggccagctg ttcaccttca gccctcgtcg ccactggacc acccaggact gcaactgctc   1080
catctaccca ggccacatct ctggacaccg tatggcttgg gacatgatga tgaactggag   1140
cccaactgcc gctctgctgg tggctcagct gctgagaatc ccacaggcca tcctggacat   1200
gatcgctggt gctcactggg gcgtgctggc tggaatggct tacttctcta tggtgggcaa   1260
ctgggccaag gtgctggtgg tgctgctgct gttcgccgga gtggacgctg aaacctacgt   1320
gaccggtggc agcgccgcta ggactactgc tggcctggct agtctgttct cccctggagc   1380
taagcagaac atccagctgg tgaacaccaa cggctcttgg cacatcaaca gcaccgccct   1440
gaactgcaac gactccctga acaccggttg gatcgctggc ctgttctacc accacaagtt   1500
caactctagc ggatgctccg aaaggctggc ttcttgcaga cctctgactg acttcgctca   1560
gggttggggt cctatcagcc acgctgatgg atctggtcca gaccagcgcc cctactgctg   1620
gcactaccct cccaagcctt gcggtatcgt gcctgctaag tccgtgtgcg gtcccgtgta   1680
ctgcttcacc ccctctcctg tggtggtggg aaccaccgac aggtctggtg ctccaaccta   1740
cagctgggga gccaacgaca ccgacgtgtt cgtgctgaac aacaccagac cacccctggg   1800
aaactggttc ggttgcacct ggatgaacag caccggcttc accaaggtgt gcggagcccc   1860
tccatgcgtg atcggaggtg tgggcaacaa caccctgcgt tgccccaccg actgcttccg   1920
caagcaccct gaggctacct actccagatg cggctctgga ccttggatca ccccaaggtg   1980
cctggtggac taccccctaca gactgtggca ctacccttgc accatcaact acaccgtgtt   2040
caaggtgcgt atgtacgtgg gcggagtgga gcacagactg gaagctgctt gtaactggac   2100
```

-continued

```
tcgcggcgac cgctgcaacc tggacgacag ggacagatct gagctgagcc ccctgctgct   2160
gtccaccacc cagtggcagg tgctgccatg cagcttcacc accctgcccg ccctgtccac   2220
tggcctgatc cacctgcacc agaacatcgt ggacgtgcag tacctgtacg gtgtgggctc   2280
ctctatcgca tcttgggcta tcaagtggga atacgtggtg ctgctgttcc tgctgctggc   2340
tgatgctcgc gtgtgctcct gcctgtggat gatgctgctg atctctcagg tggaggccgc   2400
tctggaaaac ctggtggtgc tgaacgctgc aagcctggct ggaacccacg gtctggtgtc   2460
cttcctggtg ttcttctgct tcgcttggta cctgaagggc aagtgggtgc ctggagccgt   2520
gtacgctctg tacggaatgt ggcctctgct gctgctgctg ctggccctgc cacagagagc   2580
ttacgctctg gacactgagg tggctgcttc ttgtggtggc gtggtgctgg tgggcctgat   2640
ggctctgacc ctgtctcctt actacaagag gtacatcagc tggtgcctgt ggtggctgca   2700
gtacttcctg accagaatcg aagcccagct gcacgtgtgg attcctcccc tgaacgtgcg   2760
cggcggcaga gatgccgtga tcctgctgat gtgcgtggtg caccccgctc tggtgttcga   2820
catcaccaag ctgctgctgg ccgctttcgg cccttaatct agagcccctc tccctccccc   2880
ccccctaacg ttactggccg aagccgcttg gaataaggcc ggtgtgtgtt tgtctatatg   2940
tgattttcca ccatattgcc gtcttttggc aatgtgaggg cccggaaacc tggccctgtc   3000
ttcttgacga gcattcctag gggtctttcc cctctcgcca aaggaatgca aggtctgttg   3060
aatgtcgtga aggaagcagt tcctctggaa gcttcttgaa gacaaacaac gtctgtagcg   3120
accctttgca ggcagcggaa ccccccacct ggcgacaggt gcctctgcgg ccaaaagcca   3180
cgtgtataag atacacctgc aaaggcggca caaccccagt gccacgttgt gagttggata   3240
gttgtggaaa gagtcaaatg gctctcctca agcgtagtca acaaggggct gaaggatgcc   3300
cagaaggtac cccattgtat gggaatctga tctggggcct cggtgcacat gctttacatg   3360
tgtttagtcg aggttaaaaa agctctaggc cccccgaacc acggggacgt ggttttcctt   3420
tgaaaaacac gatgataagc ttgccacaaa tgctgcctag aaggggacct aggctgggtg   3480
tgagggccac cagaaagacc tctgagagga gccagcctag aggccgccgc cagccaatcc   3540
ctaaggctcg caggcccgag ggaagaacct gggctcagcc tggttaccca tggcccctgt   3600
acggcaacga aggttgcggc tgggctggtt ggctgctgtc tccacgtggt tcccgcccct   3660
cttggggtcc tactgaccca cgccgccgca gccgcaacct gggcaaggtc atcgacaccc   3720
tgacctgcgg attcgccgac ctgatgggtt acatccctct ggtgggagct ccactgggcg   3780
gagccgctcg tgccctggct cacggagtgc gcgtgctgga ggacggtgtg aactacgcca   3840
ccggcaacct gcccggatgc agcttctcca tcttcctgct ggctctgctg tcttgtctga   3900
ctggtccagc ttccgctatg gaactgcgcc cctggctgct gtgggtggtg gctgctactg   3960
gaaccctggt gctgctagca gctgacgccc agggccagaa ggtgttcacc aacacctggg   4020
ctgtgagaat ccccggcgga cctgctgtgg ctaacagcgt ggctcgtaag cacggcttcc   4080
tgaacctggg acagattttc ggtgactact accacttctg gcaccgcgga gtgaccaaga   4140
ggagcctgtc cccacacaga ccaaggcact ccagactgca gcgtgagccc caggtgcagt   4200
ggctggaaca gcaggtggcc aagcgcagga ccaagagaga cgtgtaccag gagcctaccg   4260
acccaaagtt cccccagcag tggtatctgt ccggcgtgac ccagcgtgac ctgaacgtga   4320
aggccgcttg ggctcagggt tacaccggtc acggcatcgt ggtgtccatc ctggacgacg   4380
gcatcgagaa gaaccaccct gacctggccg gtaactacga cccaggcgct tctttcgacg   4440
tgaacgacca ggaccccgac cctcagccaa gatacaccca gatgaacgac aacagacatg   4500
```

gaaccagatg tgctggtgaa gtggctgctg tggctaacaa cggcgtgtgc ggagtgggtg 4560
tggcctacaa cgctagaatc ggtggcgtgc gtatgctgga tggagaagtg actgatgctg 4620
tggaagctag aagcctggga ctgaacccaa accacatcca catctactct gccagctggg 4680
gtccagagga tgatggaaag actgtggatg gtcctgctag actggctgag gaagccttct 4740
tccgcggcgt gagccaggga aggggaggtc tgggaagcat cttcgtgtgg gcttctggta 4800
acggcggaag agagcacgac tcctgcaact gcgacggata caccaactct atctacaccc 4860
tgagcatcag ctccgctacc cagttcggta acgtgccctg gtactccgaa gcctgctcta 4920
gcaccctggc taccacctac tcctctggca accagaacga gaagcagatc gtgaccaccg 4980
acctgcgtca gaagtgcacc gaatctcaca ctggcacctc cgcctctgct cctctggctg 5040
ctggaatcat cgccctgacc ctggaggcta acaagaacct gacctggcgc gacatgcagc 5100
acctggtggt gcagacctcc aagccagctc acctgaacgc caacgactgg gctaccaacg 5160
gcgtgggaag gaaggtgagc cactcttacg gttacggtct gctggatgct ggtgctatgg 5220
tggccctggc tcagaactgg accaccgtgg cccctcagcg caagtgcatc atcgacatcc 5280
tgaccgagcc taaggacatc ggaaagagac tggaagtgcg taagaccgtg accgcttgcc 5340
tgggagagcc caaccacatc accagactgg aacacgccca ggctcgtctg accctgtctt 5400
acaacagacg tggagacctg gccatccacc tggtgtctcc aatgggcacc cgcagcaccc 5460
tgctggctgc taggccacac gactacagcg ccgacggatt caacgactgg gctttcatga 5520
ccacccactc ctgggacgag gacccttctg gtgaatgggt gctggagatc gaaaacacca 5580
gcgaggccaa caactacggc accctgacca agttcaccct ggtgctgtac ggcaccgctc 5640
ctgagggact gccagtgccc cctgaaagct ccggttgcaa gaccctgacc tctagccagg 5700
cctgcgtggt gtgcgaggaa ggcttctccc tgcaccagaa gtcttgcgtg cagcactgcc 5760
cacccggatt cgctcctcag gtgctggaca cccactactc taccgagaac gacgtggaaa 5820
ccatcagagc cagcgtgtgc gctccttgtc acgcttcctg tgctacttgt cagggaccag 5880
ccctgactga ctgcctgtcc tgcccatctc acgccagcct ggaccccgtg gagcagacct 5940
gctccagaca gtctcagtcc tctcgtgaaa gccctccaca gcagcagccc cctagactgc 6000
cacccgaggt ggaagccggc cagagactgc gtgctggact gctgccttct cacctgccag 6060
aggtggtggc tggtctgagc tgcgctttca tcgtgctggt gttcgtgacc gtgttcctgg 6120
tgctgcagct gcgcagcggt ttctccttca ggggcgtgaa ggtgtacacc atggaccgcg 6180
gtctgatcag ctacaagggt ctgcctccag aggcttggca ggaggaatgc ccatctgaca 6240
gcgaagagga cgagggacgt ggagaacgga ctgccttcat caaagatcag agcgcactgt 6300
aataaatcga tttaattaat agcataaccc cttggggcct ctaaacgggt cttgaggggt 6360
tttttggaat tcacccagct ttcttgtaca aagtggtgat agcttgtcga gaagtactag 6420
aggatcataa tcagccatac cacatttgta gaggttttac ttgctttaaa aaacctccca 6480
cacctccccc tgaacctgaa acataaaatg aatgcaattg ttgttgttaa cttgtttatt 6540
gcagcttata atggttacaa ataaagcaat agcatcacaa atttcacaaa taaagcattt 6600
ttttcactgc attctagttg tggtttgtcc aaactcatca atgtatctta tcatgtctgg 6660
atc 6663

<210> SEQ ID NO 13
<211> LENGTH: 5829
<212> TYPE: DNA
<213> ORGANISM: Artificial Sequence -continued
<220> FEATURE:
<223> OTHER INFORMATION: YFV del108C-prM-E-IRES-human furin proprotein cassette

<400> SEQUENCE: 13

```
cgtatactcc ggaatattaa tagatcatgg agataattaa aatgataacc atctcgcaaa     60
taaataagta ttttactgtt ttcgtaacag ttttgtaata aaaaaaccta taaatattcc    120
ggattattca taccgtccca ccatcgggcg cggatcatca caagtttgta caaaaaagca    180
ggctagatct taatacgact cactatatta attaaggatc ccaaaaaatt gaaattttat    240
tttttttttt tggaatataa ataatatgag acctggacct tcaagaggtg ttcaaggatt    300
tatctttttc tttttgttca acattttgac tggaaaaaag atcacggccc acctaaagag    360
gttgtggaaa atgctggacc caagacaagg cttggctgtt ctaaggaaag ttaagagagt    420
ggtggccagt ttgatgagag gattgtcctc aaggaaacgc cgttcccatg atgttctgac    480
tgtgcaattc ctaattttgg gaatgctgtt gatgacgggt ggagtgacct tggtgcggaa    540
aaacagatgg ttgctcctaa atgtgacatc tgaggacctc gggaaaacat tctctgtggg    600
cacaggcaac tgcacaacaa acattttgga agccaagtac tggtgcccag actcaatgga    660
atacaactgt cccaatctca gtccaagaga ggagccagat gacattgatt gctggtgcta    720
tggggtggaa aacgttagag tcgcatatgg taagtgtgac tcagcaggca ggtctaggag    780
gtcaagaagg gccattgact tgcctacgca tgaaaaccat ggtttgaaga cccggcaaga    840
aaaatggatg actggaagaa tgggtgaaag gcaactccaa aagattgaga gatggctcgt    900
gaggaacccc tttttgcag  tgacagctct gaccattgcc taccttgtgg gaagcaacat    960
gacgcaacga gtcgtgattg ccctactggt cttggctgtt ggtccggcct actcagctca   1020
ctgcattgga attactgaca gggatttcat tgagggggtg catggaggaa cttgggtttc   1080
agctaccctg gagcaagaca agtgtgtcac tgttatggcc cctgacaagc cttcattgga   1140
catctcacta gagacagtag ccattgatgg acctgctgag gcgaggaaag tgtgttacaa   1200
tgcagttctc actcatgtga agattaatga caagtgcccc agcactggag aggcccacct   1260
agctgaagag aacgaagggg acaatgcgtg caagcgcact tattctgata gaggctgggg   1320
caatggctgt ggcctatttg ggaaagggag cattgtggca tgcgccaaat tcacttgtgc   1380
caaatccatg agtttgtttg aggttgatca gaccaaaatt cagtatgtca tcagagcaca   1440
attgcatgta ggggccaagc aggaaaattg gaataccgac attaagactc tcaagtttga   1500
tgccctgtca ggctcccagg aagccgagtt cactgggtat ggaaaagcta cactggaatg   1560
ccaggtgcaa actgcggtgg actttggtaa cagttacatc gctgagatgg aaaaagagag   1620
ctggatagtg gacagacagt gggcccagga cttgaccctg ccatggcaga gtggaagtgg   1680
cggggtgtgg agagagatgc atcatcttgt cgaatttgaa cctccgcatg ccgccactat   1740
cagagtactg gccctgggaa accaggaagg ctccttgaaa acagctctta ccggcgcaat   1800
gagggttaca aaggacacaa atgacaacaa cctttacaaa ctacatggtg gacatgtttc   1860
ctgcagagtg aaattgtcag ctttgacact caaggggaca tcctacaaaa tgtgcactga   1920
caaaatgtct tttgtcaaga acccaactga cactggccat ggcactgttg tgatgcaggt   1980
gaaagtgcca aaaggagccc cctgcaggat tccagtgata gtagctgatg atcttacagc   2040
ggcaatcaat aaaggcattt tggttacagt taaccccatc gcctcaacca atgatgatga   2100
agtgctgatt gaggtgaacc caccttttgg agacagctac attatcgttg ggacaggaga   2160
ttcacgtctc acttaccagt ggcacaaaga gggaagctca ataggaaagt tgttcactca   2220
```

-continued gaccatgaaa ggcgcggaac gcctggccgt catgggagac gccgcctggg atttcagctc 2280
cgctggaggg ttcttcactt cggttgggaa aggtattcat acggtgtttg gctctgcctt 2340
tcaggggcta tttggcggct tgaactggat aacaaaggtc atcatggggg cggtactcat 2400
atgggttggc atcaacacaa gaaacatgac aatgtccatg agcatgatct tggtaggagt 2460
gatcatgatg tttttgtctc taggagttgg ggcgtgagcc cctctccctc ccccccccct 2520
aacgttactg gccgaagccg cttggaataa ggccggtgtg tgtttgtcta tatgtgattt 2580
tccaccatat tgccgtcttt tggcaatgtg agggcccgga aacctggccc tgtcttcttg 2640
acgagcattc ctaggggtct ttcccctctc gccaaaggaa tgcaaggtct gttgaatgtc 2700
gtgaaggaag cagttcctct ggaagcttct tgaagacaaa caacgtctgt agcgaccctt 2760
tgcaggcagc ggaacccccc acctggcgac aggtgcctct gcggccaaaa gccacgtgta 2820
taagatacac ctgcaaaggc ggcacaaccc cagtgccacg ttgtgagttg gatagttgtg 2880
gaaagagtca aatggctctc ctcaagcgta gtcaacaagg ggctgaagga tgcccagaag 2940
gtaccccatt gtatgggaat ctgatctggg gcctcggtgc acatgcttta catgtgttta 3000
gtcgaggtta aaaaagctct aggccccccg aaccacgggg acgtggtttt cctttgaaaa 3060
acacgatgat aagcttgcca caaatggaac tgagaccttg gctgctgtgg gtggtggctg 3120
ctactggcac cctggtgctg ctagcagctg acgcccaggg ccagaaggtg ttcaccaaca 3180
cctgggctgt gagaatcccc ggcggacctg ctgtggctaa cagcgtggct cgtaagcacg 3240
gcttcctgaa cctgggacag attttcggtg actactacca cttctggcac cgcggagtga 3300
ccaagaggag cctgtcccca cacagaccaa ggcactccag actgcagcgt gagccccagg 3360
tgcagtggct ggaacagcag gtggccaagc gcaggaccaa gagagacgtg taccaggagc 3420
ctaccgaccc aaagttcccc cagcagtggt atctgtccgg cgtgacccag cgtgacctga 3480
acgtgaaggc cgcttgggct cagggttaca ccggtcacgg catcgtggtg tccatcctgg 3540
acgacggcat cgagaagaac caccctgacc tggccggtaa ctacgaccca ggcgcttctt 3600
tcgacgtgaa cgaccaggac cccgaccctc agccaagata cacccagatg aacgacaaca 3660
gacatggaac cagatgtgct ggtgaagtgg ctgctgtggc taacaacggc gtgtgcggag 3720
tgggtgtggc ctacaacgct agaatcggtg gcgtgcgtat gctggatgga gaagtgactg 3780
atgctgtgga agctagaagc ctgggactga acccaaacca catccacatc tactctgcca 3840
gctggggtcc agaggatgat ggaaagactg tggatggtcc tgctagactg gctgaggaag 3900
ccttcttccg cggcgtgagc cagggaaggg gaggtctggg aagcatcttc gtgtgggctt 3960
ctggtaacgg cggaagagag cacgactcct gcaactgcga cggatacacc aactctatct 4020
acaccctgag catcagctcc gctacccagt tcggtaacgt gccctggtac tccgaagcct 4080
gctctagcac cctggctacc acctactcct ctggcaacca gaacgagaag cagatcgtga 4140
ccaccgacct gcgtcagaag tgcaccgaat ctcacactgg cacctccgcc tctgctcctc 4200
tggctgctgg aatcatcgcc ctgaccctgg aggctaacaa gaacctgacc tggcgcgaca 4260
tgcagcacct ggtggtgcag acctccaagc cagctcacct gaacgccaac gactgggcta 4320
ccaacggcgt gggaaggaag gtgagccact cttacggtta cggtctgctg gatgctggtg 4380
ctatggtggc cctggctcag aactggacca ccgtggcccc tcagcgcaag tgcatcatcg 4440
acatcctgac cgagcctaag gacatcggaa agagactgga agtgcgtaag accgtgaccg 4500
cttgcctggg agagcccaac cacatcacca gactggaaca cgcccaggct cgtctgaccc 4560
tgtcttacaa cagacgtgga gacctggcca tccacctggt gtctccaatg ggcacccgca 4620

```
gcaccctgct ggctgctagg ccacacgact acagcgccga cggattcaac gactgggctt   4680

tcatgaccac ccactcctgg gacgaggacc cttctggtga atgggtgctg gagatcgaaa   4740

acaccagcga ggccaacaac tacggcaccc tgaccaagtt caccctggtg ctgtacggca   4800

ccgctcctga gggactgcca gtgccccctg aaagctccgg ttgcaagacc ctgacctcta   4860

gccaggcctg cgtggtgtgc gaggaaggct tctccctgca ccagaagtct tgcgtgcagc   4920

actgcccacc cggattcgct cctcaggtgc tggacaccca ctactctacc gagaacgacg   4980

tggaaaccat cagagccagc gtgtgcgctc cttgtcacgc ttcctgtgct acttgtcagg   5040

gaccagccct gactgactgc ctgtcctgcc catctcacgc cagcctggac cccgtggagc   5100

agacctgctc cagacagtct cagtcctctc gtgaaagccc tccacagcag cagcccccta   5160

gactgccacc cgaggtggaa gccggccaga gactgcgtgc tggactgctg ccttctcacc   5220

tgccagaggt ggtggctggt ctgagctgcg ctttcatcgt gctggtgttc gtgaccgtgt   5280

tcctggtgct gcagctgcgc agcggtttct ccttcagggg cgtgaaggtg tacaccatgg   5340

accgcggtct gatcagctac aagggtctgc ctccagaggc ttggcaggag gaatgcccat   5400

ctgacagcga agaggacgag ggacgtggag aacggactgc cttcatcaaa gatcagagcg   5460

cactgtaata aatcgattta attaatagca taaccccttg gggcctctaa acgggtcttg   5520

aggggttttt tggaattcac ccagctttct tgtacaaagt ggtgatagct tgtcgagaag   5580

tactagagga tcataatcag ccataccaca tttgtagagg ttttacttgc tttaaaaaac   5640

ctcccacacc tccccctgaa cctgaaacat aaaatgaatg caattgttgt tgttaacttg   5700

tttattgcag cttataatgg ttacaaataa agcaatagca tcacaaattt cacaaataaa   5760

gcattttttt cactgcattc tagttgtggt ttgtccaaac tcatcaatgt atcttatcat   5820

gtctggatc                                                           5829
```

<210> SEQ ID NO 14
<211> LENGTH: 6195
<212> TYPE: DNA
<213> ORGANISM: Artificial Sequence
<220> FEATURE:
<223> OTHER INFORMATION: HCV del108C-E1-E2-p7-IRES-human furin proprotein cassette

<400> SEQUENCE: 14

```
cgtatactcc ggaatattaa tagatcatgg agataattaa aatgataacc atctcgcaaa     60

taaataagta ttttactgtt ttcgtaacag ttttgtaata aaaaaaccta taaatattcc    120

ggattattca taccgtccca ccatcgggcg cggatcatca caagtttgta caaaaaagca    180

ggctagatct taatacgact cactatatta attaaggatc ccaaaaaatt gaaattttat    240

tttttttttt tggaatataa ataatatgct gccaagaagg ggtccaagac tcggagtgcg    300

tgccacccgc aagacctctg agcgtagcca gccaagaggc cgccgccagc caatccctaa    360

ggctcgcagg cctgaaggta gaacttgggc tcagccaggt tacccttggc cactgtacgg    420

aaacgaaggc tgcggatggg ctggatggct gctgagcccc aggggttcca gaccttcttg    480

gggtccaact gacccacgcc gccgcagccg caacctgggc aaggtcatcg acaccctgac    540

ctgcggattc gccgacctga tgggttacat cccactggtg ggagctcccc tgggcggagc    600

tgctagggcc ctggctcacg gtgtgagagt gctggaagac ggcgtgaact acgccaccgg    660

taacctgcca ggctgcagct tctccatctt cctgctggct ctgctgtcct gcctgactgg    720

accagcttct gcttaccagg tgaggaacag caccggtctg taccacgtga ccaacgactg    780
```

-continued ccccaacagc tccatcgtgt tcgaagctgc tgatgctatc ctgcacaccc caggatgcgt 840
gccttgcgtg cgtgagggta acgcttccag atgctgggtg gctgtgaccc ctaccgtggc 900
caccagagac ggcaagctgc caaccaccca gctgaggaga cacatcgacc tgctggtggg 960
tagcgccacc ctgtgctccg ctctgtacgt gggcgacctg tgcggtagcg tgttcctggt 1020
gggccagctg ttcaccttca gccctcgtcg ccactggacc acccaggact gcaactgctc 1080
catctaccca ggccacatct ctggacaccg tatggcttgg gacatgatga tgaactggag 1140
cccaactgcc gctctgctgg tggctcagct gctgagaatc ccacaggcca tcctggacat 1200
gatcgctggt gctcactggg gcgtgctggc tggaatggct tacttctcta tggtgggcaa 1260
ctgggccaag gtgctggtgg tgctgctgct gttcgccgga gtggacgctg aaacctacgt 1320
gaccggtggc agcgccgcta ggactactgc tggcctggct agtctgttct cccctggagc 1380
taagcagaac atccagctgg tgaacaccaa cggctcttgg cacatcaaca gcaccgccct 1440
gaactgcaac gactccctga acaccggttg gatcgctggc ctgttctacc accacaagtt 1500
caactctagc ggatgctccg aaaggctggc ttcttgcaga cctctgactg acttcgctca 1560
gggttggggt cctatcagcc acgctgatgg atctggtcca gaccagcgcc cctactgctg 1620
gcactaccct cccaagcctt gcggtatcgt gcctgctaag tccgtgtgcg gtcccgtgta 1680
ctgcttcacc ccctctcctg tggtggtggg aaccaccgac aggtctggtg ctccaaccta 1740
cagctgggga gccaacgaca ccgacgtgtt cgtgctgaac aacaccagac cacccctggg 1800
aaactggttc ggttgcacct ggatgaacag caccggcttc accaaggtgt gcggagcccc 1860
tccatgcgtg atcggaggtg tgggcaacaa caccctgcgt tgccccaccg actgcttccg 1920
caagcaccct gaggctacct actccagatg cggctctgga ccttggatca ccccaaggtg 1980
cctggtggac taccccctaca gactgtggca ctacccttgc accatcaact acaccgtgtt 2040
caaggtgcgt atgtacgtgg gcggagtgga gcacagactg gaagctgctt gtaactggac 2100
tcgcggcgac cgctgcaacc tggacgacag ggacagatct gagctgagcc ccctgctgct 2160
gtccaccacc cagtggcagg tgctgccatg cagcttcacc accctgcccg ccctgtccac 2220
tggcctgatc cacctgcacc agaacatcgt ggacgtgcag tacctgtacg gtgtgggctc 2280
ctctatcgca tcttgggcta tcaagtggga atacgtggtg ctgctgttcc tgctgctggc 2340
tgatgctcgc gtgtgctcct gcctgtggat gatgctgctg atctctcagg tggaggccgc 2400
tctggaaaac ctggtggtgc tgaacgctgc aagcctggct ggaacccacg gtctggtgtc 2460
cttcctggtg ttcttctgct tcgcttggta cctgaagggc aagtgggtgc ctggagccgt 2520
gtacgctctg tacggaatgt ggcctctgct gctgctgctg ctggccctgc cacagagagc 2580
ttacgctctg gacactgagg tggctgcttc ttgtggtggc gtggtgctgg tgggcctgat 2640
ggctctgacc ctgtctcctt actacaagag gtacatcagc tggtgcctgt ggtggctgca 2700
gtacttcctg accagaatcg aagcccagct gcacgtgtgg attcctcccc tgaacgtgcg 2760
cggcggcaga gatgccgtga tcctgctgat gtgcgtggtg caccccgctc tggtgttcga 2820
catcaccaag ctgctgctgg ccgctttcgg ccccttaatct agagcccctc tccctccccc 2880
ccccctaacg ttactggccg aagccgcttg gaataaggcc ggtgtgtgtt tgtctatatg 2940
tgattttcca ccatattgcc gtcttttggc aatgtgaggg cccggaaacc tggccctgtc 3000
ttcttgacga gcattcctag gggtctttcc cctctcgcca aaggaatgca aggtctgttg 3060
aatgtcgtga aggaagcagt tcctctggaa gcttcttgaa gacaaacaac gtctgtagcg 3120
accctttgca ggcagcggaa ccccccacct ggcgacaggt gcctctgcgg ccaaaagcca 3180

-continued

```
cgtgtataag atacacctgc aaaggcggca caaccccagt gccacgttgt gagttggata   3240
gttgtggaaa gagtcaaatg gctctcctca agcgtagtca acaaggggct gaaggatgcc   3300
cagaaggtac cccattgtat gggaatctga tctggggcct cggtgcacat gctttacatg   3360
tgtttagtcg aggttaaaaa agctctaggc cccccgaacc acggggacgt ggttttcctt   3420
tgaaaaacac gatgataagc ttgccacaaa tggaactgcg cccctggctg ctgtgggtgg   3480
tggctgctac tggaaccctg gtgctgctag cagctgacgc ccagggccag aaggtgttca   3540
ccaacacctg ggctgtgaga atccccggcg gacctgctgt ggctaacagc gtggctcgta   3600
agcacggctt cctgaacctg ggacagattt tcggtgacta ctaccacttc tggcaccgcg   3660
gagtgaccaa gaggagcctg tccccacaca gaccaaggca ctccagactg cagcgtgagc   3720
cccaggtgca gtggctggaa cagcaggtgg ccaagcgcag gaccaagaga gacgtgtacc   3780
aggagcctac cgacccaaag ttcccccagc agtggtatct gtccggcgtg acccagcgtg   3840
acctgaacgt gaaggccgct tgggctcagg gttacaccgg tcacggcatc gtggtgtcca   3900
tcctggacga cggcatcgag aagaaccacc ctgacctggc cggtaactac gacccaggcg   3960
cttctttcga cgtgaacgac caggaccccg accctcagcc aagatacacc cagatgaacg   4020
acaacagaca tggaaccaga tgtgctggtg aagtggctgc tgtggctaac aacggcgtgt   4080
gcggagtggg tgtggcctac aacgctagaa tcggtggcgt gcgtatgctg gatggagaag   4140
tgactgatgc tgtggaagct agaagcctgg gactgaaccc aaaccacatc cacatctact   4200
ctgccagctg gggtccagag gatgatggaa agactgtgga tggtcctgct agactggctg   4260
aggaagcctt cttccgcggc gtgagccagg gaaggggagg tctgggaagc atcttcgtgt   4320
gggcttctgg taacggcgga agagagcacg actcctgcaa ctgcgacgga tacaccaact   4380
ctatctacac cctgagcatc agctccgcta cccagttcgg taacgtgccc tggtactccg   4440
aagcctgctc tagcaccctg gctaccacct actcctctgg caaccagaac gagaagcaga   4500
tcgtgaccac cgacctgcgt cagaagtgca ccgaatctca cactggcacc tccgcctctg   4560
ctcctctggc tgctggaatc atcgccctga ccctggaggc taacaagaac ctgacctggc   4620
gcgacatgca gcacctggtg gtgcagacct ccaagccagc tcacctgaac gccaacgact   4680
gggctaccaa cggcgtggga aggaaggtga gccactctta cggttacggt ctgctggatg   4740
ctggtgctat ggtggccctg gctcagaact ggaccaccgt ggcccctcag cgcaagtgca   4800
tcatcgacat cctgaccgag cctaaggaca tcggaaagag actggaagtg cgtaagaccg   4860
tgaccgcttg cctgggagag cccaaccaca tcaccagact ggaacacgcc caggctcgtc   4920
tgaccctgtc ttacaacaga cgtggagacc tggccatcca cctggtgtct ccaatgggca   4980
cccgcagcac cctgctggct gctaggccac acgactacag cgccgacgga ttcaacgact   5040
gggctttcat gaccacccac tcctgggacg aggacccttc tggtgaatgg gtgctggaga   5100
tcgaaaacac cagcgaggcc aacaactacg gcaccctgac caagttcacc ctggtgctgt   5160
acggcaccgc tcctgaggga ctgccagtgc cccctgaaag ctccggttgc aagaccctga   5220
cctctagcca ggcctgcgtg gtgtgcgagg aaggcttctc cctgcaccag aagtcttgcg   5280
tgcagcactg cccacccgga ttcgctcctc aggtgctgga cacccactac tctaccgaga   5340
acgacgtgga aaccatcaga gccagcgtgt gcgctccttg tcacgcttcc tgtgctactt   5400
gtcagggacc agccctgact gactgcctgt cctgcccatc tcacgccagc ctggaccccg   5460
tggagcagac ctgctccaga cagtctcagt cctctcgtga aagccctcca cagcagcagc   5520
cccctagact gccacccgag gtggaagccg gccagagact gcgtgctgga ctgctgcctt   5580
```

-continued

```
ctcacctgcc agaggtggtg gctggtctga gctgcgcttt catcgtgctg gtgttcgtga   5640

ccgtgttcct ggtgctgcag ctgcgcagcg gtttctcctt caggggcgtg aaggtgtaca   5700

ccatggaccg cggtctgatc agctacaagg gtctgcctcc agaggcttgg caggaggaat   5760

gcccatctga cagcgaagag gacgagggac gtggagaacg gactgccttc atcaaagatc   5820

agagcgcact gtaataaatc gatttaatta atagcataac cccttggggc ctctaaacgg   5880

gtcttgaggg gtttttttgga attcacccag ctttcttgta caaagtggtg atagcttgtc   5940

gagaagtact agaggatcat aatcagccat accacatttg tagaggtttt acttgcttta   6000

aaaaacctcc cacacctccc cctgaacctg aaacataaaa tgaatgcaat tgttgttgtt   6060

aacttgttta ttgcagctta taatggttac aaataaagca atagcatcac aaatttcaca   6120

aataaagcat ttttttcact gcattctagt tgtggtttgt ccaaactcat caatgtatct   6180

tatcatgtct ggatc                                                    6195
```